(12) United States Patent
Badiger et al.

(10) Patent No.: US 8,530,648 B2
(45) Date of Patent: Sep. 10, 2013

(54) DIAZA-SPIRO[5.5]UNDECANES

(75) Inventors: Sangamesh Badiger, Karnataka (IN); Dirk Behnke, Grenzach-Wyhlen (DE); Claudia Betschart, Basel (CH); Vinod Chaudhari, Karnataka (IN); Simona Cotesta, Basel (CH); Jürgen Hans-Hermann Hinrichs, Schopfheim (DE); Silvio Ofner, Muenchenstein (CH); Chetan Pandit, Karnataka (IN); Jürgen Wagner, Bottmingen (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 13/517,111

(22) PCT Filed: Dec. 20, 2010

(86) PCT No.: PCT/EP2010/070263
§ 371 (c)(1),
(2), (4) Date: Jul. 5, 2012

(87) PCT Pub. No.: WO2011/076747
PCT Pub. Date: Jun. 30, 2011

(65) Prior Publication Data
US 2012/0264748 A1    Oct. 18, 2012

(30) Foreign Application Priority Data
Dec. 21, 2009    (IN) .................... 2663/DEL/2009

(51) Int. Cl.
*C07D 471/10*    (2006.01)
*A61P 3/00*    (2006.01)
*A61P 25/00*    (2006.01)
*A61P 25/28*    (2006.01)
*A61P 25/30*    (2006.01)

(52) U.S. Cl.
USPC ................................. 544/70; 544/230; 546/16

(58) Field of Classification Search
None
See application file for complete search history.

(56) References Cited

U.S. PATENT DOCUMENTS

| 7,105,526 B2 | 9/2006 | Otake et al. |
| 7,687,514 B2 | 3/2010 | Otake et al. |
| 7,803,807 B2 | 9/2010 | Otake et al. |
| 2009/0176789 A1* | 7/2009 | Breslin et al. ................. 514/249 |

OTHER PUBLICATIONS

Cai, Jiaqiang et al., "Antagonist of the Orexin Receptors", Expert Opin. Ther. Patents, 2006, pp. 631-646, vol. 16, Iss. 5.

* cited by examiner

*Primary Examiner* — Janet Andres
*Assistant Examiner* — Timothy R Rozof
(74) *Attorney, Agent, or Firm* — Scott W. Field

(57) ABSTRACT

The invention relates to compound of the formula (I), in which the substituents are as defined in the specification; in free form or in salt form; to its preparation, to its use as medicament and to medicaments comprising it.

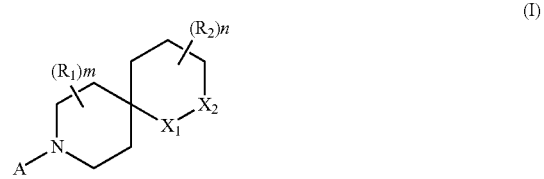

13 Claims, No Drawings

DIAZA-SPIRO[5.5]UNDECANES

The invention relates to diaza-spiro[5.5]undecanes, to their preparation, to their use as medicaments and to medicaments comprising them.

Orexins (orexin A/OX-A and orexin B/OX-B), which are also known as hypocretins, are neuropeptides. Orexin A is a 33 amino acid peptide and orexin B is a 28 amino acid peptide (Sakurai T. et al., Cell, 1998, 92, 573-585). Orexins are produced in discrete neurons of the lateral hypothalamus and bind to G-protein-coupled receptors, the orexin receptors (also known as hypocretin receptors): known are the orexin-1 receptor (OX1R) and the orexin-2 receptor (OX2R). The orexin-1 receptor has some selectivity for OX-A, whereas the orexin-2 receptor binds OX-A and OX-B with similar affinity. Orexins regulate states of sleep and wakefulness, opening potentially novel therapeutic approaches for narcolepsy as well as insomnia and other sleep disorders (Chemelli R. M. et al., Cell, 1999, 98, 437-451). Furthermore, orexins were found to stimulate food consumption in rats suggesting a physiological role for these peptides as mediators in the central feedback mechanism that regulates feeding behavior (Sakurai T. et al., Cell, 1998, 92, 573-585). Still furthermore, orexins were shown to play a role in brain reward function/motivation suggesting usefulness to treat substance-related disorders (Harris A. C. et al, Nature, 2005, 437, 556-559). Still furthermore, it has been shown that amyloid beta levels inversely correlate with orexin levels in rodents and humans (brain and/or CSF), and that an orexin receptor antagonist reduces both amyloid beta levels and amyloid plaque load in Alzheimer's transgenic mice, thus suggesting usefulness in the treatment of Alzheimers disease (Kang J. E. et al, Science 2009, 326, 1005-1007).

Orexin receptors may have numerous implications in disorders such as i) sleep disorders, e.g. sleep apnea, narcolepsy, insomnia, parasomnia, jet lag syndrome, disturbed biological and circadian rhythms; sleep disturbances associated with diseases such as neurological disorders, neuropathic pain and restless leg syndrome;
ii) eating disorders, e.g. appetite and taste disorders;
iii) substance-related disorders, e.g. substance abuse, substance dependence and substance withdrawal disorders, such as nicotine withdrawal or narcotics withdrawal;
iv) Alzheimers disease;
v) psychiatric, neurological and neurodegenerative disorders, e.g. depression; anxiety; addictions, obsessive compulsive disorder; affective neurosis; depressive neurosis; anxiety neurosis; dysthymic disorder; mood disorder; sexual dysfunction; psychosexual dysfunction; sex disorder; schizophrenia; manic depression; delirium; dementia; severe mental retardation and dyskinesias such as Huntington's disease and Tourette syndrome; Parkinson's disease; ischemic or hemorrhagic stroke; migraine; and neurodegenerative disorders including nosological entities such as disinhibition-dementia-parkinsonism-amyotrophy complex; pallido-ponto-nigral degeneration epilepsy; seizure disorders;
vi) cardiovascular diseases, diabetes; asthma; Cushing's syndrome/disease; basophile adenoma; prolactinoma; hyperprolactinemia; hypopituitarism; hypophysis tumor/adenoma; hypothalamic diseases; Froehlich's syndrome; hypophysis diseases, hypothalamic hypogonadism; Kallman's syndrome (anosmia, hyposmia); functional or psychogenic amenorrhea; hypopituitarism; hypothalamic hypothyroidism; hypothalamic-adrenal dysfunction; idiopathic hyperprolactinemia; hypothalamic disorders of growth hormone deficiency; idiopathic growth deficiency; dwarfism; gigantism; acromegaly; heart and lung diseases, acute and congestive heart failure; hypotension; hypertension; urinary retention; osteoporosis; angina pectoris; myocardial infarction; subarachnoid hemorrhage; ulcers; allergies; benign prostatic hypertrophy; chronic renal failure; renal disease; impaired glucose tolerance; vomiting and nausea; inflammatory bowel disease; gastric dyskinesia; gastric ulcers; urinary bladder incontinence e.g. urge incontinence; hyperalgesia; pain; enhanced or exaggerated sensitivity to pain such as hyperalgesia, causalgia, and allodynia; acute pain; burn pain; atypical facial pain; neuropathic pain; back pain; complex regional pain syndrome I and II; arthritic pain; sports injury pain; pain related to infection e.g. HIV, post-chemotherapy pain; post-stroke pain; post-operative pain; neuralgia; conditions associated with visceral pain such as irritable bowel syndrome, migraine and angina; and
vii) other diseases related to general orexin system dysfunction.

Orexin receptor antagonists, are considered to be useful in the treatment of a wide range of disorders, in particular sleep disorders, eating disorders and substance-related disorders.

Therefore, there is a need to provide new orexin receptor antagonists that are good drug candidates. In particular, preferred compounds should bind potently to the orexin receptors (either as OX1R or OX2R subtype selective antagonists or as dual OX1R/OX2R antagonists) whilst showing little affinity for other receptors. They should be well absorbed from the gastrointestinal tract, be sufficiently metabolically stable and possess favorable pharmacokinetic properties. When targeted against receptors in the central nervous system they should cross the blood brain barrier freely and when targeted selectively against receptors in the peripheral nervous system they should not cross the blood brain barrier. They should be non-toxic and demonstrate few side-effects. Furthermore, the ideal drug candidate will be able to exist in a physical form that is stable, non-hygroscopic and easily formulated.

The compounds of the invention are orexin receptor antagonists and are therefore potentially useful in the treatment of a wide range of disorders, particularly sleep disorders, eating disorders, substance-related disorders and Alzheimers disease.

In a first aspect, the invention relates to a compound of the formula I

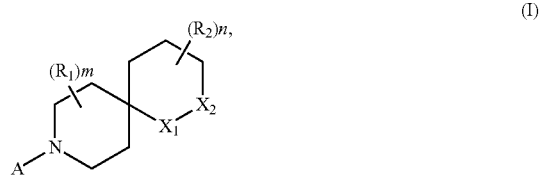

(I)

wherein
A is a eight- to ten-membered fused bicyclic aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may be substituted once or more than once by $R_3$, and wherein a substituent on a nitrogen in a heterocyclic ring system may not be halogen;
each $R_3$ independently is $C_{1-6}$alkyl, $C_{1-6}$halogenalkyl, $C_{1-6}$alkoxy, $C_{1-6}$halogenalkoxy, halogen, cyano or a three- to seven-membered monocyclic ring system which may be aromatic, saturated or unsaturated non-aromatic and which may contain from 1 to 4 hetero atoms selected from nitrogen, oxygen and sulfur, and wherein each ring system may contain not more than 2 oxygen atoms and not more than 2 sulfur atoms, and wherein each ring system may in turn be substituted once or more than once by $R_4$, and wherein a substituent on a nitrogen in a heterocyclic ring system may not be halogen;

each $R_4$ independently is $C_{1-6}$alkyl, $C_{1-6}$halogenalkyl, $C_{1-6}$alkoxy, $C_{1-6}$halogenalkoxy, halogen or cyano, or two $R_4$ at the same ring atom together are oxo;

or A is a five- to six-membered monocyclic aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system is substituted by A1 and wherein the ring system may be further substituted once or more than once by $R_5$, and wherein a substituent on a nitrogen in a heterocyclic ring system may not be halogen;

A1 is a five- to six-membered monocyclic aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may be substituted once or more than once by $R_6$, and wherein a substituent on a nitrogen in a heterocyclic ring system may not be halogen;

each $R_5$ or $R_6$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy;

m is 0, 1, 2, 3, 4, 5 or 6;

n is 0, 1, 2, 3, 4, 5 or 6;

each $R_1$ or $R_2$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy;

—$X_1$— is —C(O)— and —$X_2$— is —N(L-B)—;

or —$X_1$— is —N(L-B)— and —$X_2$— is —C(O)—;

L is —C($R_7$)$_2$—;

each $R_7$ independently is hydrogen, $C_{1-6}$alkyl, $C_{1-6}$halogenalkyl, $C_{3-7}$cycloalkyl or $C_{3-7}$cycloalkyl($C_{1-4}$alkyl);

B is a five- to ten-membered monocyclic or fused polycyclic aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may be substituted once or more than once by $R_8$, and wherein a substituent on a nitrogen in a heterocyclic ring system may not be halogen;

each $R_8$ independently $C_{1-6}$alkyl, $C_{1-6}$halogenalkyl, $C_{1-6}$hydroxyalkyl, $C_{1-4}$alkoxy-$C_{1-6}$alkyl, $C_{1-6}$aminoalkyl, $C_{1-4}$alkylamino-$C_{1-6}$alkyl, di($C_{1-4}$alkyl)amino-$C_{1-6}$alkyl, $C_{2-6}$alkenyl, $C_{2-6}$halogenalkenyl, $C_{2-6}$alkynyl, $C_{2-6}$halogenalkynyl, $C_{1-6}$alkoxy, $C_{1-6}$halogenalkoxy, $C_{1-4}$alkoxy-$C_{1-6}$alkoxy, $C_{1-6}$alkylamino, di($C_{1-6}$alkyl)amino, halogen, hydroxy, cyano, amino or a three- to seven-membered monocyclic ring system which may be aromatic, saturated or unsaturated non-aromatic and which may contain from 1 to 4 hetero atoms selected from nitrogen, oxygen and sulfur, and wherein each ring system may be attached directly to ring system B or via a $C_{1-4}$alkylene, and wherein each ring system may contain not more than 2 oxygen atoms and not more than 2 sulfur atoms, and wherein each ring system may in turn be substituted once or more than once by $C_{1-6}$alkyl, $C_{1-6}$halogenalkyl, $C_{1-6}$alkoxy, $C_{1-6}$halogenalkoxy, halogen or cyano, and wherein a substituent on a nitrogen in a heterocyclic ring system may not be halogen;

or two $R_8$ at adjacent ring atoms form together with said ring atoms a fused five- to seven-membered unsaturated non-aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may in turn be substituted once or more than once by $R_9$, and wherein a substituent on a nitrogen in a heterocyclic ring system may not be halogen; and wherein each $R_9$ independently is halogen or $C_{1-6}$alkyl, or two $R_9$ at the same ring atom together are oxo;

in free form or in salt form.

Unless indicated otherwise, the expressions used in this invention have the following meaning:

"Alkyl" represents a straight-chain or branched-chain alkyl group, for example, methyl, ethyl, n- or iso-propyl, n-, iso-, sec- or tert-butyl, n-pentyl, n-hexyl; $C_{1-6}$alkyl preferably represents a straight-chain or branched-chain $C_{1-4}$alkyl with particular preference given to methyl, ethyl, n-propyl, iso-propyl and tert-butyl.

"Alkylene" refers to a divalent alkyl group as defined herein above having 1 to 20 carbon atoms. It comprises 1 to 20 carbon atoms. Unless otherwise provided, alkylene refers to moieties having 1 to 16 carbon atoms, 1 to 10 carbon atoms, 1 to 7 carbon atoms, or 1 to 4 carbon atoms. Representative examples of alkylene include, but are not limited to, methylene, ethylene, n-propylene, iso-propylene, n-butylene, sec-butylene, iso-butylene, tert-butylene, n-pentylene, isopentylene, neopentylene, n-hexylene, 3-methylhexylene, 2,2-dimethylpentylene, 2,3-dimethylpentylene, n-heptylene, n-octylene, n-nonylene, n-decylene and the like.

Each alkyl part of "alkoxy", "halogenalkyl" and so on shall have the same meaning as described in the above-mentioned definition of "alkyl", especially regarding linearity and preferential size.

"Alkenyl" refers to a straight or branched hydrocarbon chain comprising one or more unsaturated carbon-carbon bonds, such as ethenyl and propenyl. Alkenyl groups include $C_{2-6}$alkenyl and $C_{2-4}$alkenyl groups (which have from 2 to 6 or 2 to 4 carbon atoms, respectively), such as ethenyl, allyl or isopropenyl.

"Alkynyl" refers to straight or branched hydrocarbon chains comprising one or more triple carbon-carbon bonds. Alkynyl groups include $C_{2-6}$alkynyl and $C_{2-4}$alkynyl groups, which have from 2 to 6 or 2 to 4 carbon atoms, respectively. Alkynyl groups include for example groups such as ethynyl and propynyl.

"Alkylamino" refers to a secondary or tertiary amine having the general structure —NH-alkyl or —N(alkyl)(alkyl), wherein each alkyl may be the same or different. Such groups include, for example, mono- and di-($C_{1-6}$alkyl)amino groups, in which each alkyl may be the same or different and may contain from 1 to 6 carbon atoms, as well as mono- and di-($C_{1-4}$alkyl)amino groups.

"$C_{3-7}$cycloalkyl" represents a saturated alicyclic moiety having from three to seven carbon atoms. This term refers to groups such as cyclopropyl, cyclobutyl, cyclopentyl and cyclohexyl.

A substituent being substituted "once or more than once", for example as defined for A, is preferably substituted by one to three substituents.

Halogen is generally fluorine, chlorine, bromine or iodine; preferably fluorine, chlorine or bromine. Halogenalkyl groups preferably have a chain length of 1 to 4 carbon atoms and are, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,2-trichloroethyl, 1,1,2,2-tetrafluoroethyl, 2,2,3,3-tetrafluoropropyl, 2,2,3,3,3-pentafluoropropyl or 2,2,3,4,4,4-hexafluorobutyl; preferably —$CF_3$, —$CHF_2$, —$CH_2F$, —CHF—$CH_3$, —$CF_2CH_3$, or —$CH_2CF_3$.

In the context of the invention, the definition of A and A1 as "five- to six-membered monocyclic aromatic ring system which may contain from 1 to 4 heteroatoms" encompasses a $C_6$-aromatic hydrocarbon group or a five- to six-membered heterocyclic aromatic ring system.

In the context of the invention, the definition of B as a "five- to ten-membered monocyclic or fused polycyclic aromatic ring system" encompasses a $C_6$- or $C_{10}$-aromatic hydrocarbon group or a five- to ten-membered heterocyclic aromatic ring system. "Polycyclic" means preferably bicyclic.

The term "fused polycyclic aromatic ring system" refers to an aromatic substituent which consists of multiple, e.g. two, aromatic rings that are fused together.

In the context of the invention, the definition of A as a "eight- to ten-membered fused bicyclic aromatic ring system" encompasses a $C_{10}$-aromatic hydrocarbon group or a eight- to ten-membered heterocyclic aromatic ring system.

In the context of the invention, the definition of $R_3$ and $R_8$ as a "three- to seven-membered monocyclic ring system" encompasses a $C_6$-aromatic hydrocarbon group, a five- to six-membered heterocyclic aromatic ring system and a three- to seven-membered monocyclic aliphatic or heterocyclic ring system.

In the context of the invention, the definition of two $R_8$ as a "fused five- to seven-membered unsaturated non-aromatic ring system" encompasses five- to seven-membered hydrocarbon and heterocyclic groups which comprise at least one double-bond, which is shared with the aromatic ring system they are fused to.

A $C_6$- or $C_{10}$-aromatic hydrocarbon group is typically phenyl or naphthyl, especially phenyl.

Preferably, but also depending on substituent definition, "five- to ten-membered heterocyclic aromatic ring systems" consist of 5 to 10 ring atoms of which 1-3 ring atoms are hetero atoms. Such heterocyclic aromatic ring systems may be present as a single aromatic ring system or as multiple, e.g. two, fused aromatic ring systems; preferably as single ring systems or as benz-annelated ring systems.

Examples of heterocyclic ring systems are: imidazo[2,1-b]thiazole, pyrrole, pyrroline, pyrrolidine, pyrazole, pyrazoline, pyrazolidine, imidazole, imidazoline, imidazolidine, triazole, triazoline, triazolidine, tetrazole, furane, dihydrofurane, tetrahydrofurane, furazane (oxadiazole), dioxolane, thiophene, dihydrothiophene, tetrahydrothiophene, oxazole, oxazoline, oxazolidine, isoxazole, isoxazoline, isoxazolidine, thiazole, thiazoline, thiazolidine, isothiazole, isothiazoline, isothiazolidine, thiadiazole, thiadiazoline, thiadiazolidine, pyridine, piperidine, pyridazine, pyrazine, piperazine, triazine, pyrane, tetrahydropyrane, thiopyrane, tetrahydrothiopyrane, oxazine, thiazine, dioxine, morpholine, purine, pteridine, and the corresponding benz-annelated heterocycles, e.g. indole, isoindole, coumarin, isoquinoline, quinoline, quinoxaline and the like. Further examples of heterocycles are: quinoxaline, indole, pyridine, 1H-benzo[d]imidazole, quinoline, pyrimidine, 1,3,4-oxadiazole, isoxazole, pyrrole or benzo[d]isoxazole.

Depending on substituent definition, the compounds of formula I may exist in optically active form or in form of mixtures of optical isomers, e.g. in form of racemic mixtures or diastereomeric mixtures. In particular, further asymmetrical carbon atom(s) may be present in the compounds of formula I and their salts. All optical isomers and their mixtures, including the racemic mixtures, are embraced by the invention.

As used herein, the term "isomers" refers to different compounds that have the same molecular formula but differ in arrangement and configuration of the atoms. Also as used herein, the term "an optical isomer" or "a stereoisomer" refers to any of the various stereo isomeric configurations which may exist for a given compound of the invention and includes geometric isomers. It is understood that a substituent may be attached at a chiral center of a carbon atom. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R—S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line.

The compounds described herein may contain one or more asymmetric centers and may thus give rise to enantiomers, diastereomers, and other stereoisomeric forms that may be defined, in terms of absolute stereochemistry, as (R)- or (S)-. The invention is meant to include all such possible isomers, including racemic mixtures, optically pure forms and intermediate mixtures. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration.

Any asymmetric atom (e.g. carbon or the like) of the compound(s) of the invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated bonds may, if possible, be present in cis-(Z)- or trans-(E)-form.

Accordingly, as used herein a compound of the invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Depending on substituent definition, compounds of formula I may occur in various tautomeric forms. All tautomeric forms of the compounds of formula I are embraced by the invention.

Compounds of formula I may exist in free form or as a salt. In this specification, unless otherwise indicated, language such as "compound of formula I" is to be understood as embracing the compounds in any form, for example free or acid addition salt form. Salts which are unsuitable for pharmaceutical uses but which can be employed, for example, for the isolation or purification of free compounds of formula I, such as picrates or perchlorates, are also included. For therapeutic use, only pharmaceutically acceptable salts or free compounds are employed (where applicable in the form of pharmaceutical preparations), and are therefore preferred. Salts are preferably physiologically acceptable salts, formed by the addition of an acid.

As used herein, the term "pharmaceutically acceptable salts" refers to salts that retain the biological effectiveness and properties of the compounds of this invention and, which typically are not biologically or otherwise undesirable. The compounds of the invention may be capable of forming acid salts by virtue of the presence of suitable groups, such as amino groups.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulformate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

The pharmaceutically acceptable salts of the invention can be synthesized from a parent compound by conventional chemical methods. Generally, such salts can be prepared by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are preferred, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

The invention includes all pharmaceutically acceptable isotopically-labeled compounds of the invention, i.e. compounds of formula (I), wherein (1) one or more atoms are replaced by atoms having the same atomic number, but an atomic mass or mass number different from the atomic mass or mass number usually found in nature, and/or (2) the isotopic ratio of one or more atoms is different from the naturally occurring ratio.

Examples of isotopes suitable for inclusion in the compounds of the invention comprises isotopes of hydrogen, such as $^{2}H$ and $^{3}H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulfur, such as $^{35}S$.

Certain isotopically-labeled compounds of formula (I), for example, those incorporating a radioactive isotope, are useful in drug and/or substrate tissue distribution studies. The radioactive isotopes tritium, i.e. $^{3}H$, and carbon-14, i.e. $^{14}C$, are particularly useful for this purpose in view of their ease of incorporation and ready means of detection.

Substitution with heavier isotopes such as deuterium, i.e. $^{2}H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Tomography (PET) studies for examining substrate receptor occupancy.

Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

Pharmaceutically acceptable solvates in accordance with the invention include those wherein the solvent of crystallization may be isotopically substituted, e.g. $D_2O$, $d_6$-acetone, $d_6$-DMSO.

Compounds of the invention, i.e. compounds of formula (I) that contain groups capable of acting as donors and/or acceptors for hydrogen bonds may be capable of forming co-crystals with suitable co-crystal formers. These co-crystals may be prepared from compounds of formula (I) by known co-crystal forming procedures. Such procedures include grinding, heating, co-subliming, co-melting, or contacting in solution compounds of formula I with the co-crystal former under crystallization conditions and isolating co-crystals thereby formed. Suitable co-crystal formers include those described in WO 2004/078163. Hence the invention further provides co-crystals comprising a compound of formula (I).

Compounds of the invention are either obtained in the free form, as a salt thereof, or as prodrug derivatives thereof.

The invention also provides pro-drugs of the compounds of the invention that converts in vivo to the compounds of the invention. A pro-drug is an active or inactive compound that is modified chemically through in vivo physiological action, such as hydrolysis, metabolism and the like, into a compound of this invention following administration of the prodrug to a subject. The suitability and techniques involved in making and using pro-drugs are well known by those skilled in the art. Prodrugs can be conceptually divided into two non-exclusive categories, bioprecursor prodrugs and carrier prodrugs. See *The Practice of Medicinal Chemistry*, Ch. 31-32 (Ed. Wermuth, Academic Press, San Diego, Calif., 2001). Generally, bioprecursor prodrugs are compounds, which are inactive or have low activity compared to the corresponding active drug compound, that contain one or more protective groups and are converted to an active form by metabolism or solvolysis. Both the active drug form and any released metabolic products should have acceptably low toxicity.

Carrier prodrugs are drug compounds that contain a transport moiety, e.g., that improve uptake and/or localized delivery to a site(s) of action. Desirably for such a carrier prodrug, the linkage between the drug moiety and the transport moiety is a covalent bond, the prodrug is inactive or less active than the drug compound, and any released transport moiety is acceptably non-toxic. For prodrugs where the transport moiety is intended to enhance uptake, typically the release of the transport moiety should be rapid. In other cases, it is desirable to utilize a moiety that provides slow release, e.g., certain polymers or other moieties, such as cyclodextrins. Carrier prodrugs can, for example, be used to improve one or more of the following properties: increased lipophilicity, increased duration of pharmacological effects, increased site-specificity, decreased toxicity and adverse reactions, and/or improvement in drug formulation (e.g., stability, water solubility, suppression of an undesirable organoleptic or physiochemical property). For example, lipophilicity can be increased by esterification of hydroxyl groups with lipophilic carboxylic acids (e.g., a carboxylic acid having at least one lipophilic moiety).

Exemplary prodrugs are, e.g., O-acyl derivatives of alcohols. Preferred are pharmaceutically acceptable ester derivatives convertible by solvolysis under physiological conditions to the parent carboxylic acid, e.g., lower alkyl esters, cycloalkyl esters, lower alkenyl esters, benzyl esters, mono- or di-substituted lower alkyl esters, such as the ω-(amino, mono- or di-lower alkylamino, carboxy, lower alkoxycarbonyl)-lower alkyl esters, the α-(lower alkanoyloxy, lower alkoxycarbonyl or di-lower alkylaminocarbonyl)-lower alkyl esters, such as the pivaloyloxymethyl ester and the like conventionally used in the art. In addition, amines have been masked as arylcarbonyloxymethyl substituted derivatives which are cleaved by esterases in vivo releasing the free drug and formaldehyde (Bundgaard, *J. Med. Chem.* 2503 (1989)). Moreover, drugs containing an acidic NH group, such as imidazole, imide, indole and the like, have been masked with N-acyloxymethyl groups (Bundgaard, *Design of Prodrugs*, Elsevier (1985)). Hydroxy groups have been masked as esters and ethers. EP 039,051 (Sloan and Little) discloses Mannich-base hydroxamic acid prodrugs, their preparation and use.

Furthermore, the compounds of the invention, including their salts, can also be obtained in the form of their hydrates, or include other solvents used for their crystallization.

Preferred substituents, preferred ranges of numerical values or preferred ranges of the radicals present in compounds of the formula I, Ia, Ib and the corresponding intermediate compounds are defined below. The definition of the substituents applies to the end-products as well as to the corresponding intermediates. The definitions of the substituents may be combined at will, e.g. preferred substituents $R^1$ and particularly preferred substituents $R^2$.

In especially preferred embodiments, the invention relates to one or more than one of the compounds of the formula I mentioned in the Examples hereinafter, in free form or in salt form.

In a second aspect, the invention relates to a compound of formula I

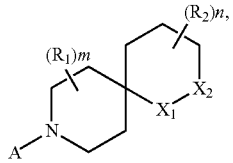

(I)

wherein
A is a eight- to ten-membered fused bicyclic aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may be substituted once or more than once by $R_3$, and wherein a substituent on a nitrogen in a heterocyclic ring system may not be halogen;

each $R_3$ independently is $C_{1-6}$alkyl, $C_{1-6}$halogenalkyl, $C_{1-6}$alkoxy, $C_{1-6}$halogenalkoxy, halogen, cyano or a three- to seven-membered monocyclic ring system which may be aromatic, saturated or unsaturated non-aromatic and which may contain from 1 to 4 hetero atoms selected from nitrogen, oxygen and sulfur, and wherein each ring system may contain not more than 2 oxygen atoms and not more than 2 sulfur atoms, and wherein each ring system may in turn be substituted once or more than once by $R_4$, and wherein a substituent on a nitrogen in a heterocyclic ring system may not be halogen;

each $R_4$ independently is $C_{1-6}$alkyl, $C_{1-6}$halogenalkyl, $C_{1-6}$alkoxy, $C_{1-6}$halogenalkoxy, halogen or cyano, or two $R_4$ at the same ring atom together are oxo;

or A is a five- to six-membered monocyclic aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system is substituted by A1 and wherein the ring system may be further substituted once or more than once by $R_5$, and wherein a substituent on a nitrogen in a heterocyclic ring system may not be halogen;

A1 is a five- to six-membered monocyclic aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may be substituted once or more than once by $R_6$, and wherein a substituent on a nitrogen in a heterocyclic ring system may not be halogen;

each $R_5$ or $R_6$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy;

m is 0, 1, 2, 3, 4, 5 or 6;
n is 0, 1, 2, 3, 4, 5 or 6;

each $R_1$ or $R_2$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy;

—$X_1$— is —C(O)— and —$X_2$— is —N(L-B)—;
or —$X_1$— is —N(L-B)— and —$X_2$— is —C(O)—;
L is —C($R_7$)$_2$—;

each $R_7$ independently is hydrogen, $C_{1-6}$alkyl, $C_{1-6}$halogenalkyl, $C_{3-7}$cycloalkyl or $C_{3-7}$cycloalkyl($C_{1-4}$alkyl);

B is a five- to ten-membered monocyclic or fused polycyclic aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may be substituted once or more than once by $R_8$, and wherein a substituent on a nitrogen in a heterocyclic ring system may not be halogen;

each $R_8$ independently is $C_{1-6}$alkyl, $C_{1-6}$halogenalkyl, $C_{1-6}$alkoxy, $C_{1-6}$halogenalkoxy, halogen, cyano or a three- to seven-membered monocyclic ring system which may be aromatic, saturated or unsaturated non-aromatic and which may contain from 1 to 4 hetero atoms selected from nitrogen, oxygen and sulfur, and wherein each ring system may contain not more than 2 oxygen atoms and not more than 2 sulfur atoms, and wherein each ring system may in turn be substituted once or more than once by $C_{1-6}$alkyl, $C_{1-6}$halogenalkyl, $C_{1-6}$alkoxy, $C_{1-6}$halogenalkoxy, halogen or cyano, and wherein a substituent on a nitrogen in a heterocyclic ring system may not be halogen;

or two $R_8$ at adjacent ring atoms form together with said ring atoms a fused five- to seven-membered unsaturated non-aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may in turn be substituted once or more than once by $R_9$, and wherein a substituent on a nitrogen in a heterocyclic ring system may not be halogen; and wherein each $R_9$ independently is halogen or $C_{1-6}$alkyl, or two $R_9$ at the same ring atom together are oxo;

in free form or in salt form.

In one class of compounds of the invention, A is a eight- to ten-membered fused bicyclic aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may be substituted once or more than once by $R_3$, and wherein a substituent on a nitrogen in a heterocyclic ring system may not be halogen. In one embodiment of said class, each $R_3$ independently is $C_{1-6}$alkyl, $C_{1-6}$halogenalkyl or halogen. In one embodiment of said class, A is unsubstituted.

In one embodiment of said class, A is quinoxalinyl, which may be substituted once or more than once by $R_3$. In one embodiment of said class, A is quinoxalin-2-yl, which may be substituted once or more than once by $R_3$.

In one class of compounds of the invention, A is a five- to six-membered monocyclic aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system is substituted by A1 and wherein the ring system may be further substituted once or more than once by $R_5$, and wherein a substituent on a nitrogen in a heterocyclic ring system may not be halogen.

In one class of compounds of the invention, m is 0, 1, 2 or 3. In one embodiment of said class, m is 0 or 1, for example m being 0.

In one class of compounds of the invention, n is 0, 1, 2 or 3. In one embodiment of said class, n is 0 or 1, for example n being 0.

In one class of compounds of the invention, each $R_1$ or $R_2$ independently is halogen, $C_{1-6}$alkyl or $C_{1-6}$halogenalkyl.

In one class of compounds of the invention, —$X_1$— is —C(O)— and —$X_2$— is —N(L-B)—.

In one class of compounds of the invention, —$X_1$— is —N(L-B)— and —$X_2$— is —C(O)—.

In one class of compounds of the invention, each $R_7$ independently is hydrogen, $C_{1-6}$alkyl or $C_{1-6}$halogenalkyl. In one embodiment of said class, each $R_7$ is hydrogen.

In one class of compounds of the invention, B is an eight- to ten-membered fused bicyclic aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may be substituted once or more than once by $R_8$, and wherein a substituent on a nitrogen in a heterocyclic ring system may not be halogen.

In one class of compounds of the invention, B is a nine-membered fused bicyclic aromatic ring system which contains from 1 to 4 hetero atoms selected from nitrogen, oxygen and sulfur, wherein the ring system may be substituted once or more than once by $R_8$, and wherein a substituent on a nitrogen in a heterocyclic ring system may not be halogen.

In one class of compounds of the invention, B is a nine-membered fused bicyclic aromatic ring system which contains from 1 to 4 hetero atoms selected from nitrogen, oxygen and sulfur, wherein the ring system may be substituted once or more than once by $R_6$, and wherein a substituent on a nitrogen in a heterocyclic ring system may not be halogen; and each $R_8$ independently is $C_{1-6}$alkyl, $C_{1-6}$halogenalkyl, $C_{1-6}$hydroxyalkyl, $C_{1-4}$alkoxy-$C_{1-6}$alkyl, $C_{1-6}$aminoalkyl, di($C_{1-4}$alkyl)amino-$C_{1-6}$alkyl, $C_{2-6}$alkenyl, $C_{2-6}$halogenalkenyl, $C_{2-6}$alkynyl, $C_{2-6}$halogenalkynyl, $C_{1-6}$alkoxy, $C_{1-6}$halogenalkoxy, $C_{1-4}$alkoxy-$C_{1-6}$alkoxy, $C_{1-6}$alkylamino, di($C_{1-6}$alkyl)amino, halogen, hydroxy, cyano, amino or a three- to seven-membered monocyclic ring system which may be aromatic, saturated or unsaturated non-aromatic and which may contain from 1 to 4 hetero atoms selected from nitrogen, oxygen and sulfur.

In one class of compounds of the invention, B is a nine-membered fused bicyclic aromatic ring system which contains from 1 to 4 hetero atoms selected from nitrogen, oxygen and sulfur, wherein the ring system may be substituted once or more than once by $R_8$, and wherein a substituent on a nitrogen in a heterocyclic ring system may not be halogen; and each $R_8$ independently is $C_{1-6}$alkyl, $C_{1-6}$alkoxy, $C_{1-6}$halogenalkyl or halogen.

In one class of compounds of the invention, B is indolyl which may be substituted once or more than once by $R_{8a}$, wherein a substituent on the nitrogen of the indolyl may not be halogen; and each $R_{8a}$ independently is $C_{1-6}$alkyl, $C_{1-6}$alkoxy, $C_{1-6}$halogenalkyl or halogen.

In one class of compounds of the invention, B is indol-3-yl which may be substituted once or more than once by $R_{8a}$, wherein a substituent on the nitrogen of the indol-3-yl may not be halogen; and each $R_{8a}$ independently is $C_{1-6}$alkyl, $C_{1-6}$alkoxy, $C_{1-6}$halogenalkyl or halogen.

In one class of compounds of the invention, B is indol-4-yl which may be substituted once or more than once by $R_{8a}$, wherein a substituent on the nitrogen of the indol-4-yl may not be halogen; and each $R_{8a}$ independently is $C_{1-6}$alkyl, $C_{1-6}$alkoxy, $C_{1-6}$halogenalkyl or halogen.

In one class of compounds of the invention, B is a five- to six-membered monocyclic aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may be substituted once or more than once by $R_8$, and wherein a substituent on a nitrogen in a heterocyclic ring system may not be halogen.

In one class of compounds of the invention, B is a six-membered monocyclic aromatic ring system which may contain 1 to 2 nitrogen atoms, wherein the ring system is substituted once by $R_{8b}$, and wherein the ring system may be further substituted once or more than once by $R_{8c}$;

$R_{8b}$ is a five- to six-membered monocyclic aromatic ring system, which may contain from 1 to 4 hetero atoms selected from nitrogen, oxygen and sulfur, and wherein the ring system may in turn be substituted once or more than once by $C_{1-6}$alkyl, $C_{1-6}$halogenalkyl, $C_{1-6}$alkoxy, $C_{1-6}$halogenalkoxy, halogen or cyano, and wherein a substituent on a nitrogen in a heterocyclic ring system may not be halogen; and each $R_{8c}$ independently is $C_{1-6}$alkyl, $C_{1-6}$halogenalkyl, $C_{1-6}$alkoxy, $C_{1-6}$halogenalkoxy, halogen or cyano.

In one class of compounds of the invention, B is a six-membered monocyclic aromatic ring system which may contain 1 to 2 nitrogen atoms, wherein the ring system is substituted once by $R_{8b}$, and wherein the ring system may be further substituted once or more than once by $R_{8c}$;

$R_{8b}$ is a six-membered monocyclic aromatic ring system, which may contain 1 to 2 nitrogen atoms, and wherein the ring system may in turn be substituted once or more than once by $C_{1-6}$alkyl, $C_{1-6}$halogenalkyl, $C_{1-6}$alkoxy, $C_{1-6}$halogenalkoxy, halogen or cyano, and wherein a substituent on a nitrogen in a heterocyclic ring system may not be halogen; and each $R_{8c}$ independently is $C_{1-6}$alkyl, $C_{1-6}$halogenalkyl, $C_{1-6}$alkoxy, $C_{1-6}$halogenalkoxy, halogen or cyano.

In one class of compounds of the invention, B is a six-membered monocyclic aromatic ring system which may contain 1 to 2 nitrogen atoms, wherein the ring system is substituted once by $R_{8b}$, and wherein the ring system may be further substituted once or more than once by $R_{8c}$;

$R_{8b}$ is a five-membered monocyclic aromatic ring system, which contains from 1 to 4 hetero atoms selected from nitrogen, oxygen and sulfur, and wherein the ring system may in turn be substituted once or more than once by $C_{1-6}$alkyl, $C_{1-6}$halogenalkyl, $C_{1-6}$alkoxy, $C_{1-6}$halogenalkoxy, halogen or cyano, and wherein a substituent on a nitrogen in a heterocyclic ring system may not be halogen; and each $R_{8c}$ independently is $C_{1-6}$alkyl, $C_{1-6}$halogenalkyl, $C_{1-6}$alkoxy, $C_{1-6}$halogenalkoxy, halogen or cyano.

In one class of compounds of the invention, B is phenyl which is substituted once by $R_{8b}$, and which may be further substituted once or more than once by $R_{8c}$;

$R_{8b}$ is a five-membered monocyclic aromatic ring system, which contains from 1 to 4 hetero atoms selected from nitrogen, oxygen and sulfur, and wherein the ring system may in turn be substituted once or more than once by $C_{1-6}$alkyl, $C_{1-6}$halogenalkyl, $C_{1-6}$alkoxy, $C_{1-6}$halogenalkoxy, halogen or cyano, and wherein a substituent on a nitrogen in a heterocyclic ring system may not be halogen; and each $R_{8c}$ independently is $C_{1-6}$alkyl, $C_{1-6}$halogenalkyl, $C_{1-6}$alkoxy, $C_{1-6}$halogenalkoxy, halogen or cyano.

In one class of compounds of the invention, B is phenyl being substituted by $R_{8b}$ in the ortho-position relative to group L, and wherein said phenyl may be further substituted once or more than once by $R_{8c}$;

$R_{8b}$ is a five-membered monocyclic aromatic ring system, which contains from 1 to 4 hetero atoms selected from nitrogen, oxygen and sulfur, and wherein the ring system may in turn be substituted once or more than once by $C_{1-6}$alkyl, $C_{1-6}$halogenalkyl, $C_{1-6}$alkoxy, $C_{1-6}$halogenalkoxy, halogen or cyano, and wherein a substituent on a nitrogen in a heterocyclic ring system may not be halogen; and each $R_{8c}$ independently is $C_{1-6}$alkyl, $C_{1-6}$halogenalkyl, $C_{1-6}$alkoxy, $C_{1-6}$halogenalkoxy, halogen or cyano.

In one class of compounds of the invention, B is phenyl being substituted by $R_{8b}$ in the ortho-position relative to group L; and $R_{8b}$ is a five-membered monocyclic aromatic ring system, which contains from 1 to 4 hetero atoms selected from nitrogen, oxygen and sulfur, and wherein the ring system may in turn be substituted once or more than once by $C_{1-6}$alkyl, $C_{1-6}$halogenalkyl, $C_{1-6}$alkoxy, $C_{1-6}$halogenalkoxy, halogen or cyano, and wherein a substituent on a nitrogen in a heterocyclic ring system may not be halogen.

In one class of compounds of the invention, B is phenyl being substituted by $R_{8b}$ in the meta-position relative to group L, and wherein said phenyl may be further substituted once or more than once by $R_{8c}$;

$R_{8b}$ is a five-membered monocyclic aromatic ring system, which contains from 1 to 4 hetero atoms selected from nitrogen, oxygen and sulfur, and wherein the ring system may in turn be substituted once or more than once by $C_{1-6}$alkyl, $C_{1-6}$halogenalkyl, $C_{1-6}$alkoxy, $C_{1-6}$halogenalkoxy, halogen or cyano, and wherein a substituent on a nitrogen in a heterocyclic ring system may not be halogen; and each $R_{8c}$ independently is $C_{1-6}$alkyl, $C_{1-6}$halogenalkyl, $C_{1-6}$alkoxy, $C_{1-6}$halogenalkoxy, halogen or cyano.

In one class of compounds of the invention, B is phenyl being substituted by $R_{8b}$ in the meta-position relative to group L; and $R_{8b}$ is a five-membered monocyclic aromatic ring system, which contains from 1 to 4 hetero atoms selected from nitrogen, oxygen and sulfur, and wherein the ring system may in turn be substituted once or more than once by $C_{1-6}$alkyl, $C_{1-6}$halogenalkyl, $C_{1-6}$alkoxy, $C_{1-6}$halogenalkoxy, halogen or cyano, and wherein a substituent on a nitrogen in a heterocyclic ring system may not be halogen.

In one class of compounds of the invention, B is a six-membered monocyclic aromatic ring system which contains 1 to 2 nitrogen atoms, wherein the ring system is substituted once by $R_{8b}$; $R_{8b}$ is a five-membered monocyclic aromatic ring system, which contains from 1 to 4 hetero atoms selected from nitrogen, oxygen and sulfur, and wherein the ring system may in turn be substituted once or more than once by $C_{1-6}$alkyl, $C_{1-6}$halogenalkyl, $C_{1-6}$alkoxy, $C_{1-6}$halogenalkoxy, halogen or cyano, and wherein a substituent on a nitrogen in a heterocyclic ring system may not be halogen.

In one class of compounds of the invention, B is a five-membered monocyclic aromatic ring system which contains from 1 to 4 hetero atoms selected from nitrogen, oxygen and sulfur, and wherein the ring system may be substituted once or more than once by $R_8$, and wherein a substituent on a nitrogen in a heterocyclic ring system may not be halogen.

In one class of compounds of the invention, B is a five-membered monocyclic aromatic ring system which contains from 1 to 4 hetero atoms selected from nitrogen, oxygen and sulfur, and wherein the ring system is substituted once by $R_{8b}$, and wherein the ring system may be further substituted once or more than once by $R_{8c}$, and wherein a substituent on a nitrogen in a heterocyclic ring system may not be halogen;

$R_{8b}$ is a five-membered monocyclic aromatic ring system, which contains from 1 to 4 hetero atoms selected from nitrogen, oxygen and sulfur, and wherein the ring system may in turn be substituted once or more than once by $C_{1-6}$alkyl, $C_{1-6}$halogenalkyl, $C_{1-6}$alkoxy, $C_{1-6}$halogenalkoxy, halogen or cyano; and each $R_{8c}$ independently is $C_{1-6}$alkyl, $C_{1-6}$halogenalkyl, $C_{1-6}$alkoxy, $C_{1-6}$halogenalkoxy, halogen or cyano.

In one class of compounds of the invention, B is a five-membered monocyclic aromatic ring system which contains from 1 to 4 hetero atoms selected from nitrogen, oxygen and sulfur, and wherein the ring system is substituted once by $R_{8b}$, and wherein the ring system may be further substituted once or more than once by $R_{8c}$, and wherein a substituent on a nitrogen in a heterocyclic ring system may not be halogen;

$R_{8b}$ is a six-membered monocyclic aromatic ring system, which may contain from 1 to 2 nitrogen atoms, and wherein the ring system may in turn be substituted once or more than once by $C_{1-6}$alkyl, $C_{1-6}$halogenalkyl, $C_{1-6}$alkoxy, $C_{1-6}$halogenalkoxy, halogen or cyano; and each $R_{8c}$ independently is $C_{1-6}$alkyl, $C_{1-6}$halogenalkyl, $C_{1-6}$alkoxy, $C_{1-6}$halogenalkoxy, halogen or cyano.

In one class of compounds of the invention, B is a five-membered monocyclic aromatic ring system which contains from 1 to 4 hetero atoms selected from nitrogen, oxygen and sulfur, and wherein the ring system is substituted once by $R_{8b}$, and wherein the ring system may be further substituted once or more than once by $R_{8c}$, and wherein a substituent on a nitrogen in a heterocyclic ring system may not be halogen;

$R_{8b}$ is phenyl, which may be substituted once or more than once by $C_{1-6}$alkyl, $C_{1-6}$halogenalkyl, $C_{1-6}$alkoxy, $C_{1-6}$halogenalkoxy, halogen or cyano; and each $R_{8c}$ independently is $C_{1-6}$alkyl, $C_{1-6}$halogenalkyl, $C_{1-6}$alkoxy, $C_{1-6}$halogenalkoxy, halogen or cyano.

In one class of compounds of the invention, B is a five-membered monocyclic aromatic ring system which contains from 1 to 4 hetero atoms selected from nitrogen, oxygen and sulfur, and wherein the ring system is substituted once by phenyl, which may in turn be substituted once or more than once by $C_{1-6}$alkyl, $C_{1-6}$halogenalkyl, $C_{1-6}$alkoxy, $C_{1-6}$halogenalkoxy, halogen or cyano.

In one class of compounds of the invention, B is a five- to six-membered monocyclic aromatic ring system which may contain from 1 to 4 hetero atoms selected from nitrogen, oxygen and sulfur, wherein the ring system may be substituted once or more than once by $R_8$, and wherein a substituent on a nitrogen in a heterocyclic ring system may not be halogen;

each $R_8$ independently is $C_{1-6}$alkyl, $C_{1-6}$halogenalkyl, $C_{1-6}$alkoxy, $C_{1-6}$halogenalkoxy, halogen, cyano or a three- to seven-membered monocyclic ring system which may be saturated or unsaturated non-aromatic and which may contain from 1 to 4 hetero atoms selected from nitrogen, oxygen and sulfur, and wherein each ring system may contain not more than 2 oxygen atoms and not more than 2 sulfur atoms, and wherein each ring system may in turn be substituted once or more than once by $C_{1-6}$alkyl, $C_{1-6}$halogenalkyl, $C_{1-6}$alkoxy, $C_{1-6}$halogenalkoxy, halogen or cyano, and wherein a substituent on a nitrogen in a heterocyclic ring system may not be halogen;

or two $R_8$ at adjacent ring atoms form together with said ring atoms a fused five- to seven-membered unsaturated non-aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may in turn be substituted once or more than once by $R_9$, and wherein a substituent on a nitrogen in a heterocyclic ring system may not be halogen; and wherein each $R_9$ independently is halogen or $C_{1-6}$alkyl, or two $R_9$ at the same ring atom together are oxo.

In one class of compounds of the invention, B is a five- to six-membered monocyclic aromatic ring system which may contain from 1 to 4 hetero atoms selected from nitrogen, oxygen and sulfur, wherein the ring system may be substituted once or more than once by $R_8$, and wherein a substituent on a nitrogen in a heterocyclic ring system may not be halogen; each $R_8$ independently is $C_{1-6}$alkyl, $C_{1-6}$halogenalkyl, $C_{1-6}$alkoxy, $C_{1-6}$halogenalkoxy, halogen, cyano.

In one class of compounds of the invention, B is a five-membered monocyclic aromatic ring system which contains from 1 to 4 hetero atoms selected from nitrogen, oxygen and sulfur, wherein the ring system may be substituted once or more than once by $R_8$, and wherein a substituent on a nitrogen in a heterocyclic ring system may not be halogen; each $R_8$ independently is $C_{1-6}$alkyl, $C_{1-6}$halogenalkyl, $C_{1-6}$alkoxy, $C_{1-6}$halogenalkoxy, halogen, cyano.

In one class of compounds of the invention, B is a six-membered monocyclic aromatic ring system which contains 1 or 2 nitrogen atoms, wherein the ring system may be substituted once or more than once by $R_8$; each $R_8$ independently is $C_{1-6}$alkyl, $C_{1-6}$halogenalkyl, $C_{1-6}$alkoxy, $C_{1-6}$halogenalkoxy, halogen, cyano.

In one class of compounds of the invention, B is phenyl which may be substituted once or more than once by $R_8$; each $R_8$ independently is $C_{1-6}$alkyl, $C_{1-6}$halogenalkyl, $C_{1-6}$alkoxy, $C_{1-6}$halogenalkoxy, halogen, cyano.

In one class of compounds of the invention, each $R_8$ independently is $C_{1-6}$alkyl, $C_{1-6}$halogenalkyl, halogen or a three- to seven-membered monocyclic ring system which may be aromatic, saturated or unsaturated non-aromatic and which may contain from 1 to 4 hetero atoms selected from nitrogen, oxygen and sulfur, and wherein each ring system may contain not more than 2 oxygen atoms and not more than 2 sulfur atoms, and wherein each ring system may in turn be substituted once or more than once by $C_{1-6}$alkyl, $C_{1-6}$halogenalkyl or halogen, and wherein a substituent on a nitrogen in a heterocyclic ring system may not be halogen.

In one class of compounds of the invention, each $R_8$ independently is $C_{1-6}$alkyl, $C_{1-6}$halogenalkyl, $C_{1-6}$hydroxyalkyl, $C_{1-4}$alkoxy-$C_{1-6}$alkyl, $C_{1-6}$-aminoalkyl, $C_{1-4}$alkylamino-$C_{1-6}$alkyl, di($C_{1-4}$alkyl)amino-$C_{1-6}$alkyl, $C_{2-6}$alkenyl, $C_{2-6}$halogenalkenyl, $C_{2-6}$alkynyl, $C_{2-6}$halogenalkynyl, $C_{1-6}$alkoxy, $C_{1-6}$halogenalkoxy, $C_{1-4}$alkoxy-$C_{1-6}$alkoxy, $C_{1-6}$alkylamino, di($C_{1-6}$alkyl)amino, halogen, hydroxy, cyano, amino or a three- to seven-membered monocyclic ring system which may be aromatic, saturated or unsaturated non-aromatic and which may contain from 1 to 4 hetero atoms selected from nitrogen, oxygen and sulfur, and wherein each ring system may be attached directly to ring system B or via a $C_{1-4}$alkylene, and wherein each ring system may contain not more than 2 oxygen atoms and not more than 2 sulfur atoms, and wherein each ring system may in turn be substituted once or more than once by $C_{1-6}$alkyl, $C_{1-6}$halogenalkyl, $C_{1-6}$alkoxy, $C_{1-6}$halogenalkoxy, halogen or cyano, and wherein a substituent on a nitrogen in a heterocyclic ring system may not be halogen.

In one class of compounds of the invention,

A is a eight- to ten-membered fused bicyclic aromatic ring system which may contain from 1 to 4 hetero atoms selected from nitrogen, oxygen and sulfur, wherein the ring system may contain not more than 2 oxygen atoms and not more than 2 sulfur atoms (e.g. quinoxalinyl or quinoxalin-2-yl), and wherein the ring system may be substituted once or more than once by $R_3$, and wherein a substituent on a nitrogen in a heterocyclic ring system may not be halogen;

each $R_3$ independently is $C_{1-6}$alkyl, $C_{1-6}$halogenalkyl or halogen;

m and n are both 0;

—$X_1$— is —C(O)— and —$X_2$— is —N(L-B)—;

L is —$CH_2$—;

B is an eight- to ten-membered fused bicyclic aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may be substituted once or more than once by $R_8$, and wherein a substituent on a nitrogen in a heterocyclic ring system may not be halogen; and each $R_8$ independently is $C_{1-6}$alkyl, $C_{1-6}$halogenalkyl or halogen.

In one class of compounds of the invention,

A is a eight- to ten-membered fused bicyclic aromatic ring system which may contain from 1 to 4 hetero atoms selected from nitrogen, oxygen and sulfur, wherein the ring system may contain not more than 2 oxygen atoms and not more than 2 sulfur atoms (e.g. quinoxalinyl or quinoxalin-2-yl), and wherein the ring system may be substituted once or more than once by $R_3$, and wherein a substituent on a nitrogen in a heterocyclic ring system may not be halogen;

each $R_3$ independently is $C_{1-6}$alkyl, $C_{1-6}$halogenalkyl or halogen;

m and n are both 0;

—$X_1$— is —C(O)— and —$X_2$— is —N(L-B)—;

L is —$CH_2$—;

B is a five- to six-membered monocyclic aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may be substituted once or more than once by $R_8$, and wherein a substituent on a nitrogen in a heterocyclic ring system may not be halogen; and each $R_8$ independently is $C_{1-6}$alkyl, $C_{1-6}$halogenalkyl or halogen.

In one class of compounds of the invention,

A is a eight- to ten-membered fused bicyclic aromatic ring system which may contain from 1 to 4 hetero atoms selected from nitrogen, oxygen and sulfur, wherein the ring system may contain not more than 2 oxygen atoms and not more than 2 sulfur atoms (e.g. quinoxalinyl or quinoxalin-2-yl), and wherein the ring system may be substituted once or more than once by $R_3$, and wherein a substituent on a nitrogen in a heterocyclic ring system may not be halogen;

each $R_3$ independently is $C_{1-6}$alkyl, $C_{1-6}$halogenalkyl or halogen;

m and n are both 0;

—$X_1$— is —C(O)— and —$X_2$— is —N(L-B)—;

L is —$CH_2$—;

B is a six-membered monocyclic aromatic ring system which may contain 1 to 2 nitrogen atoms, wherein the ring system is substituted once by $R_{8b}$, and wherein the ring system may be further substituted once or more than once by $R_{8c}$;

$R_{8b}$ is a five-membered monocyclic aromatic ring system, which contains from 1 to 4 hetero atoms selected from nitrogen, oxygen and sulfur, and wherein the ring system may in turn be substituted once or more than once by $C_{1-6}$alkyl, $C_{1-6}$halogenalkyl, $C_{1-6}$alkoxy, $C_{1-6}$halogenalkoxy, halogen or cyano, and wherein a substituent on a nitrogen in a heterocyclic ring system may not be halogen; and each $R_{8c}$ independently is $C_{1-6}$alkyl, $C_{1-6}$halogenalkyl, $C_{1-6}$alkoxy, $C_{1-6}$halogenalkoxy, halogen or cyano.

In one class of compounds of the invention,

A is a eight- to ten-membered fused bicyclic aromatic ring system which may contain from 1 to 4 hetero atoms selected from nitrogen, oxygen and sulfur, wherein the ring system may contain not more than 2 oxygen atoms and not more than 2 sulfur atoms (e.g. quinoxalinyl or quinoxalin-2-yl), and wherein the ring system may be substituted once or more than once by $R_3$, and wherein a substituent on a nitrogen in a heterocyclic ring system may not be halogen;

each $R_3$ independently is $C_{1-6}$alkyl, $C_{1-6}$halogenalkyl or halogen;

m and n are both 0;

—$X_1$— is —C(O)— and —$X_2$— is —N(L-B)—;

L is —$CH_2$—;

B is a five-membered monocyclic aromatic ring system which contains from 1 to 4 hetero atoms selected from nitrogen, oxygen and sulfur, and wherein the ring system is substituted once by $R_{8b}$, and wherein the ring system may be further substituted once or more than once by $R_{8c}$, and wherein a substituent on a nitrogen in a heterocyclic ring system may not be halogen;

$R_{8b}$ is a six-membered monocyclic aromatic ring system, which may contain from 1 to 2 nitrogen atoms, and wherein the ring system may in turn be substituted once or more than once by $C_{1-6}$alkyl, $C_{1-6}$halogenalkyl, $C_{1-6}$alkoxy, $C_{1-6}$halogenalkoxy, halogen or cyano; and each $R_{8c}$ independently is $C_{1-6}$alkyl, $C_{1-6}$halogenalkyl, $C_{1-6}$alkoxy, $C_{1-6}$halogenalkoxy, halogen or cyano.

In one class of compounds of the invention,

A is a eight- to ten-membered fused bicyclic aromatic ring system which may contain from 1 to 4 hetero atoms selected from nitrogen, oxygen and sulfur, wherein the ring system may contain not more than 2 oxygen atoms and not more than 2 sulfur atoms (e.g. quinoxalinyl or quinoxalinyl-2-yl), and wherein the ring system may be substituted once or more than once by $R_3$, and wherein a substituent on a nitrogen in a heterocyclic ring system may not be halogen;

each $R_3$ independently is $C_{1-6}$alkyl, $C_{1-6}$halogenalkyl or halogen;

m and n are both 0;

—$X_1$— is —N(L-B)— and —$X_2$— is —C(O)—;

L is —$CH_2$—;

B is an eight- to ten-membered fused bicyclic aromatic ring system which may contain from 1 to 4 hetero atoms selected from nitrogen, oxygen and sulfur, wherein the ring system may contain not more than 2 oxygen atoms and not more than 2 sulfur atoms (e.g. indolyl, indol-2-yl, indol-3-yl or indol-4-yl) and wherein the ring system may be substituted once or more than once by $R_8$, and wherein a substituent on a nitrogen in a heterocyclic ring system may not be halogen; and each $R_8$ independently is $C_{1-6}$alkyl, $C_{1-6}$halogenalkyl or halogen.

In one class of compounds of the invention,

A is a eight- to ten-membered fused bicyclic aromatic ring system which may contain from 1 to 4 hetero atoms selected from nitrogen, oxygen and sulfur, wherein the ring system may contain not more than 2 oxygen atoms and not more than 2 sulfur atoms (e.g. quinoxalinyl or quinoxalinyl-2-yl), and wherein the ring system may be substituted once or more than once by $R_3$, and wherein a substituent on a nitrogen in a heterocyclic ring system may not be halogen;

each $R_3$ independently is $C_{1-6}$alkyl, $C_{1-6}$halogenalkyl or halogen;

m and n are both 0;

—$X_1$— is —N(L-B)— and —$X_2$— is —C(O)—;

L is —$CH_2$—;

B is an five- to six-membered monocyclic aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may be substituted once or more than once by $R_8$, and wherein a substituent on a nitrogen in a heterocyclic ring system may not be halogen; and each $R_8$ independently is $C_{1-6}$alkyl, $C_{1-6}$halogenalkyl or halogen.

In one class of compounds of the invention,

A is a nine or ten-membered fused bicyclic aromatic ring system which may contain from 1 to 4 hetero atoms selected from nitrogen, oxygen and sulfur, wherein the ring system may contain not more than 2 oxygen atoms and not more than 2 sulfur atoms (e.g. quinoxalinyl, quinoxalinyl-2-yl, benzo[d]oxazolyl or benzo[d]oxazol-2-yl), and wherein the ring system may be substituted once or more than once by $R_3$, and wherein a substituent on a nitrogen in a heterocyclic ring system may not be halogen;

each $R_3$ independently is $C_{1-6}$alkyl, $C_{1-6}$halogenalkyl or halogen;

m and n are both 0;

—$X_1$— is —N(L-B)— and —$X_2$— is —C(O)—;

L is —$CH_2$—;

B is an eight- to ten-membered fused bicyclic aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may be substituted once or more than once by $R_8$, and wherein a substituent on a nitrogen in a heterocyclic ring system may not be halogen; and each $R_8$ independently is $C_{1-6}$alkyl, $C_{1-6}$halogenalkyl or halogen.

In one class of compounds of the invention,

A is a nine or ten-membered fused bicyclic aromatic ring system which may contain from 1 to 4 hetero atoms selected from nitrogen, oxygen and sulfur, wherein the ring system may contain not more than 2 oxygen atoms and not more than 2 sulfur atoms (e.g. quinoxalinyl, quinoxalinyl-2-yl, benzo[d]oxazolyl or benzo[d]oxazol-2-yl), and wherein the ring system may be substituted once or more than once by $R_3$, and wherein a substituent on a nitrogen in a heterocyclic ring system may not be halogen;

each $R_3$ independently is $C_{1-6}$alkyl, $C_{1-6}$halogenalkyl or halogen;

m and n are both 0;

—$X_1$— is —N(L-B)— and —$X_2$— is —C(O)—;

L is —$CH_2$—;

B is a five- to six-membered monocyclic aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may be substituted once or more than once by $R_8$, and wherein a substituent on a nitrogen in a heterocyclic ring system may not be halogen; and each $R_8$ independently is $C_{1-6}$alkyl, $C_{1-6}$halogenalkyl or halogen.

In one embodiment, the invention provides a compound selected from 2-((1H-indol-3-yl)methyl)-9-(quinoxalin-2-yl)-2,9-diazaspiro[5.5]undecan-1-one;
2-(naphthalen-1-ylmethyl)-9-(quinoxalin-2-yl)-2,9-diazaspiro[5.5]undecan-1-one;
2-((1H-indol-4-yl)methyl)-9-(quinoxalin-2-yl)-2,9-diazaspiro[5.5]undecan-1-one;
2-((2,3-dihydrobenzo[b][1,4]dioxin-5-yl)methyl)-9-(quinoxalin-2-yl)-2,9-diazaspiro[5.5]undecan-1-one;
2-(3-(pyridin-3-yl)benzyl)-9-(quinoxalin-2-yl)-2,9-diazaspiro[5.5]undecan-1-one;
2-benzyl-9-(quinoxalin-2-yl)-2,9-diazaspiro[5.5]undecan-1-one;
2-(naphthalen-2-ylmethyl)-9-(quinoxalin-2-yl)-2,9-diazaspiro[5.5]undecan-1-one;
2-(benzo[d][1,3]dioxol-5-ylmethyl)-9-(quinoxalin-2-yl)-2,9-diazaspiro[5.5]undecan-1-one;
2-(benzo[d][1,3]dioxol-4-ylmethyl)-9-(quinoxalin-2-yl)-2,9-diazaspiro[5.5]undecan-1-one;
9-(1H-benzo[d]imidazol-2-yl)-2-benzyl-2,9-diazaspiro[5.5]undecan-1-one;
9-(1H-benzo[d]imidazol-2-yl)-2-(naphthalen-1-ylmethyl)-2,9-diazaspiro[5.5]undecan-1-one;
9-(1-methyl-1H-benzo[d]imidazol-2-yl)-2-(naphthalen-1-ylmethyl)-2,9-diazaspiro[5.5]undecan-1-one;
2-((2-methyl-1H-indol-4-yl)methyl)-9-(quinoxalin-2-yl)-2,9-diazaspiro[5.5]undecan-1-one;
9-(quinoxalin-2-yl)-2-(3-(trifluoromethyl)benzyl)-2,9-diazaspiro[5.5]undecan-1-one;
2-(3-methylbenzyl)-9-(quinoxalin-2-yl)-2,9-diazaspiro[5.5]undecan-1-one;
2-(3,5-dimethylbenzyl)-9-(quinoxalin-2-yl)-2,9-diazaspiro[5.5]undecan-1-one;
2-(2,3-dimethylbenzyl)-9-(quinoxalin-2-yl)-2,9-diazaspiro[5.5]undecan-1-one;
2-(2,3-dimethoxybenzyl)-9-(quinoxalin-2-yl)-2,9-diazaspiro[5.5]undecan-1-one;
2-(2-methylbenzyl)-9-(quinoxalin-2-yl)-2,9-diazaspiro[5.5]undecan-1-one;
2-(2,5-dimethylbenzyl)-9-(quinoxalin-2-yl)-2,9-diazaspiro[5.5]undecan-1-one;
2-(quinolin-8-ylmethyl)-9-(quinoxalin-2-yl)-2,9-diazaspiro[5.5]undecan-1-one;
2-(biphenyl-3-ylmethyl)-9-(quinoxalin-2-yl)-2,9-diazaspiro[5.5]undecan-1-one;
9-(quinoxalin-2-yl)-2-(2-(trifluoromethyl)benzyl)-2,9-diazaspiro[5.5]undecan-1-one;
9-(quinoxalin-2-yl)-2-(4-(trifluoromethyl)benzyl)-2,9-diazaspiro[5.5]undecan-1-one;
2-((2,3-dihydrobenzo[b][1,4]dioxin-6-yl)methyl)-9-(quinoxalin-2-yl)-2,9-diazaspiro[5.5]undecan-1-one;
2-((1-methyl-1H-indol-4-yl)methyl)-9-(quinoxalin-2-yl)-2,9-diazaspiro[5.5]undecan-1-one;
2-(3-chlorobenzyl)-9-(quinoxalin-2-yl)-2,9-diazaspiro[5.5]undecan-1-one;
9-(1H-benzo[d]imidazol-2-yl)-2-(3-chlorobenzyl)-2,9-diazaspiro[5.5]undecan-1-one;
2-(3-chlorobenzyl)-9-(4-phenylpyrimidin-2-yl)-2,9-diazaspiro[5.5]undecan-1-one;
2-((1-methyl-1H-benzo[d]imidazol-2-yl)methyl)-9-(quinoxalin-2-yl)-2,9-diazaspiro[5.5]undecan-1-one;
2-((5-(4-methoxyphenyl)-1,3,4-oxadiazol-2-yl)methyl)-9-(quinoxalin-2-yl)-2,9-diazaspiro[5.5]undecan-1-one;
2-((3-methyl-5-phenylisoxazol-4-yl)methyl)-9-(quinoxalin-2-yl)-2,9-diazaspiro[5.5]undecan-1-one;
2-((2-methylquinolin-4-yl)methyl)-9-(quinoxalin-2-yl)-2,9-diazaspiro[5.5]undecan-1-one;
2-((5-methyl-3-phenylisoxazol-4-yl)methyl)-9-(quinoxalin-2-yl)-2,9-diazaspiro[5.5]undecan-1-one;
2-(3-(1H-pyrrol-1-yl)benzyl)-9-(quinoxalin-2-yl)-2,9-diazaspiro[5.5]undecan-1-one;
2-(benzo[d]isoxazol-3-ylmethyl)-9-(quinoxalin-2-yl)-2,9-diazaspiro[5.5]undecan-1-one;
2-((3,5-dimethylisoxazol-4-yl)methyl)-9-(quinoxalin-2-yl)-2,9-diazaspiro[5.5]undecan-1-one;
1-((1H-indol-4-yl)methyl)-9-(quinoxalin-2-yl)-1,9-diazaspiro[5.5]undecan-2-one;
2-(2-(3-methyl-1,2,4-oxadiazol-5-yl)benzyl)-9-(quinoxalin-2-yl)-2,9-diazaspiro[5.5]undecan-1-one;
2-((1H-indol-3-yl)methyl)-9-(benzo[d]oxazol-2-yl)-2,9-diazaspiro[5.5]undecan-1-one;
1-(2,5-dimethylbenzyl)-9-(quinoxalin-2-yl)-1,9-diazaspiro[5.5]undecan-2-one;
1-((1H-indol-4-yl)methyl)-9-(benzo[d]oxazol-2-yl)-1,9-diazaspiro[5.5]undecan-2-one;
1-((1H-indol-3-yl)methyl)-9-(quinoxalin-2-yl)-1,9-diazaspiro[5.5]undecan-2-one;
1-((1-methyl-1H-indol-4-yl)methyl)-9-(quinoxalin-2-yl)-1,9-diazaspiro[5.5]undecan-2-one;
2-((2-methoxypyridin-4-yl)methyl)-9-(quinoxalin-2-yl)-2,9-diazaspiro[5.5]undecan-1-one;
2-(3-(1H-1,2,3-triazol-1-yl)benzyl)-9-(quinoxalin-2-yl)-2,9-diazaspiro[5.5]undecan-1-one;
2-(3-(2H-1,2,3-triazol-2-yl)benzyl)-9-(quinoxalin-2-yl)-2,9-diazaspiro[5.5]undecan-1-one;
2-((1H-indol-3-yl)methyl)-9-(quinolin-3-yl)-2,9-diazaspiro[5.5]undecan-1-one;

2-(2-(2H-1,2,3-triazol-2-yl)benzyl)-9-(quinoxalin-2-yl)-2,9-diazaspiro[5.5]undecan-1-one;
2-benzyl-9-(1-methyl-1H-benzo[d]imidazol-2-yl)-2,9-diazaspiro[5.5]undecan-1-one;
2-(2-(1-methyl-1H-pyrazol-4-yl)benzyl)-9-(quinoxalin-2-yl)-2,9-diazaspiro[5.5]undecan-1-one;
2-((1H-indol-3-yl)methyl)-9-(benzo[d]thiazol-2-yl)-2,9-diazaspiro[5.5]undecan-1-one;
2-(benzo[c][1,2,5]oxadiazol-5-ylmethyl)-9-(quinoxalin-2-yl)-2,9-diazaspiro[5.5]undecan-1-one;
2-(3-(pyridin-2-yl)benzyl)-9-(quinoxalin-2-yl)-2,9-diazaspiro[5.5]undecan-1-one;
2-(isoquinolin-5-ylmethyl)-9-(quinoxalin-2-yl)-2,9-diazaspiro[5.5]undecan-1-one;
2-((2-morpholinopyridin-4-yl)methyl)-9-(quinoxalin-2-yl)-2,9-diazaspiro[5.5]undecan-1-one;
2-((1H-pyrrolo[2,3-b]pyridin-3-yl)methyl)-9-(quinoxalin-2-yl)-2,9-diazaspiro[5.5]undecan-1-one;
2-(3-(pyridin-4-yl)benzyl)-9-(quinoxalin-2-yl)-2,9-diazaspiro[5.5]undecan-1-one;
2-(3-morpholinobenzyl)-9-(quinoxalin-2-yl)-2,9-diazaspiro[5.5]undecan-1-one;
2-(3-(1H-pyrazol-1-yl)benzyl)-9-(quinoxalin-2-yl)-2,9-diazaspiro[5.5]undecan-1-one;
2-(3-(pyrimidin-2-yl)benzyl)-9-(quinoxalin-2-yl)-2,9-diazaspiro[5.5]undecan-1-one;
2-(pyridin-2-ylmethyl)-9-(quinoxalin-2-yl)-2,9-diazaspiro[5.5]undecan-1-one;
2-((2-(1H-pyrazol-1-yl)pyridin-4-yl)methyl)-9-(quinoxalin-2-yl)-2,9-diazaspiro[5.5]undecan-1-one;
2-(pyridin-3-ylmethyl)-9-(quinoxalin-2-yl)-2,9-diazaspiro[5.5]undecan-1-one;
2-(3-(pyrazin-2-yl)benzyl)-9-(quinoxalin-2-yl)-2,9-diazaspiro[5.5]undecan-1-one;
2-((1H-benzo[d][1,2,3]triazol-1-yl)methyl)-9-(quinoxalin-2-yl)-2,9-diazaspiro[5.5]undecan-1-one;
2-(pyridin-4-ylmethyl)-9-(quinoxalin-2-yl)-2,9-diazaspiro[5.5]undecan-1-one;
2-((2-methylpyridin-4-yl)methyl)-9-(quinoxalin-2-yl)-2,9-diazaspiro[5.5]undecan-1-one;
2-((2-methyl-5-m-tolylthiazol-4-yl)methyl)-9-(quinoxalin-2-yl)-2,9-diazaspiro[5.5]undecan-1-one;
2-(imidazo[1,2-a]pyridin-3-ylmethyl)-9-(quinoxalin-2-yl)-2,9-diazaspiro[5.5]undecan-1-one;
2-((2-methylimidazo[1,2-a]pyridin-3-yl)methyl)-9-(quinoxalin-2-yl)-2,9-diazaspiro[5.5]undecan-1-one;
2-((2-bromopyridin-4-yl)methyl)-9-(quinoxalin-2-yl)-2,9-diazaspiro[5.5]undecan-1-one;
2-((5-(3-fluorophenyl)-2-methylthiazol-4-yl)methyl)-9-(quinoxalin-2-yl)-2,9-diazaspiro[5.5]undecan-1-one;
2-(1-(1H-indol-3-yl)ethyl)-9-(quinoxalin-2-yl)-2,9-diazaspiro[5.5]undecan-1-one;
2-([1,2,4]triazolo[4,3-a]pyridin-3-ylmethyl)-9-(quinoxalin-2-yl)-2,9-diazaspiro[5.5]undecan-1-one;
2-((2-methyl-2H-indazol-3-yl)methyl)-9-(quinoxalin-2-yl)-2,9-diazaspiro[5.5]undecan-1-one;
2-(benzo[c][1,2,5]oxadiazol-4-ylmethyl)-9-(quinoxalin-2-yl)-2,9-diazaspiro[5.5]undecan-1-one;
2-((6-chloropyridin-3-yl)methyl)-9-(quinoxalin-2-yl)-2,9-diazaspiro[5.5]undecan-1-one;
2-(pyrazolo[1,5-a]pyridin-3-ylmethyl)-9-(quinoxalin-2-yl)-2,9-diazaspiro[5.5]undecan-1-one;
2-(3-(methoxymethyl)benzyl)-9-(quinoxalin-2-yl)-2,9-diazaspiro[5.5]undecan-1-one;
2-(4-(1H-1,2,4-triazol-1-yl)benzyl)-9-(quinoxalin-2-yl)-2,9-diazaspiro[5.5]undecan-1-one;
2-((2,3-dihydrobenzo[b][1,4]dioxin-5-yl)methyl)-9-(furo[3,2-c]pyridin-4-yl)-2,9-diazaspiro[5.5]undecan-1-one;
2-((6-(1H-pyrazol-1-yl)pyridin-2-yl)methyl)-9-(quinoxalin-2-yl)-2,9-diazaspiro[5.5]undecan-1-one;
2-((1,5-dimethyl-1H-pyrazol-3-yl)methyl)-9-(quinoxalin-2-yl)-2,9-diazaspiro[5.5]undecan-1-one;
2-(2-(1H-pyrazol-1-yl)benzyl)-9-(quinoxalin-2-yl)-2,9-diazaspiro[5.5]undecan-1-one;
2-((1-benzyl-1H-imidazol-2-yl)methyl)-9-(quinoxalin-2-yl)-2,9-diazaspiro[5.5]undecan-1-one;
2-((6-chloro-4H-benzo[d][1,3]dioxin-8-yl)methyl)-9-(quinoxalin-2-yl)-2,9-diazaspiro[5.5]undecan-1-one;
2-((5-methylisoxazol-3-yl)methyl)-9-(quinoxalin-2-yl)-2,9-diazaspiro[5.5]undecan-1-one;
2-((5-cyclobutyl-1,2,4-oxadiazol-3-yl)methyl)-9-(quinoxalin-2-yl)-2,9-diazaspiro[5.5]undecan-1-one;
9-(quinoxalin-2-yl)-2-((6-(trifluoromethyl)pyridin-3-yl)methyl)-2,9-diazaspiro[5.5]undecan-1-one;
2-((3,4-dimethoxypyridin-2-yl)methyl)-9-(quinoxalin-2-yl)-2,9-diazaspiro[5.5]undecan-1-one;
3-((1-oxo-9-(quinoxalin-2-yl)-2,9-diazaspiro[5.5]undecan-2-yl)methyl)benzonitrile
2-(isoquinolin-1-ylmethyl)-9-(quinoxalin-2-yl)-2,9-diazaspiro[5.5]undecan-1-one;
2-fluoro-5-((1-oxo-9-(quinoxalin-2-yl)-2,9-diazaspiro[5.5]undecan-2-yl)methyl)benzonitrile
2-((5-phenyloxazol-4-yl)methyl)-9-(quinoxalin-2-yl)-2,9-diazaspiro[5.5]undecan-1-one;
4-((1-oxo-9-(quinoxalin-2-yl)-2,9-diazaspiro[5.5]undecan-2-yl)methyl)quinolin-2(1H)-one;
2-((6-methylpyridin-2-yl)methyl)-9-(quinoxalin-2-yl)-2,9-diazaspiro[5.5]undecan-1-one;
2-(3-(5-methyl-1,2,4-oxadiazol-3-yl)benzyl)-9-(quinoxalin-2-yl)-2,9-diazaspiro[5.5]undecan-1-one;
4-fluoro-3-((1-oxo-9-(quinoxalin-2-yl)-2,9-diazaspiro[5.5]undecan-2-yl)methyl)benzonitrile
5-((1-oxo-9-(quinoxalin-2-yl)-2,9-diazaspiro[5.5]undecan-2-yl)methyl)picolinonitrile
2-(4-(pyrimidin-2-yl)benzyl)-9-(quinoxalin-2-yl)-2,9-diazaspiro[5.5]undecan-1-one;
2-(2-fluoro-3-methoxybenzyl)-9-(quinoxalin-2-yl)-2,9-diazaspiro[5.5]undecan-1-one;
2-((6-(pyrrolidin-1-yl)pyridin-2-yl)methyl)-9-(quinoxalin-2-yl)-2,9-diazaspiro[5.5]undecan-1-one;
2-(3-(3-methyl-1,2,4-oxadiazol-5-yl)benzyl)-9-(quinoxalin-2-yl)-2,9-diazaspiro[5.5]undecan-1-one;
2-((3-methylisoxazol-5-yl)methyl)-9-(quinoxalin-2-yl)-2,9-diazaspiro[5.5]undecan-1-one;
2-((4,6-dimethylpyridin-2-yl)methyl)-9-(quinoxalin-2-yl)-2,9-diazaspiro[5.5]undecan-1-one;
2-((1-methyl-1H-indazol-7-yl)methyl)-9-(quinoxalin-2-yl)-2,9-diazaspiro[5.5]undecan-1-one;
2-((1-methyl-1H-indazol-4-yl)methyl)-9-(quinoxalin-2-yl)-2,9-diazaspiro[5.5]undecan-1-one;

2-(4-(5-methyl-1,3,4-oxadiazol-2-yl)benzyl)-9-(quinoxalin-2-yl)-2,9-diazaspiro[5.5]undecan-1-one;
2-((1-phenyl-1H-imidazol-5-yl)methyl)-9-(quinoxalin-2-yl)-2,9-diazaspiro[5.5]undecan-1-one;
2-((1-(3-methoxyphenyl)-1H-imidazol-5-yl)methyl)-9-(quinoxalin-2-yl)-2,9-diazaspiro[5.5]undecan-1-one;
2-((1-(2-methoxyphenyl)-1H-imidazol-2-yl)methyl)-9-(quinoxalin-2-yl)-2,9-diazaspiro[5.5]undecan-1-one;
2-(benzo[c][1,2,5]thiadiazol-4-ylmethyl)-9-(quinoxalin-2-yl)-2,9-diazaspiro[5.5]undecan-1-one;
2-((5-methyl-2-(thiazol-4-yl)oxazol-4-yl)methyl)-9-(quinoxalin-2-yl)-2,9-diazaspiro[5.5]undecan-1-one;
2-(2-(3,5-dimethyl-1H-pyrazol-1-yl)benzyl)-9-(quinoxalin-2-yl)-2,9-diazaspiro[5.5]undecan-1-one;
2-((2-(furan-3-yl)-5-methyloxazol-4-yl)methyl)-9-(quinoxalin-2-yl)-2,9-diazaspiro[5.5]undecan-1-one;
9-(quinoxalin-2-yl)-2-((2,2,8-trimethyl-4H-[1,3]dioxino[4,5-c]pyridin-5-yl)methyl)-2,9-diazaspiro[5.5]undecan-1-one;
2-((1-benzyl-1H-imidazol-5-yl)methyl)-9-(quinoxalin-2-yl)-2,9-diazaspiro[5.5]undecan-1-one;
2-((4-methyl-2-phenyloxazol-5-yl)methyl)-9-(quinoxalin-2-yl)-2,9-diazaspiro[5.5]undecan-1-one;
2-((6-fluoro-4H-benzo[d][1,3]dioxin-8-yl)methyl)-9-(quinoxalin-2-yl)-2,9-diazaspiro[5.5]undecan-1-one;
2-((1H-indol-2-yl)methyl)-9-(quinoxalin-2-yl)-2,9-diazaspiro[5.5]undecan-1-one;
2-((1-phenyl-1H-tetrazol-5-yl)methyl)-9-(quinoxalin-2-yl)-2,9-diazaspiro[5.5]undecan-1-one;
2-((1H-indol-5-yl)methyl)-9-(quinoxalin-2-yl)-2,9-diazaspiro[5.5]undecan-1-one;
2-((1-oxo-9-(quinoxalin-2-yl)-2,9-diazaspiro[5.5]undecan-2-yl)methyl)benzonitrile
2-(5-methyl-2-(2H-1,2,3-triazol-2-yl)benzyl)-9-(quinoxalin-2-yl)-2,9-diazaspiro[5.5]undecan-1-one;
2-(indolin-4-ylmethyl)-9-(quinoxalin-2-yl)-2,9-diazaspiro[5.5]undecan-1-one;
2-((4-(1H-pyrazol-1-yl)pyridin-2-yl)methyl)-9-(quinoxalin-2-yl)-2,9-diazaspiro[5.5]undecan-1-one;
2-(2-methyl-5-(2H-1,2,3-triazol-2-yl)benzyl)-9-(quinoxalin-2-yl)-2,9-diazaspiro[5.5]undecan-1-one;
2-((1H-indazol-3-yl)methyl)-9-(quinoxalin-2-yl)-2,9-diazaspiro[5.5]undecan-1-one;
2-((1-methyl-1H-indol-3-yl)methyl)-9-(quinoxalin-2-yl)-2,9-diazaspiro[5.5]undecan-1-one;
2-((1H-indol-3-yl)methyl)-9-(5-chlorobenzo[d]oxazol-2-yl)-2,9-diazaspiro[5.5]undecan-1-one;
2-((3,4-dihydro-2H-benzo[b][1,4]oxazin-8-yl)methyl)-9-(quinoxalin-2-yl)-2,9-diazaspiro[5.5]undecan-1-one;
2-((2-methyl-1H-indol-3-yl)methyl)-9-(quinoxalin-2-yl)-2,9-diazaspiro[5.5]undecan-1-one;
1-benzyl-9-(quinoxalin-2-yl)-1,9-diazaspiro[5.5]undecan-2-one;
1-(benzo[d]isoxazol-3-ylmethyl)-9-(quinoxalin-2-yl)-1,9-diazaspiro[5.5]undecan-2-one;
1-((1H-indol-4-yl)methyl)-9-(5-chlorobenzo[d]oxazol-2-yl)-1,9-diazaspiro[5.5]undecan-2-one;
1-((1H-indol-4-yl)methyl)-9-(5-phenyl-1,3,4-oxadiazol-2-yl)-1,9-diazaspiro[5.5]undecan-2-one;
1-((1H-indol-4-yl)methyl)-9-(1H-benzo[d]imidazol-2-yl)-1,9-diazaspiro[5.5]undecan-2-one;
1-((1H-indol-4-yl)methyl)-9-(6-chlorobenzo[d]oxazol-2-yl)-1,9-diazaspiro[5.5]undecan-2-one;
1-((1H-indol-4-yl)methyl)-9-(5-methylbenzo[d]oxazol-2-yl)-1,9-diazaspiro[5.5]undecan-2-one;
1-((1H-pyrrolo[2,3-b]pyridin-3-yl)methyl)-9-(quinoxalin-2-yl)-1,9-diazaspiro[5.5]undecan-2-one;
2-((1-methyl-1H-indazol-3-yl)methyl)-9-(quinoxalin-2-yl)-2,9-diazaspiro[5.5]undecan-1-one;
1-((1-methyl-1H-pyrrolo[2,3-b]pyridin-3-yl)methyl)-9-(quinoxalin-2-yl)-1,9-diazaspiro[5.5]undecan-2-one;
2-((4-methyl-3,4-dihydro-2H-benzo[b][1,4]oxazin-8-yl)methyl)-9-(quinoxalin-2-yl)-2,9-diazaspiro[5.5]undecan-1-one;
2-((1-methylindolin-4-yl)methyl)-9-(quinoxalin-2-yl)-2,9-diazaspiro[5.5]undecan-1-one;
2-((1H-indol-3-yl)methyl)-9-(pyrido[3,2-b]pyrazin-7-yl)-2,9-diazaspiro[5.5]undecan-1-one;
2-(3-(5-methyloxazol-2-yl)benzyl)-9-(quinoxalin-2-yl)-2,9-diazaspiro[5.5]undecan-1-one;
2-(2-(1-methyl-1H-pyrazol-5-yl)benzyl)-9-(quinoxalin-2-yl)-2,9-diazaspiro[5.5]undecan-1-one;
2-(2-(oxazol-2-yl)benzyl)-9-(quinoxalin-2-yl)-2,9-diazaspiro[5.5]undecan-1-one;
2-(2-(furan-2-yl)benzyl)-9-(quinoxalin-2-yl)-2,9-diazaspiro[5.5]undecan-1-one;
2-(2-(pyrimidin-2-yl)benzyl)-9-(quinoxalin-2-yl)-2,9-diazaspiro[5.5]undecan-1-one;
2-((1H-indol-3-yl)methyl)-9-(1H-benzo[d]imidazol-2-yl)-2,9-diazaspiro[5.5]undecan-1-one;
2-((1H-indol-3-yl)methyl)-9-(6-methylbenzo[d]thiazol-2-yl)-2,9-diazaspiro[5.5]undecan-1-one;
2-((1H-indol-3-yl)methyl)-9-(4-phenylpyrimidin-2-yl)-2,9-diazaspiro[5.5]undecan-1-one;
2-((1H-indol-3-yl)methyl)-9-(7H-pyrrolo[2,3-d]pyrimidin-4-yl)-2,9-diazaspiro[5.5]undecan-1-one;
2-((1H-indol-3-yl)methyl)-9-(furo[3,2-c]pyridin-4-yl)-2,9-diazaspiro[5.5]undecan-1-one;
2-((1H-indol-3-yl)methyl)-9-(4-methylphthalazin-1-yl)-2,9-diazaspiro[5.5]undecan-1-one;
9-(6-(1H-imidazol-1-yl)pyrimidin-4-yl)-2-((1H-indol-3-yl)methyl)-2,9-diazaspiro[5.5]undecan-1-one;
2-((1H-indol-3-yl)methyl)-9-(5-methoxy-1H-benzo[d]imidazol-2-yl)-2,9-diazaspiro[5.5]undecan-1-one;
2-((1H-indol-3-yl)methyl)-9-(quinolin-2-yl)-2,9-diazaspiro[5.5]undecan-1-one;
2-((1H-indol-3-yl)methyl)-9-(5-(thiazol-2-yl)pyridin-2-yl)-2,9-diazaspiro[5.5]undecan-1-one;
2-((1H-indol-3-yl)methyl)-9-(isoquinolin-1-yl)-2,9-diazaspiro[5.5]undecan-1-one;
2-((1H-indol-3-yl)methyl)-9-(5-methyl-1H-benzo[d]imidazol-2-yl)-2,9-diazaspiro[5.5]undecan-1-one;
2-((1H-indol-3-yl)methyl)-9-(4-methylquinolin-2-yl)-2,9-diazaspiro[5.5]undecan-1-one;
2-((1H-indol-3-yl)methyl)-9-(6-phenylpyrimidin-4-yl)-2,9-diazaspiro[5.5]undecan-1-one;
2-((1H-indol-3-yl)methyl)-9-(4-(pyridin-4-yl)pyrimidin-2-yl)-2,9-diazaspiro[5.5]undecan-1-one;
2-((1H-indol-3-yl)methyl)-9-(pyrido[4,3-b]pyrazin-7-yl)-2,9-diazaspiro[5.5]undecan-1-one;
2-((1H-indol-3-yl)methyl)-9-(imidazo[1,2-b]pyridazin-6-yl)-2,9-diazaspiro[5.5]undecan-1-one;

2-((1H-indol-3-yl)methyl)-9-(quinazolin-2-yl)-2,9-diazaspiro[5.5]undecan-1-one;

2-((1H-indol-3-yl)methyl)-9-(3-methylquinoxalin-2-yl)-2,9-diazaspiro[5.5]undecan-1-one;

2-((1H-indol-3-yl)methyl)-9-(5-phenyl-1,3,4-thiadiazol-2-yl)-2,9-diazaspiro[5.5]undecan-1-one;

2-((1H-indol-3-yl)methyl)-9-(4-(4-fluorophenyl)thiazol-2-yl)-2,9-diazaspiro[5.5]undecan-1-one;

2-((1H-indol-3-yl)methyl)-9-(4-methyl-6-(1H-pyrazol-1-yl)pyrimidin-2-yl)-2,9-diazaspiro[5.5]undecan-1-one and 2-((1H-indol-3-yl)methyl)-9-(4-(1H-pyrazol-1-yl)pyrimidin-2-yl)-2,9-diazaspiro[5.5]undecan-1-one.

Preferably, the invention relates to a compound of formula (I) which is 2-((1H-indol-3-yl)methyl)-9-(quinoxalin-2-yl)-2,9-diazaspiro[5.5]undecan-1-one in free form or in pharmaceutically acceptable salt form.

In a further aspect, the invention also provides a process for the production of compounds of the formula I.

Compounds of the formula Ia

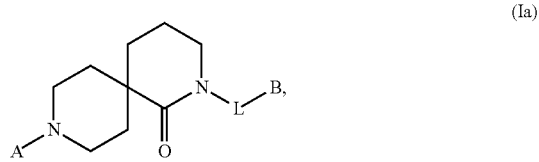

(Ia)

wherein A, L and B are as defined under formula I, are obtainable according to the following process as described in scheme 1:

Scheme 1:

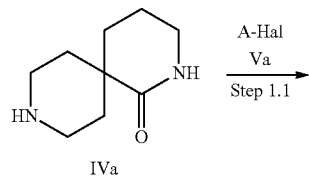

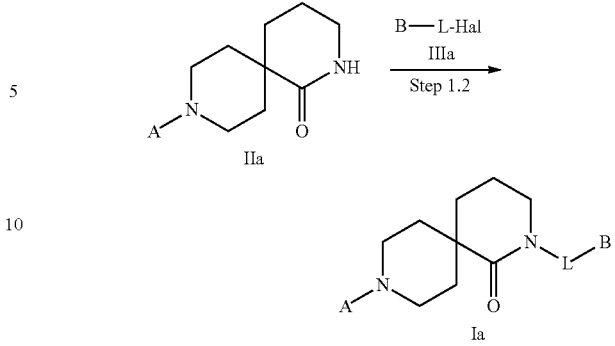

The process steps are described in more detail below:

Step 1.1

A compound of formula IIa, in which A is as defined under formula I, may be obtained by reacting the compound of formula IVa—being 2,9-diaza-spiro[5.5]undecan-1-one—with a compound of formula Va, in which A is defined under formula I and Hal is a halogen atom, such as chloro or bromo, in the presence of a base, such as $K_2CO_3$, and in the presence of a suitable solvent, such as dimethylformamide.

Step 1.2

A compound of formula Ia, in which A, L and B are as defined under formula I, may be obtained by reacting the compound of formula IIa with a compound of formula IIIa, in which B and L are as defined under formula I and Hal is a halogen atom, such as chloro or bromo, in the presence of a strong base, such as NaH, and in the presence of a suitable solvent, such as tetrahydrofuran.

Compounds of the formula Ib

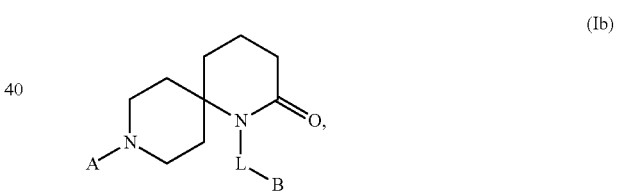

(Ib)

wherein A, L and B are as defined under formula I, are obtainable according to the following process as described in scheme 2:

Scheme 2:

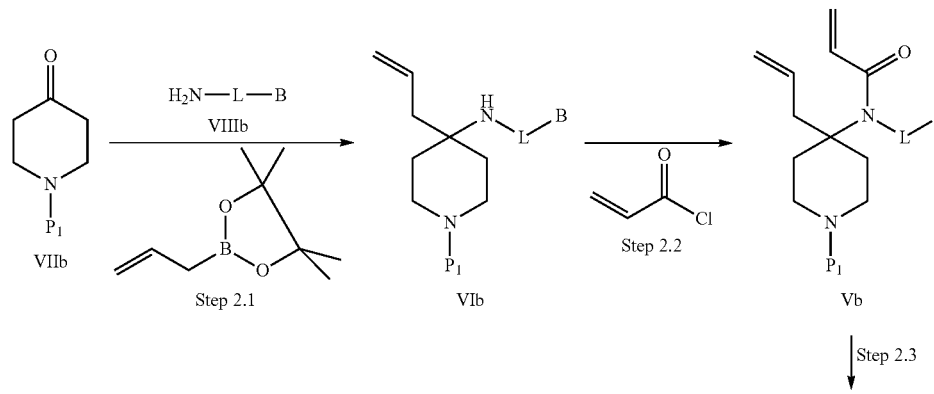

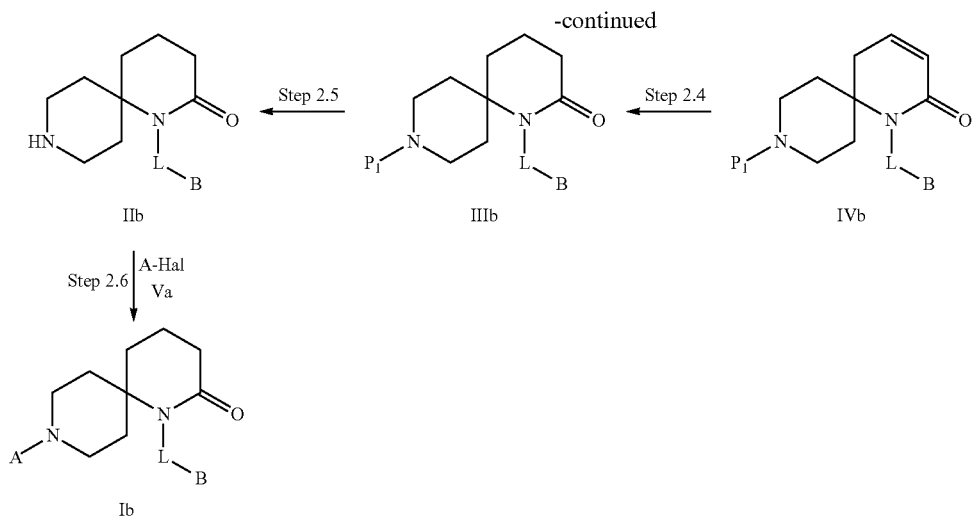

The process steps are described in more detail below:

Step 2.1

A compound of formula VIb, in which L and B are as defined under formula I and $P_1$ is a protecting group, such as tertiary-butyl-oxy-carbonyl, may be obtained by reacting a compound of formula VIIb, in which $P_1$ is a protecting group as defined under formula VIb, with a compound of formula VIIIb, in which L and B are as defined under formula I, and with allyl boronic acid pinacol ester (being depicted in scheme 2), in the presence of a water-binding agent, such as a 4 Å (4 angstroem) molecular sieve, and in the presence of a suitable solvent, such as toluene.

Step 2.2

A compound of formula Vb, in which L and B are as defined under formula I and $P_1$ is a protecting group as defined under formula VIb, may be obtained by reacting the compound of formula VIb with acroloyl chloride (being depicted in scheme 2) in the presence of a base, such as Huenig's base (DIPEA), and in the presence of a suitable solvent, such as dichloromethane.

Step 2.3

A compound of formula IVb, in which L and B are as defined under formula I and $P_1$ is a protecting group as defined under formula VIb, may be obtained by conversion of the compound of formula Vb via ring closure metathesis using a suitable catalyst, such as a Grubbs $2^{nd}$ generation catalyst, in the presence of a suitable solvent, such as dichloromethane, under an inert gas atmosphere, e.g. under an argon atmosphere.

Step 2.4

A compound of formula IIIb, in which L and B are as defined under formula I and $P_1$ is a protecting group as defined under formula VIb, may be obtained by hydrogenation of the compound of formula IVb using a suitable hydrogenation agent, such as hydrogen and a Pd/C-catalyst, in the presence of a suitable solvent, such as methanol.

Step 2.5

A compound of formula IIb, in which L and B are as defined under formula I, may be obtained by deprotecting the compound of formula IIIb with a strong acid, such as trifluoroacetic acid, in the presence of a suitable solvent, such as dichloromethane.

Step 2.6

A compound of formula Ib, in which A, L and B are as defined under formula I, may be obtained by reacting the compound of formula IIb with the compound of formula Va (said compound being described under scheme 1 above) in the presence of a base, such as $K_2CO_3$, and in the presence of a suitable solvent, such as dimethylformamide.

Further compounds of formula I may be obtainable from compounds of formula Ia or Ib—prepared as described according to scheme 1 or scheme 2—by reduction, oxidation and/or other functionalization of resulting compounds and/or by cleavage of any protecting group(s) optionally present, and of recovering the so obtainable compound of the formula I.

The reactions can be effected according to conventional methods, for example as described in the Examples.

The work-up of the reaction mixtures and the purification of the compounds thus obtainable may be carried out in accordance with known procedures.

Acid addition salts may be produced from the free bases in known manner, and vice-versa.

Compounds of the formula I can also be prepared by further conventional processes, e.g. as described in the Examples, which processes are further aspects of the invention.

The starting materials of the formulae IIIa, IVa, Va, VIIb and VIIIb are known or may be prepared according to conventional procedures starting from known compounds, for example as described in the Examples. In some cases, an intermediate of scheme 1 or scheme 2 may be known. In such a situation, said intermediate could be used as an alternative starting point for the process according to scheme 1 or scheme 2.

In a further aspect, the invention also provides a process for the production of compounds of

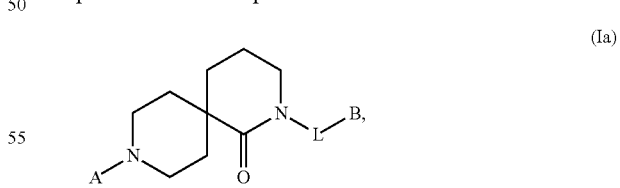
(Ia)

in which A, B and L are as defined under formula I, which comprises reacting a compound of the formula IIa

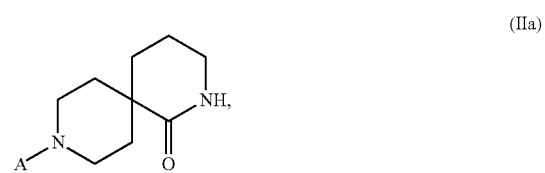
(IIa)

in which A is as defined under formula I, with a compound of the formula IIIa

B-L-Hal    (IIIa), in which B and L are as defined under formula I, and Hal is chloro or bromo, in the presence of a strong base and in the presence of a suitable solvent.

In a further aspect, the invention also provides a process for the production of compounds of the formula Ib

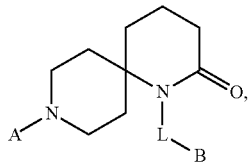
(Ib)

in which A, B and L are as defined under formula I, which comprises reacting a compound of the formula IIb

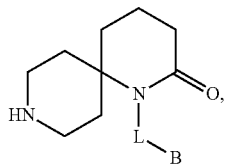
(IIb)

in which B and L are as defined under formula I, with a compound of the formula Va A-Hal    (Va), in which A is as defined under formula I, and Hal is chloro or bromo, in the presence of a base and in the presence of a suitable solvent.

In another aspect, the invention provides a pharmaceutical composition comprising a compound of the invention and a pharmaceutically acceptable carrier. The pharmaceutical composition can be formulated for particular routes of administration such as oral administration, parenteral administration, and rectal administration, etc. In addition, the pharmaceutical compositions of the invention can be made up in a solid form including capsules, tablets, pills, granules, powders or suppositories, or in a liquid form including solutions, suspensions or emulsions. The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifers and buffers etc.

Typically, the pharmaceutical compositions are tablets and gelatin capsules comprising the active ingredient together with
  a) diluents, e.g., lactose, dextrose, sucrose, mannitol, sorbitol, cellulose and/or glycine;
  b) lubricants, e.g., silica, talcum, stearic acid, its magnesium or calcium salt and/or polyethyleneglycol; for tablets also
  c) binders, e.g., magnesium aluminum silicate, starch paste, gelatin, tragacanth, methylcellulose, sodium carboxymethylcellulose and/or polyvinylpyrrolidone; if desired
  d) disintegrants, e.g., starches, agar, alginic acid or its sodium salt, or effervescent mixtures; and/or
  e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with carrier. Carriers include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They are conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

The invention further provides anhydrous pharmaceutical compositions and dosage forms comprising the compounds of the invention as active ingredients, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further provides pharmaceutical compositions and dosage forms that comprise one or more agents that reduce the rate by which the compound of the invention as an active ingredient will decompose. Such agents, which are referred to herein as "stabilizers," include, but are not limited to, antioxidants such as ascorbic acid, pH buffers, or salt buffers, etc.

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The compounds of formula I in free form or in pharmaceutically acceptable salt form, exhibit valuable pharmacological properties, e.g. orexin receptor modulating properties, e.g. as indicated in in-vitro and in-vivo tests as provided in the next sections and are therefore indicated for therapy.

Preferred compounds of formula I show an inhibition of calcium accumulation in recombinant cells expressing at least one of hOx1R or hOx2R at 10 µM of test compound of at least 10%. In one embodiment of the invention, compounds of formula I, which are described in Table 2 as showing an inhibition of calcium accumulation in recombinant cells expressing at least one of hOx1R or hOx2R at 10 µM of test compound of lower than 10%, are excluded.

Further preferred compounds of formula (I) show a Ki value for said calcium accumulation in recombinant cells expressing at least one of hOx1R or hOx2R of at least 1 µM.

Further preferred compounds of formula (I) show a Ki value for said calcium accumulation in recombinant cells expressing at least one of hOx1R or hOx2R of at least 500 nM.

Further preferred compounds of formula (I) show a Ki value for said calcium accumulation in recombinant cells expressing at least one of hOx1R or hOx2R of at least 100 nM.

Further preferred compounds of formula (I) show a Ki value for said calcium accumulation in recombinant cells expressing at least one of hOx1R or hOx2R of at least 50 nM.

In an embodiment, the invention provides a method of inhibiting orexin receptor activity in a subject, wherein the method comprises administering to the subject a therapeutically effective amount of the compound of the invention.

In an embodiment, the invention relates to the use of a compound of the invention for the treatment of a disorder or disease in a subject mediated by orexin receptors.

In another embodiment, the invention relates to the use of a compound of the invention for the treatment of a disorder or disease in a subject characterized by an abnormal activity of orexin receptors.

Compounds of the invention may be useful in the treatment of an indication selected from:
i) sleep disorders;
ii) eating disorders;
iii) substance-related disorders;
iv) Alzheimers disease;
v) psychiatric, neurological and neurodegenerative disorders, such as depression; anxiety; addictions, obsessive compulsive disorder; affective neurosis; depressive neurosis; anxiety neurosis; dysthymic disorder; mood disorder; sexual dysfunction; psychosexual dysfunction; sex disorder; schizophrenia; manic depression; delirium; dementia; severe mental retardation and dyskinesias such as Huntington's disease and Tourette syndrome; Parkinson's disease; ischemic or haemorrhagic stroke; migraine; and neurodegenerative disorder including nosological entities such as disinhibition-dementia-parkinsonism-amyotrophy complex; pallido-ponto-nigral degeneration epilepsy; seizure disorders;
vi) cardiovascular diseases, diabetes; asthma; Cushing's syndrome/disease; basophil adenoma; prolactinoma; hyperprolactinemia; hypopituitarism; hypophysis tumour/adenoma; hypothalamic diseases; Froehlich's syndrome; hypophysis diseases, hypothalamic hypogonadism; Kallman's syndrome (anosmia, hyposmia); functional or psychogenic amenorrhea; hypopituitarism; hypothalamic hypothyroidism; hypothalamic-adrenal dysfunction; idiopathic hyperprolactinemia; hypothalamic disorders of growth hormone deficiency; idiopathic growth deficiency; dwarfism; gigantism; acromegaly; heart and lung diseases, acute and congestive heart failure; hypotension; hypertension; urinary retention; osteoporosis; angina pectoris; myocardial infarction; subarachnoid haemorrhage; ulcers; allergies; benign prostatic hypertrophy; chronic renal failure; renal disease; impaired glucose tolerance; vomiting and nausea; inflammatory bowel disease; gastric dyskinesia; gastric ulcers; urinary bladder incontinence e.g. urge incontinence; hyperalgesia; pain; enhanced or exaggerated sensitivity to pain such as hyperalgesia, causalgia, and allodynia; acute pain; burn pain; atypical facial pain; neuropathic pain; back pain; complex regional pain syndrome I and II; arthritic pain; sports injury pain; pain related to infection e.g. HIV, post-chemotherapy pain; post-stroke pain; post-operative pain; neuralgia; conditions associated with visceral pain such as irritable bowel syndrome, migraine and angina; and
vii) other diseases related to general orexin system dysfunction.

Compounds of the invention may be especially useful in the treatment of an indication selected from: sleep disorders, eating disorders, substance-related disorders and Alzheimers disease.

"Eating disorders" may be defined as comprising metabolic dysfunction; dysregulated appetite control; compulsive obesities; emeto-bulimia or anorexia nervosa. This pathologically modified food intake may result from disturbed appetite (attraction or aversion for food); altered energy balance (intake vs expenditure); disturbed perception of food quality (high fat or carbohydrates, high palatability); disturbed food availability (unrestricted diet or deprivation) or disrupted water balance.

"Sleep disorders" include insomnias, narcolepsy and other disorders of excessive sleepiness, sleep-related dystonias; restless leg syndrome; sleep apneas; jet-lag syndrome; shift-work syndrome, delayed or advanced sleep phase syndrome. Insomnias are defined as comprising sleep disorders associated with aging; intermittent treatment of chronic insomnia; situational transient insomnia (new environment, noise) or short-term insomnia due to stress; grief; pain or illness.

"Substance-related disorders" include substance abuse, substance dependence and substance withdrawal disorders, e.g. nicotine withdrawal or narcotics withdrawal.

Thus, as a further embodiment, the invention provides the use of a compound of formula (I) in free form or in pharmaceutically acceptable salt form as a medicament.

As a further embodiment, the invention provides the use of a compound of formula (I) in free form or in pharmaceutically acceptable salt form in therapy.

In a further embodiment, the therapy is selected from a disease which is ameliorated by modulation, preferably antagonism, of orexin receptors. In another embodiment, the disease is selected from the afore-mentioned list, suitably sleep disorders, eating disorders, substance-related disorders or Alzheimers disease.

In another embodiment, the invention provides a method of treating a disease which is ameliorated by modulation, preferably antagonism, of orexin receptors comprising administration of a therapeutically acceptable amount of a compound of formula (I) in free form or in pharmaceutically acceptable salt form. In a further embodiment, the disease is selected from the afore-mentioned list, suitably sleep disorders, eating disorders or Alzheimers disease.

The term "a therapeutically effective amount" of a compound of the invention refers to an amount of the compound of the invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the invention that, when administered to a subject, is effective to (1) at least partially alleviating, inhibiting, preventing and/or ameliorating a condition, or a disorder or a disease (i) mediated by orexin receptors, or (ii) associated with orexin receptor activity, or (iii) characterized by abnormal activity of orexin receptors; or (2) reducing or inhibiting the activity of orexin receptors; or (3) reducing or inhibiting the expression of orexin receptors. In another non-limiting embodiment, the term "a therapeutically effective amount" refers to the amount of the compound of the invention that, when administered to a cell, or a tissue, or a non-cellular biological material, or a medium, is effective to at least partially reducing or inhibiting the activity of orexin receptors; or at least partially reducing or inhibiting the expression of orexin receptors.

As used herein, the term "subject" refers to an animal. Preferably, the animal is a mammal. A subject also refers to for example, primates (e.g., humans), cows, sheep, goats, horses, dogs, cats, rabbits, rats, mice, fish, birds and the like. In a preferred embodiment, the subject is a human.

As used herein, the term "inhibition" or "inhibiting" refers to the reduction or suppression of a given condition, symptom, or disorder, or disease, or a significant decrease in the baseline activity of a biological activity or process.

As used herein, the term "treating" or "treatment" of any disease or disorder refers in one embodiment, to ameliorating the disease or disorder (i.e., slowing or arresting or reducing the development of the disease or at least one of the clinical symptoms thereof). In another embodiment "treating" or "treatment" refers to alleviating or ameliorating at least one physical parameter including those which may not be discernible by the patient. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to preventing or delaying the onset or development or progression of the disease or disorder.

The pharmaceutical composition or combination of the invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the invention can be applied in vitro in the form of solutions, e.g., preferably aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, or between about 1-100 mg/kg.

The activity of a compound according to the invention can be assessed by in vitro & in vivo methods described herein.

The compound of the invention may be administered either simultaneously with, or before or after, at least one other therapeutic agent. Thus, a combination comprising a therapeutically effective amount of the compound of the invention and one or more therapeutically active agents is covered by the present invention. The compound of the invention may be administered separately, by the same or different route of administration, or together in the same pharmaceutical composition.

The following Examples illustrate the invention, but do not limit it.

Abbreviations:
AcOH acetic acid
Boc tert-butoxycarbonyl
d day(s)
DBU 1,8-diazabicyclo[5.4.0]undec-7-en
1,2-DCE 1,2-dichloroethane
DCM dichloromethane
DIC dicyclohexylcarbodiimide
DIPEA N-ethyl-N-isopropylpropan-2-amine (Diisopropylethylamine)
DMAP N,N-dimethylpyridin-4-amine
DMF dimethylformamide
DMSO dimethylsulfoxide
EDC 1-(3-dimethylaminopropyl)-3-ethylcarbodiimide
ESIMS electrospray ionization mass spectrometry EtOAc ethyl acetate
Et$_2$O diethyl ether
h hour(s)
Hex hexane
HOBt 1-Hydroxybenzotriazole trihydrate
HPLC high pressure liquid chromatography
LCMS liquid chromatography mass spectroscopy
LDA lithium diisopropylamide
min minute(s)
NMP N-methyl-2-pyrrolidone (1-methyl-2-pyrrolidone)
NMR nuclear magnetic resonance spectrometry
quant. quantitative
Rt retention time
rt room temperature
TBAI tetrabutylammonium iodide
TBME tert-butyl methyl ether
THF tetrahydrofuran
TFA trifluoroacetic acid
TLC thin layer chromatography
Ts Tosyl
UPLC ultra performance liquid chromatography
HPLC Conditions (For Examples 1 to 38):
Method A (Rt$_A$=Retention Time A)
 Agilent 1100 & 1200 series; Column—Zorbax XDB—C18 5μ, 150×4.6 mm; gradient: A—0.01% TFA in water/B—acetonitrile:methanol (1:1); 0-1 min 70 A-30 B; 1-6 min 30 A-100 B; 6-10 min 0 A-30 B; 10-12 min 70 A-30 B; column temperature 40° C.
Method B (Rt$_B$=Retention Time B)
 Agilent 1100 & 1200 series; Column—Zorbax XDB—C18 5μ, 150×4.6 mm; gradient: A—0.01% TFA in water/B—acetonitrile:methanol (1:1); 0-1 min 95 A-05 B; 1-6 min 95 A-100 B; 6-10 min 0 A-05 B; 10-12 min 95 A-05 B; flow 1.0 ml/min; column temperature 40° C.
Method C (Rt$_C$=Retention Time C)
 Agilent 1100 & 1200 series; Column—Zorbax XDB—C18 5μ, 150×4.6 mm; gradient: A—5 mM Ammonium acetate in water/B—acetonitrile; 0-1 min 70 A-30 B; 1-6 min 30 A-100 B; 6-10 min 0 A-30 B; 10-12 min 70 A-30 B; flow 1.0 ml/min; column temperature 40° C.
Method D (Rt$_D$=Retention Time D)
 Agilent 1100 & 1200 series; Column—Zorbax XDB—C18 5μ, 150×4.6 mm; gradient: A—5 mM Ammonium acetate in water/B—acetonitrile; 0-1 min 95 A-05 B; 1-6 min 95 A-100 B; 6-10 min 0 A-05 B; 10-12 min 95 A-05 B; flow 1.0 ml/min; column temperature 40° C.
Method E (Rt$_E$=Retention Time E)
 Agilent 1100series; Column—Chiralpak AD-H 5μ, 250×4.6 mm; isocratic: A—n-Heptane/B—Ethanol, 80:20; Flow 0.8 ml/min; column temperature 40° C.
LCMS Conditions (%=percent by volume) (for examples 1 to 38):
Method A (Rt$_A$=Retention Time A)
 Agilent 1100series; LC-MSD; column Mercury MS Synergi 2μ, 20×4.0 mm; A—0.1% formic acid in water/B—acetonitrile; 0-0.5 min 70 A-30 B; 1.5-2.4 min 5 A-95 B; 2.5-3.0 min 70 A-30 B; flow 2.0 ml/min; column temperature 30° C.
Method B (Rt$_B$=Retention Time B)
 Agilent 1100series; LC-MSD; column Mercury MS Synergi 2μ, 20×4.0 mm; A—0.1% formic acid in water/B—acetonitrile; 0-0.5 min 30 A-70 B; 1.5-2.4 min 100 A-0 B; 2.5-3.0 min 30 A-70 B; flow 2.0 ml/min; column temperature 30° C.
Method C (Rt$_C$=Retention Time C)
 Agilent 1100series; LC-MSD; column Mercury MS Synergi 2μ, 20×4.0 mm; A—0.1% formic acid in water/B—acetonitrile; 0-0.5 min 30 A-70 B; 1.5-2.4 min 10 A-90 B; 2.5-3.0 min 30 A-70 B; flow 2.0 ml/min; column temperature 30° C.
Method D (Rt$_D$=Retention Time D)
 Agilent 1100series; LC-MS; column Zorbax SB-C18 1.8μ, 30×3.0 mm; A—0.05% trifluoroacetic acid in water/B—0.05% trifluoroacetic acid in acetonitrile; 30 A-100 B in 3.25 min 100 B in 0.75 min 100 A-30 B in 0.25 min; flow 0.7 ml/min; column temperature 35° C.
Method E (Rt$_E$=Retention Time E)
 Acquity HPLC/MS Waters, column Acquity 1.8μ, 2.1×50 mm; A—0.05% formic acid in water/B—acetonitrile; 98 A-2 B in 1.2 min, 98 B in 0.95 min; 98 A-2 B in 0.04 min; flow 0.4 ml/min; column temperature 50° C.
Method F (Rt$_F$=Retention Time F)
 Agilent 1200 HPLC equipped with 6110 MSD (UV 215 nm, pos. mode with ESI ion source); column Agilent TC C18, 5 um, 2.1×50 mm; A: 0.1% TFA in water, B: 0.05% TFA in acetonitrile; 0.0 min 90 A-10 B, 3.4 min 0 A-100 B, 3.9 min 0 A-100 B, 3.91 min 90 A-10 B, 4.5 min 90 A-10 B; flow 0.8 ml/min; column temperature 50° C.
LCMS Conditions (%=percent by volume) (For Examples 39 to 176):
Method A (Rt$_A$=Retention Time A)
 Acquity HPLC/MS Waters, column Waters Acquity HSS T3 1.8 μm, 2.1×50 mm; A: water+0.05% formic acid+0.05% ammonium acetate/B: acetonitrile+0.04% formic acid; 98% A to 98% B in 1.4 min, 98% B 0.75 min; to 98% A in 0.05 min; flow 1.2 ml/min; column temperature 50° C.
Method B (Rt$_B$=Retention Time B)
 HP-1100 LC/MS Agilent technology, column Zorbax SB-C18 1.8 μm, 3×30 mm; A: water+0.05% trifluoroacetic acid/B: acetonitrile+0.05% trifluoroacetic acid; 30% A to 100% B in 3.25 min, 100% B 0.75 min; to 30% A in 0.02 min; flow 0.7 ml/min; column temperature 35° C.
Method C (Rt$_C$=Retention Time C)
 Agilent 1100series; LC-MS; column Zorbax SB-C18 1.8 μm, 3.0×30 mm; A: water+0.05% trifluoroacetic acid/B: acetonitrile+0.05% trifluoroacetic acid in; 90% A to 100% B in 3.25 min, 100% B 0.75 min, to 90% A in 0.25 min; flow 0.7 ml/min; column temperature 35° C.
Method D (Rt$_D$=Retention Time D)
 Agilent 1100series; LC-MS; column Zorbax SB-C18 1.8 μm, 3.0×30 mm; A: water+0.05% trifluoroacetic acid/B: acetonitrile+0.05% trifluoroacetic acid in; 70% A to 100% B in 3.25 min, 100% B 0.75 min, to 70% A in 0.25 min; flow 0.7 ml/min; column temperature 35° C.
Method E (Rt$_E$=Retention Time E)
 Agilent 1100series; Agilent MSD vsl Single quad mass spectrometer; column Mercury MS Synergi 2μ, 20×4.0 mm; A: water+0.1% formic acid/B—acetonitrile; 0-0.5 min 70 A-30 B; 1.5-2.4 min 5 A-95 B; 2.5-3.0 min 70 A-30 B; flow 2.0 ml/min; column temperature 30° C.
Method F (Rt$_F$=Retention Time F)
 Agilent 1100series; Applied Biosystem MDS SCIEX API 2000 Triple quad mass spectrometer; column Mercury MS Synergi 2μ, 20×4.0 mm; A: water+0.1% formic acid/B—acetonitrile; 0-0.5 min 70 A-30 B; 1.5-2.4 min 5 A-95 B; 2.5-3.0 min 70 A-30 B; flow 2.0 ml/min; column temperature 30° C.
Method G (Rt$_G$=Retention Time G)
 Agilent 1100series; LC-MS; column Ascentis Express FusedCore 2.1×30 mm 2.7 μm C18; A: water+0.05% trifluoroacetic acid/B: acetonitrile+0.04% trifluoroacetic acid in; 90% A to 95% B in 1.7 min, 95% B 0.7 min, to 90% A in 0.05 min; flow 1.4 ml/min; column temperature 50° C.

Method H (Rt$_H$=Retention Time H)

Agilent 1100 series; LC-MS; column—Ascentis Express FusedCore—C18 2.1×30 mm 2.7 μm; gradient: A: water+ 0.05% TFA/B: acetonitrile+0.04% TFA; 98% A to 98% B in 1.4 min, 98% B 0.75 min, to 98% A in 0.04 min; flow 1.2 ml/min; column temperature 50° C.

Method I (Rt$_I$=Retention Time I)

Agilent 1100 series; LC-MS; column—Ascentis Express FusedCore—C18 2.1×30 mm 2.7 μm; gradient: A: water+ 0.05% TFA/B: acetonitrile+0.04% TFA; 90% A to 95% B in 1.7 min, 95% B 0.7 min, to 90% A in 0.05 min; flow 1.4 ml/min; column temperature 50° C.

$^1$H-NMR Instruments: Varian Mercury (300 MHz), Bruker BioSpin (600 MHz), Bruker, (400 MHz), Varian (400 MHz)

EXAMPLES

Method A

Example 1

2-((1H-indol-3-yl)methyl)-9-(quinoxalin-2-yl)-2,9-diazaspiro[5.5]undecan-1-one

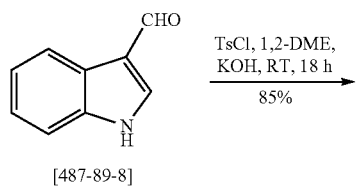

[487-89-8]

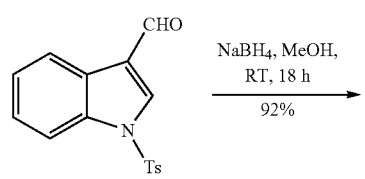

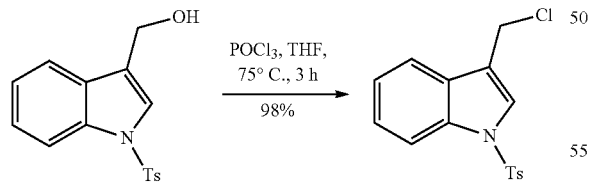

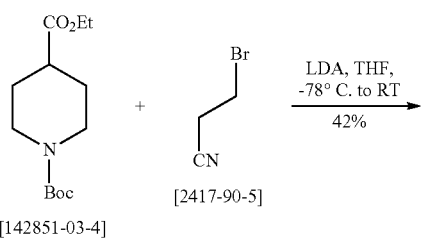

[142851-03-4]    [2417-90-5]

-continued

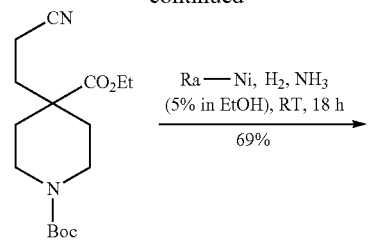

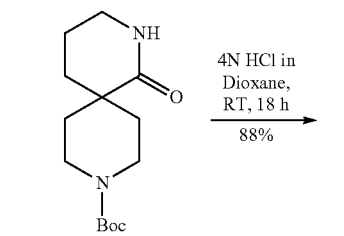

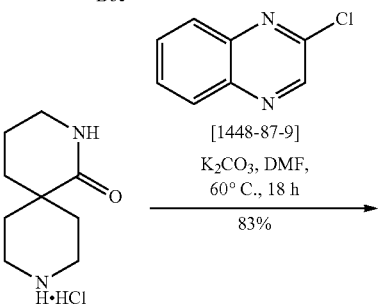

[1448-87-9]

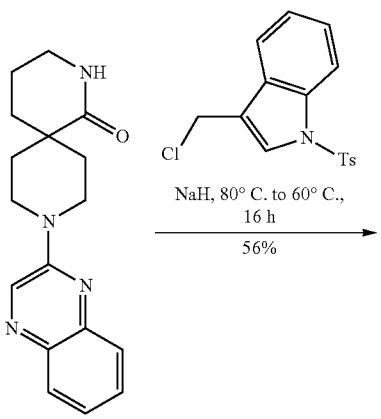

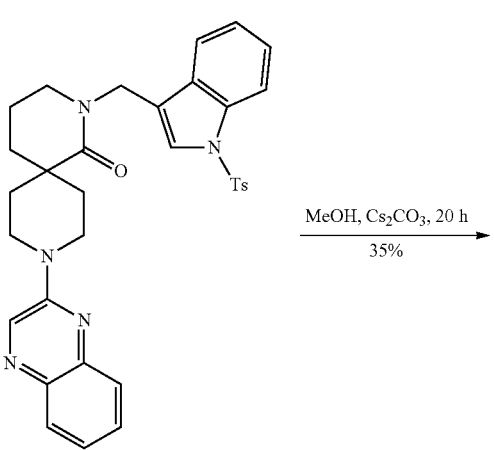

-continued

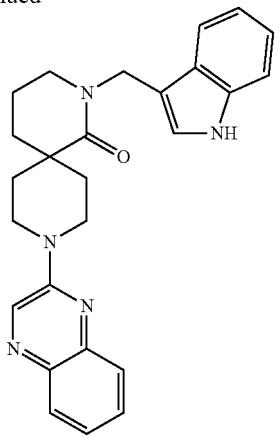

a) 1-tosyl-1H-indole-3-carbaldehyde

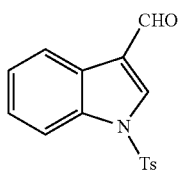 [SMILES: Cc1ccc(S(=O)(=O)n2cc(C=O)c3ccccc32)cc1]

To a solution of indole-3-carbaldehyde (4.0 g, 27.586 mmol) in 1,2-dimethoxyethane (40 mL) KOH (4.63 g, 82.758 mmol) was added at rt and stirred for 10 min. p-toluene sulfonyl chloride (5.785 g, 30.345 mmol) was added to the solution at rt and stirred for 18 h.

The solvent was removed under reduced pressure at 45° C. Ethyl acetate was added to the crude reaction mixture and the organic layer was washed with water and brine. The organic layer was dried over anhydrous sodium sulfate and concentrated under reduced pressure to yield a white solid (7.0 g, 85%). [$^1$H-NMR (CDCl$_3$, 300 MHz) δ 10.12 (s, 1H), 8.31-8.19 (m, 2H), 8.03-7.80 (m, 3H), 7.25-7.48 (m, 4H 2.19 (s, 3H)].

b) (1-tosyl-1H-indol-3-yl)methanol

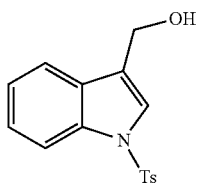 [SMILES: Cc1ccc(S(=O)(=O)n2cc(CO)c3ccccc32)cc1]

To a solution of 1-tosyl-1H-indole-3-carbaldehyde (7 g, 23.385 mmol) in MeOH (70 mL), NaBH$_4$ (1.77 g, 46.769 mmol) was added at 0° C. and the mixture was stirred for 10 min. The reaction mixture was allowed to warm to rt and stirring was continued for 18 h. The solvent was removed under reduced pressure at 45° C. and the crude reaction mixture was quenched with saturated aqueous ammonium chloride solution. Ethyl acetate was added and the organic layer was washed with water and brine. The organic layer was dried over anhydrous sodium sulfate. The organic layer was concentrated under reduced pressure to yield a solid (6.5 g, 92%). [$^1$H-NMR (CDCl$_3$, 300 MHz) δ 8.02-7.95 (m, 1H), 7.82-7.75 (m, 2H), 7.65-7.53 (m, 2H), 7.40-7.19 (m, 4H)].

c) 3-(chloromethyl)-1-tosyl-1H-indole

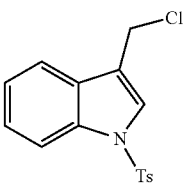 [SMILES: Cc1ccc(S(=O)(=O)n2cc(CCl)c3ccccc32)cc1]

To a solution of (1-tosyl-1H-indol-3-yl)methanol (1.0 g, 3.318 mmol) in dry THF (10 mL), POCl$_3$ (0.661 g, 4.314 mmol) was added at 0° C. and the mixture was stirred for 10 min. The reaction mixture was allowed to warm to ambient temperature and refluxed for 3 h. The solvent was removed under reduced pressure at 45° C. and the crude reaction mixture was quenched with saturated NaHCO$_3$ solution and extracted with DCM. The organic layer was separated and dried over anhydrous sodium sulfate, filtered and concentrated under reduced pressure to yield the title compound as a solid (1.04 g, 98%).

d) 1-tert-butyl 4-ethyl 4-(2-cyanoethyl)piperidine-1,4-dicarboxylate

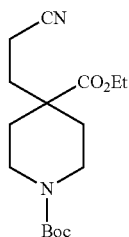

To a solution of ethyl N-Boc-piperidine-4-carboxylate (10.0 g, 38.86 mmol) in THF (200 mL) was added LDA (2 M solution in Hexane, 38.86 mL, 77.72 mmol) at −78° C. and stirred for 30 min. 3-bromo propionitrile (6.25 g, 46.63 mmol) was then added at −78° C. The resulting reaction mixture was stirred at −60° C. for 4 h and quenched with saturated NH$_4$Cl solution. Ethyl acetate was added and the organic layer was extracted with water and brine. The organic layer was dried over Na$_2$SO$_4$, filtered and concentrated. The crude product was purified by column chromatography using 10% ethyl acetate in hexane to yield the title compound as a pale yellow liquid (5.0 g, 40%). [$^1$H-NMR (DMSO-d$_6$, 300 MHz): δ 4.15 (q, 2H), 3.78-3.54 (m, 2H), 2.93-2.72 (m, 2H), 2.43 (t, 2H), 2.02-1.78 (m, 4H), 1.45-1.29 (m, 11H), 1.22 (t, 3H); HPLC Rt$_A$=4.703 min (93%); LCMS Rt$_A$=1.881, [M+H-Boc]$^+$=211.1].

e) tert-butyl 1-oxo-2,9-diazaspiro[5.5]undecane-9-carboxylate

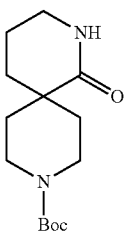

A heterogeneous mixture of Raney Ni (5.0 g) in ethanolic ammonia (~20% v/v) and 1-tert-butyl 4-ethyl 4-(2-cyanoethyl)piperidine-1,4-dicarboxylate (8.5 g, 27.42 mmol) was hydrogenated at 100 psi for 48 h at rt in an autoclave. After completion of the reaction, the catalyst was filtered off and washed with ethanol. The combined filtrate was concentrated under reduced pressure and triturated with n-pentane to yield a solid which was purified by column chromatography (eluent=6% methanol in chloroform) to furnish the title compound as a white solid (3.0 g, 41%). [$^1$H-NMR (DMSO-d$_6$, 300 MHz): δ 7.38 (s, 1H), 3.68-3.60 (m, 2H), 3.18-2.95 (m, 4H), 1.89-1.58 (m, 4H), 1.45-1.22 (m, 13H); HPLC Rt$_A$=3.835 min (96%); LCMS Rt$_A$=1.630, [M+H-Boc]$^+$=169.1].

f) 2,9-diazaspiro[5.5]undecan-1-one hydrochloride

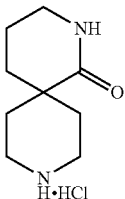

To the stirred solution of tert-butyl 1-oxo-2,9-diazaspiro[5.5]undecane-9-carboxylate (3.0 g, 11.19 mmol) in DCM (60 mL) was added 4N HCl in dioxane (20 mL) and the mixture was stirred at rt for 18 h. The solvent was removed under reduced pressure and triturated with diethyl ether (2×5 mL) to yield the title compound as a solid (2.2 g, 96%). Note: The product is moisture sensitive. [$^1$H-NMR (DMSO-d$_6$, 300 MHz): δ 9.25-8.68 (m, 2H), 7.43 (s, 1H), 7.20-6.25 (m, 2H), 3.61-2.90 (m, 5H), 2.12-1.95 (m, 2H), 1.76-1.49 (m, 5H); LCMS Rt$_A$=0.326, [M+H]$^+$=169.0].

g) 9-(quinoxalin-2-yl)-2,9-diazaspiro[5.5]undecan-1-one

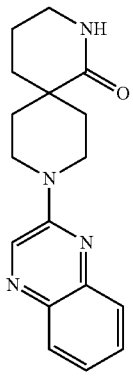

To the stirred solution of 2,9-diazaspiro[5.5]undecan-1-one hydrochloride (2.2 g, 10.78 mmol) in DMF (15 mL) was added K$_2$CO$_3$ (4.45 g, 32.24 mmol) and 2-chloro quinoxaline (1.94 g, 11.82 mmol). The mixture was heated at 60° C. for 18 h. The reaction mixture was cooled to rt and concentrated under reduced pressure. To the crude mixture water was added and extracted with ethyl acetate. The organic layer was dried over anhydride sodium sulfate, filtered and concentrated to obtain a yellow solid which was triturated with n-pentane to yield a yellow solid (2.5 g, 78%). [$^1$H-NMR (DMSO-d$_6$, 300 MHz): δ 8.91 (s, 1H), 7.81 (d, 1H), 7.62-7.55 (m, 2H), 7.42-7.33 (m, 2H), 4.33-4.19 (m, 2H), 3.52-3.33 (m, 2H), 3.20-3.05 (m, 2H), 2.12-1.98 (m, 2H), 1.95-1.64 (m, 4H), 1.59-1.48 (m, 2H); HPLC Rt$_A$=3.665 min (97%); LCMS Rt$_A$=0.377, [M+H]$^+$=297.1].

h) 2-((1H-indol-3-yl)methyl)-9-(quinoxalin-2-yl)-2,9-diazaspiro[5.5]undecan-1-one

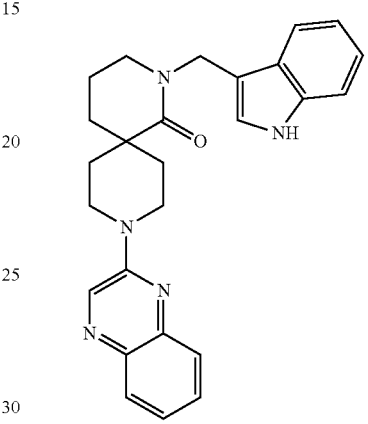

NaH (1.42 g, 5.938 mmol) was added to a stirred solution of 9-(quinoxalin-2-yl)-2,9-diazaspiro[5.5]undecan-1-one (0.8 g, 2.699 mmol) in THF (20 mL) and the resulting mixture was heated under reflux for 10 min. The reaction mixture was allowed to warm to rt. Then, 3-(chloromethyl)-1-tosyl-1H-indole (1.035 g, 3.239 mmol) was added and the mixture was heated at 60° C. for 16 h. The mixture was cooled to rt and saturated aqueous NH$_4$Cl solution was added and the solution was extracted with ethyl acetate. The organic layer was washed with water and brine, filtered and dried over anhydrous sodium sulfate. The organic layer was concentrated under reduced pressure. The purification of the product was attempted by flash-column chromatography over Silicagel (Eluent: ~1% methanol in chloroform) to yield a solid (0.43 g). [HPLC Rt$_A$=6.77 min (56%); LCMS Rt$_A$=0.377, [M+H]$^+$=580.3]. This product was directly taken for the next step for detosylation to furnish the title compound as follows:

To the stirred solution of 2-((1H-indol-3-yl)methyl)-9-(quinoxalin-2-yl)-2,9-diazaspiro[5.5]undecan-1-one (0.43 g, 0.742 mmol) in methanol (10 mL) Cs$_2$CO$_3$ (1.446 g, 4.45 mmol) was added and the mixture was stirred at reflux for 20 h. The solvent was removed under reduced pressure at 45° C. and the crude reaction mixture was taken up in ethyl acetate. The ethyl acetate layer was washed with water and brine, and dried over anhydrous sodium sulfate. The organic layer was filtered and concentrated under reduced pressure to obtain a pale yellow solid. Purification of the crude product by preparative HPLC under neutral conditions furnished the title compound as a pale yellow solid (0.112 g, 35%); M.P: 109-111° C.; [$^1$H-NMR (CDCl$_3$, 300 MHz): δ 8.6 (s, 1H), 8.17 (brs, 1H), 7.91-7.85 (m, 1H), 7.72-7.64 (m, 2H), 7.61-7.53 (m, 1H), 7.43-7.34 (m, 2H), 7.28-7.11 (m, 3H), 4.78 (s, 2H), 4.35-4.22 (m, 2H), 3.67-3.51 (m, 2H), 3.28 (t, 2H), 2.42-2.30 (m, 2H), 1.78-1.72 (m, 4H), 1.71-1.58 (m, 2H); HPLC Rt$_A$=5.170 min (98%); LCMS Rt$_C$=0.41, [M+H]$^+$=426.2].

Method B

Example 2

2-(naphthalen-1-ylmethyl)-9-(quinoxalin-2-yl)-2,9-diazaspiro[5.5]undecan-1-one

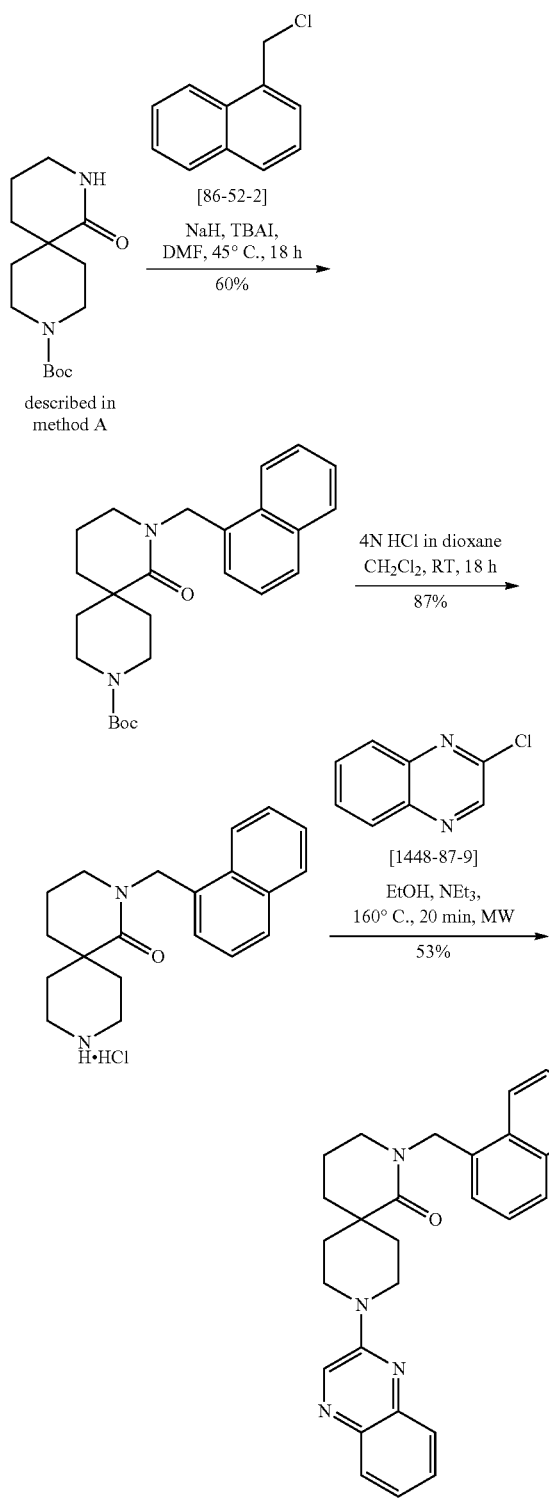

a) tert-butyl 2-(naphthalen-1-yl)methyl)-1-oxo-2,9-diazaspiro[5.5]undecane-9-carboxylate

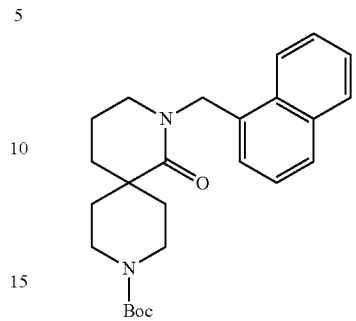

A solution of tert-butyl 1-Oxo-2,9-diaza-spiro[5.5]undecane-9-carboxylate (400 mg, 1.5 mmol) in DMF (2 ml) was added slowly at rt to a suspension of sodium hydride 95% (54 mg, 2.24 mmol) in THF (6 ml). The reaction mixture was stirred for 20 min at rt. Then a solution of 1-(chloromethyl)naphthalene (0.33 ml, 2.24 mmol) in THF (2 ml) was added dropwise followed by the addition of tetrabutylammonium iodide (55 mg, 0.15 mmol). The mixture was stirred at 45° C. for 18 h. The reaction mixture was quenched with $H_2O$ (50 ml) and extracted twice with EtOAc (50 ml). The combined organic layer was dried over $Na_2SO_4$, filtered and evaporated. The residue was purified by flash chromatography (hexane/EtOAc 2:1) to yield 377 mg (61%) of the title compound. [$^1$H NMR (DMSO, 400 MHz) δ 8.01 (m, 1H), 7.93 (m, 1H), 7.85 (m, 1H), 7.55-7.42 (m, 3H), 7.30 (m, 1H), 4.95 (s, 2H), 3.72 (m, 2H), 3.15-2.95 (m, 4H), 1.98-1.82 (m, 2H), 1.78-1.62 (m, 4H), 1.48-1.38 (m, 2H), 1.39 (s, 9H)].

b) 2-(naphthalen-1-ylmethyl)-9-(quinoxalin-2-yl)-2,9-diazaspiro[5.5]undecan-1-one

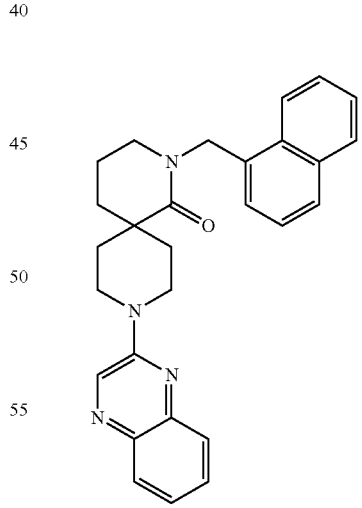

HCl (4M in dioxane, 5 ml) was added to a solution of tert-butyl 2-(naphthalen-1-ylmethyl)-1-oxo-2,9-diazaspiro[5.5]undecane-9-carboxylate (377 mg, 0.9 mmol) in $CH_2Cl_2$ (2 ml) and the mixture was stirred at rt for 18 h. The volatiles were evaporated to afford 270 mg (87%) of crude 2-(naphthalen-1-ylmethyl)-2,9-diazaspiro[5.5]undecan-1-one hydrochloride, which was used without further purification.

Crude 2-naphthalen-1-yl-methyl-2,9-diaza-spiro[5.5]undecan-1-one hydrochloride (100 mg, 0.29 mmol), 2-chloroquinoxaline (81 mg, 0.49 mmol) and triethylamine (0.12 ml, 0.87 mmol) were dissolved in EtOH (1 ml) in a microwave tube. The tube was sealed and the suspension was heated at 160° C. over 20 min under microwave conditions. The solvent was removed under reduced pressure and the resulting crude product was purified by preparative reverse phase chromatography (Sun Fire C18 column, 16 min linear gradient: elution 20-60% ($CH_3CN$ in $H_2O$ (0.1% TFA)); flow rate 50 ml/min) to yield 87 mg (53%) of the title compound. [$^1$H NMR (DMSO, 600 MHz) δ 8.86 (s, 1H), 8.07-8.00 (m, 1H), 7.98-7.91 (m, 1H), 7.86 (d, 1H, J=8.28 Hz), 7.82 (d, 1H, J=8.02 Hz), 7.64-7.56 (m, 2H), 7.56-7.50 (m, 2H), 7.48 (t, 1H), 7.38 (t, 1H), 7.34 (d, 1H, J=7.06 Hz), 4.98 (s, 2H), 4.37-4.26 (m, 2H), 3.46 (t, 2H), 3.23-3.10 (m, 2H), 2.20-2.08 (m, 2H), 1.93-1.82 (m, 2H), 1.80-1.70 (m, 2H), 1.67-1.53 (m, 2H), LCMS $Rt_D$=3.10 min, $[M+H]^+$=437.2].

Example 3

2-((1H-indol-4-yl)methyl)-9-(quinoxalin-2-yl)-2,9-diazaspiro[5.5]undecan-1-one

Example 3 was synthesized according to method A using 4-(bromomethyl)-1-tosyl-1H-indole [78118-62-4] in the amide alkylation step.

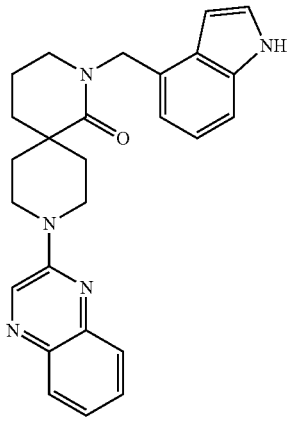 [SMILES: O=C1N(Cc2cccc3[nH]ccc23)CCCC12CCN(c1cnc3ccccc3n1)CC2]

To a solution of 9-quinoxalin-2-yl-2,9-diaza-spiro[5.5]undecan-1-one (100 mg, 0.34 mmol) in THF (5 ml) sodium hydride 95% (18 mg, 0.74 mmol) was added and the mixture was stirred for 10 min at rt. Then 4-bromomethyl-1-(toluene-4-sulfonyl)-1H-indole (147 mg, 0.4 mmol) was added and the reaction mixture was heated at 50° C. over 18 h. Saturated aqueous $NH_4Cl$ solution (50 ml) was added and the reaction mixture was extracted with methylene chloride. The organic layer was dried over $Na_2SO_4$, filtered and concentrated under reduced pressure. The resulting crude product was purified by flash chromatography (EtOAc/hexane 4:6) to yield 80 mg (55%) of the title compound. [$^1$H NMR (DMSO, 600 MHz) δ 11.14 (br.s, 1H), 8.84 (s, 1H), 7.81 (d, 1H, J=8.28 Hz), 7.63-7.52 (m, 2H), 7.44-7.34 (m, 2H), 7.34-7.25 (m, 2H), 7.03 (t, 1H), 6.82 (d, 1H, J=7.06 Hz), 6.43 (br.s, 1H), 4.76 (s, 2H), 4.35-4.25 (m, 2H), 3.48-3.38 (2H, m), 3.13 (t, 2H), 2.21-2.04 (m, 2H), 1.91-1.80 (m, 2H), 1.77-1.65 (m, 2H), 1.62-1.52 (m, 2H), LCMS $Rt_E$=2.70 min, $[M+H]^+$=426.4].

Example 4

2-((2,3-dihydrobenzo[b][1,4]dioxin-5-yl)methyl)-9-(quinoxalin-2-yl)-2,9-diazaspiro[5.5]undecan-1-one Example 4 was synthesized according to method A using 5-(bromomethyl)-2,3-dihydrobenzo[b][1,4]dioxine [214894-89-0] in the amide alkylation step.

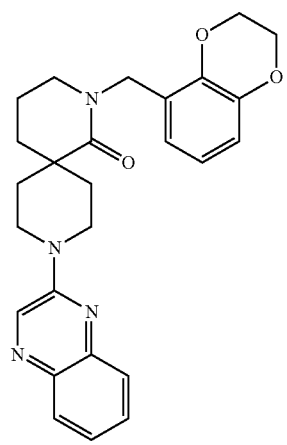 [SMILES: O=C1N(Cc2cccc3c2OCCO3)CCCC12CCN(c1cnc3ccccc3n1)CC2]

To a solution of 9-quinoxalin-2-yl-2,9-diaza-spiro[5.5]undecan-1-one (50 mg, 0.169 mmol) in THF (2 ml) sodium hydride 95% (6.07 mg, 0.253 mmol) was added and the mixture was stirred for 20 min. Then 5-bromomethyl-2,3-dihydro-benzo[1,4]dioxin (77 mg, 0.337 mmol) was added and the reaction mixture was heated at 50° C. over 18 h. Saturated aqueous $NH_4Cl$ solution (50 ml) was added and the reaction mixture was extracted with methylene chloride. The organic layer was dried over $Na_2SO_4$, filtered and concentrated under reduced pressure. The resulting crude product was purified by flash chromatography (EtOAc/hexane 70:30) to yield 60 mg (79%) of the title compound. [$^1$H NMR (600 MHz, DMSO-$d_6$) δ 1.54-1.66 (2H, m) 1.76-1.84 (2H, m) 1.87-1.93 (2H, m) 2.02-2.12 (2H, m) 3.23 (2H, t) 3.39-3.47 (2H, m) 4.20-4.23 (2H, m) 4.24-4.27 (3H, m) 4.27-4.30 (1H, m) 4.41 (2H, s) 6.54 (1H, m) 6.72-6.75 (1H, m) 6.75-6.79 (1H, m) 7.32-7.41 (1H, m) 7.49-7.63 (2H, m) 7.80 (1H, d, J=8.07 Hz), 8.82 (1H, s), LCMS $Rt_D$=3.27 min, $[M+H]^+$=445.2].

Example 5

2-(3-(pyridin-3-yl)benzyl)-9-(quinoxalin-2-yl)-2,9-diazaspiro[5.5]undecan-1-one

Example 5 was synthesized according to method A using 3-(3-(chloromethyl)phenyl)pyridine [1092656-83-1] in the amide alkylation step.

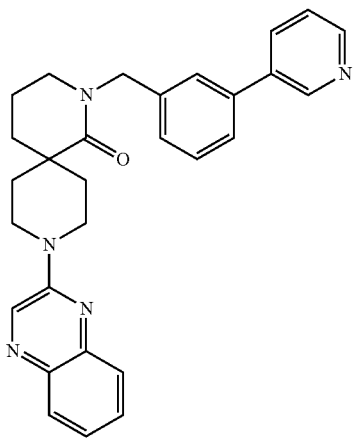 [SMILES: O=C1N(Cc2cccc(-c3cccnc3)c2)CCCC12CCN(c1cnc3ccccc3n1)CC2]

To a stirred solution of 9-(quinoxalin-2-yl)-2,9-diazaspiro[5.5]undecan-1-one (0.035 g, 0.12 mmol) in dry THF (4.0 mL), NaH (0.014 g, 0.36 mmol) was added at rt and the mixture was stirred for 10 min. 3-(3-Chloromethyl-phenyl)-pyridine (0.05 g, 0.24 mmol) was then added and the reaction mixture was heated to 60° C. for 6 h. The mixture was quenched with 1 ml saturated aqueous NH$_4$Cl solution, diluted with 50 ml water and the resulting mixture was extracted with ethyl acetate (100 mL). The organic layer was washed with water and brine. The organic layer was dried over Na$_2$SO$_4$, filtered and concentrated to obtain the crude product. Preparative HPLC purification furnished the title compound as a pale yellow sticky solid (0.025 g, 46%). [$^1$H-NMR (CDCl$_3$, 300 MHz): δ 8.84-8.81 (m, 1H), 8.66-8.58 (m, 2H), 7.92-7.81 (m, 2H), 7.72-7.65 (m, 1H), 7.35-7.61 (m, 6H), 4.68 (s, 2H), 4.31-4.20 (m, 2H), 3.70-3.55 (m, 2H), 3.31 (t, 2H), 2.43-2.29 (m, 2H), 1.96-1.82 (m, 4H), 1.75-1.63 (dt, 2H); HPLC Rt$_A$=4.635 min (96%); LCMS Rt$_C$=0.395, [M+H]$^+$=464.0].

TABLE 1a

Compounds of Formula (I)

Examples 6-26 and 30-37 were synthesized according to synthetic method A or B. Examples 27-29 were synthesized according to synthetic method B.

| No | Structure | Name | LCMS Rt [min] (method) | [M + H]$^+$ |
|---|---|---|---|---|
| 1 | 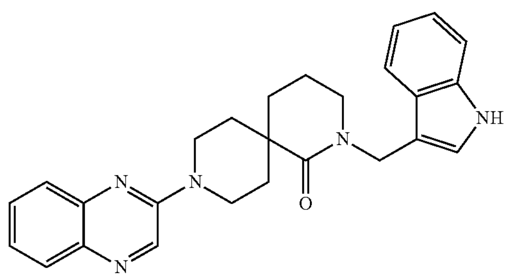 [SMILES: O=C1N(Cc2c[nH]c3ccccc23)CCCC12CCN(c1cnc3ccccc3n1)CC2] | 2-((1H-indol-3-yl)methyl)-9-(quinoxalin-2-yl)-2,9-diazaspiro[5.5]undecan-1-one | 0.41 (C) | 426.2 |
| 2 | 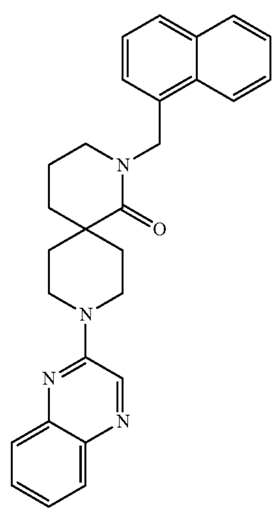 [SMILES: O=C1N(Cc2cccc3ccccc23)CCCC12CCN(c1cnc3ccccc3n1)CC2] | 2-(naphthalen-1-ylmethyl)-9-(quinoxalin-2-yl)-2,9-diazaspiro[5.5]undecan-1-one | 3.10 (D) | 437.3 |

TABLE 1a-continued

Compounds of Formula (I)
Examples 6-26 and 30-37 were synthesized according to synthetic method A or B. Examples 27-29 were synthesized according to synthetic method B.

| No | Structure | Name | LCMS Rt [min] (method) | [M + H]+ |
|---|---|---|---|---|
| 3 | 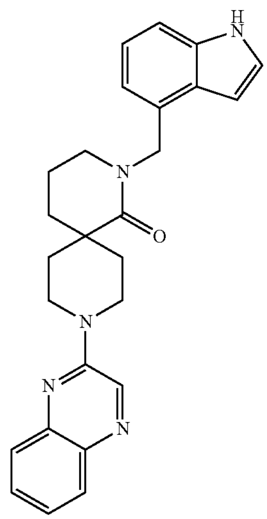 [SMILES: O=C1N(Cc2cccc3[nH]ccc23)CCCC12CCN(c1cnc3ccccc3n1)CC2] | 2-((1H-indol-4-yl)methyl)-9-(quinoxalin-2-yl)-2,9-diazaspiro[5.5]undecan-1-one | 2.70 (E) | 426.4 |
| 4 | 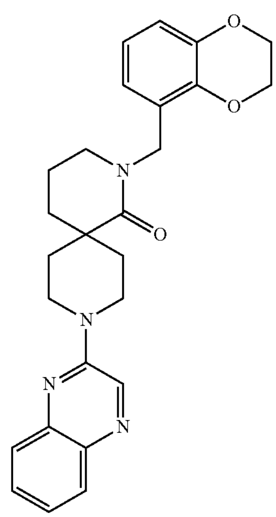 [SMILES: O=C1N(Cc2cccc3c2OCCO3)CCCC12CCN(c1cnc3ccccc3n1)CC2] | 2-((2,3-dihydrobenzo[b][1,4]dioxin-5-yl)methyl)-9-(quinoxalin-2-yl)-2,9-diazaspiro[5.5]undecan-1-one | 3.27 (D) | 445.2 |
| 5 | 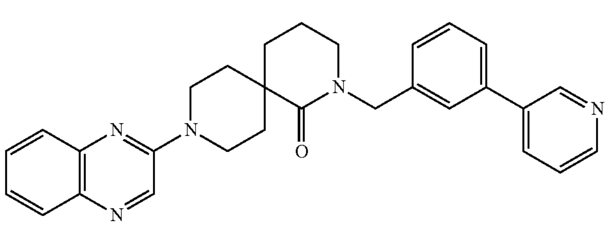 [SMILES: O=C1N(Cc2cccc(-c3cccnc3)c2)CCCC12CCN(c1cnc3ccccc3n1)CC2] | 2-(3-(pyridin-3-yl)benzyl)-9-(quinoxalin-2-yl)-2,9-diazaspiro[5.5]undecan-1-one | 0.39 (C) | 464.0 |

TABLE 1a-continued

Compounds of Formula (I)
Examples 6-26 and 30-37 were synthesized according to synthetic method A or B. Examples 27-29 were synthesized according to synthetic method B.

| No | Structure | Name | LCMS Rt [min] (method) | [M + H]+ |
|---|---|---|---|---|
| 6 | 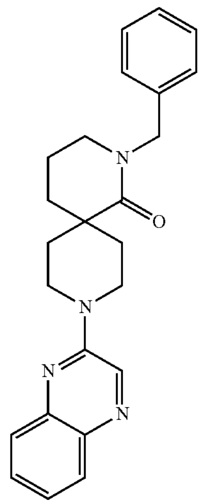 [SMILES: O=C1N(Cc2ccccc2)CCCC12CCN(c1cnc3ccccc3n1)CC2] | 2-benzyl-9-(quinoxalin-2-yl)-2,9-diazaspiro[5.5]undecan-1-one | 3.29 (D) | 387.2 |
| 7 | 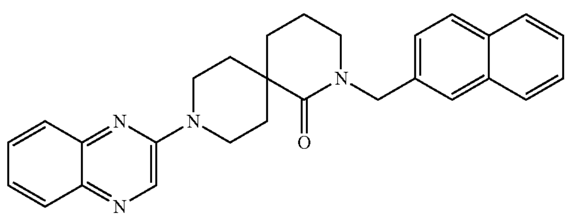 [SMILES: O=C1N(Cc2ccc3ccccc3c2)CCCC12CCN(c1cnc3ccccc3n1)CC2] | 2-(naphthalen-2-ylmethyl)-9-(quinoxalin-2-yl)-2,9-diazaspiro[5.5]undecan-1-one | 3.08 (D) | 437.3 |
| 8 | 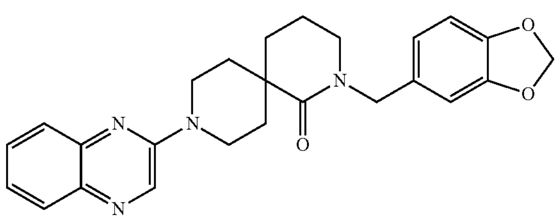 [SMILES: O=C1N(Cc2ccc3c(c2)OCO3)CCCC12CCN(c1cnc3ccccc3n1)CC2] | 2-(benzo[d][1,3]dioxol-5-ylmethyl)-9-(quinoxalin-2-yl)-2,9-diazaspiro[5.5]undecan-1-one | 2.38 (D) | 431.2 |
| 9 | 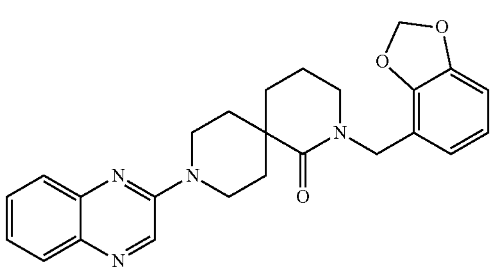 [SMILES: O=C1N(Cc2cccc3c2OCO3)CCCC12CCN(c1cnc3ccccc3n1)CC2] | 2-(benzo[d][1,3]dioxol-4-ylmethyl)-9-(quinoxalin-2-yl)-2,9-diazaspiro[5.5]undecan-1-one | 2.87 (E) | 431.4 |

TABLE 1a-continued

Compounds of Formula (I)
Examples 6-26 and 30-37 were synthesized according to synthetic method A or B. Examples 27-29 were synthesized according to synthetic method B.

| No | Structure | Name | LCMS Rt [min] (method) | [M + H]+ |
|---|---|---|---|---|
| 10 | 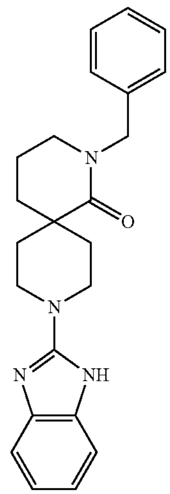 [SMILES: O=C1N(Cc2ccccc2)CCCC12CCN(c1nc3ccccc3[nH]1)CC2] | 9-(1H-benzo[d]imidazol-2-yl)-2-benzyl-2,9-diazaspiro[5.5]undecan-1-one | 2.90 (D) | 375.2 |
| 11 | 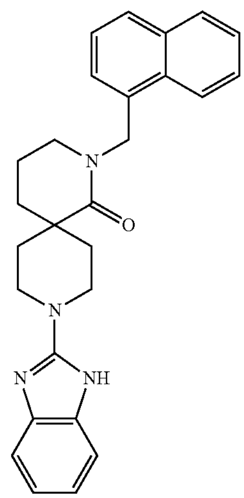 [SMILES: O=C1N(Cc2cccc3ccccc23)CCCC12CCN(c1nc3ccccc3[nH]1)CC2] | 9-(1H-benzo[d]imidazol-2-yl)-2-(naphthalen-1-ylmethyl)-2,9-diazaspiro[5.5]undecan-1-one | 2.35 (D) | 426.2 |
| 12 | 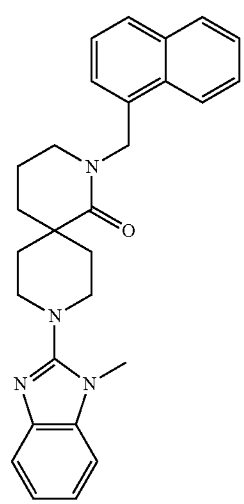 [SMILES: Cn1c(N2CCC3(CCCN(Cc4cccc5ccccc45)C3=O)CC2)nc2ccccc21] | 9-(1-methyl-1H-benzo[d]imidazol-2-yl)-2-(naphthalen-1-ylmethyl)-2,9-diazaspiro[5.5]undecan-1-one | 3.28 (D) | 439.2 |

TABLE 1a-continued

Compounds of Formula (I)
Examples 6-26 and 30-37 were synthesized according to synthetic method A or B. Examples 27-29 were synthesized according to synthetic method B.

| No | Structure | Name | LCMS Rt [min] (method) | [M + H]+ |
|---|---|---|---|---|
| 13 | 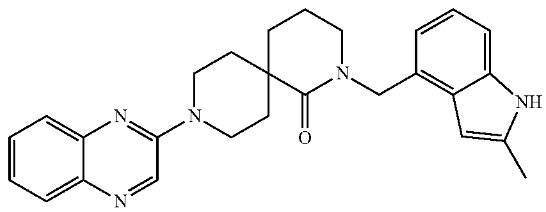 [SMILES: Cc1cc2c(CN3CCCC4(CCN(c5cnc6ccccc6n5)CC4)C3=O)cccc2[nH]1] | 2-((2-methyl-1H-indol-4-yl)methyl)-9-(quinoxalin-2-yl)-2,9-diazaspiro[5.5]undecan-1-one | 2.85 (E) | 440.4 |
| 14 | 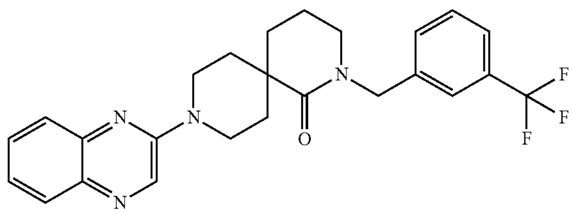 [SMILES: O=C1N(Cc2cccc(C(F)(F)F)c2)CCCC12CCN(c1cnc3ccccc3n1)CC2] | 9-(quinoxalin-2-yl)-2-(3-(trifluoromethyl)benzyl)-2,9-diazaspiro[5.5]undecan-1-one | 3.02 (D) | 455.2 |
| 15 | 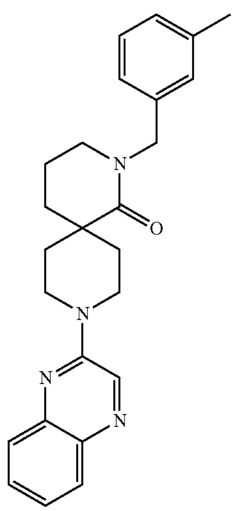 [SMILES: Cc1cccc(CN2CCCC3(CCN(c4cnc5ccccc5n4)CC3)C2=O)c1] | 2-(3-methylbenzyl)-9-(quinoxalin-2-yl)-2,9-diazaspiro[5.5]undecan-1-one | 3.43 (D) | 401.2 |
| 16 | 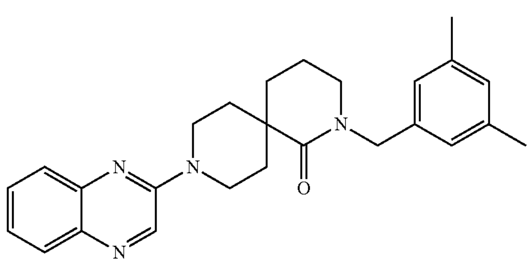 [SMILES: Cc1cc(C)cc(CN2CCCC3(CCN(c4cnc5ccccc5n4)CC3)C2=O)c1] | 2-(3,5-dimethylbenzyl)-9-(quinoxalin-2-yl)-2,9-diazaspiro[5.5]undecan-1-one | 2.19 (E) | 415.4 |
| 17 | 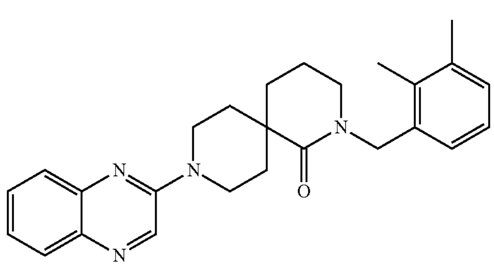 [SMILES: Cc1cccc(CN2CCCC3(CCN(c4cnc5ccccc5n4)CC3)C2=O)c1C] | 2-(2,3-dimethylbenzyl)-9-(quinoxalin-2-yl)-2,9-diazaspiro[5.5]undecan-1-one | 3.29 (E) | 415.4 |

TABLE 1a-continued

Compounds of Formula (I)
Examples 6-26 and 30-37 were synthesized according to synthetic method A or B. Examples 27-29 were synthesized according to synthetic method B.

| No | Structure | Name | LCMS Rt [min] (method) | [M + H]+ |
|---|---|---|---|---|
| 18 | 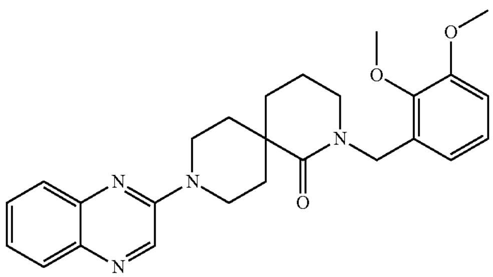 [SMILES: COc1cccc(CN2CCCC3(CCN(c4cnc5ccccc5n4)CC3)C2=O)c1OC] | 2-(2,3-dimethoxybenzyl)-9-(quinoxalin-2-yl)-2,9-diazaspiro[5.5]undecan-1-one | 2.89 (E) | 447.3 |
| 19 | 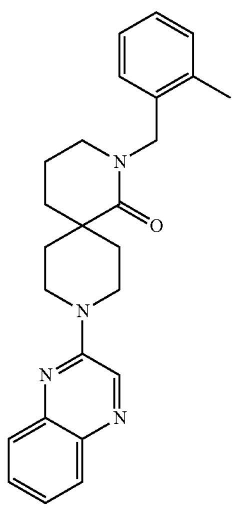 [SMILES: Cc1ccccc1CN1CCCC2(CCN(c3cnc4ccccc4n3)CC2)C1=O] | 2-(2-methylbenzyl)-9-(quinoxalin-2-yl)-2,9-diazaspiro[5.5]undecan-1-one | 3.41 (D) | 401.2 |
| 20 | 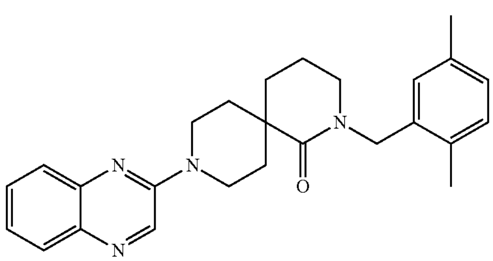 [SMILES: Cc1ccc(C)c(CN2CCCC3(CCN(c4cnc5ccccc5n4)CC3)C2=O)c1] | 2-(2,5-dimethylbenzyl)-9-(quinoxalin-2-yl)-2,9-diazaspiro[5.5]undecan-1-one | 3.31 (E) | 415.4 |
| 21 | 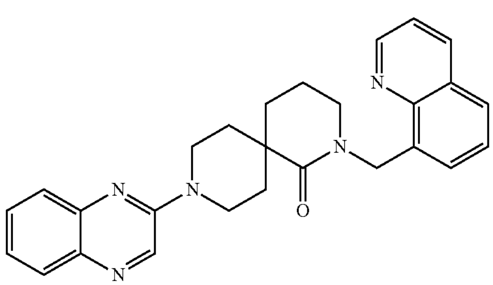 [SMILES: O=C1N(Cc2cccc3cccnc23)CCCC12CCN(c1cnc3ccccc3n1)CC2] | 2-(quinolin-8-ylmethyl)-9-(quinoxalin-2-yl)-2,9-diazaspiro[5.5]undecan-1-one | 2.73 (E) | 438.3 |

TABLE 1a-continued

Compounds of Formula (I)

Examples 6-26 and 30-37 were synthesized according to synthetic method A or B. Examples 27-29 were synthesized according to synthetic method B.

| No | Structure | Name | LCMS Rt [min] (method) | [M + H]+ |
|---|---|---|---|---|
| 22 | 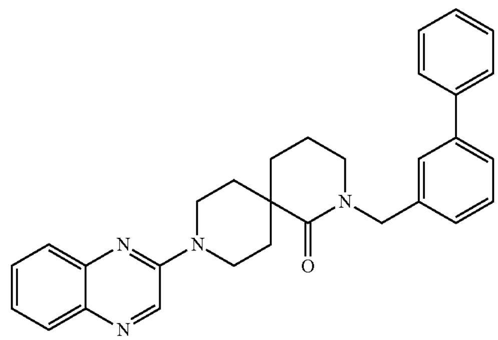 [SMILES: O=C1N(Cc2cccc(-c3ccccc3)c2)CCCC12CCN(c1cnc3ccccc3n1)CC2] | 2-(biphenyl-3-ylmethyl)-9-(quinoxalin-2-yl)-2,9-diazaspiro[5.5]undecan-1-one | 3.49 (E) | 463.4 |
| 23 | 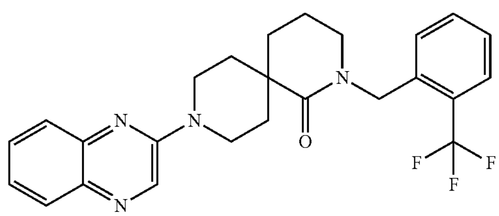 [SMILES: O=C1N(Cc2ccccc2C(F)(F)F)CCCC12CCN(c1cnc3ccccc3n1)CC2] | 9-(quinoxalin-2-yl)-2-(2-(trifluoromethyl)benzyl)-2,9-diazaspiro[5.5]undecan-1-one | 3.02 (D) | 455.2 |
| 24 | 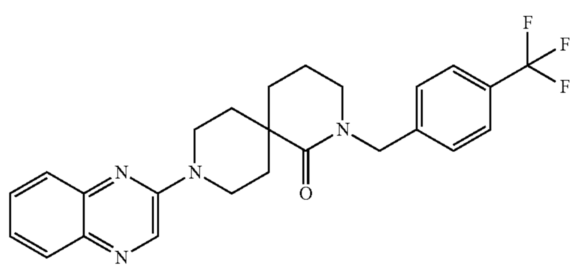 [SMILES: O=C1N(Cc2ccc(C(F)(F)F)cc2)CCCC12CCN(c1cnc3ccccc3n1)CC2] | 9-(quinoxalin-2-yl)-2-(4-(trifluoromethyl)benzyl)-2,9-diazaspiro[5.5]undecan-1-one | 3.02 (D) | 455.2 |
| 25 | 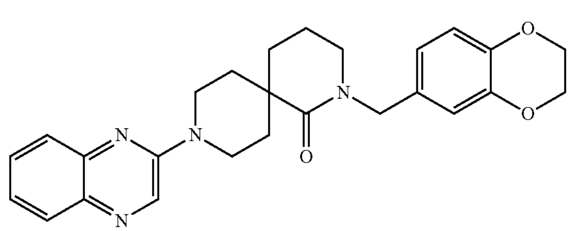 [SMILES: O=C1N(Cc2ccc3c(c2)OCCO3)CCCC12CCN(c1cnc3ccccc3n1)CC2] | 2-((2,3-dihydrobenzo[b][1,4]dioxin-6-yl)methyl)-9-(quinoxalin-2-yl)-2,9-diazaspiro[5.5]undecan-1-one | 2.39 (D) | 445.2 |
| 26 | 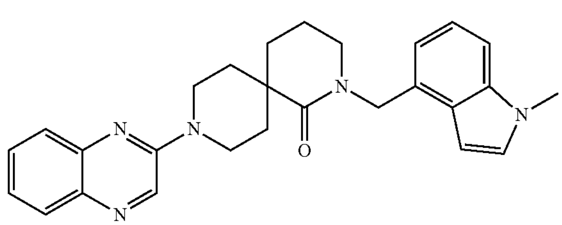 [SMILES: Cn1ccc2c(CN3CCCC4(CCN(c5cnc6ccccc6n5)CC4)C3=O)cccc21] | 2-((1-methyl-1H-indol-4-yl)methyl)-9-(quinoxalin-2-yl)-2,9-diazaspiro[5.5]undecan-1-one | 3.06 (E) | 440.4 |

TABLE 1a-continued

Compounds of Formula (I)
Examples 6-26 and 30-37 were synthesized according to synthetic method A or B. Examples 27-29 were synthesized according to synthetic method B.

| No | Structure | Name | LCMS Rt [min] (method) | [M + H]+ |
|---|---|---|---|---|
| 27 | 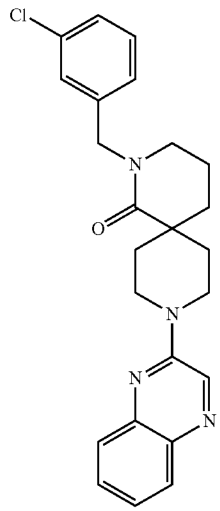 [SMILES: O=C1N(Cc2cccc(Cl)c2)CCCC12CCN(c1cnc3ccccc3n1)CC2] | 2-(3-chlorobenzyl)-9-(quinoxalin-2-yl)-2,9-diazaspiro[5.5]undecan-1-one | 2.94 (F) | 421.1 |
| 28 | 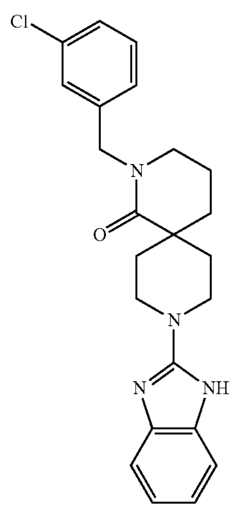 [SMILES: O=C1N(Cc2cccc(Cl)c2)CCCC12CCN(c1nc3ccccc3[nH]1)CC2] | 9-(1H-benzo[d]imidazol-2-yl)-2-(3-chlorobenzyl)-2,9-diazaspiro[5.5]undecan-1-one | 2.43 (F) | 409.1 |
| 29 | 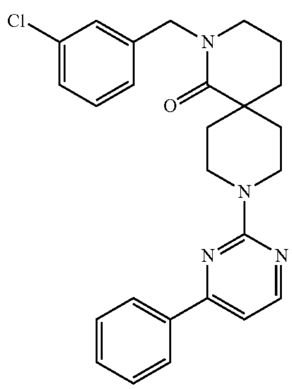 [SMILES: O=C1N(Cc2cccc(Cl)c2)CCCC12CCN(c1nccc(-c3ccccc3)n1)CC2] | 2-(3-chlorobenzyl)-9-(4-phenylpyrimidin-2-yl)-2,9-diazaspiro[5.5]undecan-1-one | 3.14 (F) | 447.2 |

TABLE 1a-continued

Compounds of Formula (I)

Examples 6-26 and 30-37 were synthesized according to synthetic method A or B. Examples 27-29 were synthesized according to synthetic method B.

| No | Structure | Name | LCMS Rt [min] (method) | [M + H]+ |
|---|---|---|---|---|
| 30 | 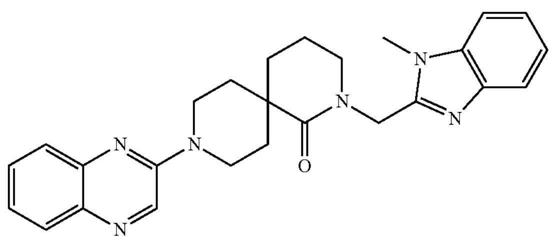 [SMILES: Cn1c(CN2CCCC3(CCN(c4cnc5ccccc5n4)CC3)C2=O)nc2ccccc21] | 2-((1-methyl-1H-benzo[d]imidazol-2-yl)methyl)-9-(quinoxalin-2-yl)-2,9-diazaspiro[5.5]undecan-1-one | 0.31 (C) | 441.1 |
| 31 | 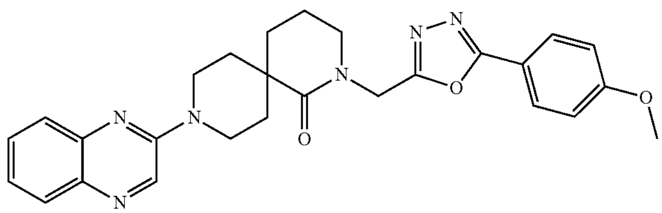 [SMILES: COc1ccc(-c2nnc(CN3CCCC4(CCN(c5cnc6ccccc6n5)CC4)C3=O)o2)cc1] | 2-((5-(4-methoxyphenyl)-1,3,4-oxadiazol-2-yl)methyl)-9-(quinoxalin-2-yl)-2,9-diazaspiro[5.5]undecan-1-one | 0.39 (C) | 485.3 |
| 32 | 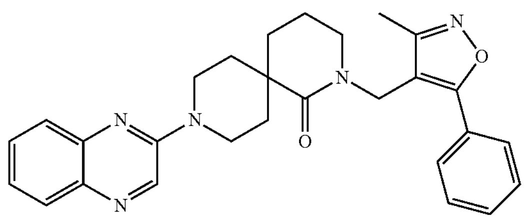 [SMILES: Cc1noc(-c2ccccc2)c1CN1CCCC2(CCN(c3cnc4ccccc4n3)CC2)C1=O] | 2-((3-methyl-5-phenylisoxazol-4-yl)methyl)-9-(quinoxalin-2-yl)-2,9-diazaspiro[5.5]undecan-1-one | 0.46 (C) | 468.4 |
| 33 | 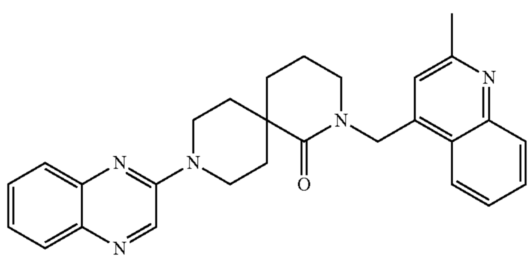 [SMILES: Cc1cc(CN2CCCC3(CCN(c4cnc5ccccc5n4)CC3)C2=O)c2ccccc2n1] | 2-((2-methylquinolin-4-yl)methyl)-9-(quinoxalin-2-yl)-2,9-diazaspiro[5.5]undecan-1-one | 0.28 (A) | 452.1 |
| 34 | 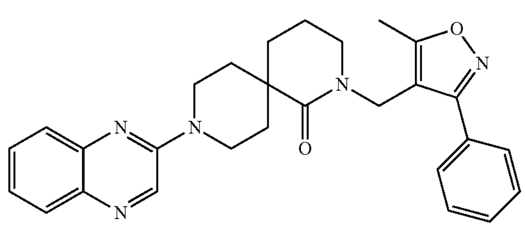 [SMILES: Cc1onc(-c2ccccc2)c1CN1CCCC2(CCN(c3cnc4ccccc4n3)CC2)C1=O] | 2-((5-methyl-3-phenylisoxazol-4-yl)methyl)-9-(quinoxalin-2-yl)-2,9-diazaspiro[5.5]undecan-1-one | 1.67 (A) | 468.2 |
| 35 | 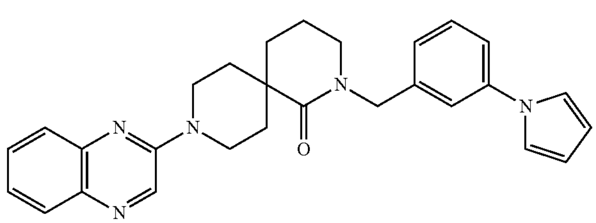 [SMILES: O=C1N(Cc2cccc(-n3cccc3)c2)CCCC12CCN(c1cnc3ccccc3n1)CC2] | 2-(3-(1H-pyrrol-1-yl)benzyl)-9-(quinoxalin-2-yl)-2,9-diazaspiro[5.5]undecan-1-one | 1.78 (A) | 452.1 |

TABLE 1a-continued

Compounds of Formula (I)
Examples 6-26 and 30-37 were synthesized according to synthetic method A or B. Examples 27-29 were synthesized according to synthetic method B.

| No | Structure | Name | LCMS Rt [min] (method) | [M + H]+ |
|---|---|---|---|---|
| 36 | 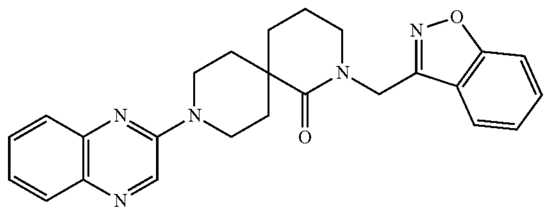 [SMILES: O=C1N(Cc2noc3ccccc23)CCCC12CCN(c1cnc3ccccc3n1)CC2] | 2-(benzo[d]isoxazol-3-ylmethyl)-9-(quinoxalin-2-yl)-2,9-diazaspiro[5.5]undecan-1-one | 0.47 (C) | 428.2 |
| 37 | 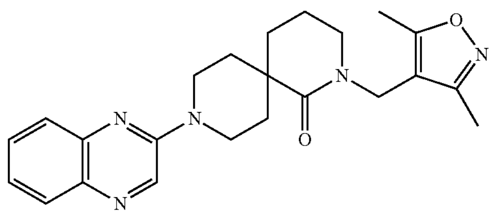 [SMILES: Cc1noc(C)c1CN1CCCC2(CCN(c3cnc4ccccc4n3)CC2)C1=O] | 2-((3,5-dimethylisoxazol-4-yl)methyl)-9-(quinoxalin-2-yl)-2,9-diazaspiro[5.5]undecan-1-one | 1.31 (A) | 406.1 |

Method C

Example 38

1-((1H-indol-4-yl)methyl)-9-(Quinoxalin-2-yl)-1,9-diazaspiro[5.5]undecan-2-one

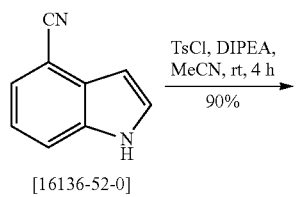

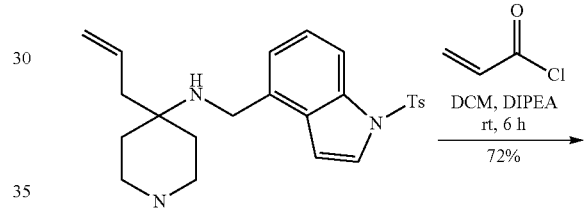

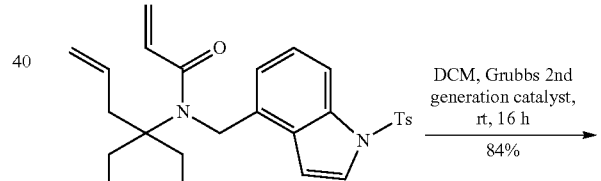

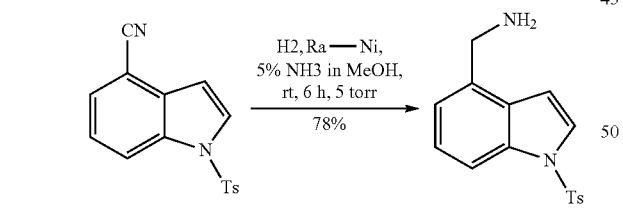

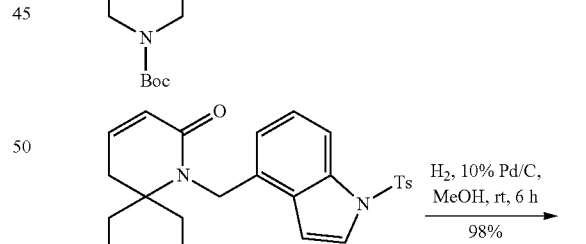

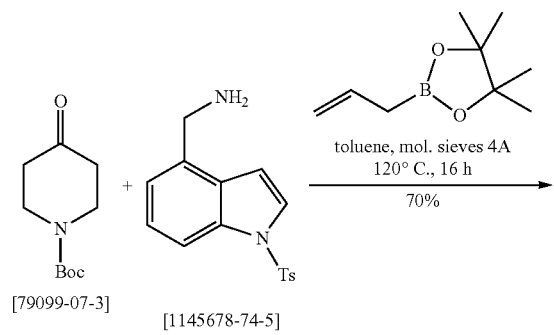

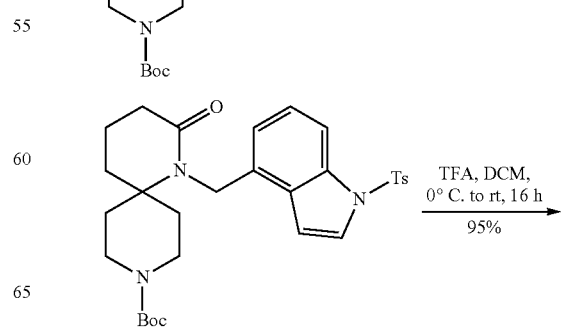

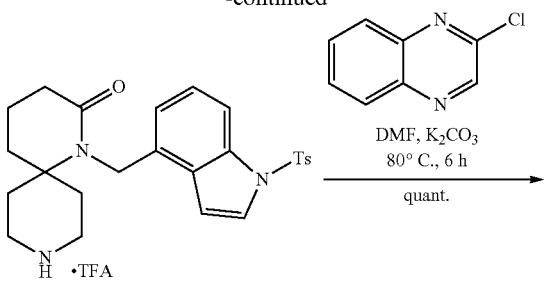
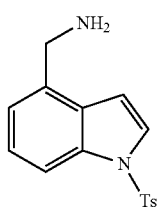 [SMILES: Cc1ccc(S(=O)(=O)n2ccc3c(CN)cccc32)cc1]

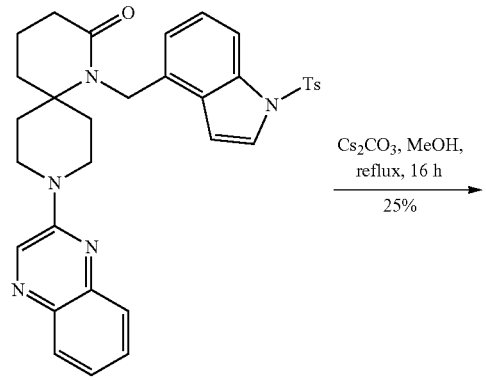

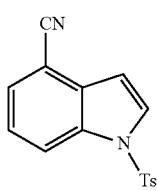

a) 1-tosyl-1H-indole-4-carbonitrile

To a stirred solution of 4-Cyano indole (0.5 g, 3.5 mmol), diisopropylethylamine (1.8 mL, 10.5 mmol) in acetonitrile (5.0 mL), p-toluene sulfonyl chloride (0.8 g, 4.22 mmol) was added and the mixture was stirred at rt for 4 h. The solvent was evaporated under reduced pressure and the residue was diluted with ethyl acetate. The organic layer was washed with water, dried over anhydrous sodium sulfate and concentrated to yield the title compound as brown colored solid (0.95 g, 90%). [$^1$H-NMR (CDCl$_3$, 300 MHz): δ 8.22 (d, 1H), 7.81-7.72 (m, 3H), 7.56 (d, 1H), 7.38 (t, 1H), 7.29-7.22 (m, 2H), 6.88 (d, 1H), 2.39 (s, 3H)].

b) (1-tosyl-1H-indol-4-yl)methanamine

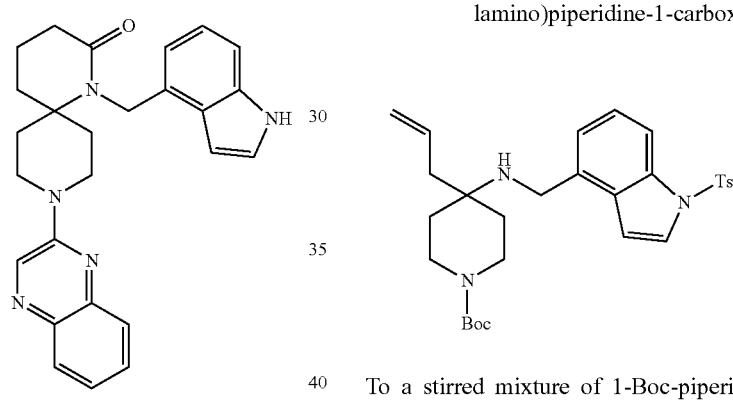

A mixture of 1-tosyl-1H-indole-4-carbonitrile (0.5 g, 1.69 mmol), 5% NH$_3$ in methanol (5.0 mL) and Raney Nickel (0.2 g) in methanol (15.0 ml) was hydrogenated at 5 Torr for 6 h at rt. After completion of the reaction, the Raney Nickel was filtered off through a pad of celite under vacuum and washed with methanol (5×2 mL). The combined filtrates were evaporated to dryness under reduced pressure. The residue was washed with 10% diethyl ether in pentane to yield the title compound as a white solid (0.45 g, 78%). [$^1$H-NMR (CDCl$_3$, 300 MHz): δ 7.72-7.59 (m, 3H), 7.44-7.52 (m, 1H), 7.33-6.72 (m, 5H), 4.12-4.01 (m, 2H), 2.27 (s, 3H)].

c) tert-butyl 4-allyl-4-((1-tosyl-1H-indol-4-yl)methylamino)piperidine-1-carboxylate To a stirred mixture of 1-Boc-piperidin-4-one (0.25 g, 1.256 mmol), 4 Å molecular sieves (0.25 g), allyl boronic acid pinacol ester (0.255 g, 1.507 mmol) in toluene (10.0 mL), 1-tosyl-1H-indol-4-yl)methanamine (0.45 g, 1.507 mmol) was added and the reaction mixture was heated to reflux for 16 h. The mixture was filtered through a pad of celite. The filtrate was concentrated under reduced pressure and the residue was purified by column chromatography (eluent: 10% ethyl acetate in hexane) to yield the title compound as a white solid (0.2 g, 70%). LCMS Rt$_A$=0.341, [M+H]$^+$=524.0 d) tert-butyl 4-allyl-4-(N-((1-tosyl-1H-indol-4-yl)methyl)acrylamido)piperidine-1-carboxylate

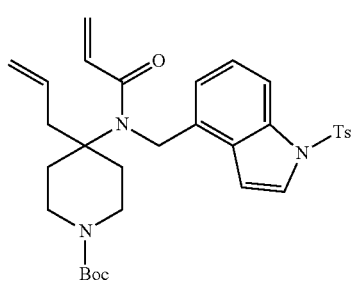 [SMILES: C=CCC1(N(Cc2cccc3c2ccn3S(=O)(=O)c2ccc(C)cc2)C(=O)C=C)CCN(C(=O)OC(C)(C)C)CC1]

Acryloyl chloride (0.360 g, 0.401 mmol) was added at 0° C. to a stirred solution of tert-butyl 4-allyl-4-((1-tosyl-1H-indol-4-yl)methylamino)piperidine-1-carboxylate (0.2 g, 0.382 mmol), diisopropylethylamine (0.32 mL, 1.91 mmol) in DCM (5.0 mL). The reaction mixture was stirred at 0° C. for 30 min and was then allowed to warm to rt and stirred for 4 h. The reaction mixture was concentrated under reduced pressure and the crude product was purified by column chromatography (eluent: 5% ethyl acetate in hexane) to yield the title compound as a white solid (0.16 g, 72%). LCMS $Rt_A$=0.774, $[M+H-Boc]^+$=477.9 e) tert-butyl 2-oxo-1-((1-tosyl-1H-indol-4-yl)methyl)-1,9-diazaspiro[5.5]undec-3-ene-9-carboxylate

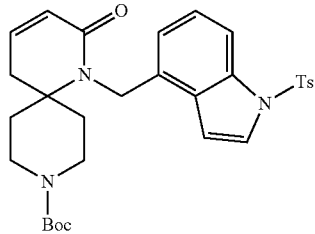 [SMILES: Cc1ccc(S(=O)(=O)n2ccc3c(CN4C(=O)C=CCC45CCN(C(=O)OC(C)(C)C)CC5)cccc32)cc1]

To a solution of tert-butyl 4-allyl-4-(N-((1-tosyl-1H-indol-4-yl)methyl)acrylamido)piperidine-1-carboxylate (0.075 g, 0.13 mmol) in DCM (5.0 mL) was added Grubbs $2^{nd}$ generation catalyst (0.006 g, 0.006 mmol) under argon and the reaction mixture was stirred at rt overnight. The dark brown solution was concentrated under reduced pressure and the crude product was purified by column chromatography (eluent: 25% ethyl acetate in hexane) to yield the title compound as a solid (0.060 g, 84%). LCMS $Rt_A$=0.523, $[M+H]^+$=549.8 f) tert-butyl 2-oxo-1-((1-tosyl-1H-indol-4-yl)methyl)-1,9-diazaspiro[5.5]undecane-9-carboxylate

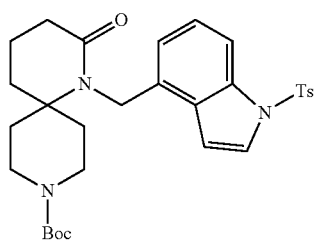

To a solution of tert-butyl 2-oxo-1-((1-tosyl-1H-indol-4-yl)methyl)-1,9-diazaspiro[5.5]undec-3-ene-9-carboxylate (0.12 g, 0.218 mmol) in methanol (6.0 mL) was added 10% Pd/C and the reaction mixture was stirred for 6 h under hydrogen (1 atm. pressure) at rt. The reaction mixture was filtered through a pad of celite and washed with methanol. The filtrate was concentrated and the product was isolated as a white solid (0.120 g, 99%). LCMS $Rt_A$=0.511, $[M+H]^+$=551.9 g) 1-((1-tosyl-1H-indol-4-yl)methyl)-1,9-diazaspiro[5.5]undecan-2-one (TFA Salt)

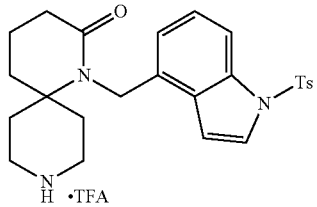 [SMILES: Cc1ccc(S(=O)(=O)n2ccc3c(CN4C(=O)CCCC45CCNCC5)cccc32)cc1]

To a stirred solution of tert-butyl 2-oxo-1-((1-tosyl-1H-indol-4-yl)methyl)-1,9-diazaspiro[5.5]undecane-9-carboxylate (0.12 g, 0.21 mmol) in DCM (5.0 mL), TFA (0.5 mL) was added at 0° C. and the reaction mixture was stirred for 16 h at rt under a nitrogen atmosphere. The reaction mixture was concentrated to yield the title compound as colourless oil (0.11 g, 95%) which was used in the next step.

h) 9-(quinoxalin-2-yl)-1-((1-tosyl-1H-indol-4-yl)methyl)-1,9-diazaspiro[5.5]undecan-2-one

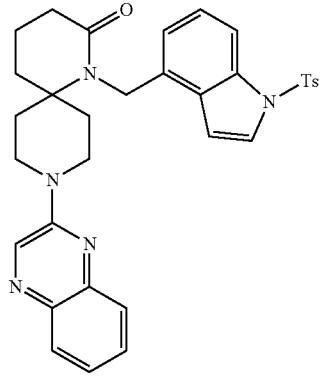 [SMILES: Cc1ccc(S(=O)(=O)n2ccc3c(CN4C(=O)CCCC45CCN(c4cnc6ccccc6n4)CC5)cccc32)cc1]

To a stirred solution of 1-((1-tosyl-1H-indol-4-yl)methyl)-1,9-diazaspiro[5.5]undecan-2-one (TFA salt) (0.11 g, 0.201 mmol) in 5.0 mL DMF, 2-chloroquinoxaline (0.04 g, 0.241 mmol) and $K_2CO_3$ (0.084 g, 0.603 mmol) were added and the reaction mixture was stirred for 6 h at 80° C. under a nitrogen atmosphere. The reaction mixture was quenched with ice-cold water and extracted with ethyl acetate (2×25 mL), dried over anhydrous $Na_2SO_4$, filtered and concentrated under reduced pressure to yield the title compound as a pale yellow solid (0.120 g). LCMS $Rt_A$=0.512, $[M+H]^+$=579.9 i) 1-((1H-indol-4-yl)methyl)-9-(quinoxalin-2-yl)-1,9-diazaspiro[5.5]undecan-2-one

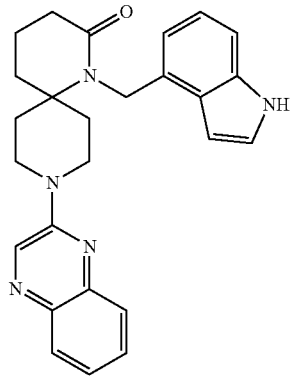 [SMILES: O=C1CCCC2(CCN(c3cnc4ccccc4n3)CC2)N1Cc1cccc2[nH]ccc12]

Cs₂CO₃ (0.201 g, 0.621 mmol) was added to a stirred solution of 9-(quinoxalin-2-yl)-1-((1-tosyl-1H-indol-4-yl)methyl)-1,9-diazaspiro[5.5]undecan-2-one (0.12 g, 0.207 mmol) in methanol (8.0 mL) and stirring was continued for 16 h at 80° C. under a nitrogen atmosphere. The reaction mixture was quenched with ice-cold water and extracted with ethyl acetate (2×125 mL), dried over anhydrous Na₂SO₄, filtered and concentrated. The crude product was purified by preparative HPLC under neutral conditions to yield the title compound as a yellow solid (0.022 g, 25%). [¹H-NMR (CDCl₃, 300 MHz): δ 8.5 (s, 1H), 8.21 (brs, 1H), 7.88 (d, 1H), 7.91-7.55 (m, 2H), 7.42 (t, 1H), 7.19-7.08 (m, 2H), 6.85 (d, 1H), 6.49-6.42 (m, 1H), 4.99 (s, 2H), 4.49-4.36 (m, 2H), 3.12 (t, 2H), 2.69 (t, 2H), 2.25-2.10 (m, 4H), 2.03-1.90 (m, 2H), 1.78 (d, 2H); HPLC Rt$_A$=4.393 min (98%); LCMS Rt$_E$=1.753, [M+H]⁺=426.1].

Method D

Example 39

2-(2-(3-methyl-1,2,4-oxadiazol-5-yl)benzyl)-9-(quinoxalin-2-yl)-2,9-diazaspiro[5.5]undecan-1-one

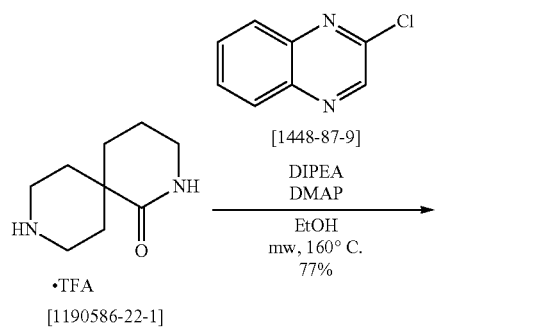

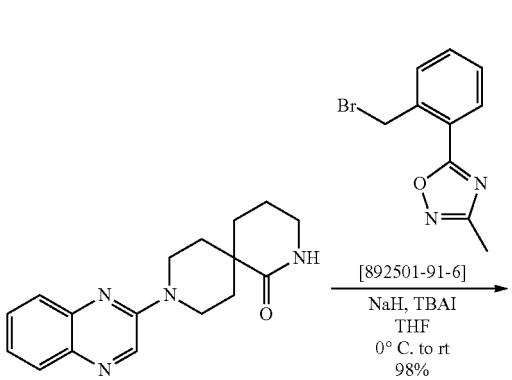

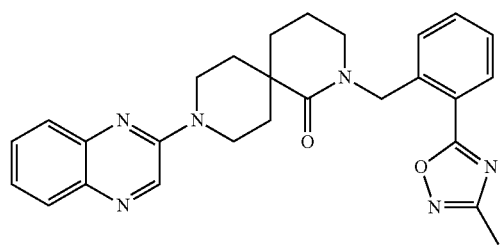

a) 9-(quinoxalin-2-yl)-2,9-diazaspiro[5.5]undecan-1-one

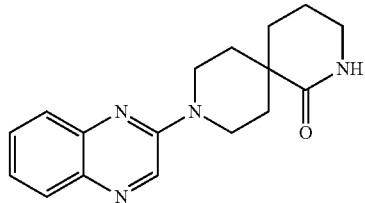 [SMILES: O=C1NCCCC12CCN(c1cnc3ccccc3n1)CC2]

The mixture of 2,9-diazaspiro[5.5]undecan-1-one TFA salt ([1190586-22-1], 1.0 g, 3.5 mmol), 2-chloroquinoxaline ([1448-87-9], 0.77 g, 4.6 mmol), DIPEA (3.7 ml, 21 mmol) and DMAP (22 mg, 0.18 mmol) in ethanol (10 ml) was placed in a microwave tube. The tube was sealed and the suspension was heated at 160° C. for 2 h under microwave conditions. The mixture was filtered and the residue washed with ethanol. The filtrate was concentrated and the precipitate filtered and washed with ethanol. The combined solid material was dissolved in ethyl acetate, washed with water and dried over anhydrous sodium sulfate, filtered and concentrated under reduced pressure to afford 0.81 g (77%) of the title compound as a pale yellow solid which was not further purified. [1H NMR (400 MHz, DMSO-d₆) ♀ ppm 8.79 (s, 1H), 7.78 (d, J=7.8 Hz, 1H), 7.53-7.58 (m, 2H), 7.31-7.39 (m, 2H), 4.22 (dt, J=13.5, 4.4 Hz, 2H), 3.37-3.49 (m, 2H), 3.06-3.15 (m, 2H), 1.91-2.05 (m, 2H), 1.75-1.83 (m, 2H), 1.65-1.75 (m, 2H), 1.44-1.55 (m, 2H); LCMS Rt$_B$=2.80 min, [M+H]⁺=297.2].

b) 2-(2-(3-methyl-1,2,4-oxadiazol-5-yl)benzyl)-9-(quinoxalin-2-yl)-2,9-diazaspiro[5.5]undecan-1-one

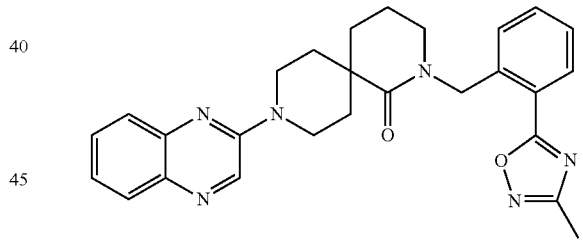

To a suspension of 9-(quinoxalin-2-yl)-2,9-diazaspiro[5.5]undecan-1-one (41 mg, 0.14 mmol) and TBAI (2.6 mg, 6.9 µmol) in THF (0.6 ml) was added sodium hydride (7.0 mg, 95%, 2.8 mmol) at 0° C. The yellow suspension was stirred for 20 min at 0° C. under argon. A solution of 5-(2-(bromomethyl)phenyl)-3-methyl-1,2,4-oxadiazole in dry THF (0.4 ml) was added and stirring was continued for 2 h at rt. To the reaction mixture was added water and ethyl acetate. The aqueous phase was extracted with ethyl acetate. The organic phases were washed with water and brine, combined and dried over sodium sulfate, filtered and evaporated to give 64 mg (98%) of a pale brown oil. [1H NMR (600 MHz, DMSO-d₆) ♀ ppm 8.84 (s, 1H), 8.05 (d, J=7.9 Hz, 1H), 7.81 (d, J=8.3 Hz, 1H), 7.68 (t, J=7.7 Hz, 1H), 7.55-7.62 (m, 2H), 7.51 (t, J=7.8 Hz, 2H), 7.34-7.41 (m, 1H), 7.27 (d, J=7.7 Hz, 1H), 4.91 (s, 2H), 4.23-4.34 (m, 2H), 3.46 (t, J=11.1 Hz, 2H), 3.26-3.32 (m, 2H), 2.44 (s, 3H), 2.04-2.12 (m, 2H), 1.93-2.01 (m, 2H), 1.83-1.92 (m, 2H), 1.66 (d, J=13.5 Hz, 2H); LCMS Rt$_D$=2.63 min, [M+H]⁺=469.2].

Method E

Example 40

2-((1H-indol-3-1/1)methyl)-9-(benzo[d]oxazol-2-yl)-2,9-diazaspiro[5.5]undecan-1-one

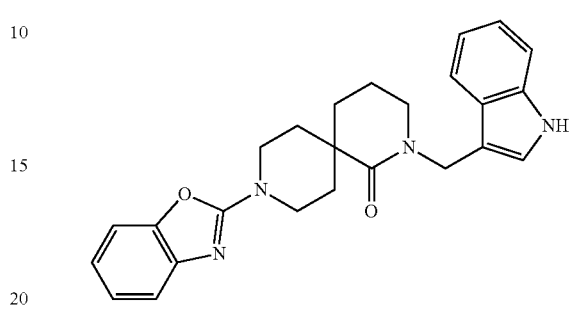

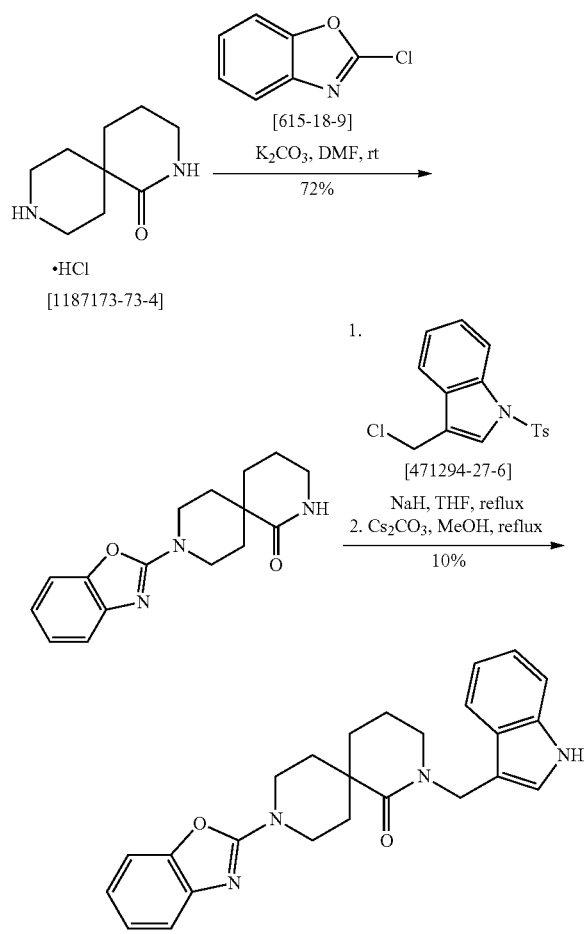

a) 9-(benzo[d]oxazol-2-yl)-2,9-diazaspiro[5.5]undecan-1-one

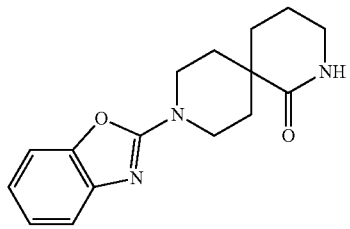 [SMILES: O=C1NCCCC12CCN(c1nc3ccccc3o1)CC2]

To the stirred solution of 2,9-diazaspiro[5.5]undecan-1-one hydrochloride [1187173-73-4] (100 mg, 0.49 mmol) in DMF (3 mL) was added K$_2$CO$_3$ (203 mg, 1.47 mmol) and 2-chloro benzoxazole [615-18-9] (82.8 mg, 0.54 mmol). The mixture was heated at 60° C. for 18 h. The reaction mixture was cooled to rt and concentrated under reduced pressure. To the crude mixture water was added and extracted with ethyl acetate. The organic layer was dried over anhydrous sodium sulfate, filtered and concentrated to obtain a yellow solid which was washed with diethyl ether and n-pentane to yield the title compound as solid (100 mg, 72%). [LCMS Rt$_F$=0.36 min, [M+H]$^+$=286.1]

b) 2-((1H-indol-3-yl)methyl)-9-(benzo[d]oxazol-2-yl)-2,9-diazaspiro[5.5]undecan-1-one NaH (28 mg, 1.16 mmol) was added to a stirred solution of 9-(benzo[d]oxazol-2-yl)-2,9-diazaspiro[5.5]undecan-1-one (150 mg, 0.53 mmol) in THF (5 mL) and the resulting mixture was heated under reflux for 30 min. The reaction mixture was allowed to warm to rt. Then, 3-(chloromethyl)-1-tosyl-1H-indole [471294-27-6] (201 mg, 0.63 mmol) was added and the mixture was heated at 60° C. for 18 h. The mixture was cooled to rt and saturated aqueous NH$_4$Cl solution was added and the solution was extracted with ethyl acetate. The organic layer was washed with water and brine, filtered and dried over anhydrous sodium sulfate. The organic layer was concentrated under reduced pressure to yield a pale brown solid. This product was directly taken for the next step for detosylation to furnish the title compound as follows:

To the stirred solution of the obtained solid in methanol/THF (v/v 2:1, 3 mL) Cs$_2$CO$_3$ (855 mg, 2.63 mmol) was added and the mixture was stirred at reflux for 20 h. The solvent was removed under reduced pressure at 45° C. and the crude reaction mixture was taken up in ethyl acetate. The ethyl acetate layer was washed with water and brine, and dried over anhydrous sodium sulfate. The organic layer was filtered and concentrated under reduced pressure to obtain a pale yellow solid. The crude product was purified by preparative HPLC under neutral conditions to yield the title compound as a pale yellow solid (22 mg, 10%). [$^1$H-NMR (CDCl$_3$, 300 MHz): δ 8.14 (br s, 1H), 7.70 (d, 1H), 7.38 (t, 2H), 7.28-7.15 (m, 5H), 7.06-6.98 (m, 1H), 4.78 (s, 2H), 4.20-4.08 (m, 2H), 3.68-3.55 (m, 2H), 3.28 (t, 2H), 2.38-2.25 (m, 2H), 1.83-1.72 (m, 4H), 1.71-1.52 (m, 2H); LCMS Rt$_F$=0.41 min, [M+H]$^+$=415.0].

Method F

Example 41

1-(2,5-dimethylbenzyl)-9-(quinoxalin-2-yl)-1,9-diazaspiro[5.5]undecan-2-one

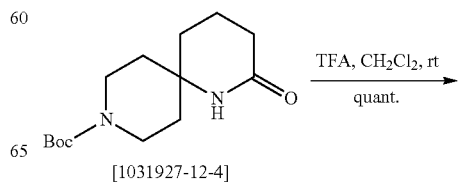

a) 1,9-diazaspiro[5.5]undecan-2-one (TFA Salt)

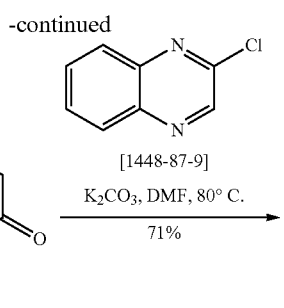

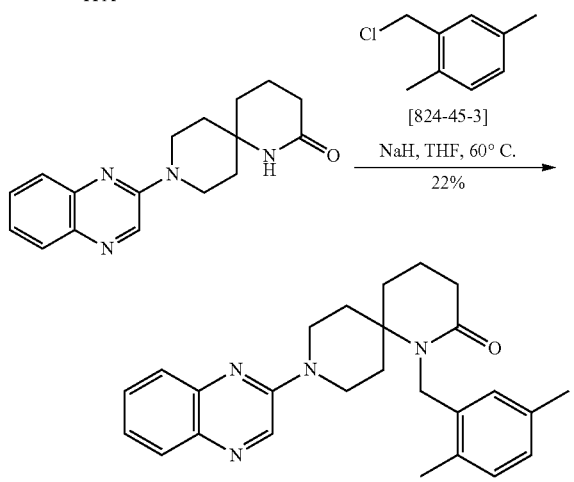

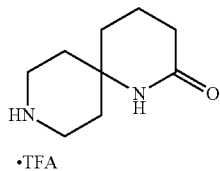

To a solution of tert-butyl 2-oxo-1,9-diazaspiro[5.5]undecane-9-carboxylate [1031927-12-4] (920 mg, 3.26 mmol) in dichloromethane (10 mL) was added TFA (2.53 mL, 32.6 mmol). The solution was stirred for 40 min at rt. After completion of the reaction the mixture was evaporated under reduced pressure and dried under high vacuum (1.90 g, 100%). [$^1$H NMR (400 MHz, DMSO-d$_6$) ♀ ppm 8.59-8.35 (m, 2H), 7.83 (s, 1H), 3.27-3.14 (m, 2H), 3.12-2.98 (m, 2H), 2.17-2.04 (m, 2H), 1.80-1.57 (m, 8H); LCMS Rt$_A$=0.20 min, [M+H]$^+$=169.2].

b) 9-(quinoxalin-2-yl)-1,9-diazaspiro[5.5]undecan-2-one

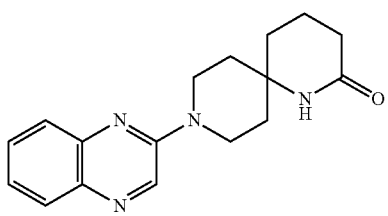 [SMILES: O=C1CCCC2(CCN(c3cnc4ccccc4n3)CC2)N1]

To a stirred solution of 1,9-diazaspiro[5.5]undecan-2-one (TFA salt) (800 mg, 4.76 mmol) in 10 mL DMF, 2-chloroquinoxaline (937 mg, 5.71 mmol) and K$_2$CO$_3$ (3.3 g, 23.8 mmol) were added and the reaction mixture was stirred for 18 h at 80° C. under a nitrogen atmosphere. The reaction mixture was quenched with ice-cold water and extracted with ethyl acetate (2×50 mL), dried over anhydrous Na$_2$SO$_4$, filtered and concentrated under reduced pressure. The crude mixture was purified by flash column chromatography (eluent: 3% methanol in chloroform) to yield the title compound (1.0 g, 71%). [LCMS Rt$_F$=0.37 min, [M+H]$^+$=297.2]

c) 1-(2,5-dimethylbenzyl)-9-(quinoxalin-2-yl)-1,9-diazaspiro[5.5]undecan-2-one

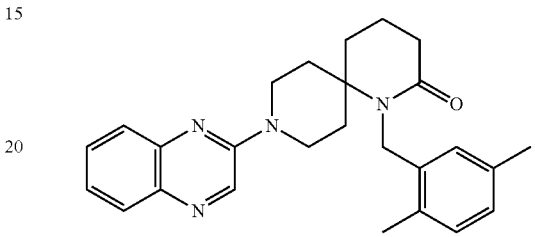

To a solution of 9-(quinoxalin-2-yl)-1,9-diazaspiro[5.5]undecan-2-one (80 mg, 0.27 mmol) in THF (5 mL) sodium hydride 95% (32 mg, 0.81 mmol) was added and the mixture was stirred for 10 min at rt. Then 2,5-dimethylbenzylchloride (70 mg, 0.35 mmol) was added and the reaction mixture was heated at 60° C. over 18 h. Saturated aqueous NH$_4$Cl solution (40 mL) was added and the reaction mixture was extracted with ethyl acetate (100 mL). The organic layer was dried over Na$_2$SO$_4$, filtered and concentrated under reduced pressure. The resulting crude product was purified by reversed phase preparative HPLC (column Zorbax eclipseXDB C18, flow 20 mL/min, mobile phase 0.1% TFA in water (A): acetonitrile (B) gradient) to yield the title compound (49 mg, 22%). [$^1$H NMR (300 MHz, CDCl$_3$) δ 8.55 (s, 1H), 7.88 (d, 1H), 7.70-7.55 (m, 2H), 7.48-7.35 (t, 1H), 7.05-6.85 (m, 2H), 6.72 (s, 1H), 4.55 (s, 2H), 4.55-4.39 (m, 2H), 3.12 (t, 2H), 2.65 (t, 2H), 2.30 (s, 3H), 2.15 (s, 3H), 2.20-1.88 (m, 6H), 1.85-1.63 (m, 2H); LCMS Rt$_E$=1.64 min, [M+H]$^+$=415.2].

Method G

Example 42

1-((1H-indol-4-yl)methyl)-9-(benzo[d]oxazol-2-yl)-1,9-diazaspiro[5.5]undecan-2-one

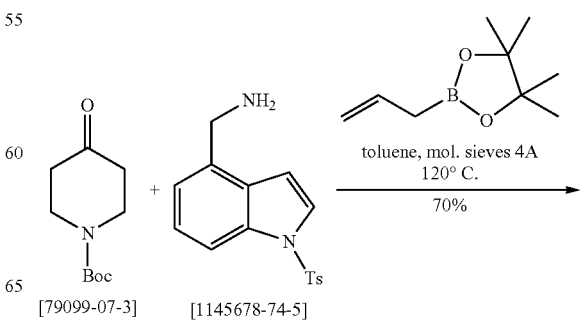

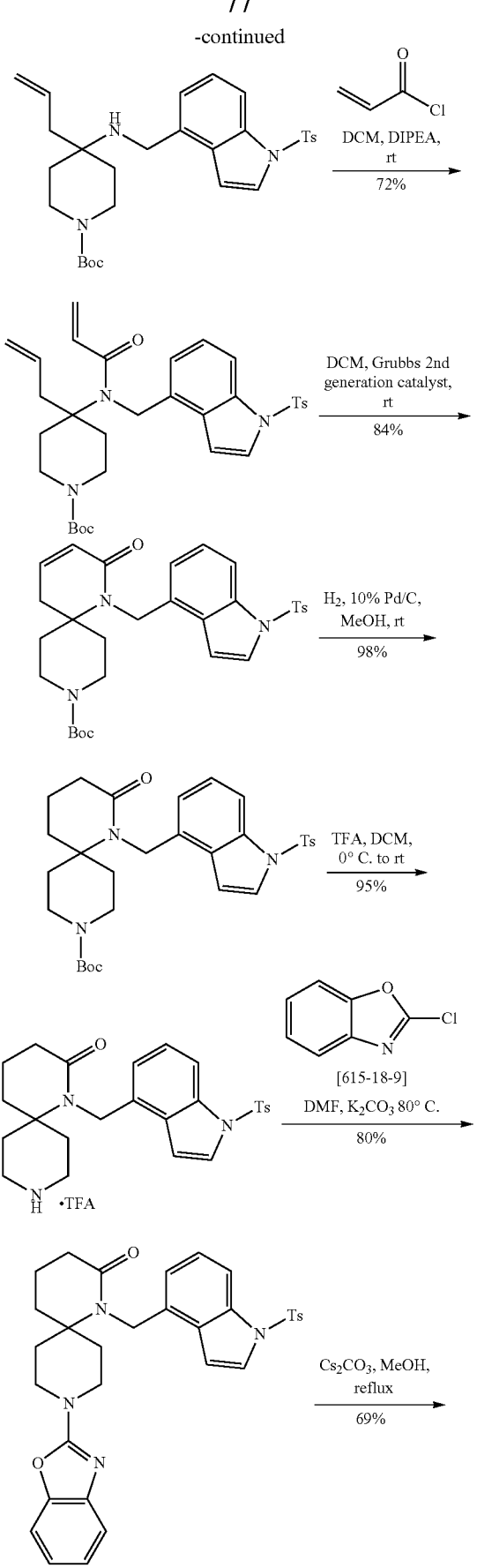

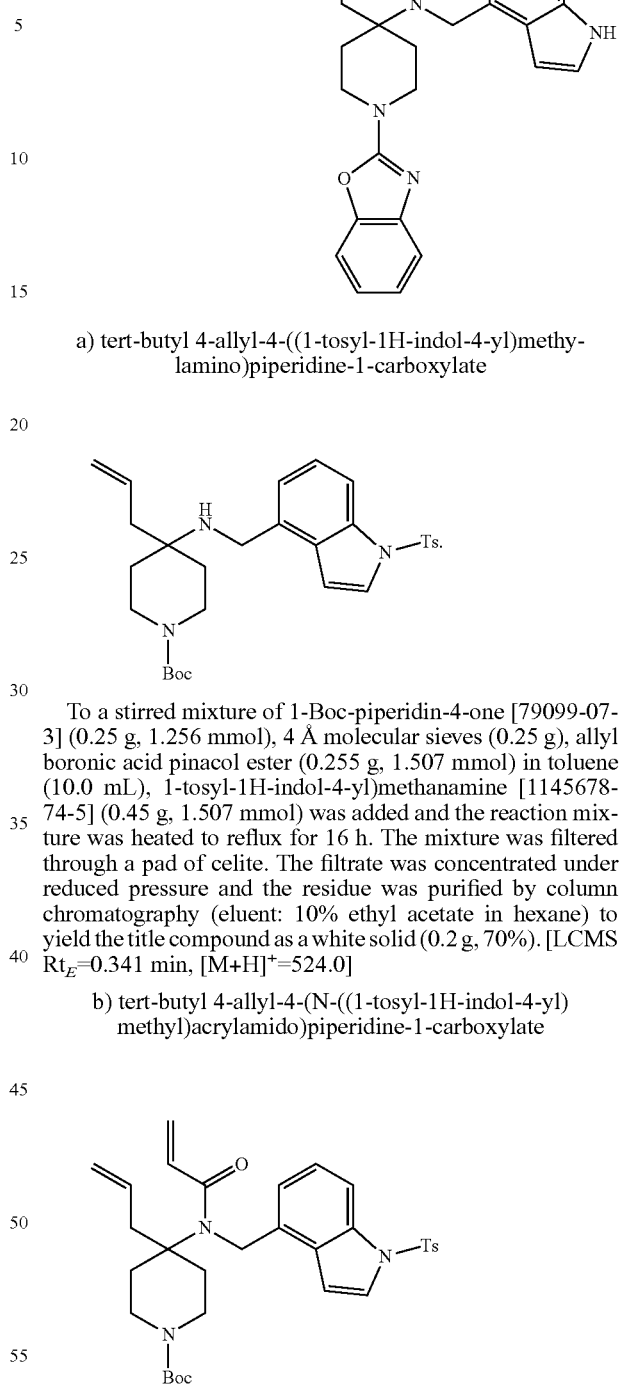

a) tert-butyl 4-allyl-4-((1-tosyl-1H-indol-4-yl)methylamino)piperidine-1-carboxylate

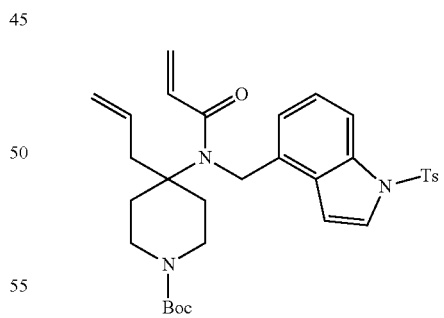

To a stirred mixture of 1-Boc-piperidin-4-one [79099-07-3] (0.25 g, 1.256 mmol), 4 Å molecular sieves (0.25 g), allyl boronic acid pinacol ester (0.255 g, 1.507 mmol) in toluene (10.0 mL), 1-tosyl-1H-indol-4-yl)methanamine [1145678-74-5] (0.45 g, 1.507 mmol) was added and the reaction mixture was heated to reflux for 16 h. The mixture was filtered through a pad of celite. The filtrate was concentrated under reduced pressure and the residue was purified by column chromatography (eluent: 10% ethyl acetate in hexane) to yield the title compound as a white solid (0.2 g, 70%). [LCMS $Rt_E$=0.341 min, $[M+H]^+$=524.0]

b) tert-butyl 4-allyl-4-(N-((1-tosyl-1H-indol-4-yl)methyl)acrylamido)piperidine-1-carboxylate Acryloyl chloride (0.360 g, 0.401 mmol) was added at 0° C. to a stirred solution of tert-butyl 4-allyl-4-((1-tosyl-1H-indol-4-yl)methylamino)piperidine-1-carboxylate (0.2 g, 0.382 mmol), diisopropylethylamine (0.32 mL, 1.91 mmol) in dichloromethane (5.0 mL). The reaction mixture was stirred at 0° C. for 30 min and was then allowed to warm to it and stirred for 4 h. The reaction mixture was concentrated under reduced pressure and the crude product was purified by column chromatography (eluent: 5% ethyl acetate in hexane) to yield the title compound as a white solid (0.16 g, 72%). [LCMS $Rt_E$=0.774 min, $[M+H-Boc]^+$=477.9]

c) tert-butyl 2-oxo-1-((1-tosyl-1H-indol-4-yl)methyl)-1,9-diazaspiro[5.5]undec-3-ene-9-carboxylate

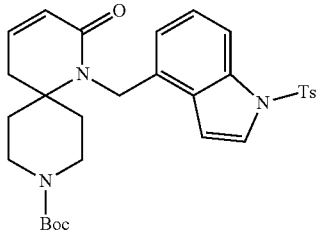 [SMILES: Cc1ccc(S(=O)(=O)n2ccc3c(CN4C(=O)C=CCC45CCN(C(=O)OC(C)(C)C)CC5)cccc32)cc1]

To a solution of tert-butyl 4-allyl-4-(N-((1-tosyl-1H-indol-4-yl)methyl)acrylamido)piperidine-1-carboxylate (0.075 g, 0.13 mmol) in dichloromethane (5.0 mL) was added Grubbs $2^{nd}$ generation catalyst (0.006 g, 0.006 mmol) under argon and the reaction mixture was stirred at it overnight. The dark brown solution was concentrated under reduced pressure and the crude product was purified by column chromatography (eluent: 25% ethyl acetate in hexane) to yield the title compound as a solid (0.060 g, 84%). [LCMS $Rt_E$=0.523 min, [M+H]$^+$=549.8]

d) tert-butyl 2-oxo-1-((1-tosyl-1H-indol-4-yl)methyl)-1,9-diazaspiro[5.5]undecane-9-carboxylate

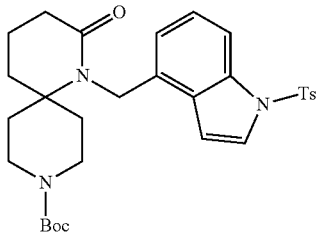 [SMILES: Cc1ccc(S(=O)(=O)n2ccc3c(CN4C(=O)CCCC45CCN(C(=O)OC(C)(C)C)CC5)cccc32)cc1]

To a solution of tert-butyl 2-oxo-1-((1-tosyl-1H-indol-4-yl)methyl)-1,9-diazaspiro[5.5]undec-3-ene-9-carboxylate (0.12 g, 0.218 mmol) in methanol (6.0 mL) was added 10% Pd/C and the reaction mixture was stirred for 6 h under hydrogen (1 atm. pressure) at rt. The reaction mixture was filtered through a pad of celite and washed with methanol. The filtrate was concentrated and the product was isolated as a white solid (0.120 g, 99%). [LCMS $Rt_E$=0.511 min, [M+H]$^+$=551.9]

e) 1-((1-tosyl-1H-indol-4-yl)methyl)-1,9-diazaspiro[5.5]undecan-2-one (TFA Salt)

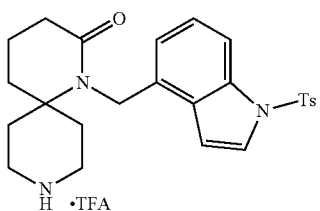 [SMILES: Cc1ccc(S(=O)(=O)n2ccc3c(CN4C(=O)CCCC45CCNCC5)cccc32)cc1]

To a stirred solution of tert-butyl 2-oxo-1-((1-tosyl-1H-indol-4-yl)methyl)-1,9-diazaspiro[5.5]undecane-9-carboxylate (0.12 g, 0.21 mmol) in dichloromethane (5.0 mL), TFA (0.5 mL) was added at 0° C. and the reaction mixture was stirred for 16 h at rt under a nitrogen atmosphere. The reaction mixture was concentrated to yield the title compound as colourless oil (0.11 g, 95%) which was used in the next step.

f) 9-(benzo[d]oxazol-2-yl)-1-((1-tosyl-1H-indol-4-yl)methyl)-1,9-diazaspiro[5.5]undecan-2-one

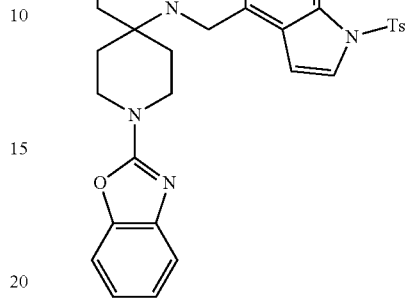

To the stirred solution of 1-((1-tosyl-1H-indol-4-yl)methyl)-1,9-diazaspiro[5.5]undecan-2-one (TFA salt) (300 mg, 0.55 mmol) in DMF (6 mL) were added $K_2CO_3$ (380 mg, 2.75 mmol) and 2-chloro benzoxazole (101 mg, 0.66 mmol). The mixture was heated at 80° C. for 18 h. The reaction mixture was cooled to rt and concentrated under reduced pressure. To the crude mixture water was added and extracted with ethyl acetate. The organic layer was dried over anhydride sodium sulfate, filtered and concentrated to obtain a solid which was purified by flash column chromatography (eluent: 3% methanol in chloroform) to yield the title compound (250 mg, 80%). [LCMS $Rt_E$=1.75 min, [M+H]$^+$=569.1].

q) 1-((1H-indol-4-yl)methyl)-9-(benzo[d]oxazol-2-yl)-1,9-diazaspiro[5.5]undecan-2-one

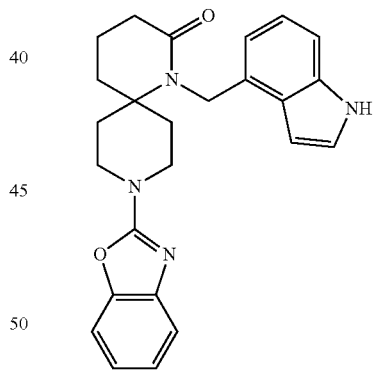

$Cs_2CO_3$ (430 mg, 1.32 mmol) was added to a stirred solution of 9-(benzo[d]oxazol-2-yl)-1-((1-tosyl-1H-indol-4-yl)methyl)-1,9-diazaspiro[5.5]undecan-2-one (250 mg, 0.44 mmol) in methanol (10 mL) and stirring was continued for 18 h at 78° C. The reaction mixture was concentrated, water was added to the residue and extracted with ethyl acetate (2×50 mL), dried over anhydrous $Na_2SO_4$, filtered and concentrated. The crude product was purified by reversed phase HPLC (column Zorbax eclipseXDB C18 21.2×150 mm 5 μm, flow 20 mL/min, eluent: gradient water/acetonitrile) to yield the title compound (126 mg, 69%). [$^1$H NMR (400 MHz, CDCl$_3$) δ ppm 8.30 (br s, 1H), 7.36-6.96 (m, 7H), 6.78 (d, 1H), 6.46 (m, 1H), 4.95 (s, 2H), 4.16 (dd, 2H), 3.18 (t, 2H), 2.65 (t, 2H), 2.20-2.05 (m, 4H), 1.95-1.88 (m, 2H), 1.75-1.61 (m, 2H); LCMS $Rt_E$=1.32 min, [M+H]$^+$=415.1].

Method H

Example 43

1-((1H-indol-3-yl)methyl)-9-(quinoxalin-2-yl)-1,9-diazaspiro[5.5]undecan-2-one

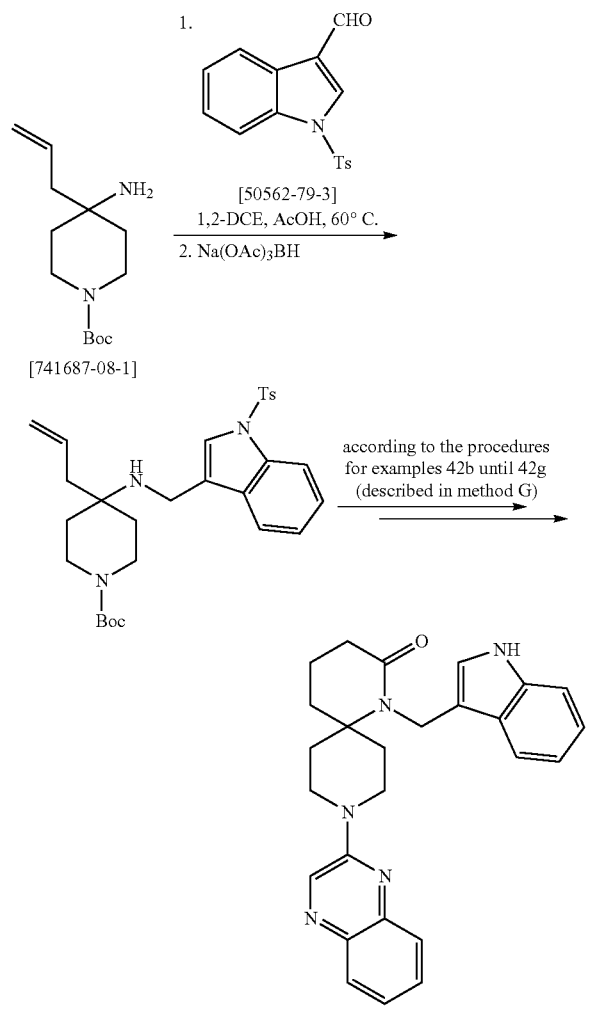

a) tert-butyl 4-allyl-4-((1-tosyl-1H-indol-3-yl)methylamino)piperidine-1-carboxylate

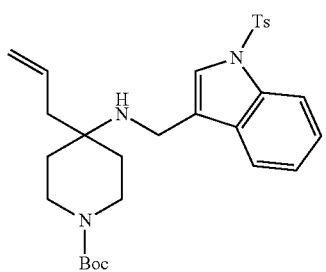 [SMILES: C=CCC1(NCc2cn(S(=O)(=O)c3ccc(C)cc3)c3ccccc23)CCN(C(=O)OC(C)(C)C)CC1]

To a solution of 1-tosyl-1H-indole-3-carbaldehyde [50562-79-3] (1.90 g, 6.35 mmol) in 1,2-dichloroethane (30 mL) were added tert-butyl 4-allyl-4-aminopiperidine-1-carboxylate [741687-08-1] (1.52 g, 6.35 mmol) and acetic acid (381 mg, 6.35 mmol). The resulting solution was heated at 60° C. for 3 h. Then NaBH(OAc)$_3$ was added and the reaction mixture was heated at 60° C. for 38 h. The mixture was cooled to rt, saturated NaHCO$_3$ solution (30 mL) was added and extracted with ethyl acetate (3×50 mL). The combined organic layers were washed with water and brine, then dried over anhydrous Na$_2$SO$_4$, filtered and concentrated under reduced pressure. The crude mixture was purified by flash-column chromatography over silicagel (eluent: 20% ethyl acetate/hexane) to yield the title compound (2.0 g, 60%). [LCMS Rt$_E$=0.34 min, [M+H]$^+$=524.0]

b) 1-((1H-indol-3-yl)methyl)-9-(quinoxalin-2-yl)-1,9-diazaspiro[5.5]undecan-2-one

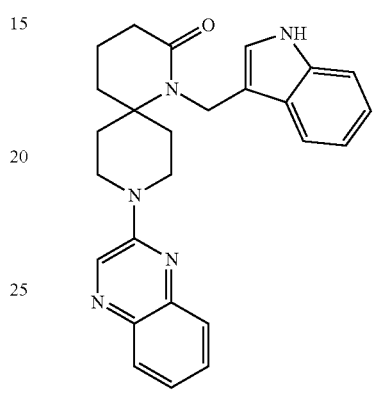

The title compound was synthesized from tert-butyl 4-allyl-4-((1-tosyl-1H-indol-3-yl)methylamino)piperidine-1-carboxylate (example 5a) according to the procedures for examples 4b to 4g (described in method D).

[$^1$H NMR (400 MHz, CDCl$_3$) ♀ ppm 8.55 (s, 1H), 7.98 (br s, 1H), 7.90 (d, 1H), 7.70 (d, 1H), 7.62 (t, 1H), 7.50-7.40 (m, 2H), 7.33 (d, 1H), 7.15 (t, 1H), 7.10 (s, 1H), 7.00 (t, 1H), 4.78 (s, 2H), 4.43 (dd, 2H), 3.15 (t, 2H), 2.60 (t, 2H), 2.40-2.20 (m, 2H), 2.15-2.05 (m, 2H), 1.95-1.80 (m, 2H), 1.75-1.61 (m, 2H); LCMS Rt$_F$=1.44 min, [M+H]$^+$=426.0].

Method I

Example 44

1-((1-methyl-1H-indol-4-yl)methyl)-9-(quinoxalin-2-yl)-1,9-diazaspiro[5.5]undecan-2-one

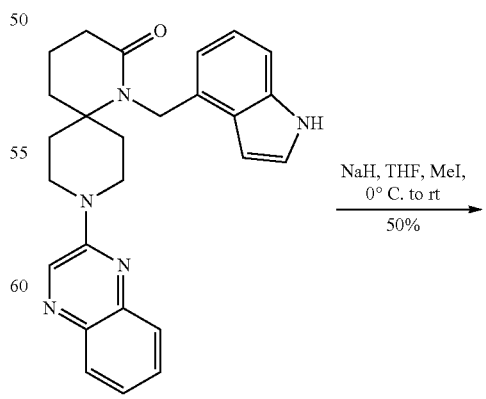

synthesized according to synthesis method G

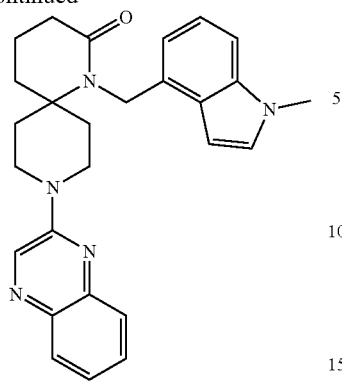

The title compound was synthesized from 1-((1H-indol-4-yl)methyl)-9-(quinoxalin-2-yl)-1,9-diazaspiro[5.5]undecan-2-one (prepared according to method G) via methylation as follows: NaH (7 mg, 0.18 mmol, 60% in mineral oil) was added to an ice-cold solution of 1-((1H-indol-4-yl)methyl)-9-(quinoxalin-2-yl)-1,9-diazaspiro[5.5]undecan-2-one (synthesized according to method G) (25 mg, 0.06 mmol) in THF (5 mL). The resulting mixture was stirred at rt for 10 min. The mixture was cooled to 0° C., methyl iodide (26 mg, 0.18 mmol) was added at 0° C. and stirring was continued at 0° C. for 1 h. Then the mixture was allowed to warm to rt over a period of 1 h. The mixture was poured into water and the solution was extracted twice with ethyl acetate. The combined organic layers were washed with water and brine, filtered and dried over anhydrous sodium sulfate. The organic layer was concentrated under reduced pressure. The product was purified by preparative reversed phase HPLC (column Zorbax eclipseXDB C18 21.2×150 mm 5 μm, flow 20 mL/min, eluent: gradient water/acetonitrile) to yield the title compound (13 mg, 50%). [$^1$H NMR (300 MHz, CDCl$_3$) δ ppm 8.49 (s, 1H), 7.88 (d, 1H), 7.68-7.50 (m, 2H), 7.45-7.35 (m, 1H), 7.21-7.08 (m, 2H), 6.95 (d, 1H), 6.73 (d, 1H), 6.35 (d, 1H), 4.98 (s, 2H), 4.40 (d, 2H), 3.78 (s, 3H), 3.15 (t, 2H), 2.68 (t, 2H), 2.25-2.05 (m, 4H), 2.00-1.85 (m, 2H), 1.80-1.70 (m, 2H); LCMS Rt$_F$=1.50 min, [M+H]$^+$=440.0].

Method K

Example 45

2-((2-methoxypyridin-4-yl)methyl)-9-(quinoxalin-2-yl)-2,9-diazaspiro[5.5]undecan-1-one

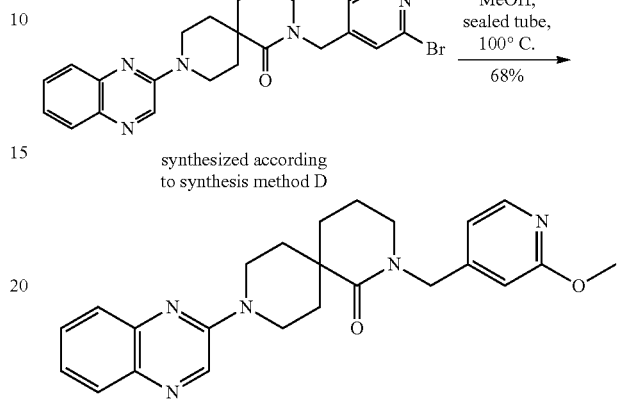

synthesized according to synthesis method D

The title compound was synthesized from 2-((2-bromopyridin-4-yl)methyl)-9-(quinoxalin-2-yl)-2,9-diazaspiro[5.5]undecan-1-one (prepared according to method D) as follows: A stirred solution of 2-((2-bromopyridin-4-yl)methyl)-9-(quinoxalin-2-yl)-2,9-diazaspiro[5.5]undecan-1-one (synthesized according to method D) (70 mg, 0.15 mmol) and NaOMe (40.6 mg, 0.75 mmol) in MeOH (2 mL) was heated at 100° C. for 18 h. The reaction mixture was cooled to rt and the solvent was evaporated under reduced pressure. Water was added and the mixture was extracted with ethyl acetate. The combined organic layer was dried over anhydrous sodium sulfate, filtered and concentrated under reduced pressure. The crude product was washed with hexane to yield the title compound (55 mg, 68%). [$^1$H NMR (300 MHz, CDCl$_3$) δ ppm 8.60 (s, 1H), 8.12 (d, 1H), 7.85 (d, 1H), 7.68 (d, 1H), 7.56 (t, 1H), 7.38 (t, 1H), 6.75 (d, 1H), 6.55 (s, 1H), 4.56 (s, 2H), 4.31-4.13 (m, 2H), 3.92 (s, 3H), 3.70-3.55 (m, 2H), 3.25 (br s, 2H), 2.40-2.25 (m, 2H), 1.98-1.80 (m, 4H), 1.78-1.50 (m, 2H); LCMS Rt$_F$=1.30 min, [M+H]$^+$=418.0].

Method L

Example 46

2-(3-(1H-1,2,3-triazol-1-yl)benzyl)-9-(quinoxalin-2-yl)-2,9-diazaspiro[5.5]undecan-1-one Example 47

2-(3-(2H-1,2,3-triazol-2-yl)benzyl)-9-(quinoxalin-2-yl)-2,9-diazaspiro[5.5]undecan-1-one

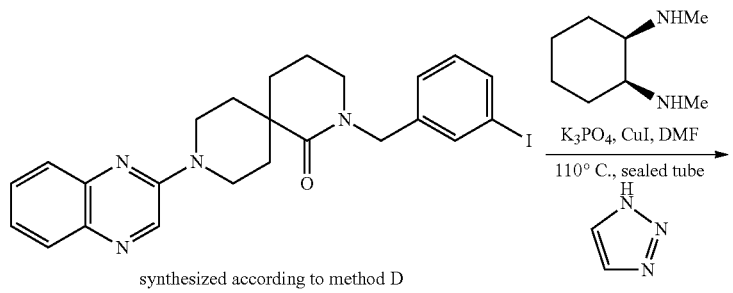

synthesized according to method D

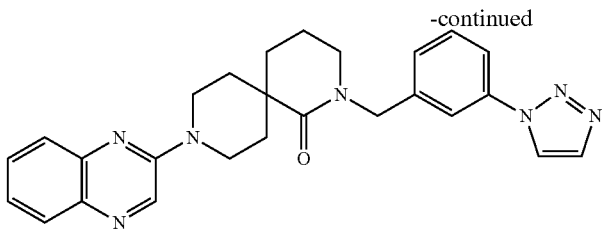

example 46

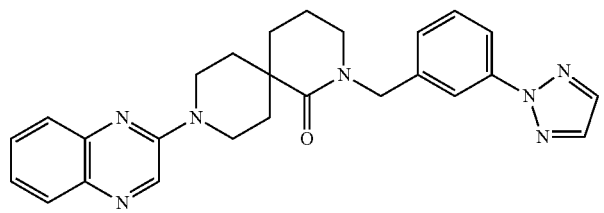

example 47 a) 2-(3-iodobenzyl)-9-(quinoxalin-2-yl)-2,9-diaza-spiro[5.5]undecan-1-one

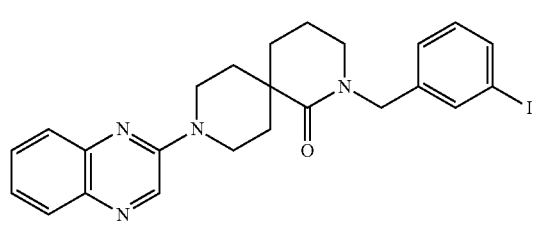 [SMILES: O=C1N(Cc2cccc(I)c2)CCCC12CCN(c1cnc3ccccc3n1)CC2]

The title compound was synthesized in analogy to method A from 2,9-diazaspiro[5.5]undecan-1-one (TFA salt) [1190586-22-1], 3-iodobenzyl bromide [49617-83-6] and 2-chloroquinoxaline [1448-87-9]. [LCMS Rt$_F$=1.99 min, [M+H]$^+$=513.0].

b) 2-(3-(1H-1,2,3-triazol-1-yl)benzyl)-9-(quinoxalin-2-yl)-2,9-diazaspiro[5.5]undecan-1-one and 2-(3-(2H-1,2,3-triazol-2-yl)benzyl)-9-(quinoxalin-2-yl)-2,9-diazaspiro[5.5]undecan-1-one example 46

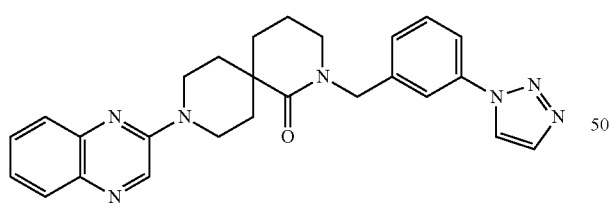

example 47

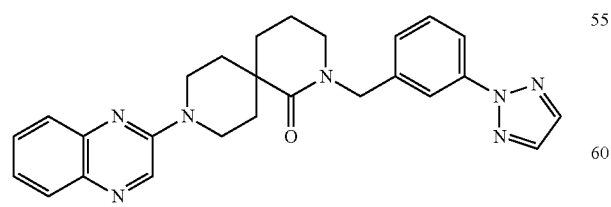

To a mixture of 2-(3-iodobenzyl)-9-(quinoxalin-2-yl)-2,9-diazaspiro[5.5]undecan-1-one (104 mg, 0.20 mmol), 1H-1,2,3-triazole (28 mg, 0.40 mmol), trans-N,N'-dimethylcyclohexane-1,2-diamine [68737-65-5] (6 mg, 0.04 mmol) and K$_3$PO$_4$ (127 mg, 0.60 mmol) in DMF (2 mL), CuI (15 mg, 0.08 mmol) was added and the reaction mixture was stirred at 110° C. for 24 h. The reaction mixture was cooled to it and filtered to remove the solids. The filtrate was concentrated under reduced pressure. The residue was purified by reversed phase preparative HPLC (column AG/PP/C-18-15/025, flow 20 mL/min, mobile phase water (A): acetonitrile (B) gradient) to yield the regioisomeric title compounds (example 8: 28 mg, 31% and example 9: 54 mg, 60%).

Example 46

[$^1$H NMR (400 MHz, CDCl$_3$) ♀ ppm 8.62 (s, 1H), 8.01 (s, 1H), 7.90-7.88 (m, 2H), 7.70-7.64 (m, 3H), 7.60-7.49 (m, 2H), 7.42-7.33 (m, 2H), 4.68 (s, 2H), 4.28-4.23 (m, 2H), 3.67-3.60 (m, 2H), 3.35-3.33 (m, 2H), 2.40-2.32 (m, 2H), 1.93-1.90 (m, 4H), 1.73-1.57 (m, 2H); LCMS Rt$_F$=1.65 min, [M+H]$^+$=454.1].

Example 47

[$^1$H NMR (400 MHz, CDCl$_3$) ♀ ppm 8.62 (s, 1H), 8.01 (d, 1H), 7.97 (s, 1H), 7.88 (d, 1H), 7.83 (s, 2H), 7.68 (d, 1H), 7.57 (t, 1H), 7.47 (t, 1H), 7.39 (t, 1H), 7.27-7.24 (m, 1H), 4.69 (s, 2H), 4.29-4.23 (m, 2H), 3.70-3.63 (m, 2H), 3.35-3.32 (m, 2H), 2.42-2.35 (m, 2H), 1.92-1.88 (m, 4H), 1.74-1.59 (m, 2H); LCMS Rt$_F$=1.90 min, [M+H]$^+$=454.1].

Method M

Example 48

2-((1H-indol-3-yl)methyl)-9-(quinolin-3-yl)-2,9-diazaspiro[5.5]undecan-1-one

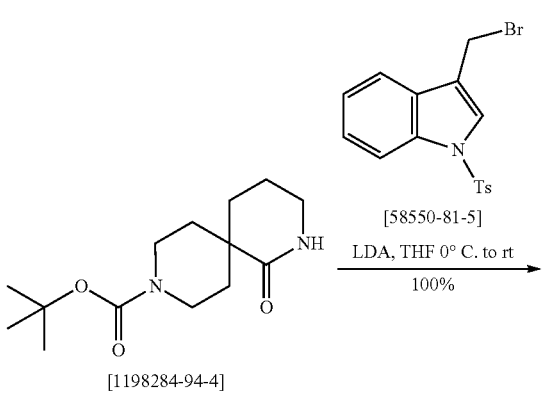

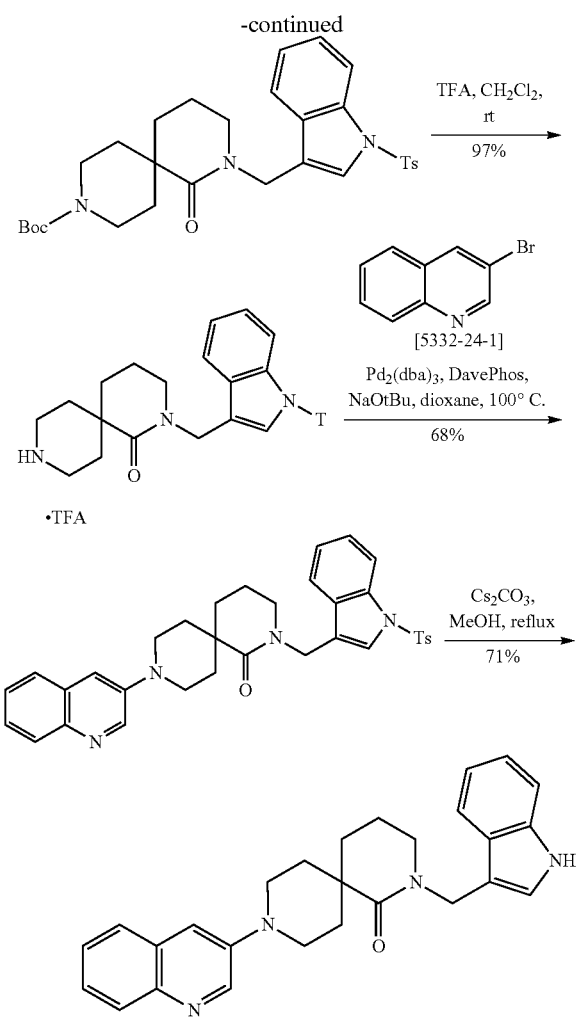

a) tert-butyl 1-oxo-2-((1-tosyl-1H-indol-3-yl)methyl)-2,9-diazaspiro[5.5]undecane-9-carboxylate To a solution of diisopropylamine (1.238 mL, 8.60 mmol) in THF (40 mL) n-butyllithium (6.01 mL, 9.61 mmol) was added at 0° C. and the mixture was stirred for 30 min at 0° C. Then a solution of tert-butyl 1-oxo-2,9-diazaspiro[5.5]undecane-9-carboxylate [1198284-94-4] (2.57 g, 9.28 mmol) in THF (10 mL) was added within 3 min and the mixture was stirred for 30 min at 0° C. 3-(bromomethyl)-1-tosyl-1H-indole [58550-81-5] (3.2 g, 8.43 mmol) in THF (10 mL) was dropped to the reaction mixture within 15 min. The mixture was stirred at 0° C. for 1 h and allowed to warm to room temperature overnight. The reaction mixture was quenched with ice-cold water and extracted with TBME (2×150 mL). The combined organic layers were washed with 5% aqueous citric acid and brine, dried over anhydrous Na$_2$SO$_4$, filtered and concentrated (5.3 g, 100%). [$^1$H NMR (400 MHz, DMSO-d$_8$) ♀ ppm 7.88 (d, J=8.28 Hz, 1H), 7.81 (d, J=8.28 Hz, 2H), 7.74 (s, 1H), 7.55 (d, J=7.78 Hz, 1H), 7.36 (d, J=8.03 Hz, 2H), 7.32 (t, J=7.91 Hz, 1H), 7.25-7.21 (m, 1H), 4.58 (s, 2H), 3.75-3.63 (m, 2H), 3.09 (t, J=5.77 Hz, 2H), 2.99 (br. s., 2H), 2.30 (s, 3H), 1.90-1.80 (m, 2H), 1.72-1.57 (m, 4H), 1.39 (s, 9H), 1.36-1.28 (m, 2H); LCMS Rt$_A$=1.37 min, [M+H]$^+$=552.3].

b) 2-((1-tosyl-1H-indol-3-yl)methyl)-2,9-diazaspiro[5.5]undecan-1-one (TFA Salt)

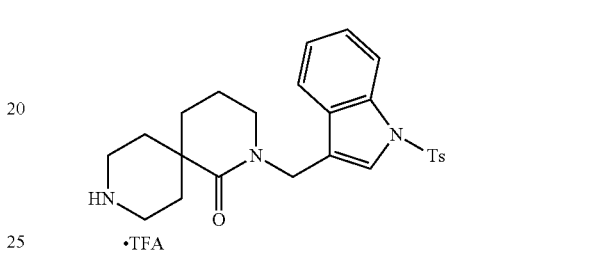

To a solution of tert-butyl 1-oxo-2-((1-tosyl-1H-indol-3-yl)methyl)-2,9-diazaspiro[5.5]undecane-9-carboxylate (5.3 g, 8.45 mmol) in dichloromethane (30 mL) was added TFA (4.93 mL, 63.4 mmol). The solution was stirred for 70 min at rt. After completion of the reaction the mixture was evaporated to dryness. The residue was crystallized in THF/heptane 3:1 to yield the title compound as white crystals (5.5 g, quant.). [$^1$H NMR (400 MHz, DMSO-d$_6$) ♀ ppm 8.43 (br. s, 2H), 7.89 (d, J=8.28 Hz, 1H), 7.82 (d, J=8.28 Hz, 2H), 7.78 (s, 1H), 7.56 (d, J=7.78 Hz, 1H), 7.38-7.31 (m, 3H), 7.24-7.20 (m, 1H), 4.59 (s, 2H), 3.29-3.19 (m, 2H), 3.12 (t, J=5.77 Hz, 2H), 3.07-2.95 (m, 2H), 2.30 (s, 3H), 2.10 (ddd, J=14.24, 10.35, 4.02 Hz, 2H), 1.75-1.59 (m, 4H), 1.58-1.48 (m, 2H); LCMS Rt$_A$=0.88 min, [M+H]$^+$=452.3].

c) 9-(quinolin-3-yl)-2-((1-tosyl-1H-indol-3-yl)methyl)-2,9-diazaspiro[5.5]undecan-1-one

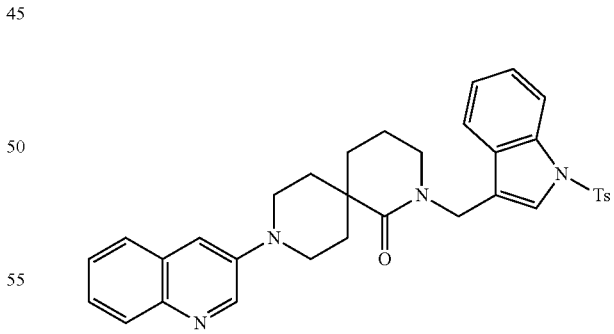

The mixture of 2-((1-tosyl-1H-indol-3-yl)methyl)-2,9-diazaspiro[5.5]undecan-1-one (100 mg, 0.15 mmol, contains 1.7 moleq TFA), 3-bromoquinoline (49 mg, 0.23 mmol), Pd$_2$dba$_3$ (7 mg, 7.7 μmol), sodium t-butanolate (45 mg, 0.46 mmol), 2-(2-dicyclohexylphosphanylphenyl)-N,N-dimethylaniline (DavePhos, 6.1 mg, 0.015 mmol) and dry dioxane (2 mL) was placed in a microwave tube and flushed with argon. The tube was sealed and the suspension was heated at 100° C. for 1 h under microwave conditions. The reaction mixture was diluted with ethyl acetate and washed with water and brine and dried over anhydrous sodium sulfate, filtered and concentrated under reduced pressure. The resulting brown oil was purified by flash chromatography (EtOAc/heptane 3:1) to yield the title compound (63 mg, 68%). [LCMS Rt$_A$=1.31 min, [M+H]$^+$=579.2].

d) 2-((1H-indol-3-yl)methyl)-9-(quinolin-3-yl)-2,9-diazaspiro[5.5]undecan-1-one

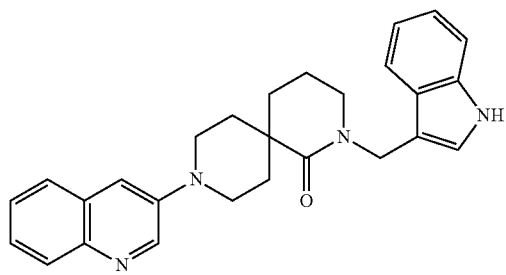 [SMILES: O=C1N(Cc2c[nH]c3ccccc23)CCCC12CCN(c1cnc3ccccc3c1)CC2]

The mixture of 9-(quinolin-3-yl)-2-((1-tosyl-1H-indol-3-yl)methyl)-2,9-diazaspiro[5.5]undecan-1-one (60 mg, 0.1 mmol) and Cs$_2$CO$_3$ (150 mg, 0.46 mmol) in methanol (2 mL) was heated under reflux for 18 h. The reaction mixture was diluted with ethyl acetate and washed with water and brine and dried over anhydrous sodium sulfate, filtered and concentrated under reduced pressure to afford the title compound (31 mg, 71%). [$^1$H NMR (600 MHz, DMSO-d$_6$) ♀ ppm 10.94 (br. s., 1H), 8.86 (d, 1H), 7.86-7.83 (m, 1H), 7.77-7.75 (m, 1H), 7.56-7.52 (m, 2H), 7.48-7.43 (m, 2H), 7.34 (d, 1H), 7.28 (d, 1H), 7.06 (t, 1H), 6.95 (t, 1H), 4.64 (s, 2H), 3.77-3.68 (m, 2H), 3.19-3.13 (m, 2H), 3.06 (t, 2H), 2.30-2.19 (m, 2H), 1.80-1.72 (m, 2H), 1.72-1.63 (m, 2H), 1.60-1.50 (m, 2H); LCMS Rt$_A$=1.05 min, [M+H]$^+$=425.3].

Method N

Example 49

2-(2-(2H-1,2,3-triazol-2-yl)benzyl)-9-(quinoxalin-2-yl)-2,9-diazaspiro[5.5]undecan-1-one

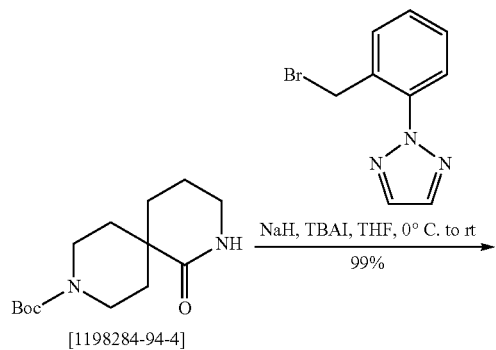

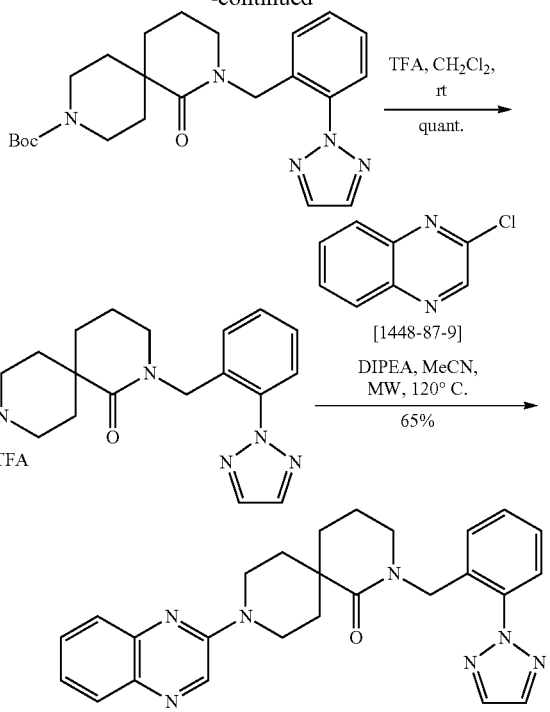

a) tert-butyl 2-(2-(2H-1,2,3-triazol-2-yl)benzyl)-1-oxo-2,9-diazaspiro[5.5]undecane-9-carboxylate

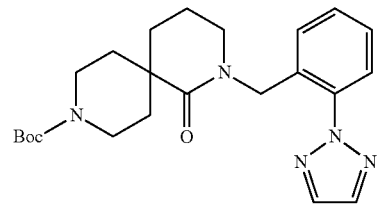 [SMILES: CC(C)(C)OC(=O)N1CCC2(CCCN(Cc3ccccc3-n3nccn3)C2=O)CC1]

NaH (308 mg, 7.69 mmol, 60% in mineral oil) was added to an ice-cold solution of tert-butyl 1-oxo-2,9-diazaspiro[5.5]undecane-9-carboxylate [1198284-94-4] (1.127 g, 4.08 mmol), 2-(2-(bromomethyl)phenyl)-2H-1,2,3-triazole (described separately as building block) (1.0 g, 4.16 mmol) and TBAI (78 mg, 0.208 mmol) in THF (30 mL). The resulting mixture was stirred at 0° C. for 1 h. The reaction mixture was allowed to warm to rt and stirred for 4 h. To the mixture water was added and the solution was extracted twice with ethyl acetate. The organic layer was washed with water and brine, filtered and dried over anhydrous sodium sulfate. The organic layer was concentrated under reduced pressure. The product was purified by flash-column chromatography over silicagel (eluent: gradient 5%-65% ethyl acetate/heptane) to yield the title compound (1.77 g, 99%). [$^1$H NMR (400 MHz, DMSO-d$_6$) ♀ ppm 8.11 (s, 2H), 7.61-7.59 (m, 1H), 7.52-7.46 (m, 2H), 7.23 (d, 1H), 4.53 (s, 2H), 3.69-3.65 (m, 2H), 3.11-3.07 (m, 2H), 3.03 (br s, 2H), 1.86-1.72 (m, 6H), 1.45-1.40 (m, 2H), 1.38 (s, 9H); LCMS Rt$_A$=1.17, [M+H]$^+$=426.4].

b) 2-(2-(2H-1,2,3-triazol-2-yl)benzyl)-2,9-diazaspiro[5.5]undecan-1-one (TFA Salt)

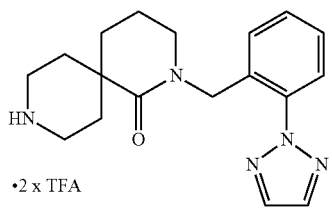 [SMILES: O=C1N(Cc2ccccc2-n2nccn2)CCCC12CCNCC2]

•2 x TFA

To a solution of tert-butyl 2-(2-(2H-1,2,3-triazol-2-yl)benzyl)-1-oxo-2,9-diazaspiro[5.5]-undecane-9-carboxylate (1.76 g, 4.09 mmol) in dichloromethane (15 mL) was added TFA (3.15 mL, 40.9 mmol). The solution was stirred for 25 min at rt. After completion of the reaction the mixture was evaporated to dryness. The residue was dried under high vacuum to yield the title compound as a solid (2.79 g, quant.). [$^1$H NMR (400 MHz, DMSO-$d_6$) ♀ ppm 8.42 (br s, 2H), 8.11 (s, 2H), 7.64-7.60 (m, 1H), 7.51-7.47 (m, 2H), 7.24 (d, 1H), 4.55 (s, 2H), 3.24-3.18 (m, 2H), 3.13-3.11 (m, 2H), 3.09-2.97 (m, 2H), 2.13-2.04 (m, 2H), 1.82-1.70 (m, 4H), 1.65-1.55 (m, 2H); LCMS Rt$_A$=0.60, [M+H]$^+$=326.3].

c) 2-(2-(2H-1,2,3-triazol-2-yl)benzyl)-9-(quinoxalin-2-yl)-2,9-diazaspiro[5.5]undecan-1-one

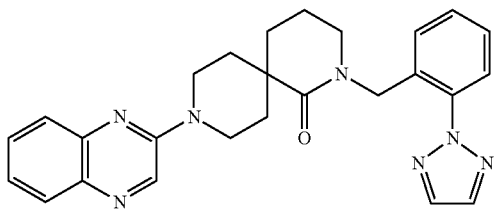 [SMILES: O=C1N(Cc2ccccc2-n2nccn2)CCCC12CCN(c1cnc3ccccc3n1)CC2]

To a stirred solution of 2-(2-(2H-1,2,3-triazol-2-yl)benzyl)-2,9-diazaspiro[5.5]undecan-1-one (TFA salt) (200 mg, 0.354 mmol, contains 2.0 moleq. TFA) and diisopropylethylamine (0.64 mL, 3.61 mmol) in acetonitrile (1 mL) was added 2-chloroquinoxaline [1448-87-9] (121 mg, 0.72 mmol). The mixture was heated at 120° C. for 40 min under microwave conditions. The reaction mixture was cooled to rt and concentrated under reduced pressure. The crude mixture was purified by flash-column chromatography over silicagel (eluent: gradient 10%-100% ethyl acetate/heptane) to yield the title compound (106 mg, 65%). [$^1$H NMR (400 MHz, DMSO-$d_6$) ♀ ppm 8.81 (s, 1H), 8.11 (s, 2H), 7.80 (d, 1H), 7.59-7.63 (m, 1H), 7.56-7.59 (m, 2H), 7.44-7.55 (m, 2H), 7.33-7.40 (m, 1H), 7.24-7.29 (m, 1H), 4.54 (br. s, 2H), 4.19-4.29 (m, 2H), 3.39-3.49 (m, 2H), 3.13 (t, 2H), 1.99-2.10 (m, 2H), 1.84-1.92 (m, 2H), 1.73-1.83 (m, 2H), 1.54-1.65 (m, 2H); LCMS Rt$_A$=1.16, [M+H]$^+$=454.4].

Method O

Example 50

2-benzyl-9-(1-methyl-1H-benzo[d]imidazol-2-yl)-2,9-diazaspiro[5.5]undecan-1-one (TFA Salt)

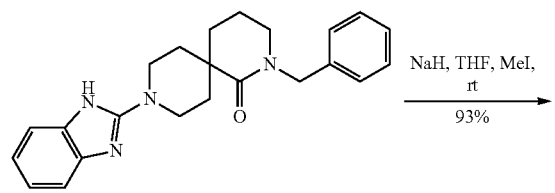

synthesized according to synthesis method N

NaH, THF, MeI, rt
→
93%

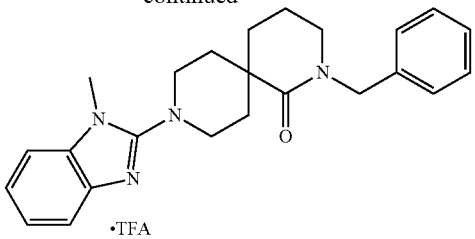

•TFA

The title compound was synthesized from 9-(1H-benzo[d]imidazol-2-yl)-2-benzyl-2,9-diazaspiro[5.5]undecan-1-one (prepared according to method N) via methylation as follows:
NaH (5.3 mg, 0.22 mmol, 95%) was added to an ice-cold solution of 9-(1H-benzo[d]imidazol-2-yl)-2-benzyl-2,9-diazaspiro[5.5]undecan-1-one (prepared according to method N) (50 mg, 0.1 mmol) in THF (2 mL). The resulting mixture was stirred at 0° C. for 20 min. Then methyl iodide (0.014 mL, 0.22 mmol) was added at 0° C. and the reaction mixture was allowed to warm to rt over a period of 18 h. The reaction was quenched with HCl 2 N (1 mL) and the solution mixture was evaporated under vacuum. The product was purified by preparative reverse phase LC SunFire C18 OBD 5 mm 30×100 mm with flow rate 50 ml/min in 16 min linear gradient (mobile phase 0.1% TFA in water (A): acetonitrile (B) gradient) to yield the title compound as TFA salt (48 mg, 93%). [$^1$H NMR (600 MHz, DMSO-$d_6$) ♀ ppm 1.63-1.73 (m, 2H) 1.74-1.82 (m, 2H) 1.82-1.93 (m, 2H) 2.14-2.28 (m, 2H) 3.15-3.31 (m, 2H) 3.46-3.62 (m, 2H) 3.74 (s, 3H) 3.76-3.90 (m, 3H) 4.51 (s, 2H) 7.20 (d, J=7.27 Hz, 2H) 7.22-7.29 (m, 2H) 7.33 (t, J=7.47 Hz, 2H) 7.35-7.39 (m, 2H) 7.43-7.52 (m, 1H) 7.55-7.69 (m, 1H); LCMS Rt$_B$=1.65, [M+H]$^+$=389.2].

Method P

Example 51

2-(2-(1-methyl-1H-pyrazol-4-yl)benzyl)-9-(quinoxalin-2-yl)-2,9-diazaspiro[5.5]undecan-1-one

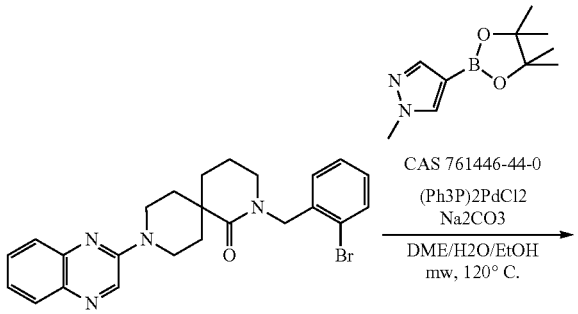

CAS 761446-44-0
(Ph3P)2PdCl2
Na2CO3
DME/H2O/EtOH
mw, 120° C.

synthesized accroding to method D

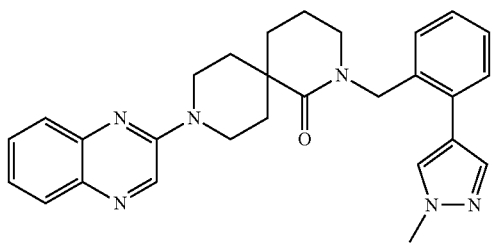

a) 2-(2-bromobenzyl)-9-(quinoxalin-2-yl)-2,9-diazaspiro[5.5]undecan-1-one

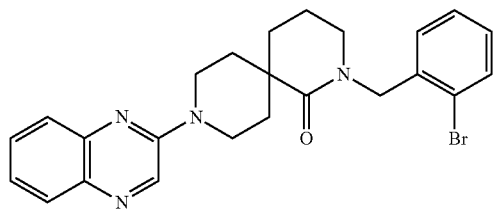 [SMILES: O=C1N(Cc2ccccc2Br)CCCC12CCN(c1cnc3ccccc3n1)CC2]

2-(2-bromobenzyl)-9-(quinoxalin-2-yl)-2,9-diazaspiro[5.5]undecan-1-one was synthesized according to method D. [$^1$H NMR (400 MHz, DMSO-$d_6$) ♀ ppm 8.81 (s, 1H), 7.79 (d, J=7.8 Hz, 1H), 7.61 (d, J=8.2 Hz, 1H), 7.53-7.59 (m, 2H), 7.32-7.41 (m, 2H), 7.21 (t, J=7.6 Hz, 1H), 7.09 (d, J=7.8 Hz, 1H), 4.49 (s, 2H), 4.19-4.31 (m, 2H), 3.45 (br. t, J=10.6, 10.6 Hz, 2H), 3.25 (t, J=5.9 Hz, 2H), 2.00-2.12 (m, 2H), 1.89-1.97 (m, 2H), 1.79-1.89 (m, 2H), 1.58-1.68 (m, 2H); LCMS Rt$_D$=2.88 min, [M+H]$^+$=465.0/467.0].

b) 2-(2-(1-methyl-1H-pyrazol-4-yl)benzyl)-9-(quinoxalin-2-yl)-2,9-diazaspiro[5.5]undecan-1-one

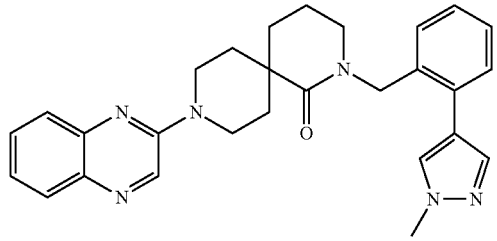 [SMILES: Cn1cc(-c2ccccc2CN2CCCC3(CCN(c4cnc5ccccc5n4)CC3)C2=O)cn1]

The mixture of 2-(2-bromobenzyl)-9-(quinoxalin-2-yl)-2,9-diazaspiro[5.5]undecan-1-one (58 mg, 0.11 mmol), 1-methyl-4-(4,4,5,5-tetramethyl-1,3,2-dioxaborolan-2-yl)-1H-pyrazole [761446-44-0] (34 mg, 0.16 mmol), (Ph$_3$P)$_2$PdCl$_2$ and sodium carbonate (39 mg, 0.37 mmol) in the solvent mixture DME/H$_2$O/EtOH (2 ml, 7:3:2) was placed in a microwave tube. The tube was sealed and the suspension was heated at 120° C. over 1 h under microwave conditions. The reaction mixture was concentrated under reduced pressure. Methanol was added and the mixture filtered through PL-thiol MP SPE cartridge (previously washed with MeOH) and evaporated to give 100 mg of a yellow oil which was purified by preparative HPLC (column Waters Sunfire C18, 5 um, 4.6×50 mm, flow 5 ml/min, solvent A: Water+0.1% TFA; Solvent B: Acetonitrile+0.1% TFA/gradient 5-100% B in 2.5 min). The product containing fractions were adjusted to pH 7 with aqueous sodium bicarbonate an extracted with ethyl acetate to yield the title compound (35 mg, 66%). [$^1$H NMR (600 MHz, DMSO-$d_6$) ppm 8.84 (s, 1H), 7.92 (s, 1H), 7.81 (d, J=8.1 Hz, 1H), 7.54-7.64 (m, 3H), 7.32-7.42 (m, 2H), 7.22-7.31 (m, 2H), 7.02-7.11 (m, 1H), 4.59 (s, 2H), 4.22-4.34 (m, 2H), 3.44 (t, J=11.1 Hz, 2H), 3.13 (t, J=5.9 Hz, 2H), 2.02-2.13 (m, 2H), 1.86-1.95 (m, 2H), 1.75-1.85 (m, 2H), 1.61 (d, J=13.5 Hz, 2H); LCMS Rt$_C$=3.11 min, [M+H]$^+$=467.2].

Method Q

Example 52

2-((1H-indol-3-yl)methyl)-9-(benzo[d]thiazol-2-yl)-2,9-diazaspiro[5.5]undecan-1-one

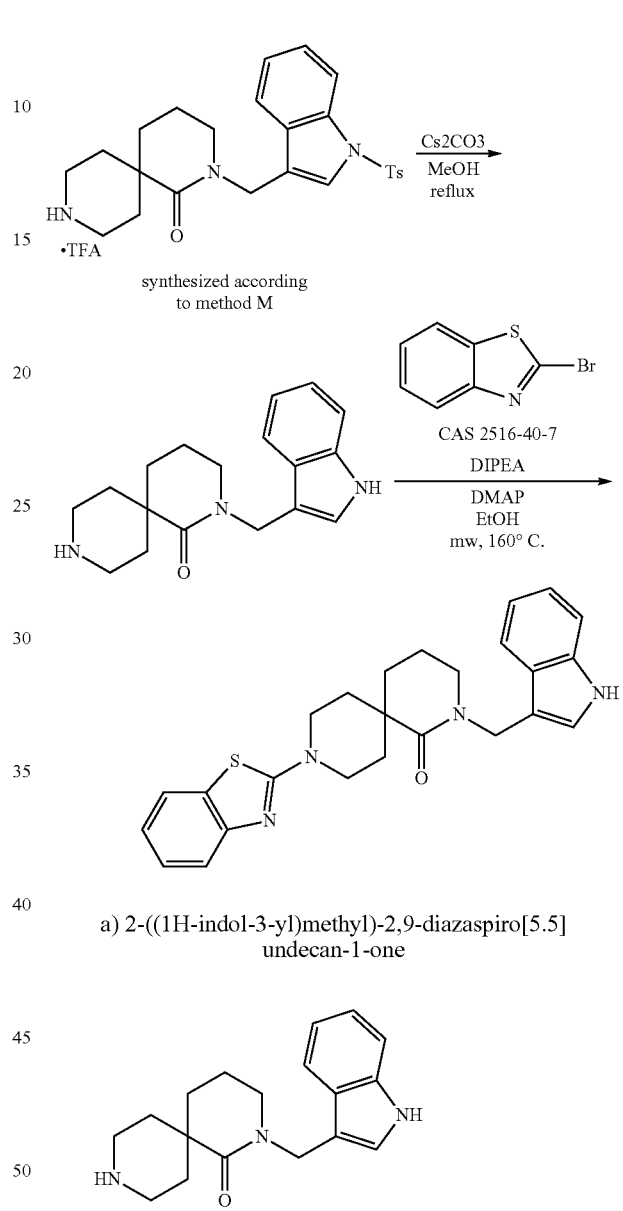

a) 2-((1H-indol-3-yl)methyl)-2,9-diazaspiro[5.5]undecan-1-one

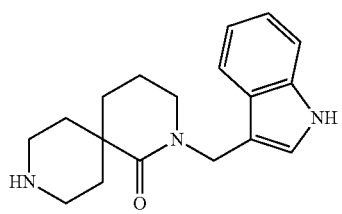 [SMILES: O=C1N(Cc2c[nH]c3ccccc23)CCCC12CCNCC2]

The mixture of 2-((1-tosyl-1H-indol-3-yl)methyl)-2,9-diazaspiro[5.5]undecan-1-one (15 g, 23 mmol) and Cs$_2$CO$_3$ (45 g, 139 mmol) in methanol (170 ml) was heated under reflux for 2.5 h. The solution was diluted with water, the pH adjusted to 7 with a saturated aqueous potassium carbonate solution and the aqueous phase extracted with dichloromethane. The organic layer was washed with brine and dried over anhydrous sodium sulfate, filtered and concentrated under reduced pressure to afford 6.69 g (99%) of the title compound as a beige foam which was not further purified. [$^1$H NMR (400 MHz, DMSO-$d_6$) ♀ ppm 10.91 (br. s., 1H), 7.48-7.55 (m, 1H), 7.32 (d, J=8.2 Hz, 1H), 7.24 (d, J=2.0 Hz, 1H), 7.04 (t, J=7.6 Hz, 1H), 6.88-6.96 (m, 1H), 4.60 (s, 2H), 3.10 (t, J=6.1 Hz, 2H), 2.71-2.89 (m, 2H), 2.51-2.69 (m, 2H), 2.01 (s, 3H), 1.54-1.73 (m, 4H), 1.25-1.38 (m, 2H); LCMS Rt$_C$=2.44 min, [M+H]$^+$=298.2].

b) 2-((1H-indol-3-yl)methyl)-9-(benzo[d]thiazol-2-yl)-2,9-diazaspiro[5.5]undecan-1-one

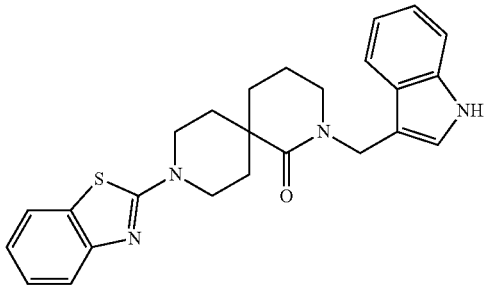

To the solution of 2-((1H-indol-3-yl)methyl)-2,9-diazaspiro[5.5]undecan-1-one (60 mg, 0.20 mmol) and 2-bromobenzo[d]thiazole [2516-40-7] (56 mg, 0.26 mmol) in ethanol (0.7 ml) was added DIPEA (176 μl, 1.0 mmol) and DMAP (1.2 mg, 0.01 mmol). The mixture was heated at 160° C. for 1.25 h under microwave conditions. The solvent was evaporated and the residue was purified by flash chromatography (EtOAc/hexane 2:3) to yield 51 mg (56%) of the title compound as a pale yellow solid. [$^1$H NMR (600 MHz, DMSO-$d_6$) ♀ ppm 10.96 (br. s., 1H), 7.76 (d, J=7.9 Hz, 1H), 7.54 (d, J=8.1 Hz, 1H), 7.44 (d, J=7.9 Hz, 1H), 7.34 (d, J=8.1 Hz, 1H), 7.22-7.32 (m, 2H), 7.01-7.11 (m, 2H), 6.96 (t, J=7.3 Hz, 1H), 4.63 (s, 2H), 3.82-3.96 (m, 2H), 3.38-3.49 (m, 2H), 3.17 (t, J=5.9 Hz, 2H), 2.06-2.18 (m, 2H), 1.74-1.84 (m, 2H), 1.61-1.74 (m, 2H), 1.53 (d, J=13.7 Hz, 2H); LCMS $Rt_C$=2.37 min, [M+H]$^+$=431.2].

Table 1b: Compounds of Formula (I)

Examples (Ex) 53-176 were synthesized according to respective synthetic methods (SM) D to Q. LCMS: LCMS Rt, [min], (method).

| Ex. | Structure | Name | SM | LCMS | [M + H]$^+$ |
|---|---|---|---|---|---|
| 53 | 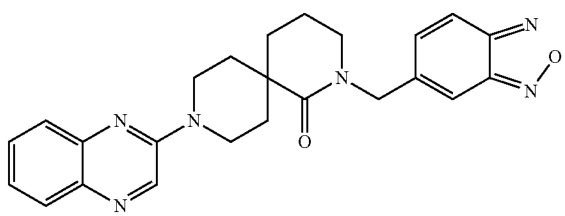 [SMILES: N=C1C=CC(CN2CCCC3(CCN(c4cnc5ccccc5n4)CC3)C2=O)=C/C1=N/O] | 2-(benzo[c][1,2,5]oxadiazol-5-ylmethyl)-9-(quinoxalin-2-yl)-2,9-diazaspiro[5.5]undecan-1-one | D | 0.45 (F) | 429.4 |
| 54 | 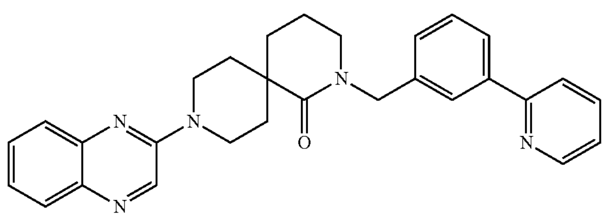 [SMILES: O=C1N(Cc2cccc(-c3ccccn3)c2)CCCC12CCN(c1cnc3ccccc3n1)CC2] | 2-(3-(pyridin-2-yl)benzyl)-9-(quinoxalin-2-yl)-2,9-diazaspiro[5.5]undecan-1-one | D | 0.41 (F) | 464.3 |
| 55 | 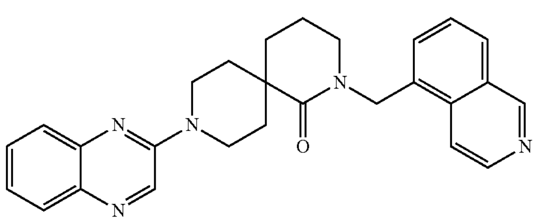 [SMILES: O=C1N(Cc2cccc3cnccc23)CCCC12CCN(c1cnc3ccccc3n1)CC2] | 2-(isoquinolin-5-ylmethyl)-9-(quinoxalin-2-yl)-2,9-diazaspiro[5.5]undecan-1-one | D | 0.36 (F) | 437.9 |
| 56 | 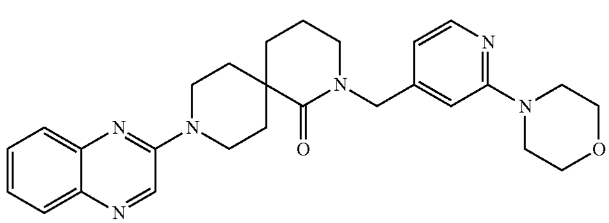 [SMILES: O=C1N(Cc2ccnc(N3CCOCC3)c2)CCCC12CCN(c1cnc3ccccc3n1)CC2] | 2-((2-morpholinopyridin-4-yl)methyl)-9-(quinoxalin-2-yl)-2,9-diazaspiro[5.5]undecan-1-one | D | 0.35 (F) | 473.1 |

-continued

| Ex. | Structure | Name | SM | LCMS | [M + H]+ |
|---|---|---|---|---|---|
| 57 | 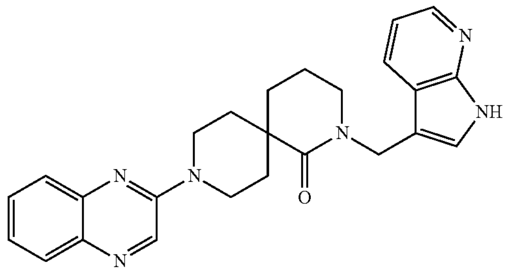 [SMILES: O=C1N(Cc2c[nH]c3ncccc23)CCCC12CCN(c1cnc3ccccc3n1)CC2] | 2-((1H-pyrrolo[2,3-b]pyridin-3-yl)methyl)-9-(quinoxalin-2-yl)-2,9-diazaspiro[5.5]undecan-1-one | D | 0.37 (F) | 427.2 |
| 58 | 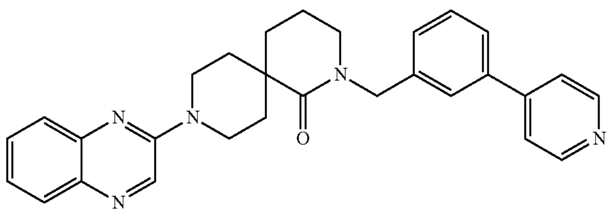 [SMILES: O=C1N(Cc2cccc(-c3ccncc3)c2)CCCC12CCN(c1cnc3ccccc3n1)CC2] | 2-(3-(pyridin-4-yl)benzyl)-9-(quinoxalin-2-yl)-2,9-diazaspiro[5.5]undecan-1-one | D | 0.37 (F) | 464.4 |
| 59 | 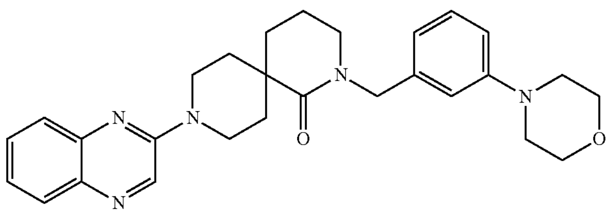 [SMILES: O=C1N(Cc2cccc(N3CCOCC3)c2)CCCC12CCN(c1cnc3ccccc3n1)CC2] | 2-(3-morpholinobenzyl)-9-(quinoxalin-2-yl)-2,9-diazaspiro[5.5]undecan-1-one | D | 1.49 (E) | 472.2 |
| 60 | 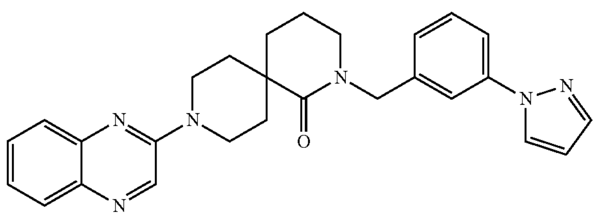 [SMILES: O=C1N(Cc2cccc(-n3cccn3)c2)CCCC12CCN(c1cnc3ccccc3n1)CC2] | 2-(3-(1H-pyrazol-1-yl)benzyl)-9-(quinoxalin-2-yl)-2,9-diazaspiro[5.5]undecan-1-one | D | 1.69 (F) | 453.1 |
| 61 | 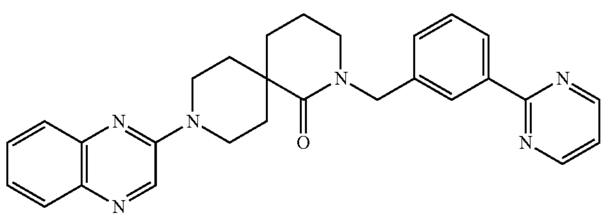 [SMILES: O=C1N(Cc2cccc(-c3ncccn3)c2)CCCC12CCN(c1cnc3ccccc3n1)CC2] | 2-(3-(pyrimidin-2-yl)benzyl)-9-(quinoxalin-2-yl)-2,9-diazaspiro[5.5]undecan-1-one | D | 1.55 (F) | 464.7 |
| 62 | 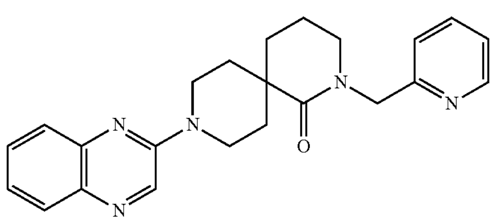 [SMILES: O=C1N(Cc2ccccn2)CCCC12CCN(c1cnc3ccccc3n1)CC2] | 2-(pyridin-2-ylmethyl)-9-(quinoxalin-2-yl)-2,9-diazaspiro[5.5]undecan-1-one | D | 0.28 (E) | 388.1 |
| 63 | 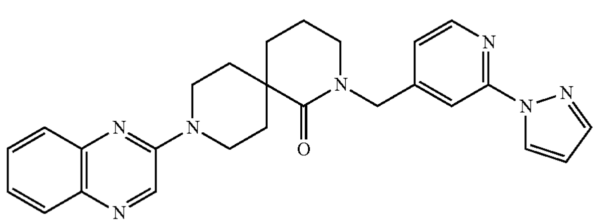 [SMILES: O=C1N(Cc2ccnc(-n3cccn3)c2)CCCC12CCN(c1cnc3ccccc3n1)CC2] | 2-((2-(1H-pyrazol-1-yl)pyridin-4-yl)methyl)-9-(quinoxalin-2-yl)-2,9-diazaspiro[5.5]undecan-1-one | D | 1.49 (F) | 454.1 |

| Ex. | Structure | Name | SM | LCMS | [M + H]+ |
|---|---|---|---|---|---|
| 64 | 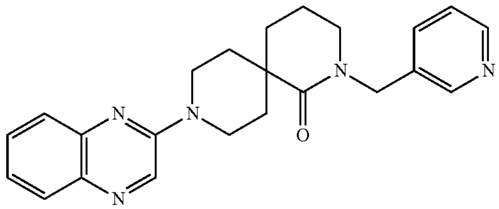 [SMILES: O=C1N(Cc2cccnc2)CCCC12CCN(c1cnc3ccccc3n1)CC2] | 2-(pyridin-3-ylmethyl)-9-(quinoxalin-2-yl)-2,9-diazaspiro[5.5]undecan-1-one | D | 0.25 (F) | 388.1 |
| 65 | 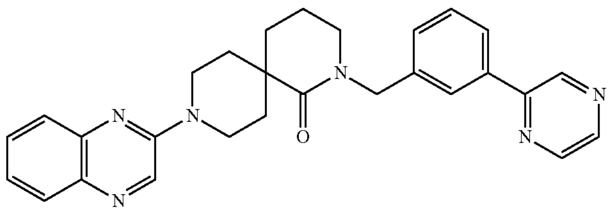 [SMILES: O=C1N(Cc2cccc(-c3cnccn3)c2)CCCC12CCN(c1cnc3ccccc3n1)CC2] | 2-(3-(pyrazin-2-yl)benzyl)-9-(quinoxalin-2-yl)-2,9-diazaspiro[5.5]undecan-1-one | D | 1.49 (E) | 465.2 |
| 66 | 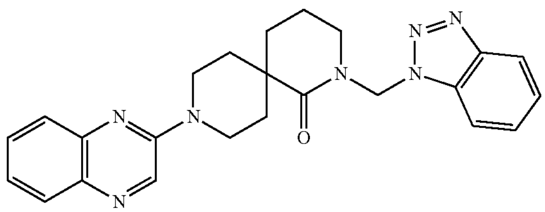 [SMILES: O=C1N(Cn2nnc3ccccc32)CCCC12CCN(c1cnc3ccccc3n1)CC2] | 2-((1H-benzo[d][1,2,3]triazol-1-yl)methyl)-9-(quinoxalin-2-yl)-2,9-diazaspiro[5.5]undecan-1-one | D | 1.48 (E) | 428.2 |
| 67 | 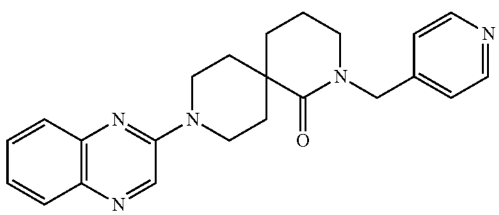 [SMILES: O=C1N(Cc2ccncc2)CCCC12CCN(c1cnc3ccccc3n1)CC2] | 2-(pyridin-4-ylmethyl)-9-(quinoxalin-2-yl)-2,9-diazaspiro[5.5]undecan-1-one | D | 0.12 (E) | 388.1 |
| 68 | 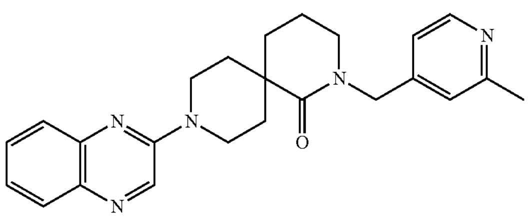 [SMILES: Cc1cc(CN2CCCC3(CCN(c4cnc5ccccc5n4)CC3)C2=O)ccn1] | 2-((2-methylpyridin-4-yl)methyl)-9-(quinoxalin-2-yl)-2,9-diazaspiro[5.5]undecan-1-one | D | 0.12 (E) | 402.1 |
| 69 | 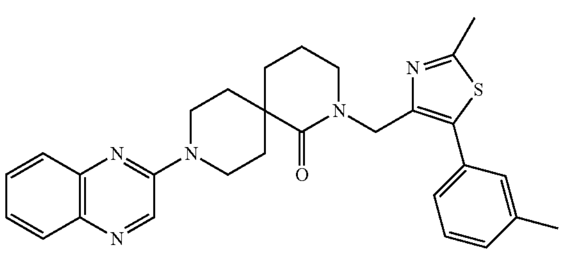 [SMILES: Cc1cccc(-c2sc(C)nc2CN2CCCC3(CCN(c4cnc5ccccc5n4)CC3)C2=O)c1] | 2-((2-methyl-5-m-tolylthiazol-4-yl)methyl)-9-(quinoxalin-2-yl)-2,9-diazaspiro[5.5]undecan-1-one | D | 1.80 (F) | 497.9 |
| 70 | 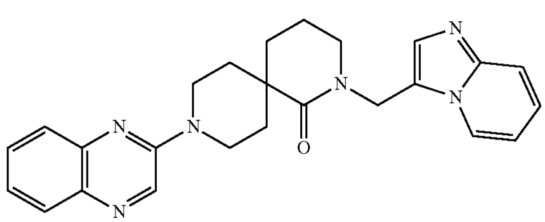 [SMILES: O=C1N(Cc2cnc3ccccn23)CCCC12CCN(c1cnc3ccccc3n1)CC2] | 2-(imidazo[1,2-a]pyridin-3-ylmethyl)-9-(quinoxalin-2-yl)-2,9-diazaspiro[5.5]undecan-1-one | D | 0.26 (F) | 426.9 |

| Ex. | Structure | Name | SM | LCMS | [M + H]+ |
|---|---|---|---|---|---|
| 71 | 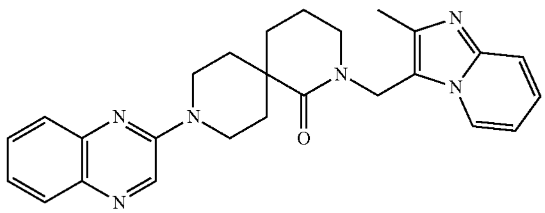 [SMILES: Cc1nc2ccccn2c1CN1CCCC2(CCN(c3cnc4ccccc4n3)CC2)C1=O] | 2-((2-methylimidazo[1,2-a]pyridin-3-yl)methyl)-9-(quinoxalin-2-yl)-2,9-diazaspiro[5.5]undecan-1-one | D | 0.22 (E) | 441.2 |
| 72 | 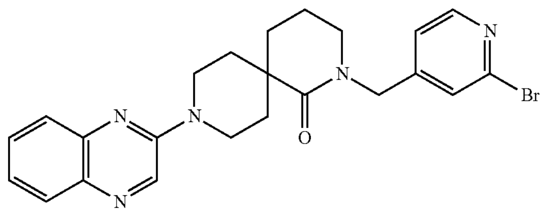 [SMILES: O=C1N(Cc2ccnc(Br)c2)CCCC12CCN(c1cnc3ccccc3n1)CC2] | 2-((2-bromopyridin-4-yl)methyl)-9-(quinoxalin-2-yl)-2,9-diazaspiro[5.5]undecan-1-one | D | 1.40 (F) | 466.0/ 468.0 |
| 73 | 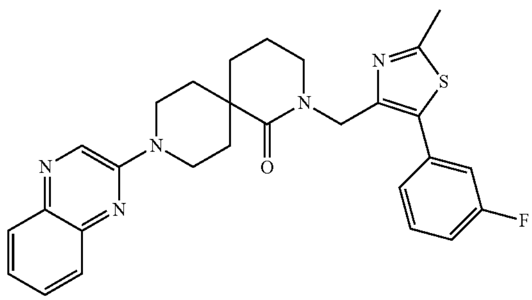 [SMILES: Cc1nc(CN2CCCC3(CCN(c4cnc5ccccc5n4)CC3)C2=O)c(-c2cccc(F)c2)s1] | 2-((5-(3-fluorophenyl)-2-methylthiazol-4-yl)methyl)-9-(quinoxalin-2-yl)-2,9-diazaspiro[5.5]undecan-1-one | D | 0.41 (F) | not found |
| 74 | 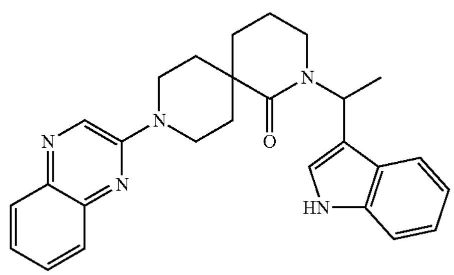 [SMILES: CC(c1c[nH]c2ccccc12)N1CCCC2(CCN(c3cnc4ccccc4n3)CC2)C1=O] | 2-(1-(1H-indol-3-yl)ethyl)-9-(quinoxalin-2-yl)-2,9-diazaspiro[5.5]undecan-1-one | D | 1.60 (F) | 439.9 |
| 75 | 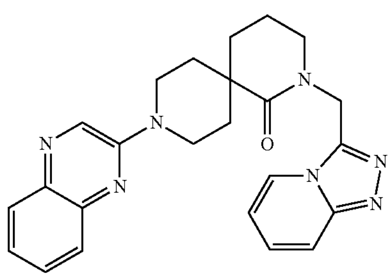 [SMILES: O=C1N(Cc2nnc3ccccn23)CCCC12CCN(c1cnc3ccccc3n1)CC2] | 2-([1,2,4]triazolo[4,3-a]pyridin-3-ylmethyl)-9-(quinoxalin-2-yl)-2,9-diazaspiro[5.5]undecan-1-one | D | 0.54 (F) | 428.0 |
| 76 | 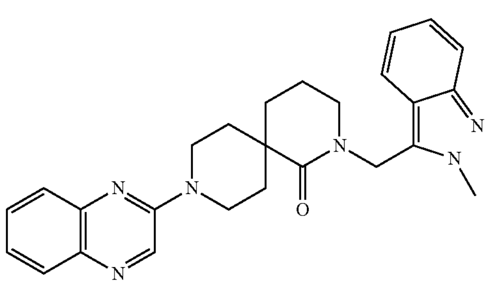 [SMILES: CN/C(CN1CCCC2(CCN(c3cnc4ccccc4n3)CC2)C1=O)=C1/C=CC=CC1=N] | 2-((2-methyl-2H-indazol-3-yl)methyl)-9-(quinoxalin-2-yl)-2,9-diazaspiro[5.5]undecan-1-one | E[1] | 1.44 (E) | 440.8 |

-continued

| Ex. | Structure | Name | SM | LCMS | [M + H]+ |
|---|---|---|---|---|---|
| 77 | 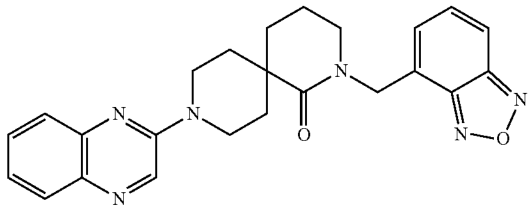 [SMILES: O=C1N(Cc2cccc3nonc23)CCCC12CCN(c1cnc3ccccc3n1)CC2] | 2-(benzo[c][1,2,5]oxadiazol-4-ylmethyl)-9-(quinoxalin-2-yl)-2,9-diazaspiro[5.5]undecan-1-one | D | 1.59 (E) | 428.8 |
| 78 | 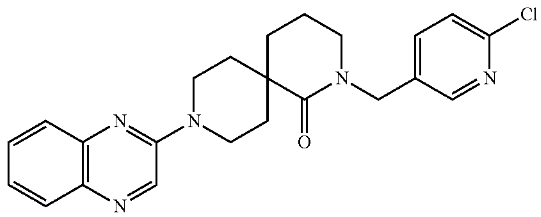 [SMILES: O=C1N(Cc2ccc(Cl)nc2)CCCC12CCN(c1cnc3ccccc3n1)CC2] | 2-((6-chloropyridin-3-yl)methyl)-9-(quinoxalin-2-yl)-2,9-diazaspiro[5.5]undecan-1-one | D | 1.42 (F) | 421.8 |
| 79 | 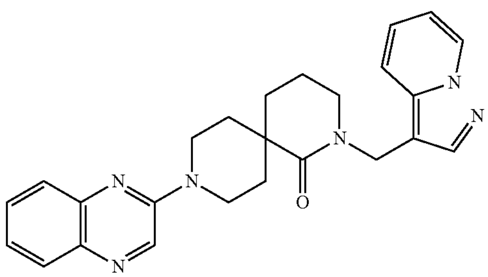 [SMILES: N=C/C(CN1CCCC2(CCN(c3cnc4ccccc4n3)CC2)C1=O)=C1/C=CC=CN1] | 2-(pyrazolo[1,5-a]pyridin-3-ylmethyl)-9-(quinoxalin-2-yl)-2,9-diazaspiro[5.5]undecan-1-one | D | 1.34 (F) | 426.9 |
| 80 | 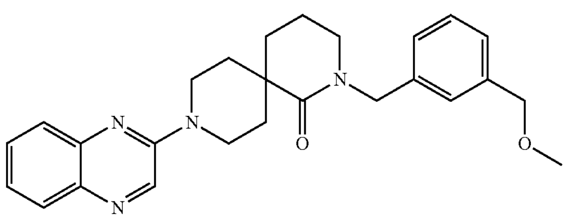 [SMILES: COCc1cccc(CN2CCCC3(CCN(c4cnc5ccccc5n4)CC3)C2=O)c1] | 2-(3-(methoxymethyl)benzyl)-9-(quinoxalin-2-yl)-2,9-diazaspiro[5.5]undecan-1-one | D | 2.33 (D) | 431.2 |
| 81 | 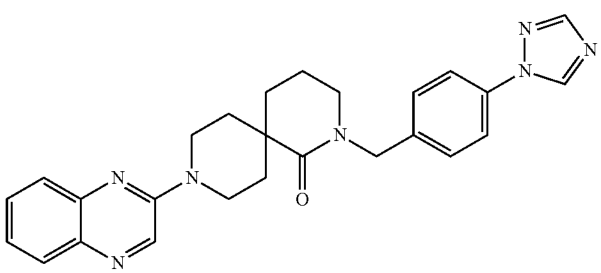 [SMILES: O=C1N(Cc2ccc(-n3cncn3)cc2)CCCC12CCN(c1cnc3ccccc3n1)CC2] | 2-(4-(1H-1,2,4-triazol-1-yl)benzyl)-9-(quinoxalin-2-yl)-2,9-diazaspiro[5.5]undecan-1-one | D | 2.90 (C) | 454.2 |
| 82 | 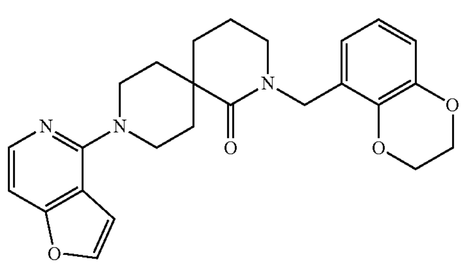 [SMILES: O=C1N(Cc2cccc3c2OCCO3)CCCC12CCN(c1nccc3occc13)CC2] | 2-((2,3-dihydrobenzo[b][1,4]dioxin-5-yl)methyl)-9-(furo[3,2-c]pyridin-4-yl)-2,9-diazaspiro[5.5]undecan-1-one | D | 0.22 (E) | 434.1 |

-continued

| Ex. | Structure | Name | SM | LCMS | [M + H]⁺ |
|---|---|---|---|---|---|
| 83 | 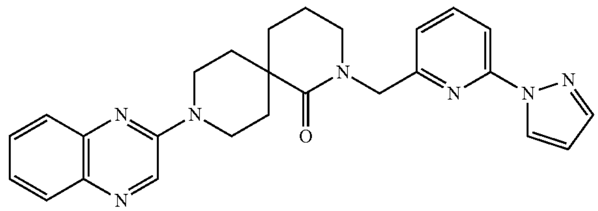 [SMILES: O=C1N(Cc2cccc(-n3cccn3)n2)CCCC12CCN(c1cnc3ccccc3n1)CC2] | 2-((6-(1H-pyrazol-1-yl)pyridin-2-yl)methyl)-9-(quinoxalin-2-yl)-2,9-diazaspiro[5.5]undecan-1-one | D | 1.56 (E) | 454.2 |
| 84 | 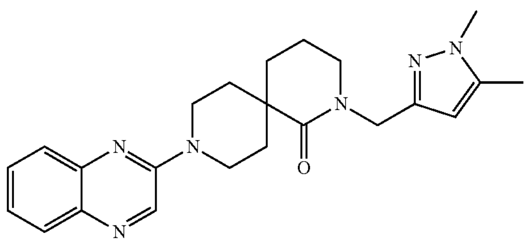 [SMILES: Cc1cc(CN2CCCC3(CCN(c4cnc5ccccc5n4)CC3)C2=O)nn1C] | 2-((1,5-dimethyl-1H-pyrazol-3-yl)methyl)-9-(quinoxalin-2-yl)-2,9-diazaspiro[5.5]undecan-1-one | D | 2.78 (C) | 405.2 |
| 85 | 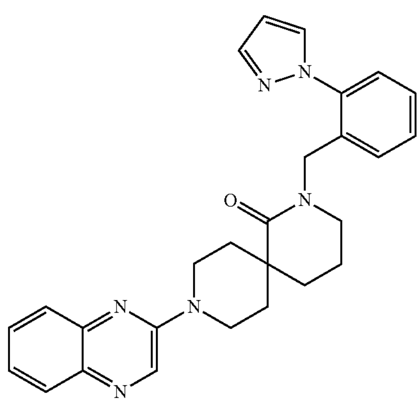 [SMILES: O=C1N(Cc2ccccc2-n2cccn2)CCCC12CCN(c1cnc3ccccc3n1)CC2] | 2-(2-(1H-pyrazol-1-yl)benzyl)-9-(quinoxalin-2-yl)-2,9-diazaspiro[5.5]undecan-1-one | D | 0.98 (H) | 453.6 |
| 86 | 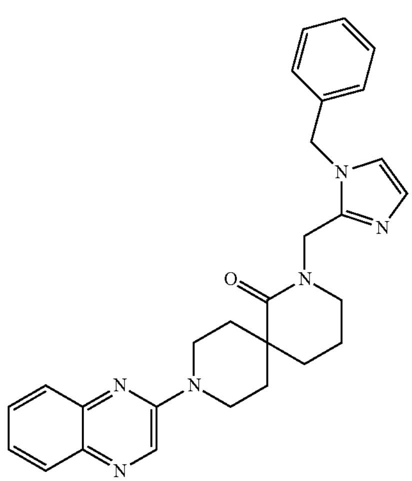 [SMILES: O=C1N(Cc2nccn2Cc2ccccc2)CCCC12CCN(c1cnc3ccccc3n1)CC2] | 2-((1-benzyl-1H-imidazol-2-yl)methyl)-9-(quinoxalin-2-yl)-2,9-diazaspiro[5.5]undecan-1-one | D | 0.85 (H) | 467.6 |

-continued
| Ex. | Structure | Name | SM | LCMS | [M + H]+ |
|---|---|---|---|---|---|
| 87 | 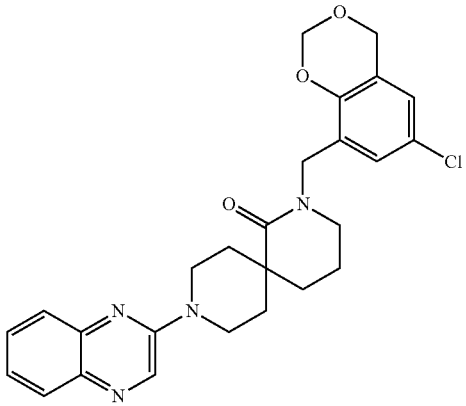 [SMILES: O=C1N(Cc2cc(Cl)cc3c2OCOC3)CCCC12CCN(c1cnc3ccccc3n1)CC2] | 2-((6-chloro-4H-benzo[d][1,3]dioxin-8-yl)methyl)-9-(quinoxalin-2-yl)-2,9-diazaspiro[5.5]undecan-1-one | D | 1.08 (H) | 478.0 |
| 88 | 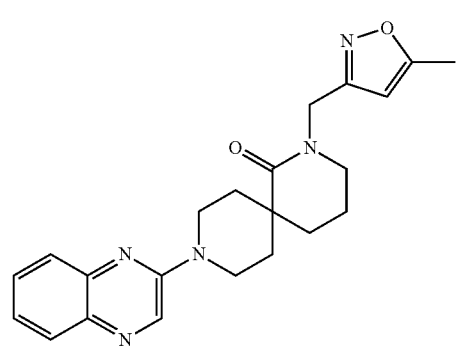 [SMILES: Cc1cc(CN2CCCC3(CCN(c4cnc5ccccc5n4)CC3)C2=O)no1] | 2-((5-methylisoxazol-3-yl)methyl)-9-(quinoxalin-2-yl)-2,9-diazaspiro[5.5]undecan-1-one | D | 0.90 (H) | 392.5 |
| 89 | 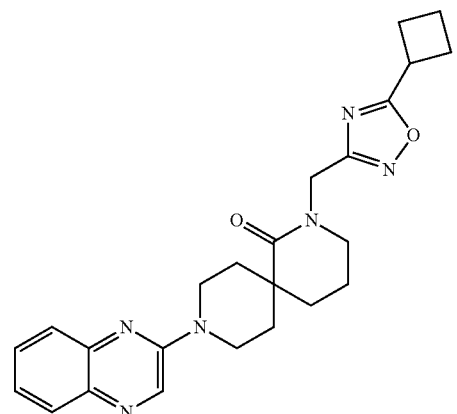 | 2-((5-cyclobutyl-1,2,4-oxadiazol-3-yl)methyl)-9-(quinoxalin-2-yl)-2,9-diazaspiro[5.5]undecan-1-one | D | 0.98 (H) | 433.5 |
| 90 | 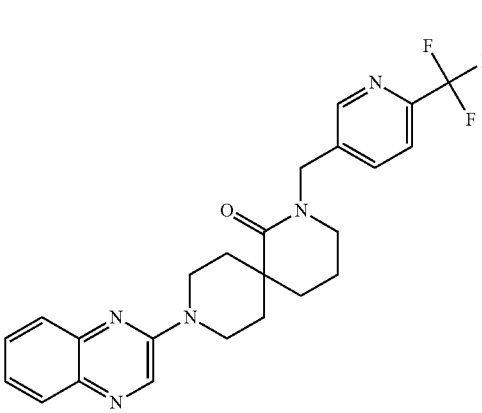 | 9-(quinoxalin-2-yl)-2-((6-(trifluoromethyl)pyridin-3-yl)methyl)-2,9-diazaspiro[5.5]undecan-1-one | D | 1.00 (H) | 456.5 |

-continued

| Ex. | Structure | Name | SM | LCMS | [M + H]+ |
|---|---|---|---|---|---|
| 91 | 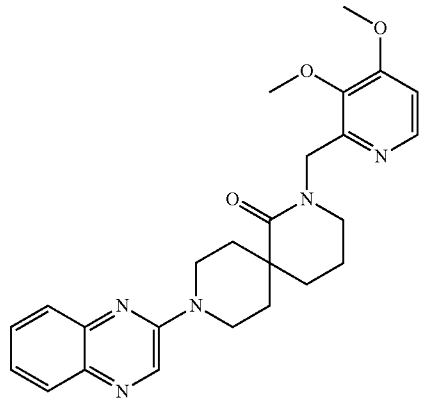 [SMILES: COc1ccnc(CN2CCCC3(CCN(c4cnc5ccccc5n4)CC3)C2=O)c1OC] | 2-((3,4-dimethoxypyridin-2-yl)methyl)-9-(quinoxalin-2-yl)-2,9-diazaspiro[5.5]undecan-1-one | D | 0.89 (H) | 448.5 |
| 92 | 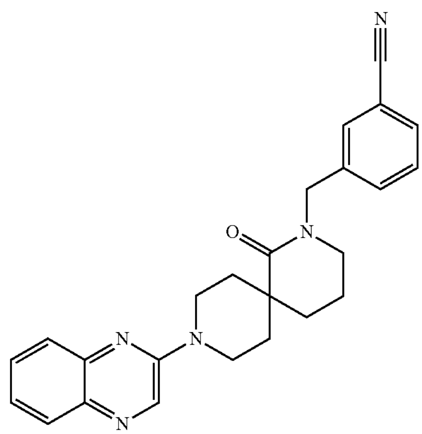 [SMILES: N#Cc1cccc(CN2CCCC3(CCN(c4cnc5ccccc5n4)CC3)C2=O)c1] | 3-((1-oxo-9-(quinoxalin-2-yl)-2,9-diazaspiro[5.5]undecan-2-yl)methyl)benzonitrile | D | 0.98 (H) | 412.5 |
| 93 | 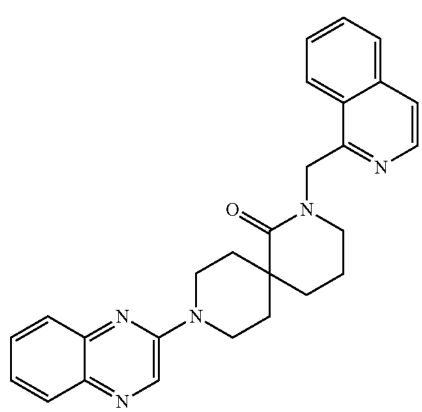 [SMILES: O=C1N(Cc2nccc3ccccc23)CCCC12CCN(c1cnc3ccccc3n1)CC2] | 2-(isoquinolin-1-ylmethyl)-9-(quinoxalin-2-yl)-2,9-diazaspiro[5.5]undecan-1-one | D | 0.83 (H) | 438.6 |
| 94 | 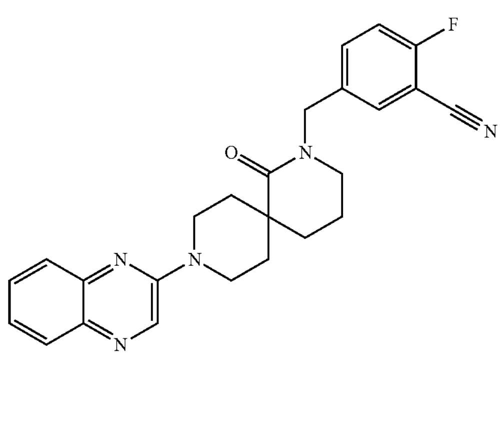 [SMILES: N#Cc1cc(CN2CCCC3(CCN(c4cnc5ccccc5n4)CC3)C2=O)ccc1F] | 2-fluoro-5-((1-oxo-9-(quinoxalin-2-yl)-2,9-diazaspiro[5.5]undecan-2-yl)methyl)benzonitrile | D | 1.01 (H) | 430.5 |

-continued

| Ex. | Structure | Name | SM | LCMS | [M + H]+ |
|---|---|---|---|---|---|
| 95 | 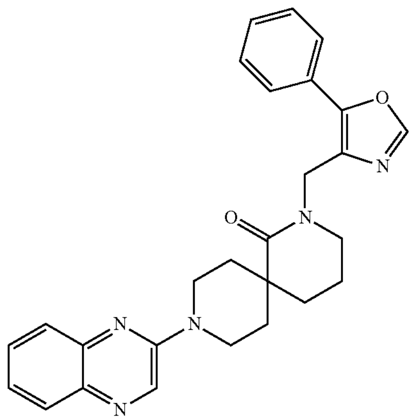 [SMILES: O=C1N(Cc2ncoc2-c2ccccc2)CCCC12CCN(c1cnc3ccccc3n1)CC2] | 2-((5-phenyloxazol-4-yl)methyl)-9-(quinoxalin-2-yl)-2,9-diazaspiro[5.5]undecan-1-one | D | 2.50 (D) | 454.2 |
| 96 | 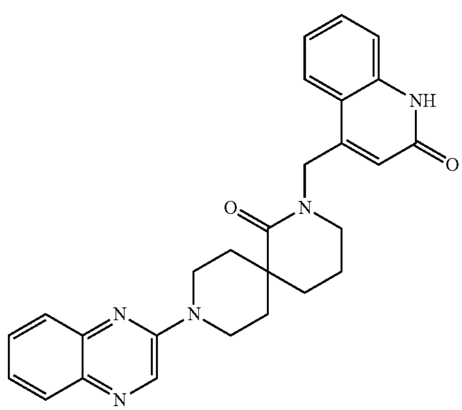 [SMILES: O=C1N(Cc2cc(=O)[nH]c3ccccc23)CCCC12CCN(c1cnc3ccccc3n1)CC2] | 4-((1-oxo-9-(quinoxalin-2-yl)-2,9-diazaspiro[5.5]undecan-2-yl)methyl)quinolin-2(1H)-one | D | 0.87 (H) | 454.6 |
| 97 | 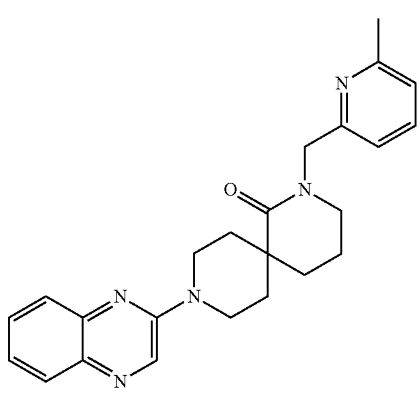 [SMILES: Cc1cccc(CN2CCCC3(CCN(c4cnc5ccccc5n4)CC3)C2=O)n1] | 2-((6-methylpyridin-2-yl)methyl)-9-(quinoxalin-2-yl)-2,9-diazaspiro[5.5]undecan-1-one | D | 0.75 (H) | 402.5 |

-continued

| Ex. | Structure | Name | SM | LCMS | [M + H]⁺ |
|---|---|---|---|---|---|
| 98 | 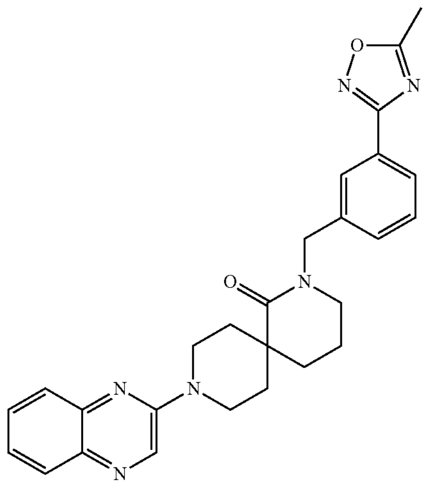 [SMILES: Cc1nc(-c2cccc(CN3CCCC4(CCN(c5cnc6ccccc6n5)CC4)C3=O)c2)no1] | 2-(3-(5-methyl-1,2,4-oxadiazol-3-yl)benzyl)-9-(quinoxalin-2-yl)-2,9-diazaspiro[5.5]undecan-1-one | D | 1.02 (H) | 469.6 |
| 99 | 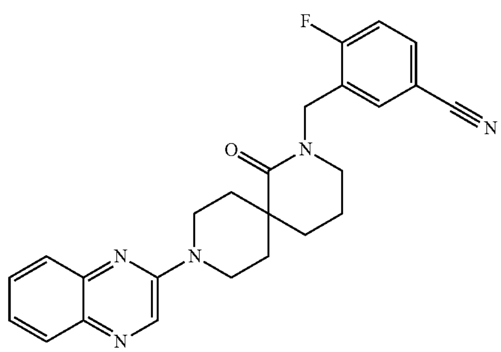 [SMILES: N#Cc1ccc(F)c(CN2CCCC3(CCN(c4cnc5ccccc5n4)CC3)C2=O)c1] | 4-fluoro-3-((1-oxo-9-(quinoxalin-2-yl)-2,9-diazaspiro[5.5]undecan-2-yl)methyl)benzonitrile | D | 1.00 (H) | 430.5 |
| 100 | 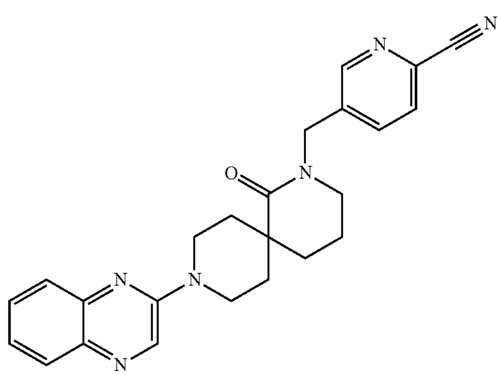 [SMILES: N#Cc1ccc(CN2CCCC3(CCN(c4cnc5ccccc5n4)CC3)C2=O)cn1] | 5-((1-oxo-9-(quinoxalin-2-yl)-2,9-diazaspiro[5.5]undecan-2-yl)methyl)picolinonitrile | D | 0.90 (H) | 413.5 |
| 101 | 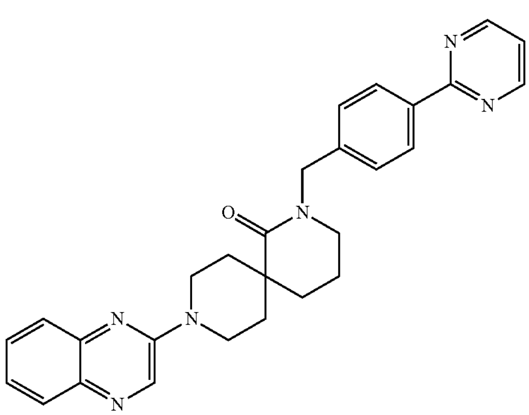 [SMILES: O=C1N(Cc2ccc(-c3ncccn3)cc2)CCCC12CCN(c1cnc3ccccc3n1)CC2] | 2-(4-(pyrimidin-2-yl)benzyl)-9-(quinoxalin-2-yl)-2,9-diazaspiro[5.5]undecan-1-one | D | 0.98 (H) | 465.6 |

| Ex. | Structure | Name | SM | LCMS | [M + H]+ |
|---|---|---|---|---|---|
| 102 | 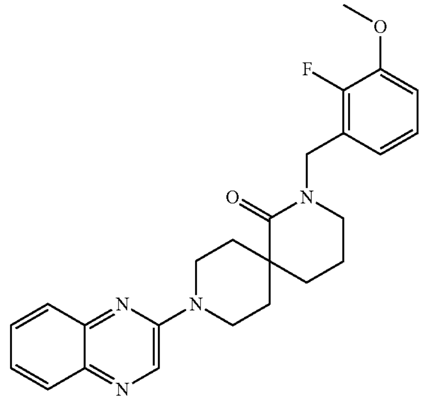 [SMILES: COc1cccc(CN2CCCC3(CCN(c4cnc5ccccc5n4)CC3)C2=O)c1F] | 2-(2-fluoro-3-methoxybenzyl)-9-(quinoxalin-2-yl)-2,9-diazaspiro[5.5]undecan-1-one | D | 1.02 (H) | 435.5 |
| 103 | 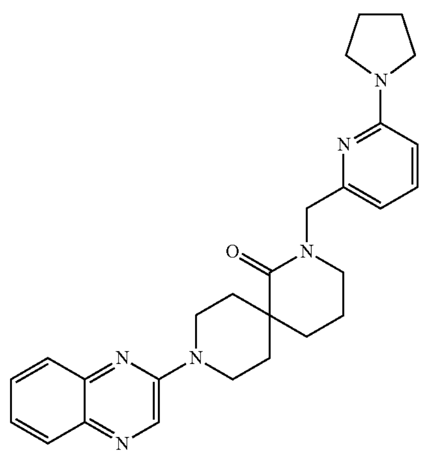 [SMILES: O=C1N(Cc2cccc(N3CCCC3)n2)CCCC12CCN(c1cnc3ccccc3n1)CC2] | 2-((6-(pyrrolidln-1-yl)pyridin-2-yl)methyl)-9-(quinoxalin-2-yl)-2,9-diazaspiro[5.5]undecan-1-one | D | 0.84 (H) | 457.6 |
| 104 | 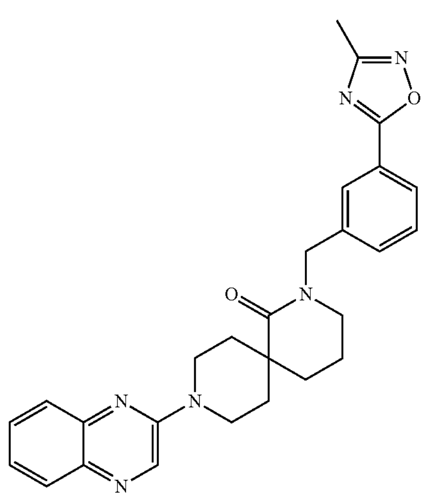 [SMILES: Cc1noc(-c2cccc(CN3CCCC4(CCN(c5cnc6ccccc6n5)CC4)C3=O)c2)n1] | 2-(3-(3-methyl-1,2,4-oxadiazol-5-yl)benzyl)-9-(quinoxalin-2-yl)-2,9-diazaspiro[5.5]undecan-1-one | D | 1.02 (H) | 469.6 |

-continued

| Ex. | Structure | Name | SM | LCMS | [M + H]+ |
|---|---|---|---|---|---|
| 105 | 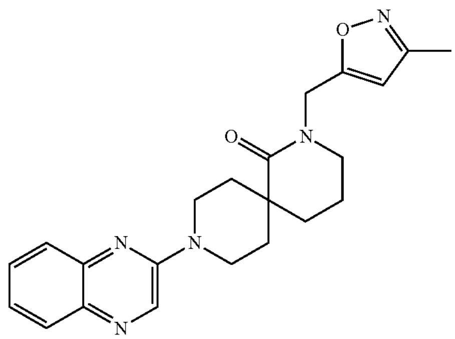 [SMILES: Cc1cc(CN2CCCC3(CCN(c4cnc5ccccc5n4)CC3)C2=O)on1] | 2-((3-methylisoxazol-5-yl)methyl)-9-(quinoxalin-2-yl)-2,9-diazaspiro[5.5]undecan-1-one | D | 0.89 (H) | 392.5 |
| 106 | 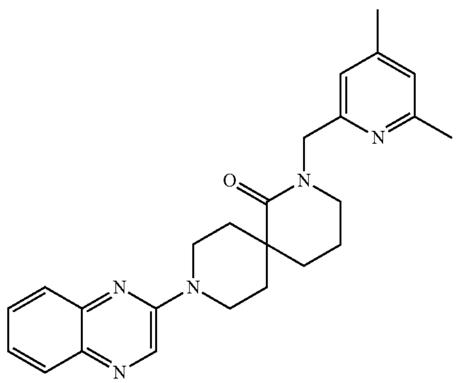 [SMILES: Cc1cc(C)nc(CN2CCCC3(CCN(c4cnc5ccccc5n4)CC3)C2=O)c1] | 2-((4,6-dimethylpyridin-2-yl)methyl)-9-(quinoxalin-2-yl)-2,9-diazaspiro[5.5]undecan-1-one | D | 0.77 (H) | 416.5 |
| 107 | 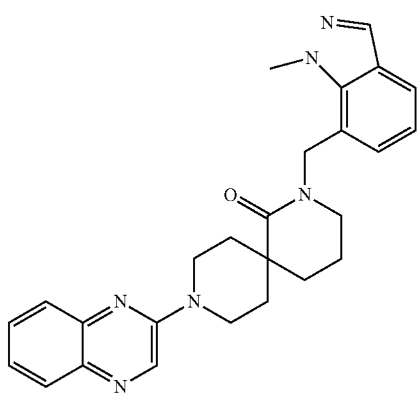 [SMILES: CNc1c(C=N)cccc1CN1CCCC2(CCN(c3cnc4ccccc4n3)CC2)C1=O] | 2-((1-methyl-1H-indazol-7-yl)methyl)-9-(quinoxalin-2-yl)-2,9-diazaspiro[5.5]undecan-1-one | D | 0.98 (H) | 441.6 |
| 108 | 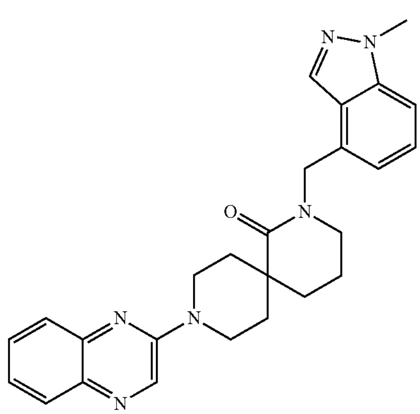 [SMILES: Cn1ncc2c(CN3CCCC4(CCN(c5cnc6ccccc6n5)CC4)C3=O)cccc21] | 2-((1-methyl-1H-indazol-4-yl)methyl)-9-(quinoxalin-2-yl)-2,9-diazaspiro[5.5]undecan-1-one | D | 0.97 (H) | 441.6 |

| Ex. | Structure | Name | SM | LCMS | [M + H]+ |
|---|---|---|---|---|---|
| 109 | 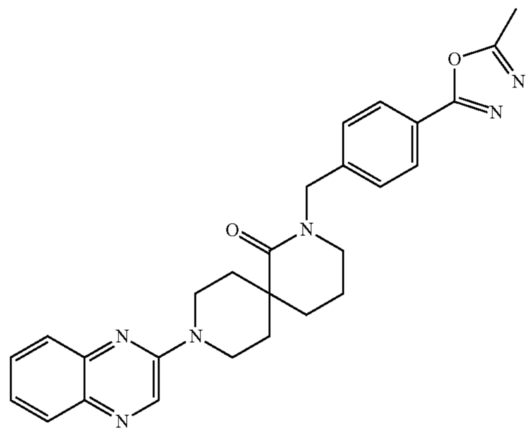 [SMILES: CC(=N)OC(=N)c1ccc(CN2CCCC3(CCN(c4cnc5ccccc5n4)CC3)C2=O)cc1] | 2-(4-(5-methyl-1,3,4-oxadiazol-2-yl)benzyl)-9-(quinoxalin-2-yl)-2,9-diazaspiro[5.5]undecan-1-one | D | 0.93 (H) | 469.6 |
| 110 | 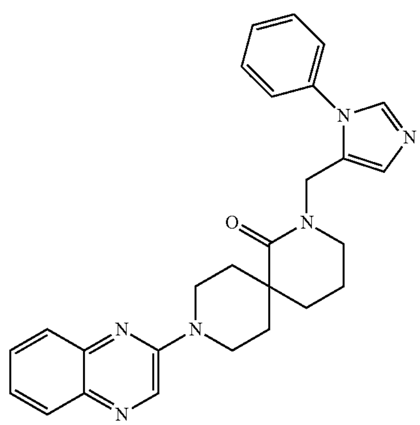 [SMILES: O=C1N(Cc2cncn2-c2ccccc2)CCCC12CCN(c1cnc3ccccc3n1)CC2] | 2-((1-phenyl-1H-imidazol-5-yl)methyl)-9-(quinoxalin-2-yl)-2,9-diazaspiro[5.5]undecan-1-one | D | 0.80 (H) | 453.6 |
| 111 | 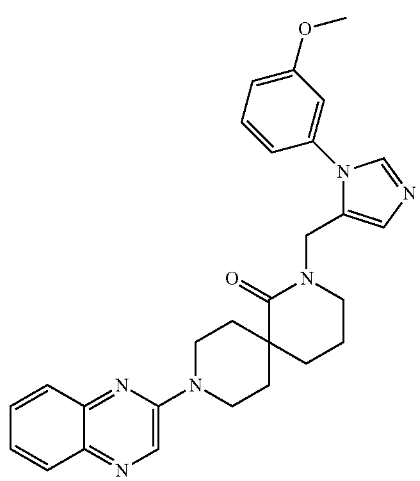 [SMILES: COc1cccc(-n2cncc2CN2CCCC3(CCN(c4cnc5ccccc5n4)CC3)C2=O)c1] | 2-((1-(3-methoxyphenyl)-1H-imidazol-5-yl)methyl)-9-(quinoxalin-2-yl)-2,9-diazaspiro[5.5]undecan-1-one | D | 0.82 (H) | 483.6 |

-continued

| Ex. | Structure | Name | SM | LCMS | [M + H]+ |
|---|---|---|---|---|---|
| 112 | 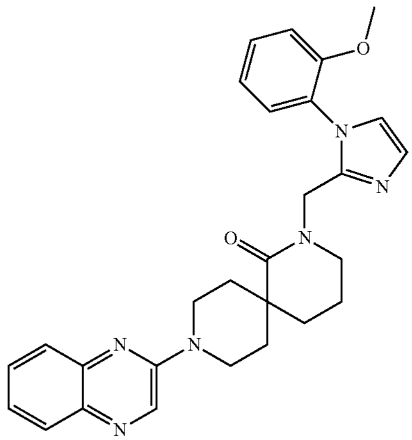 [SMILES: COc1ccccc1-n1ccnc1CN1CCCC2(CCN(c3cnc4ccccc4n3)CC2)C1=O] | 2-((1-(2-methoxyphenyl)-1H-imidazol-2-yl)methyl)-9-(quinoxalin-2-yl)-2,9-diazaspiro[5.5]undecan-1-one | D | 0.83 (H) | 483.6 |
| 113 | 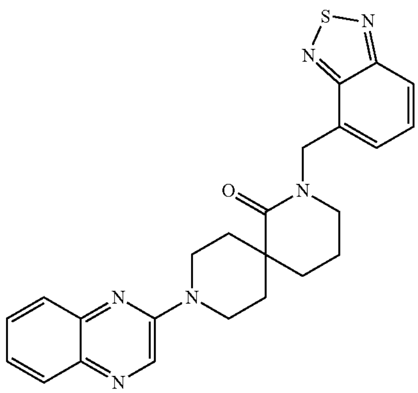 [SMILES: O=C1N(Cc2cccc3nsnc23)CCCC12CCN(c1cnc3ccccc3n1)CC2] | 2-(benzo[c][1,2,5]thiadiazol-4-ylmethyl)-9-(quinoxalin-2-yl)-2,9-diazaspiro[5.5]undecan-1-one | D | 1.02 (H) | 445.6 |
| 114 | 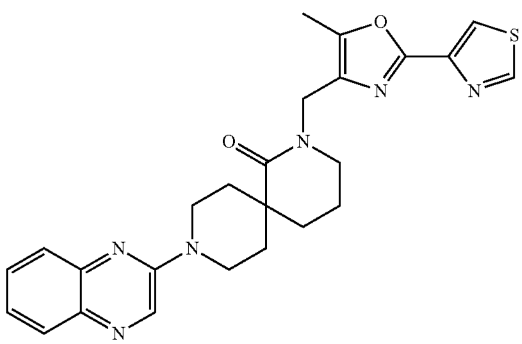 [SMILES: Cc1oc(-c2cscn2)nc1CN1CCCC2(CCN(c3cnc4ccccc4n3)CC2)C1=O] | 2-((5-methyl-2-(thiazol-4-yl)oxazol-4-yl)methyl)-9-(quinoxalin-2-yl)-2,9-diazaspiro[5.5]undecan-1-one | D | 0.90 (H) | 475.6 |
| 115 | 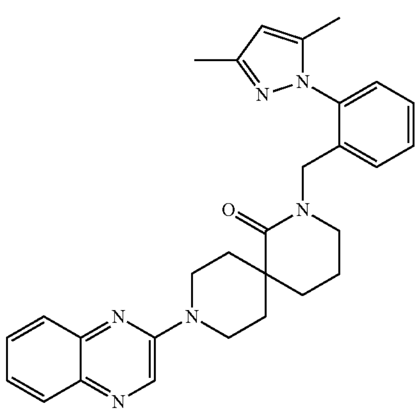 [SMILES: Cc1cc(C)n(-c2ccccc2CN2CCCC3(CCN(c4cnc5ccccc5n4)CC3)C2=O)n1] | 2-(2-(3,5-dimethyl-1H-pyrazol-1-yl)benzyl)-9-(quinoxalin-2-yl)-2,9-diazaspiro[5.5]undecan-1-one | D | 1.00 (H) | 481.6 |

| Ex. | Structure | Name | SM | LCMS | [M + H]+ |
|---|---|---|---|---|---|
| 116 | 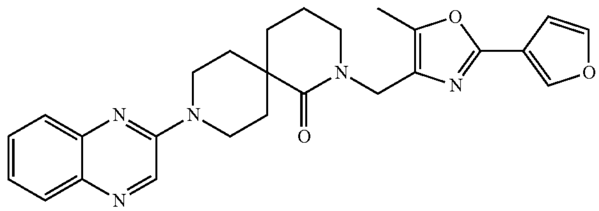 [SMILES: Cc1oc(-c2ccoc2)nc1CN1CCCC2(CCN(c3cnc4ccccc4n3)CC2)C1=O] | 2-((2-(furan-3-yl)-5-methyloxazol-4-yl)methyl)-9-(quinoxalin-2-yl)-2,9-diazaspiro[5.5]undecan-1-one | D | 2.36 (D) | 458.2 |
| 117 | 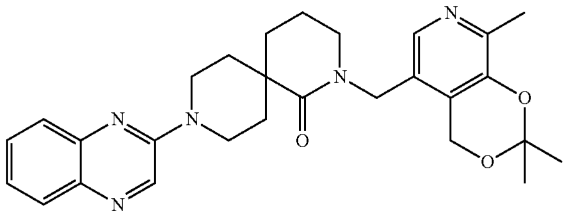 [SMILES: Cc1ncc(CN2CCCC3(CCN(c4cnc5ccccc5n4)CC3)C2=O)c2c1OC(C)(C)OC2] | 9-(quinoxalin-2-yl)-2-((2,2,8-trimethyl-4H-[1,3]dioxino[4,5-c]pyridin-5-yl)methyl)-2,9-diazaspiro[5.5]undecan-1-one | D | 2.71 (C) | 488.2 |
| 118 | 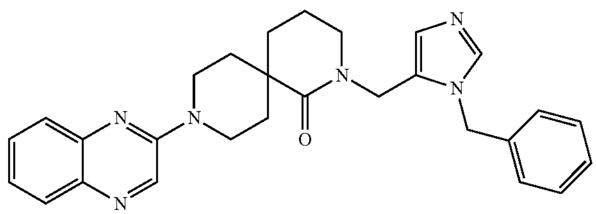 [SMILES: O=C1N(Cc2cncn2Cc2ccccc2)CCCC12CCN(c1cnc3ccccc3n1)CC2] | 2-((1-benzyl-1H-imidazol-5-yl)methyl)-9-(quinoxalin-2-yl)-2,9-diazaspiro[5.5]undecan-1-one | D | 2.72 (D) | 467.2 |
| 119 | 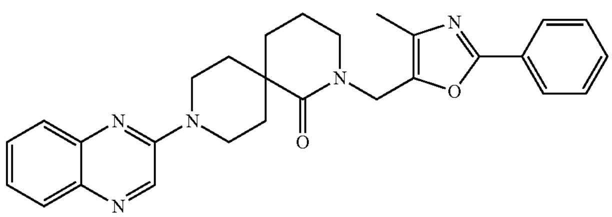 [SMILES: Cc1nc(-c2ccccc2)oc1CN1CCCC2(CCN(c3cnc4ccccc4n3)CC2)C1=O] | 2-((4-methyl-2-phenyloxazol-5-yl)methyl)-9-(quinoxalin-2-yl)-2,9-diazaspiro[5.5]undecan-1-one | D | 3.30 (C) | 468.2 |
| 120 | 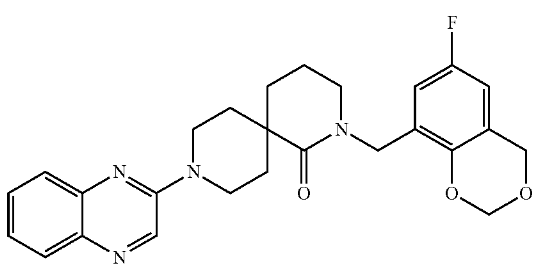 [SMILES: O=C1N(Cc2cc(F)cc3c2OCOC3)CCCC12CCN(c1cnc3ccccc3n1)CC2] | 2-((6-fluoro-4H-benzo[d][1,3]dioxin-8-yl)methyl)-9-(quinoxalin-2-yl)-2,9-diazaspiro[5.5]undecan-1-one | D | 3.20 (C) | 463.2 |
| 121 | 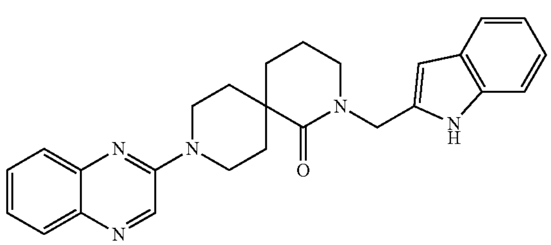 [SMILES: O=C1N(Cc2cc3ccccc3[nH]2)CCCC12CCN(c1cnc3ccccc3n1)CC2] | 2-((1H-indol-2-yl)methyl)-9-(quinoxalin-2-yl)-2,9-diazaspiro[5.5]undecan-1-one | D | 2.71 (D) | 426.2 |
| 122 | 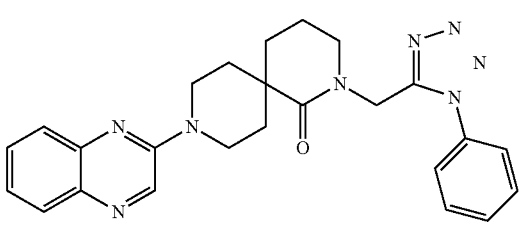 | 2-((1-phenyl-1H-tetrazol-5-yl)methyl)-9-(quinoxalin-2-yl)-2,9-diazaspiro[5.5]undecan-1-one | D | 3.00 (C) | 455.2 |

-continued

| Ex. | Structure | Name | SM | LCMS | [M + H]+ |
|---|---|---|---|---|---|
| 123 | 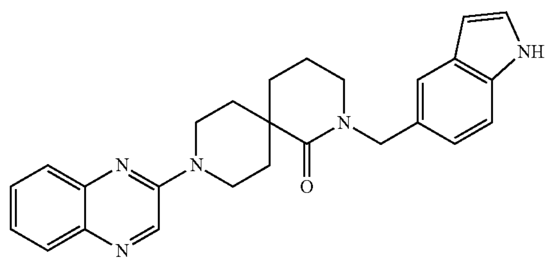 [SMILES: O=C1N(Cc2ccc3[nH]ccc3c2)CCCC12CCN(c1cnc3ccccc3n1)CC2] | 2-((1H-indol-5-yl)methyl)-9-(quinoxalin-2-yl)-2,9-diazaspiro[5.5]undecan-1-one | D | 2.31 (D) | 426.2 |
| 124 | 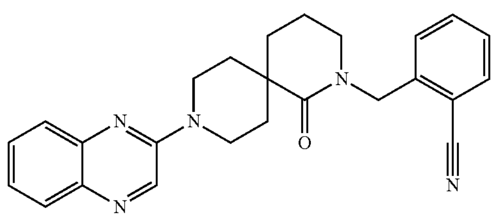 [SMILES: N#Cc1ccccc1CN1CCCC2(CCN(c3cnc4ccccc4n3)CC2)C1=O] | 2-((1-oxo-9-(quinoxalin-2-yl)-2,9-diazaspiro[5.5]undecan-2-yl)methyl)benzonitrile | D | 3.13 (C) | 412.2 |
| 125 | 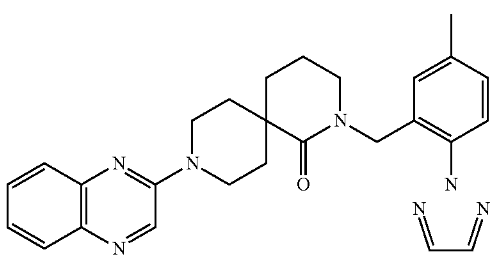 | 2-(5-methyl-2-(2H-1,2,3-triazol-2-yl)benzyl)-9-(quinoxalin-2-yl)-2,9-diazaspiro[5.5]undecan-1-one | D | 1.65 (E) | 468.2 |
| 126 | 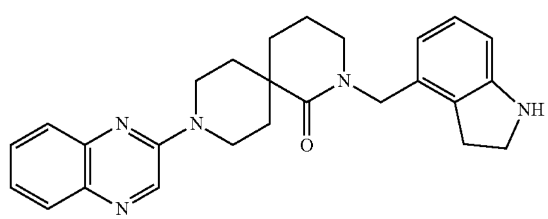 [SMILES: O=C1N(Cc2cccc3c2CCN3)CCCC12CCN(c1cnc3ccccc3n1)CC2] | 2-(indolin-4-ylmethyl)-9-(quinoxalin-2-yl)-2,9-diazaspiro[5.5]undecan-1-one | D[2] | 0.21 (F) | 428.2 |
| 127 | 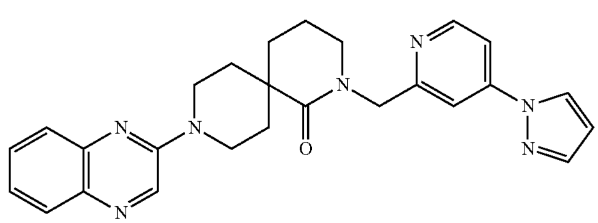 [SMILES: O=C1N(Cc2cc(-n3cccn3)ccn2)CCCC12CCN(c1cnc3ccccc3n1)CC2] | 2-((4-(1H-pyrazol-1-yl)pyridin-2-yl)methyl)-9-(quinoxalin-2-yl)-2,9-diazaspiro[5.5]undecan-1-one | D | 1.36 (F) | 454.1 |
| 128 | 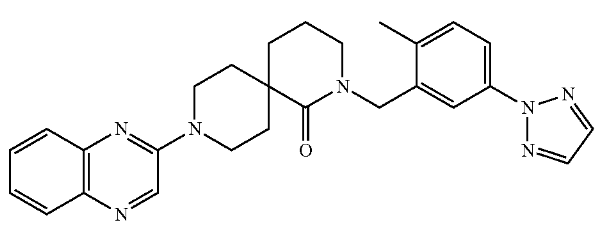 [SMILES: Cc1ccc(-n2nccn2)cc1CN1CCCC2(CCN(c3cnc4ccccc4n3)CC2)C1=O] | 2-(2-methyl-5-(2H-1,2,3-triazol-2-yl)benzyl)-9-(quinoxalin-2-yl)-2,9-diazaspiro[5.5]undecan-1-one | D | 1.95 (F) | 468.1 |

| Ex. | Structure | Name | SM | LCMS | [M + H]+ |
|---|---|---|---|---|---|
| 129 | 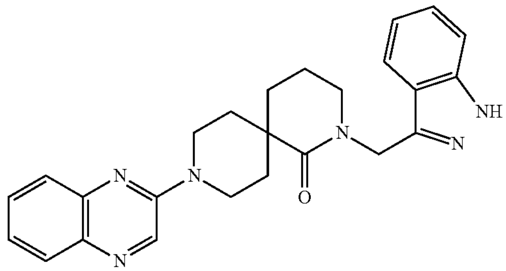 [SMILES: N=C(CN1CCCC2(CCN(c3cnc4ccccc4n3)CC2)C1=O)c1ccccc1N] | 2-((1H-indazol-3-yl)methyl)-9-(quinoxalin-2-yl)-2,9-diazaspiro[5.5]undecan-1-one | D | 1.38 (E) | 427.2 |
| 130 | 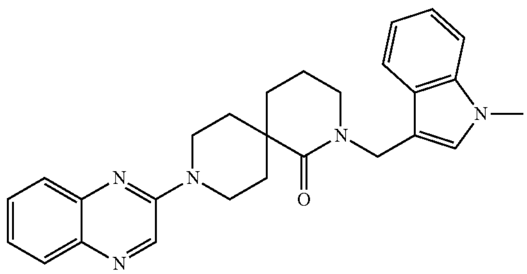 [SMILES: Cn1cc(CN2CCCC3(CCN(c4cnc5ccccc5n4)CC3)C2=O)c2ccccc21] | 2-((1-methyl-1H-indol-3-yl)methyl)-9-(quinoxalin-2-yl)-2,9-diazaspiro[5.5]undecan-1-one | $Q^1$ | 2.80 (D) | 440.2 |
| 131 | 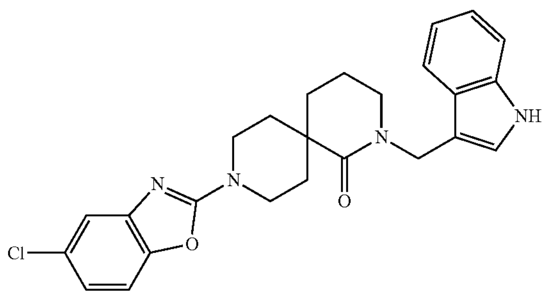 [SMILES: O=C1N(Cc2c[nH]c3ccccc23)CCCC12CCN(c1nc3cc(Cl)ccc3o1)CC2] | 2-((1H-indol-3-yl)methyl)-9-(5-chlorobenzo[d]oxazol-2-yl)-2,9-diazaspiro[5.5]undecan-1-one | E | 1.73 (E) | 449.1 |
| 132 | 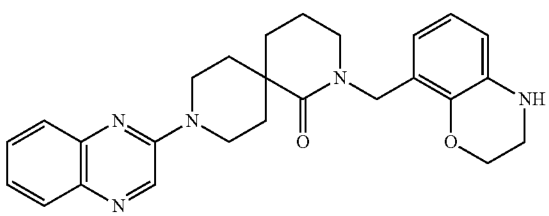 [SMILES: O=C1N(Cc2cccc3c2OCCN3)CCCC12CCN(c1cnc3ccccc3n1)CC2] | 2-((3,4-dihydro-2H-benzo[b][1,4]oxazin-8-yl)methyl)-9-(quinoxalin-2-yl)-2,9-diazaspiro[5.5]undecan-1-one | $E^3$ | 1.32 (E) | 444.2 |
| 133 | 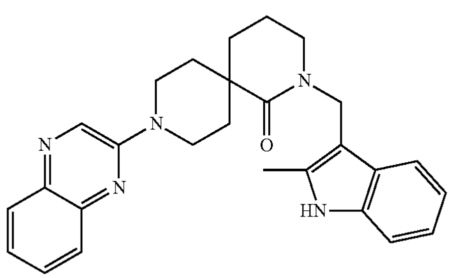 [SMILES: Cc1[nH]c2ccccc2c1CN1CCCC2(CCN(c3cnc4ccccc4n3)CC2)C1=O] | 2-((2-methyl-1H-indol-3-yl)methyl)-9-(quinoxalin-2-yl)-2,9-diazaspiro[5.5]undecan-1-one | E | 1.61 (F) | 440.0 |
| 134 | 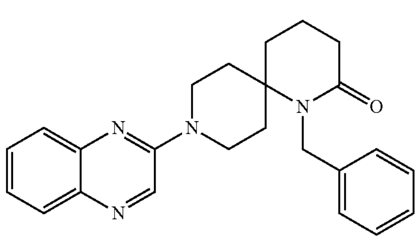 [SMILES: O=C1CCCC2(CCN(c3cnc4ccccc4n3)CC2)N1Cc1ccccc1] | 1-benzyl-9-(quinoxalin-2-yl)-1,9-diazaspiro[5.5]undecan-2-one | F | 1.59 (E) | 387.3 |

| Ex. | Structure | Name | SM | LCMS | [M + H]⁺ |
|---|---|---|---|---|---|
| 135 | 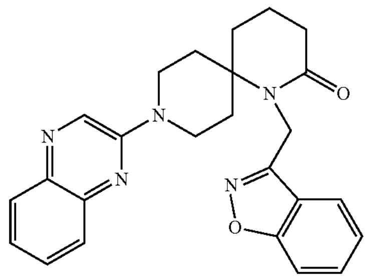 [SMILES: O=C1CCCC2(CCN(c3cnc4ccccc4n3)CC2)N1Cc1noc2ccccc12] | 1-(benzo[d]isoxazol-3-ylmethyl)-9-(quinoxalin-2-yl)-1,9-diazaspiro[5.5]undecan-2-one | F | 1.46 (E) | 428.1 |
| 136 | 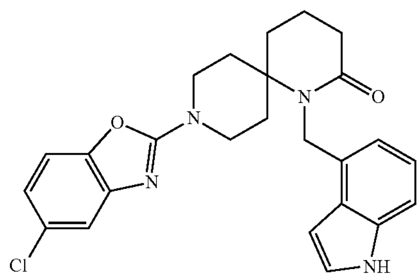 [SMILES: O=C1CCCC2(CCN(c3nc4cc(Cl)ccc4o3)CC2)N1Cc1cccc2[nH]ccc12] | 1-((1H-indol-4-yl)methyl)-9-(5-chlorobenzo[d]oxazol-2-yl)-1,9-diazaspiro[5.5]undecan-2-one | G | 1.57 (E) | 449.1 |
| 137 | 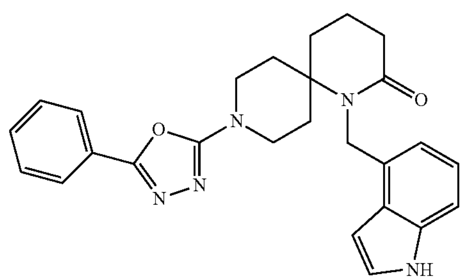 [SMILES: O=C1CCCC2(CCN(c3nnc(-c4ccccc4)o3)CC2)N1Cc1cccc2[nH]ccc12] | 1-((1H-indol-4-yl)methyl)-9-(5-phenyl-1,3,4-oxadiazol-2-yl)-1,9-diazaspiro[5.5]undecan-2-one | G | 1.29 (F) | 442.2 |
| 138 | 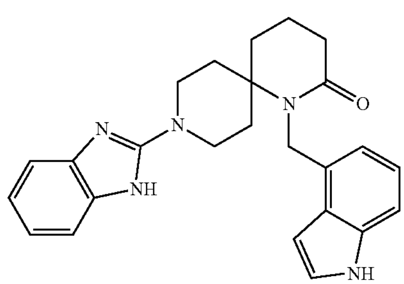 [SMILES: O=C1CCCC2(CCN(c3nc4ccccc4[nH]3)CC2)N1Cc1cccc2[nH]ccc12] | 1-((1H-indol-4-yl)methyl)-9-(1H-benzo[d]imidazol-2-yl)-1,9-diazaspiro[5.5]undecan-2-one | G | 0.12 (E) | 414.1 |
| 139 | 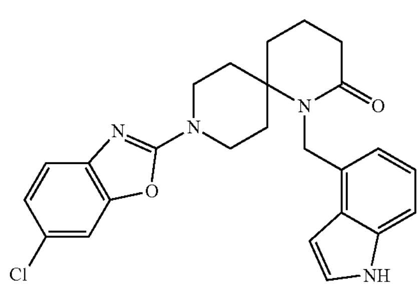 [SMILES: O=C1CCCC2(CCN(c3nc4ccc(Cl)cc4o3)CC2)N1Cc1cccc2[nH]ccc12] | 1-((1H-indol-4-yl)methyl)-9-(6-chlorobenzo[d]oxazol-2-yl)-1,9-diazaspiro[5.5]undecan-2-one | G | 1.54 (F) | 449.0 |

-continued

| Ex. | Structure | Name | SM | LCMS | [M + H]⁺ |
|---|---|---|---|---|---|
| 140 | 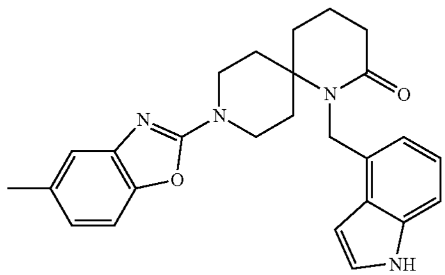 [SMILES: Cc1ccc2oc(N3CCC4(CCCC(=O)N4Cc4cccc5[nH]ccc45)CC3)nc2c1] | 1-((1H-indol-4-yl)methyl)-9-(5-methylbenzo[d]oxazol-2-yl)-1,9-diazaspiro[5.5]undecan-2-one | G | 1.43 (F) | 429.0 |
| 141 | 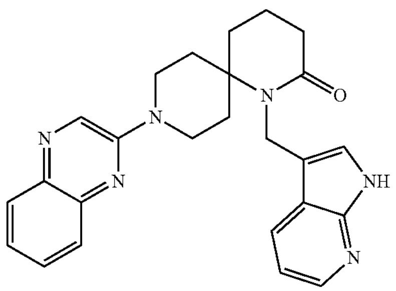 [SMILES: O=C1CCCC2(CCN(c3cnc4ccccc4n3)CC2)N1Cc1c[nH]c2ncccc12] | 1-((1H-pyrrolo[2,3-b]pyridin-3-yl)methyl)-9-(quinoxalin-2-yl)-1,9-diazaspiro[5.5]undecan-2-one | H | 0.28 (E) | 427.2 |
| 142 | 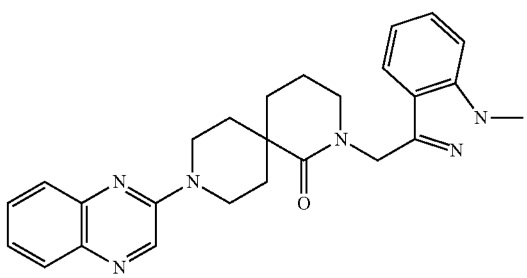 [SMILES: CNc1ccccc1C(=N)CN1CCCC2(CCN(c3cnc4ccccc4n3)CC2)C1=O] | 2-((1-methyl-1H-indazol-3-yl)methyl)-9-(quinoxalin-2-yl)-2,9-diazaspiro[5.5]undecan-1-one | D¹ | 1.82 (F) | 441.0 |
| 143 | 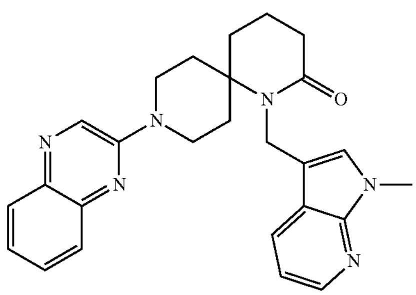 [SMILES: Cn1cc(CN2C(=O)CCCC23CCN(c2cnc4ccccc4n2)CC3)c2cccnc21] | 1-((1-methyl-1H-pyrrolo[2,3-b]pyridin-3-yl)methyl)-9-(quinoxalin-2-yl)-1,9-diazaspiro[5.5]undecan-2-one | H⁴ | 0.83 (F) | 441.2 |
| 144 | 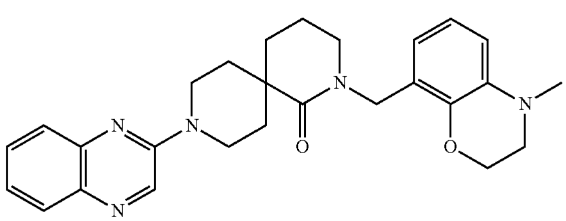 [SMILES: CN1CCOc2c(CN3CCCC4(CCN(c5cnc6ccccc6n5)CC4)C3=O)cccc21] | 2-((4-methyl-3,4-dihydro-2H-benzo[b][1,4]oxazin-8-yl)methyl)-9-(quinoxalin-2-yl)-2,9-diazaspiro[5.5]undecan-1-one | E⁵ | 1.66 (E) | 458.2 |
| 145 | 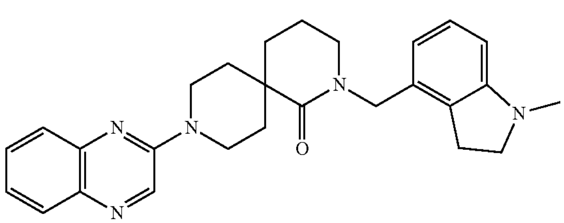 [SMILES: CN1CCc2c(CN3CCCC4(CCN(c5cnc6ccccc6n5)CC4)C3=O)cccc21] | 2-((1-methylindolin-4-yl)methyl)-9-(quinoxalin-2-yl)-2,9-diazaspiro[5.5]undecan-1-one | D⁶ | 1.79 (F) | 442.1 |

-continued

| Ex. | Structure | Name | SM | LCMS | [M + H]+ |
|---|---|---|---|---|---|
| 146 | 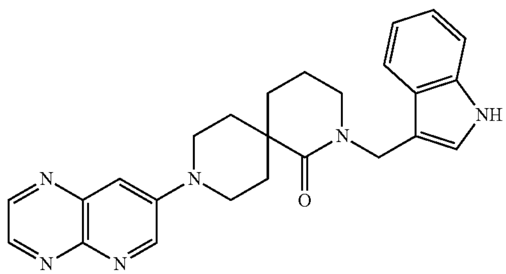 [SMILES: O=C1N(Cc2c[nH]c3ccccc23)CCCC12CCN(c1cnc3nccnc3c1)CC2] | 2-((1H-indol-3-yl)methyl)-9-(pyrido[3,2-b]pyrazin-7-yl)-2,9-diazaspiro[5.5]undecan-1-one | M | 0.87 (A) | 427.0 |
| 147 | 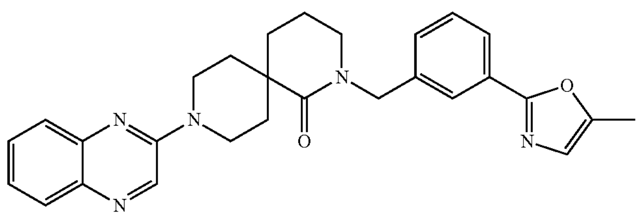 [SMILES: Cc1cnc(-c2cccc(CN3CCCC4(CCN(c5cnc6ccccc6n5)CC4)C3=O)c2)o1] | 2-(3-(5-methyloxazol-2-yl)benzyl)-9-(quinoxalin-2-yl)-2,9-diazaspiro[5.5]undecan-1-one | N | 1.22 (A) | 468.5 |
| 148 | 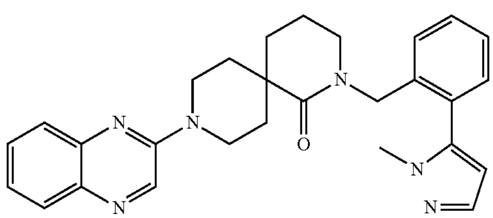 [SMILES: CN/C(=C\C=N)c1ccccc1CN1CCCC2(CCN(c3cnc4ccccc4n3)CC2)C1=O] | 2-(2-(1-methyl-1H-pyrazol-5-yl)benzyl)-9-(quinoxalin-2-yl)-2,9-diazaspiro[5.5]undecan-1-one | P | 3.11 (C) | 467.2 |
| 149 | 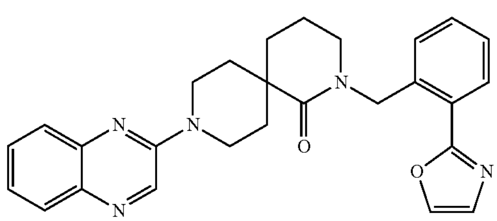 [SMILES: O=C1N(Cc2ccccc2-c2ncco2)CCCC12CCN(c1cnc3ccccc3n1)CC2] | 2-(2-(oxazol-2-yl)benzyl)-9-(quinoxalin-2-yl)-2,9-diazaspiro[5.5]undecan-1-one | P | 3.21 (C) | 454.2 |
| 150 | 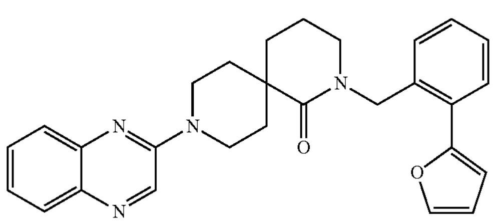 [SMILES: O=C1N(Cc2ccccc2-c2ccco2)CCCC12CCN(c1cnc3ccccc3n1)CC2] | 2-(2-(furan-2-yl)benzyl)-9-(quinoxalin-2-yl)-2,9-diazaspiro[5.5]undecan-1-one | P | 2.96 (D) | 453.2 |
| 151 | 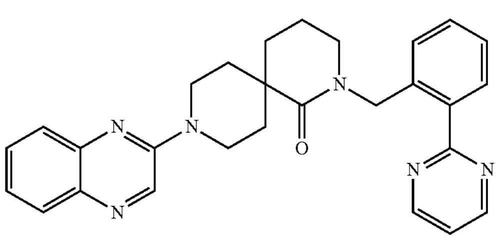 [SMILES: O=C1N(Cc2ccccc2-c2ncccn2)CCCC12CCN(c1cnc3ccccc3n1)CC2] | 2-(2-(pyrimidin-2-yl)benzyl)-9-(quinoxalin-2-yl)-2,9-diazaspiro[5.5]undecan-1-one | P | 2.97 (C) | 465.2 |

-continued

| Ex. | Structure | Name | SM | LCMS | [M + H]+ |
|---|---|---|---|---|---|
| 152 | 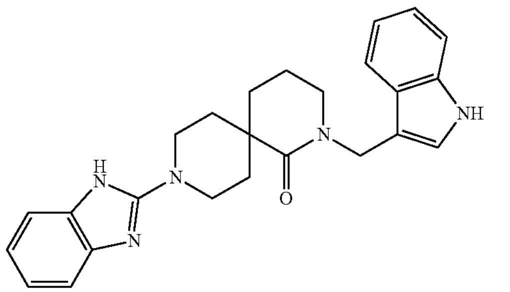 [SMILES: O=C1N(Cc2c[nH]c3ccccc23)CCCC12CCN(c1nc3ccccc3[nH]1)CC2] | 2-((1H-indol-3-yl)methyl)-9-(1H-benzo[d]imidazol-2-yl)-2,9-diazaspiro[5.5]undecan-1-one | Q | 0.75 (A) | 414.1 |
| 153 | 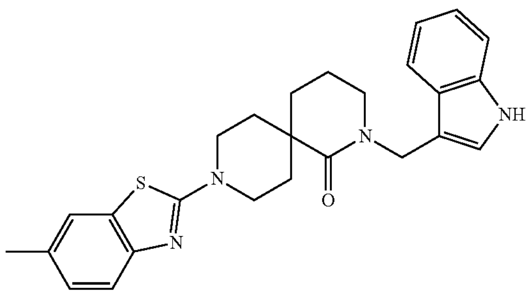 [SMILES: Cc1ccc2nc(N3CCC4(CCCN(Cc5c[nH]c6ccccc56)C4=O)CC3)sc2c1] | 2-((1H-indol-3-yl)methyl)-9-(6-methylbenzo[d]thiazol-2-yl)-2,9-diazaspiro[5.5]undecan-1-one | Q | 2.54 (D) | 445.2 |
| 154 | 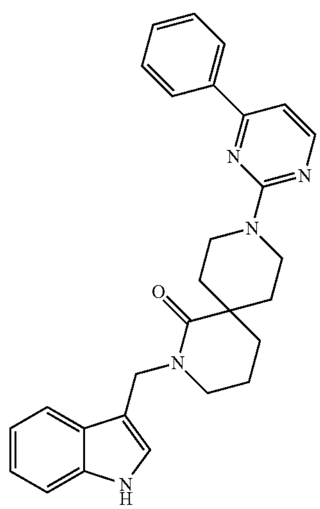 [SMILES: O=C1N(Cc2c[nH]c3ccccc23)CCCC12CCN(c1nccc(-c3ccccc3)n1)CC2] | 2-((1H-indol-3-yl)methyl)-9-(4-phenylpyrimidin-2-yl)-2,9-diazaspiro[5.5]undecan-1-one | Q | 1.13 (I) | 452.6 |
| 155 | 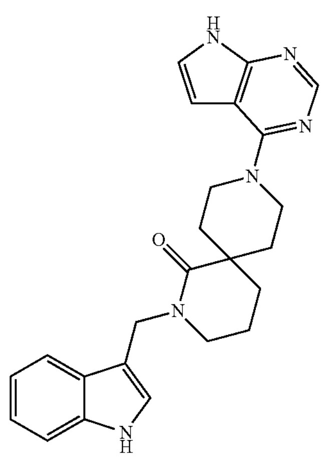 [SMILES: O=C1N(Cc2c[nH]c3ccccc23)CCCC12CCN(c1ncnc3[nH]ccc13)CC2] | 2-((1H-indol-3-yl)methyl)-9-(7H-pyrrolo[2,3-d]pyrimidin-4-yl)-2,9-diazaspiro[5.5]undecan-1-one | Q | 0.85 (A) | 415.8 |

| Ex. | Structure | Name | SM | LCMS | [M + H]+ |
|---|---|---|---|---|---|
| 156 | 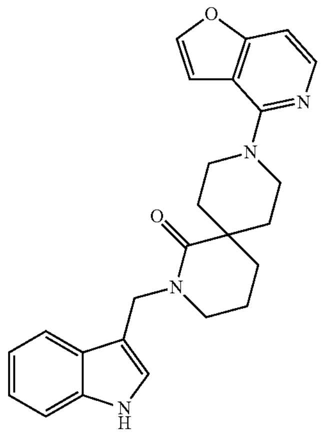 [SMILES: O=C1N(Cc2c[nH]c3ccccc23)CCCC12CCN(c1nccc3occc13)CC2] | 2-((1H-indol-3-yl)methyl)-9-(furo[3,2-c]pyridin-4-yl)-2,9-diazaspiro[5.5]undecan-1-one | Q | 2.84 (C) | 415.2 |
| 157 | 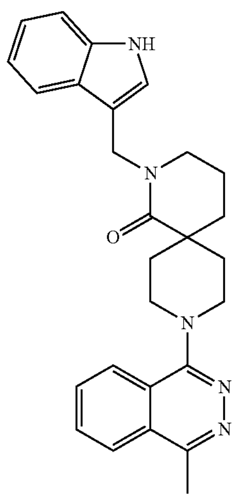 [SMILES: Cc1nnc(N2CCC3(CCCN(Cc4c[nH]c5ccccc45)C3=O)CC2)c2ccccc12] | 2-((1H-indol-3-yl)methyl)-9-(4-methylphthalazin-1-yl)-2,9-diazaspiro[5.5]undecan-1-one | Q | 0.81 (I) | 440.6 |
| 158 | 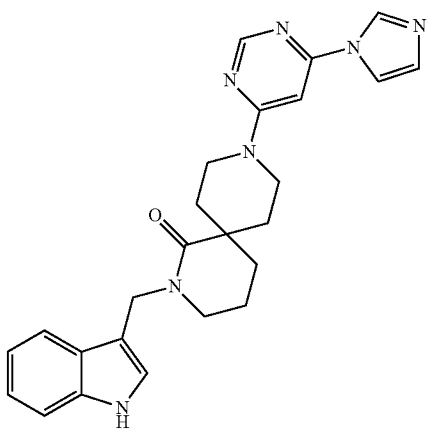 [SMILES: O=C1N(Cc2c[nH]c3ccccc23)CCCC12CCN(c1cc(-n3ccnc3)ncn1)CC2] | 9-(6-(1H-imidazo-1-yl)pyrimidin-4-yl)-2-((1H-indol-3-yl)methyl)-2,9-diazaspiro[5.5]undecan-1-one | Q | 0.81 (I) | 442.5 |
| 159 | 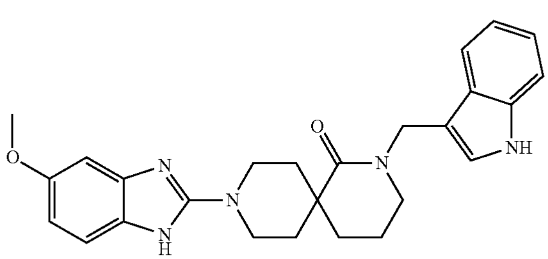 [SMILES: COc1ccc2[nH]c(N3CCC4(CCCN(Cc5c[nH]c6ccccc56)C4=O)CC3)nc2c1] | 2-((1H-indol-3-yl)methyl)-9-(5-methoxy-1H-benzo[d]imidazol-2-yl)-2,9-diazaspiro[5.5]undecan-1-one | Q | 0.82 (I) | 444.6 |

-continued

| Ex. | Structure | Name | SM | LCMS | [M + H]⁺ |
|---|---|---|---|---|---|
| 160 | 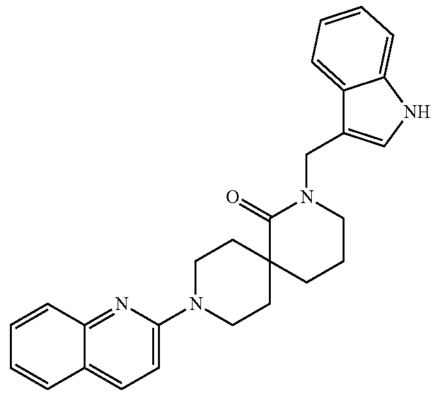 [SMILES: O=C1N(Cc2c[nH]c3ccccc23)CCCC12CCN(c1ccc3ccccc3n1)CC2] | 2-((1H-indol-3-yl)methyl)-9-(quinolin-2-yl)-2,9-diazaspiro[5.5]undecan-1-one | Q | 0.84 (I) | 425.6 |
| 161 | 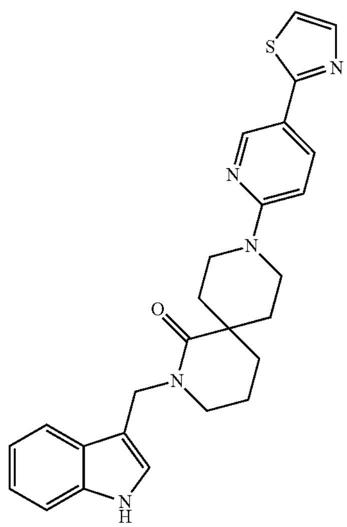 [SMILES: O=C1N(Cc2c[nH]c3ccccc23)CCCC12CCN(c1ccc(-c3nccs3)cn1)CC2] | 2-((1H-indol-3-yl)methyl)-9-(5-(thiazol-2-yl)pyridin-2-yl)-2,9-diazaspiro[5.5]undecan-1-one | Q | 0.89 (I) | 458.6 |
| 162 | 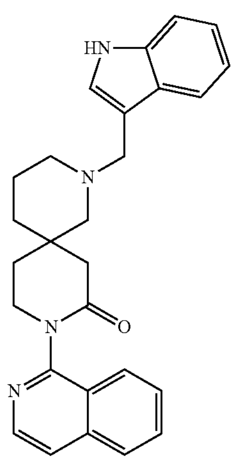 [SMILES: O=C1CC2(CCCN(Cc3c[nH]c4ccccc34)C2)CCN1c1nccc2ccccc12] | 2-((1H-indol-3-yl)methyl)-9-(isoquinolin-1-yl)-2,9-diazaspiro[5.5]undecan-1-one | Q | 0.85 (I) | 425.6 |
| 163 | 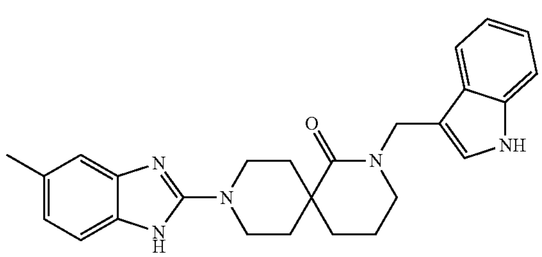 [SMILES: Cc1ccc2[nH]c(N3CCC4(CCCN(Cc5c[nH]c6ccccc56)C4=O)CC3)nc2c1] | 2-((1H-indol-3-yl)methyl)-9-(5-methyl-1H-benzo[d]imidazol-2-yl)-2,9-diazaspiro[5.5]undecan-1-one | Q | 0.84 (I) | 428.6 |

-continued

| Ex. | Structure | Name | SM | LCMS | [M + H]+ |
|---|---|---|---|---|---|
| 164 | 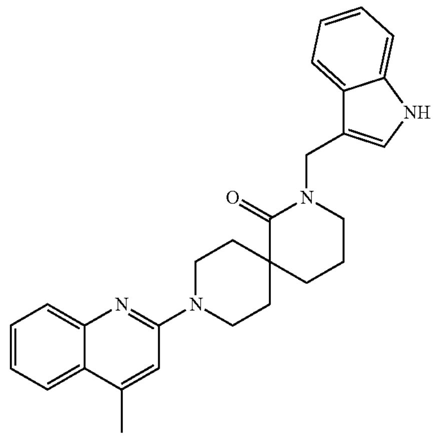 [SMILES: Cc1cc(N2CCC3(CCCN(Cc4c[nH]c5ccccc45)C3=O)CC2)nc2ccccc12] | 2-((1H-indol-3-yl)methyl)-9-(4-methylquinolin-2-yl)-2,9-diazaspiro[5.5]undecan-1-one | Q | 0.88 (I) | 439.6 |
| 165 | 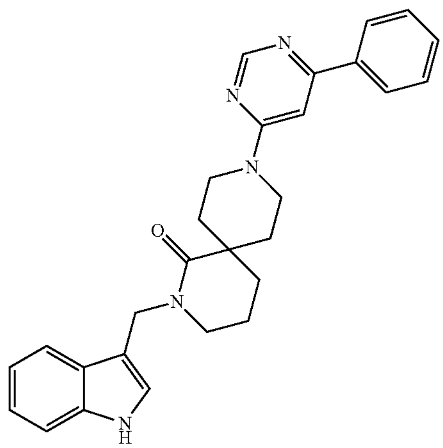 [SMILES: O=C1N(Cc2c[nH]c3ccccc23)CCCC12CCN(c1cc(-c3ccccc3)ncn1)CC2] | 2-((1H-indol-3-yl)methyl)-9-(6-phenylpyrimidin-4-yl)-2,9-diazaspiro[5.5]undecan-1-one | Q | 0.93 (A) | 452.8 |
| 166 | 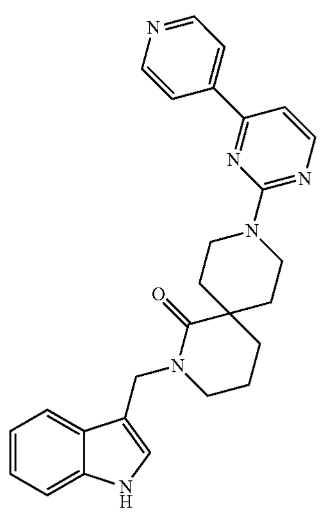 | 2-((1H-indol-3-yl)methyl)-9-(4-(pyridin-4-yl)pyrimidin-2-yl)-2,9-diazaspiro[5.5]undecan-1-one | Q | 0.87 (I) | 453.6 |
| 167 | 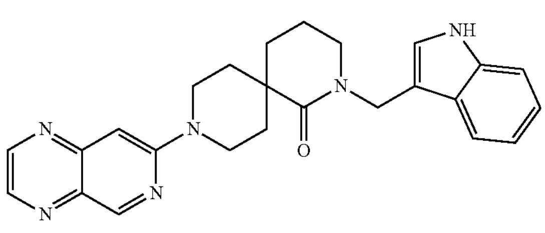 [SMILES: O=C1N(Cc2c[nH]c3ccccc23)CCCC12CCN(c1cc3nccnc3cn1)CC2] | 2-((1H-indol-3-yl)methyl)-9-(pyrido[4,3-b]pyrazin-7-yl)-2,9-diazaspiro[5.5]undecan-1-one | Q | 1.05 (A) | 427.8 |

-continued

| Ex. | Structure | Name | SM | LCMS | [M + H]+ |
|---|---|---|---|---|---|
| 168 | 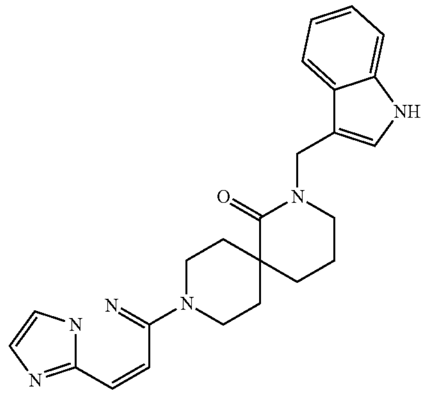 [SMILES: N=C(/C=C\c1ncc[nH]1)N1CCC2(CCCN(Cc3c[nH]c4ccccc34)C2=O)CC1] | 2-((1H-indol-3-yl)methyl)-9-(imidazo[1,2-b]pyridazin-6-yl)-2,9-diazaspiro[5.5]undecan-1-one | Q | 0.79 (I) | 415.5 |
| 169 | 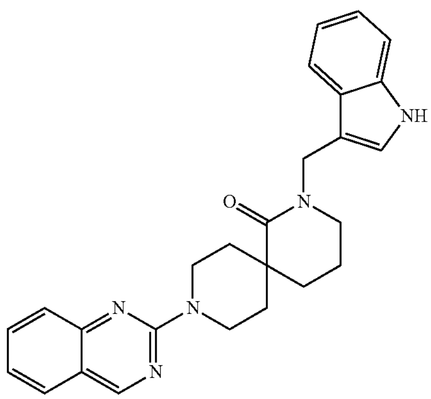 [SMILES: O=C1N(Cc2c[nH]c3ccccc23)CCCC12CCN(c1ncc3ccccc3n1)CC2] | 2-((1H-indol-3-yl)methyl)-9-(quinazolin-2-yl)-2,9-diazaspiro[5.5]undecan-1-one | Q | 0.90 (I) | 426.5 |
| 170 | 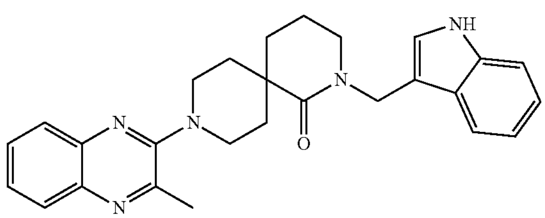 [SMILES: Cc1nc2ccccc2nc1N1CCC2(CCCN(Cc3c[nH]c4ccccc34)C2=O)CC1] | 2-((1H-indol-3-yl)methyl)-9-(3-methylquinoxalin-2-yl)-2,9-diazaspiro[5.5]undecan-1-one | Q | 1.19 (I) | 440.6 |
| 171 | 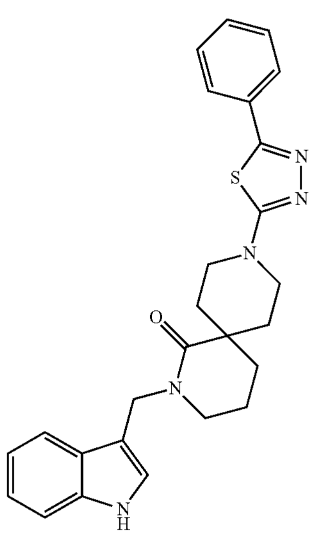 [SMILES: O=C1N(Cc2c[nH]c3ccccc23)CCCC12CCN(c1nnc(-c3ccccc3)s1)CC2] | 2-((1H-indol-3-yl)methyl)-9-(5-phenyl-1,3,4-thiadiazol-2-yl)-2,9-diazaspiro[5.5]undecan-1-one | Q | 1.18 (I) | 458.6 |

| Ex. | Structure | Name | SM | LCMS | [M + H]⁺ |
|---|---|---|---|---|---|
| 172 | 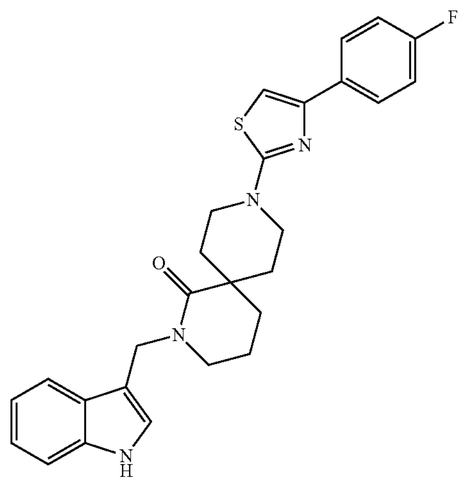 [SMILES: O=C1N(Cc2c[nH]c3ccccc23)CCCC12CCN(c1nc(-c3ccc(F)cc3)cs1)CC2] | 2-((1H-indol-3-yl)methyl)-9-(4-(4-fluorophenyl)thiazol-2-yl)-2,9-diazaspiro[5.5]undecan-1-one | Q | 1.32 (I) | 475.6 |
| 173 | 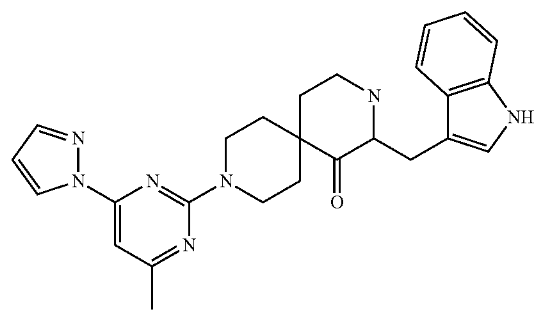 [SMILES: Cc1cc(-n2cccn2)nc(N2CCC3(CCNC(Cc4c[nH]c5ccccc45)C3=O)CC2)n1] | 2-((1H-indol-3-yl)methyl)-9-(4-methyl-6-(1H-pyrazol-1-yl)pyrimidin-2-y))-2,9-diazaspiro[5.5]undecan-1-one | Q | 1.24 (A) | 456.4 |
| 174 | 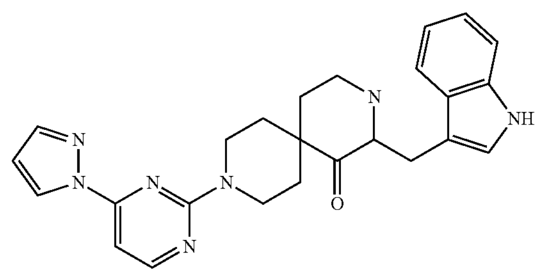 [SMILES: O=C1C(Cc2c[nH]c3ccccc23)NCCC12CCN(c1nccc(-n3cccn3)n1)CC2] | 2-((1H-indol-3-yl)methyl)-9-(4-(1H-pyrazol-1-yl)pyrimidin-2-yl)-2,9-diazaspiro[5.5]undecan-1-one | Q | 1.15 (A) | 442.4 |
| 175 | 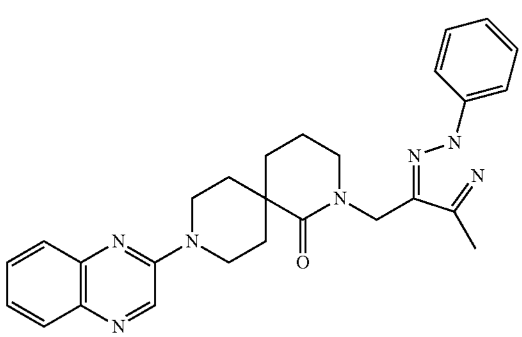 [SMILES: CC(=N)/C(CN1CCCC2(CCN(c3cnc4ccccc4n3)CC2)C1=O)=N\Nc1ccccc1] | 2-((5-methyl-2-phenyl-2H-1,2,3-triazol-4-yl)methyl)-9-(quinoxalin-2-yl)-2,9-diazaspiro[5.5]undecan-1-one | D | 1.80 (E) | 468.1 |

-continued

| Ex. | Structure | Name | SM | LCMS | [M + H]⁺ |
|---|---|---|---|---|---|
| 176 | 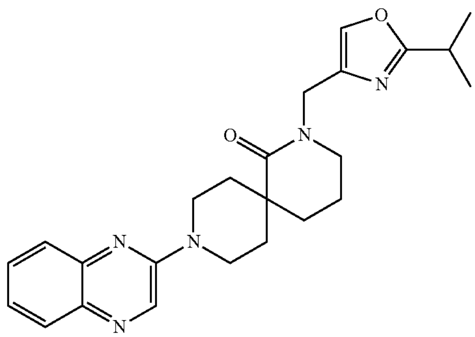 [SMILES: CC(C)c1nc(CN2CCCC3(CCN(c4cnc5ccccc5n4)CC3)C2=O)co1] | 2-((2-isopropyloxazol-4-yl)methyl)-9-(quinoxalin-2-yl)-2,9-diazaspiro[5.5]undecan-1-one | D | 0.95 (H) | 420.5 |

[1] synthesized according to the indicated synthesis method followed by alkylation with methyl iodide in the last step
[2] synthesized according to synthesis method D using building block A126 followed by deprotection with TFA in the last step
[3] synthesized according to method E using an N-tosyl protected building block, followed by deprotection with NaOMe in THF:MeOH. at 110° C. in the last step
[4] synthesized from example 141 by alkylation with methyl iodide
[5] synthesized from example 132 by alkylation with methyl iodide
[6] synthesized from example 126 by alkylation with methyl iodide Building block K49:
2-(2-(bromomethyl)phenyl)-2H-1,2,3-triazole

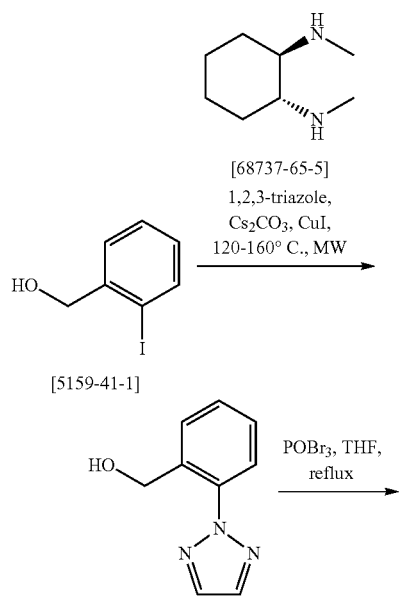

a) (2-(2H-1,2,3-triazol-2-yl)phenyl)methanol

To a mixture of (2-iodophenyl)methanol [5159-41-1] (1.50 g, 6.41 mmol), 1H-1,2,3-triazole (0.797 g, 11.54 mmol), trans-N,N'-dimethylcyclohexane-1,2-diamine [68737-65-5] (0.091 g, 0.641 mmol) and $Cs_2CO_3$ (3.76 g, 11.54 mmol) in DMF (15 mL), CuI (0.61 g, 3.20 mmol) was added and the reaction mixture was stirred for 20 min at 120° C. and 15 min at 160° C. in the microwave. The reaction mixture was cooled to rt and filtered to remove the solids. The filtrate was concentrated under reduced pressure. The residue was purified by flash-column chromatography over silicagel (eluent: gradient 10%-100% ethyl acetate/heptane) to yield the title compound (1.46 g, 64%). [¹H NMR (400 MHz, DMSO-$d_6$) ♀ ppm 8.10 (s, 2H), 7.74 (d, J=7.53 Hz, 1H), 7.61 (dd, J=8.03, 1.25 Hz, 1H), 7.52 (td, J=7.53, 1.25 Hz, 1H), 7.44 (m, 1H), 5.26 (t, J=5.40 Hz, 1H), 4.59 (d, J=5.02 Hz, 2H); LCMS $Rt_A$=0.68, [M+H]⁺=176.1].

b) 2-(2-(bromomethyl)phenyl)-2H-1,2,3-triazole

To a stirred solution of (2-(2H-1,2,3-triazol-2-yl)phenyl)methanol (37 mg, 0.209 mmol) in THF (1 mL), $PBr_3$ (0.024 mL, 0.251 mmol) was added and the mixture was heated at 70° C. for 20 min. The mixture was cooled to rt, poured into saturated aqueous $NaHCO_3$ solution and extracted with dichloromethane (2×). The organic layer was dried over anhydrous $Na_2SO_4$, filtered and concentrated under reduced pressure. The residue was purified by flash-column chromatography over silicagel (eluent: gradient 10%-100% ethyl acetate/heptane) to yield the title compound (28 mg, 54%). [¹H NMR (400 MHz, DMSO-$d_6$) ♀ ppm 8.17 (s, 2H), 7.69 (ddd, J=7.59, 3.58, 1.63 Hz, 2H), 7.53 (dqd, J=14.74, 7.51, 7.51, 7.51, 1.63 Hz, 2H), 4.96 (s, 2H); LCMS $Rt_A$=1.02, [M+H]⁺=238.2/240.2].

Building block A57:
3-(chloromethyl)-1-tosyl-1H-pyrrolo[2,3-b]pyridine

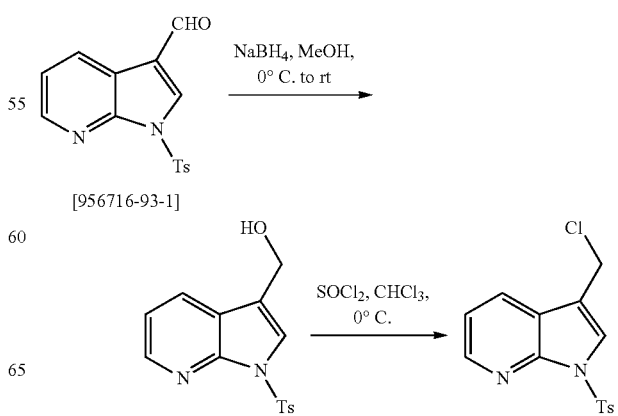

a) (1-tosyl-1H-pyrrolo[2,3-b]pyridin-3-yl)methanol

To a stirred solution of 1-tosyl-1H-pyrrolo[2,3-b]pyridine-3-carbaldehyde [956716-93-1] (2.0 g, 6.66 mmol) in methanol (20 mL) NaBH$_4$ (0.756 g, 20 mmol) was added in portions at 0° C. Then the mixture was allowed to warm to rt and stirred for 18 h. Methanol was evaporated under reduced pressure and water was added to the stirred residue. The resulting precipitate was filtered off and dried under vacuum to yield the title compound as a white solid (1.6 g, 80%). [$^1$H NMR (400 MHz, CHLOROFORM-d) ♀ ppm 8.45 (dd, J=4.8, 3.2 Hz, 1H), 8.07 (d, J=8.4 Hz, 2H), 7.96 (dd, J=8.0, 1.6 Hz, 1H), 7.70 (s, 1H), 7.26 (d, J=8.4 Hz, 2H), 7.20 (dd, J=7.6, 4.8 Hz, 1H), 4.83 (d, J=5.2 Hz, 2H), 2.37 (s, 3H), 1.73 (t, J=5.2 Hz, 1H); LCMS Rt$_E$=0.85, [M+H]$^+$=302.8].

b) 3-(chloromethyl)-1-tosyl-1H-pyrrolo[2,3-b]pyridine

To a stirred solution of (1-tosyl-1H-pyrrolo[2,3-b]pyridin-3-yl)methanol (100 mg, 0.331 mmol) in THF (5 mL) POCl$_3$ (76.2 mg, 0.496 mmol) was added dropwise at 0° C. and stirred for 15 min and then refluxed for 2 h. Then the reaction mixture was quenched with saturated aqueous NaHCO$_3$ solution and extracted with ethyl acetate (2×). The organic layer was dried over anhydrous Na$_2$SO$_4$, filtered and concentrated under reduced pressure at 45° C. The title compound was obtained as a solid (80 mg, 76%). Due to the instability, this compound was used immediately for the next step. [LCMS Rt$_E$=1.75, [M+H]$^+$=320.7].

Building block A58: 4-(3-(chloromethyl)phenyl)pyridine

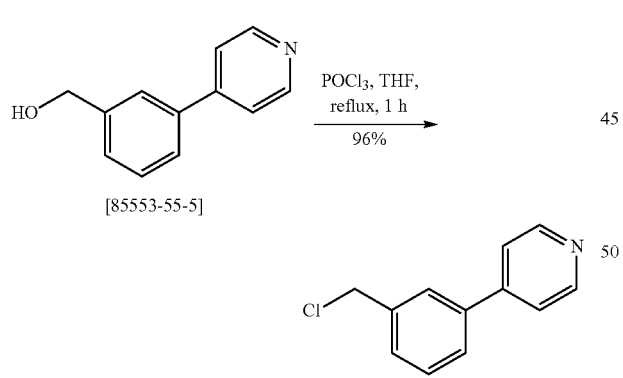

To a stirred solution of (3-(pyridin-4-yl)phenyl)methanol [85553-55-5] (200 mg, 1.08 mmol) in THF (5 mL) POCl$_3$ (215 mg, 1.40 mmol) was added dropwise at 0° C. and stirred for 15 min and then refluxed for 1 h. Then the reaction mixture was quenched with saturated aqueous NaHCO$_3$ solution (50 mL) and extracted with ethyl acetate (2×50 mL). The organic layer was dried over anhydrous Na$_2$SO$_4$, filtered and concentrated under reduced pressure at 45° C. to yield title compound (212 mg, 97%). [LCMS Rt$_F$=0.35 min, [M+H]$^+$=203.9].

Building block A61: 2-(3-(bromomethyl)phenyl)pyrimidine

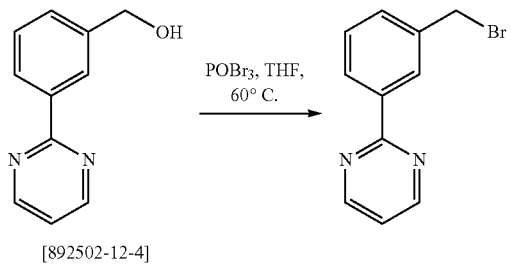 [SMILES: OCc1cccc(-c2ncccn2)c1 ; BrCc1cccc(-c2ncccn2)c1]

To a stirred solution of (3-(pyrimidin-2-yl)phenyl)methanol [892502-12-4] (2.48 g, 12.92 mmol) in THF (25 mL), POBr$_3$ (4.81 g, 16.79 mmol) was added and the mixture was heated at 60° C. for 90 min. The mixture was cooled to rt, poured into saturated aqueous NaHCO$_3$ solution and extracted with ethyl acetate (2×). The combined organic layers were dried over anhydrous Na$_2$SO$_4$, filtered and concentrated under reduced pressure. The residue was purified by flash-column chromatography over silicagel (eluent: gradient 5%-40% ethyl acetate/heptane) to yield the title compound (2.59 g, 80%). [$^1$H NMR (400 MHz, DMSO-d$_6$) ♀ ppm 8.92 (d, J=5.0 Hz, 2H), 8.48 (t, J=1.6 Hz, 1H), 8.32 (dt, J=7.7, 1.4 Hz, 1H), 7.58-7.62 (m, 1H), 7.49-7.54 (m, 1H), 7.47 (t, J=4.8 Hz, 1H), 4.82 (s, 2H); LCMS Rt$_A$=1.04, [M+H]$^+$=249.2/251.2].

Building block A63: 4-(bromomethyl)-2-(1H-pyrazol-1-yl)pyridine

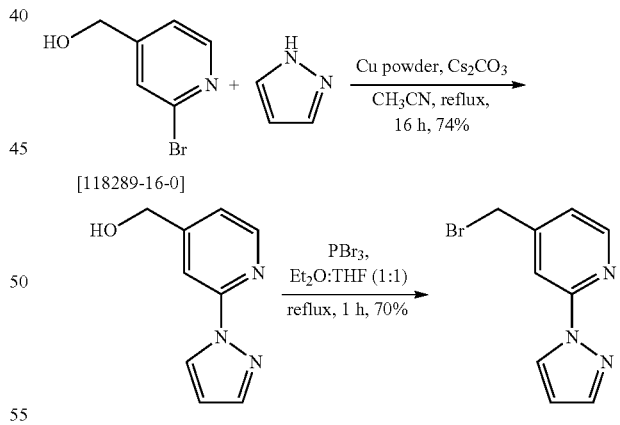

a) (2-(1H-pyrazol-1-yl)pyridin-4-yl)methanol

A mixture of (2-bromopyridin-4-yl)methanol [118289-16-0] (370 mg, 2.00 mmol), 1H-pyrazole (204 mg, 3.00 mmol), Cu powder (26 mg, 0.40 mmol) and Cs$_2$CO$_3$ (1.30 g, 4.00 mmol) in acetonitrile (4 mL) was heated under reflux for 16 h. The reaction mixture was cooled to rt and concentrated under reduced pressure. The residue was taken up in ethyl acetate and washed with water and brine, dried over anhydrous b) 4-(bromomethyl)-2-(1H-pyrazol-1-yl)pyridine To a stirred solution of (2-(1H-pyrazol-1-yl)pyridin-4-yl)methanol (175 mg, 1.00 mmol) in diethyl ether (5 mL), PBr$_3$ (0.11 mL, 1.00 mmol) was added dropwise at 0° C. Then THF (5 mL) was added to the resulting white precipitate and the mixture was heated at 65° C. for 1 h. The mixture was cooled to rt, diluted with ethyl acetate (5 mL) and poured into saturated aqueous NaHCO$_3$ solution (5 mL). The layers were separated and the aqueous layer was extracted with ethyl acetate (2×5 mL). The combined organic layers were washed with brine and dried over anhydrous Na$_2$SO$_4$, filtered and concentrated under reduced pressure to yield the title compound (165 mg, 70%). [LCMS Rt$_E$=1.33 min, [M+H]$^+$= 237.9/239.9].

Building block A65:
2-(3-(bromomethyl)phenyl)pyrazine

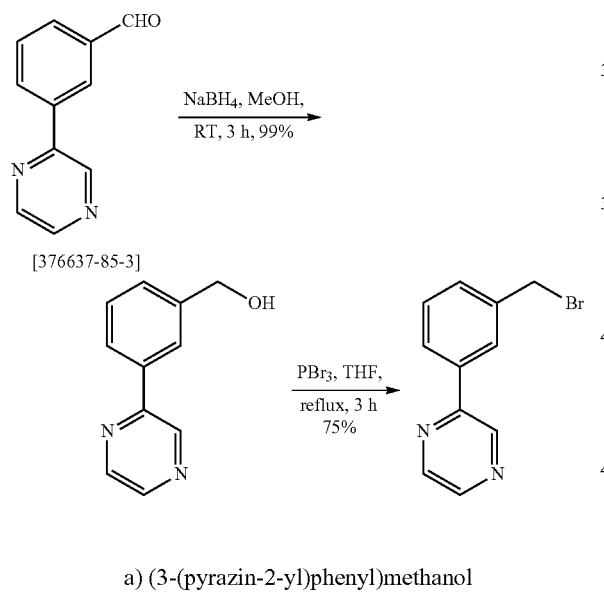

a) (3-(pyrazin-2-yl)phenyl)methanol

To a stirred solution of 3-(pyrazin-2-yl)benzaldehyde [376637-85-3] (200 mg, 1.09 mmol) in methanol (5 mL), NaBH$_4$ (82 mg, 2.17 mmol) was added at 0° C. and stirred for 10 min. Then the mixture was allowed to warm to rt and stirred for 3 h. The mixture was concentrated under reduced pressure at 45° C., saturated aqueous NH$_4$Cl solution was added and extracted with ethyl acetate (2×5 mL). The combined organic layers were washed with brine and dried over anhydrous Na$_2$SO$_4$, filtered and concentrated under reduced pressure to yield the title compound as a liquid (200 mg, 99%). [LCMS Rt$_E$=0.20 min, [M+H]$^+$=187.0; TLC R$_f$=0.26 (ethyl acetate/hexane 50:50)].

b) 2-(3-(bromomethyl)phenyl)pyrazine

To a stirred solution of (3-(pyrazin-2-yl)phenyl)methanol (200 mg, 1.08 mmol) in THF (5 mL), PBr$_3$ (349 mg, 1.29 mmol) was added dropwise at 0° C. and stirred for 10 min. Then, the reaction mixture was refluxed for 3 h. The mixture was cooled to rt, poured into ice-cold saturated aqueous NaHCO$_3$ solution (5 mL) and extracted with ethyl acetate (2×). The combined organic layers were washed with brine and dried over anhydrous Na$_2$SO$_4$, filtered and concentrated under reduced pressure to yield the title compound (200 mg, 75%). [TLC R$_f$=0.54 (ethyl acetate/hexane 50:50)].

Building block A69:
4-(chloromethyl)-2-methyl-5-m-tolylthiazole

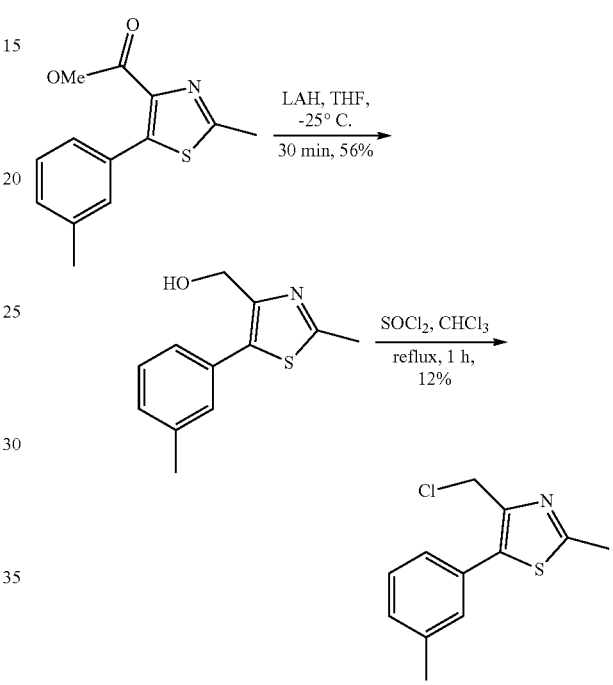

a) (2-methyl-5-m-tolylthiazol-4-yl)methanol

To a stirred suspension of lithium aluminiumhydride (139 mg, 3.64 mmol) in THF (5 mL) a solution of methyl 2-methyl-5-m-tolylthiazole-4-carboxylate [1007873-98-4] (600 mg, 2.43 mmol) in THF (5 mL) was added at −25° C. and stirred for 30 min. Then water (5 mL) was added dropwise and the mixture was extracted with ethyl acetate (100 mL). The organic layer was washed with brine and dried over anhydrous Na$_2$SO$_4$, filtered and concentrated under reduced pressure. The residue was purified by flash column chromatography (eluent: 50% ethyl acetate in hexane) to yield the title compound (300 mg, 56%). [LCMS Rt$_F$=0.32 min, [M+H]$^+$=219.9; TLC R$_f$=0.20 (methanol/chloroform 10:90)].

b) 4-(chloromethyl)-2-methyl-5-m-tolylthiazole

To a stirred solution of (2-methyl-5-m-tolylthiazol-4-yl)methanol (300 mg, 1.37 mmol) in chloroform (10 mL), thionyl chloride (162 mg, 1.37 mmol) was added dropwise at rt and stirred for 30 min and then refluxed for 1 h. The reaction mixture was cooled to rt and absorbed directly on silicagel (10 g). Subsequent flash column chromatography (eluent: 7% ethyl acetate in hexane) yielded the title compound (40 mg, 12%). [LCMS Rt$_F$=1.70 min, [M+H]$^+$=238.0; TLC R$_f$=0.54 (methanol/chloroform 10:90)].

Building block A73: 4-(chloromethyl)-5-(3-fluorophenyl)-2-methylthiazole

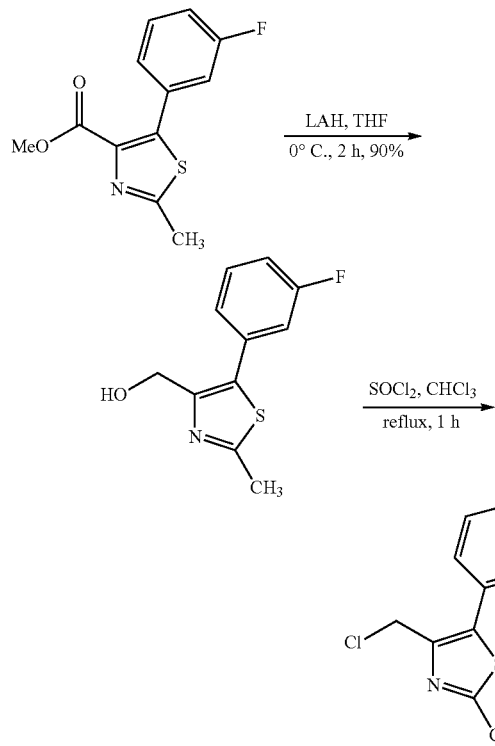

The title compound was synthesized in 2 steps in analogy to building block A32 from methyl 5-(3-fluorophenyl)-2-methylthiazole-4-carboxylate [1007874-04-5].

[TLC $R_f$=0.57 (methanol/chloroform 10:90)].

Building block A125: 2-(2-(chloromethyl)-4-methylphenyl)-2H-1,2,3-triazole

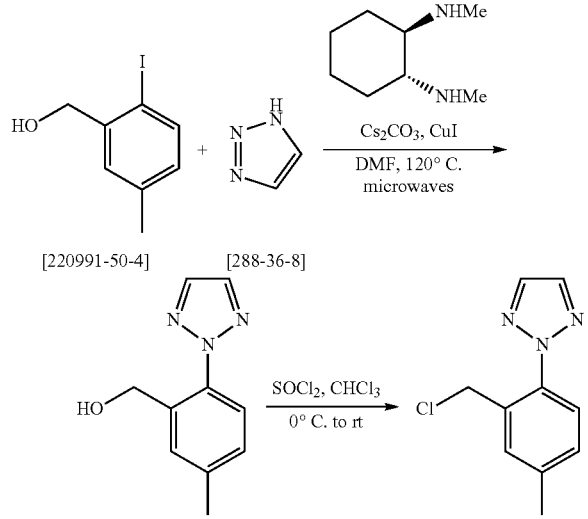

a) (5-methyl-2-(2H-1,2,3-triazol-2-yl)phenyl)methanol

The title compound was synthesized in analogy to the procedure described for building block K11 from (2-iodo-5-methylphenyl)methanol [220991-50-4] and 1H-1,2,3-triazole.

[LCMS $Rt_E$=0.47 min, $[M-H_2O+H]^+$=172.1; TLC $R_f$=0.27 (ethyl acetate/hexane 30:70)].

b) 2-(2-(chloromethyl)-4-methylphenyl)-2H-1,2,3-triazole

To a stirred solution of (5-methyl-2-(2H-1,2,3-triazol-2-yl)phenyl)methanol (100 mg, 0.53 mmol) in chloroform (3 mL), thionyl chloride (76 mg, 0.63 mmol) was added dropwise at 0° C. and stirred for 1 h. Then the mixture was allowed to warm to rt and stirred overnight. The reaction mixture was concentrated under reduced pressure. Saturated aqueous $NaHCO_3$ solution (5 mL) was added and extracted with ethyl acetate (2×). The combined organic layers were washed with brine and dried over anhydrous $Na_2SO_4$, filtered and evaporated under reduced pressure to yield the title compound (100 mg, 91%). [TLC $R_f$=0.59 (ethyl acetate/hexane 30:70)].

Building block A126: tert-butyl 4-(chloromethyl)indoline-1-carboxylate

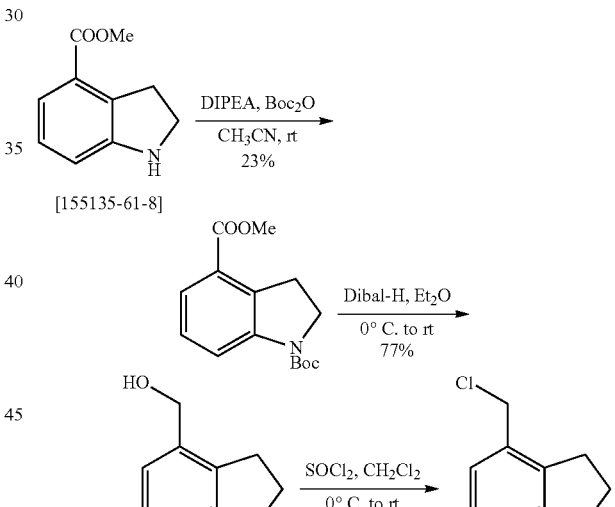

a) 1-tert-butyl 4-methyl indoline-1,4-dicarboxylate

To a stirred solution of methyl indoline-4-carboxylate [155135-61-8] (1.2 g, 6.78 mmol) in acetonitrile (60 mL), $Boc_2O$ (1.87 mL, 8.14 mmol) and DMAP (166 mg, 1.36 mmol) were added and stirred at rt for 16 h. The reaction mixture was concentrated under reduced pressure. Water (30 mL) was added and extracted with ethyl acetate (2×30 mL). The combined organic layers were washed with brine and dried over anhydrous $Na_2SO_4$, filtered and evaporated under reduced pressure. The crude product was purified flash column chromatography (eluent: 2% ethyl acetate in hexane) to yield the title compound (430 mg, 23%). [LCMS $Rt_E$=1.86 min, $[M-Boc+H]^+$=178.1; TLC $R_f$=0.64 (ethyl acetate/hexane 20:80)].

b) tert-butyl 4-(hydroxymethyl)indoline-1-carboxylate

To a stirred solution of methyl 1-tert-butyl 4-methyl indoline-1,4-dicarboxylate (330 mg, 1.19 mmol) in diethyl ether (5 mL), diisobutyl aluminiumhydride (2.97 mL, 2.97 mmol, 1M in toluene) was added and stirred at rt for 16 h. The reaction mixture was quenched with saturated aqueous NH$_4$Cl solution and extracted with ethyl acetate (2×). The combined organic layers were washed with brine and dried over anhydrous Na$_2$SO$_4$, filtered and concentrated under reduced pressure. The crude product was purified flash column chromatography (eluent: 15% ethyl acetate in hexane) to yield the title compound (230 mg, 77%). [LCMS Rt$_E$=1.32 min, [M-Boc+H]$^+$=150.1; TLC R$_f$=0.21 (ethyl acetate/hexane 30:70)].

c) tert-butyl 4-(chloromethyl)indoline-1-carboxylate

To a stirred solution of tert-butyl 4-(hydroxymethyl)indoline-1-carboxylate (230 mg, 0.92 mmol) in dichloromethane (3 mL), thionyl chloride (0.123 mL, 1.02 mmol) was added dropwise at 0° C. and stirred for 1 h. Then the mixture was allowed to warm to rt and stirred overnight. The reaction mixture was concentrated under reduced pressure and dried under high vacuum to yield the title compound (217 mg, crude). The compound was directly used for the next step. [TLC R$_f$=0.86 (ethyl acetate/hexane 20:80)].

Building block A127: 2-(bromomethyl)-4-(1H-pyrazol-1-yl)pyridine

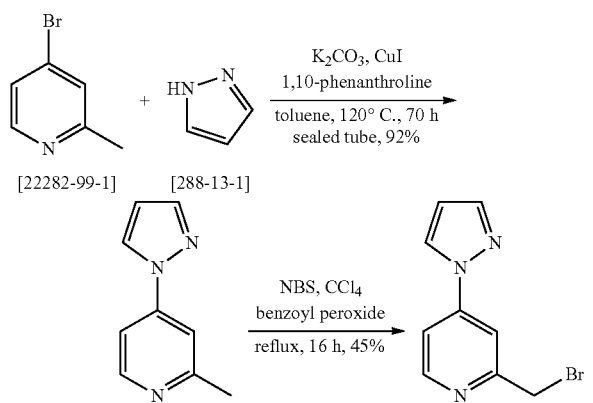

a) 2-methyl-4-(1H-pyrazol-1-yl)pyridine

To a mixture of 4-bromo-2-methylpyridine [22282-99-1] (350 mg, 2.05 mmol), 1H-pyrazole (140 mg, 2.05 mmol), 1,10-phenanthroline (74 mg, 0.41 mmol) and K$_2$CO$_3$ (567 mg, 4.1 mmol) in toluene (2 mL), CuI (19 mg, 0.1 mmol) was added and the reaction mixture was heated at 120° C. for 70 h in a sealed tube. The reaction mixture was cooled to rt, quenched with water (50 mL) and extracted with dichloromethane (150 mL). The organic layer was washed with brine and dried over anhydrous Na$_2$SO$_4$, filtered and concentrated under reduced pressure. The crude product was purified flash column chromatography (eluent: 30% ethyl acetate in hexane) to yield the title compound (300 mg, 92%). [$^1$H NMR (300 MHz, CDCl$_3$) δ ppm 8.53 (d, 1H), 8.02 (d, 1H), 7.77 (d, 1H), 7.55 (d, 1H), 7.44-7.40 (m, 1H), 6.52 (t, 1H), 2.62 (s, 3H); TLC R$_f$=0.28 (ethyl acetate/hexane 30:70)].

b) 2-(bromomethyl)-4-(1H-pyrazol-1-yl)pyridine

To a stirred solution of 2-methyl-4-(1H-pyrazol-1-yl)pyridine (300 mg, 1.9 mmol) in CCl$_4$ (25 mL), N-bromo succinimide (304 mg, 1.71 mmol) and benzoyl peroxide (23 mg, 0.09 mmol) were added and heated to reflux for 16 h. The reaction mixture was cooled to rt and precipitated succinimide was filtered. The filtrate was absorbed on silicagel and concentrated under reduced pressure. The crude product was purified flash column chromatography (eluent: 5% ethyl acetate in hexane) to yield the title compound (100 mg, 45%). [TLC R$_f$=0.34 (ethyl acetate/hexane 30:70)].

Building block A128: 2-(3-(chloromethyl)-4-methylphenyl)-2H-1,2,3-triazole

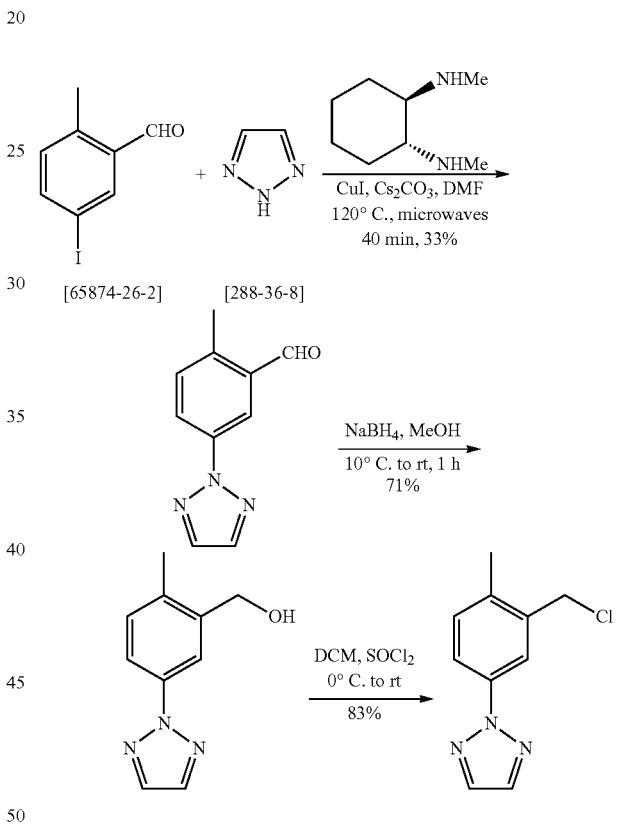

a) 2-methyl-5-(2H-1,2,3-triazol-2-yl)benzaldehyde

The title compound was synthesized in analogy to the procedure described for building block K49 from 5-iodo-2-methylbenzaldehyde [65874-26-2] and 1H-1,2,3-triazole.
[TLC R$_f$=0.34 (ethyl acetate/hexane 5:95)].

b) (2-methyl-5-(2H-1,2,3-triazol-2-yl)phenyl)methanol

To a stirred solution of 2-methyl-5-(2H-1,2,3-triazol-2-yl) benzaldehyde (140 mg, 0.75 mmol) in methanol (10 mL), NaBH$_4$ (42 mg, 1.1 mmol) was added at 10° C. and stirred for 10 min. Then the mixture was allowed to warm to rt and stirred for 1 h. The mixture was quenched with saturated aqueous NH$_4$Cl solution (0.3 mL) and filtered over hyflow.

The filtrate was dried over anhydrous Na₂SO₄, filtered and concentrated under reduced pressure. The crude product was purified flash column chromatography (eluent: 30% ethyl acetate in hexane) to yield the title compound (100 mg, 71%). [TLC R$_f$=0.18 (ethyl acetate/hexane 30:70)].

c) 2-(3-(chloromethyl)-4-methylphenyl)-2H-1,2,3-triazole

To a stirred solution of (2-methyl-5-(2H-1,2,3-triazol-2-yl) phenyl)methanol (100 mg, 0.53 mmol) in dichloromethane (5 mL), thionyl chloride (155 mg, 1.3 mmol) was added dropwise at 0° C. and stirred for 1 h. Then the mixture was allowed to warm to rt and stirred overnight. The reaction mixture was concentrated under reduced pressure at rt and dried under high vacuum to yield the title compound (90 mg, 83%). The compound was directly used for the next step without further purification. [TLC R$_f$=0.66 (ethyl acetate/hexane 30:70)].

Building block B133:
3-(chloromethyl)-2-methyl-1-tosyl-1H-indole

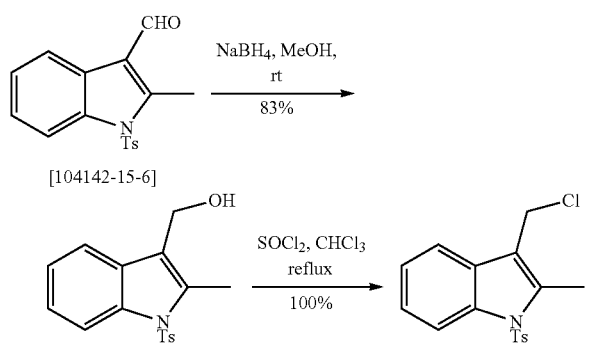

a) (2-methyl-1-tosyl-1H-indol-3-yl)methanol

To a stirred solution of 2-methyl-1-tosyl-1H-indole-3-carbaldehyde [104142-15-6] (1.2 g, 3.83 mmol) in methanol (40 mL), NaBH₄ (145 mg, 3.83 mmol) was added at 0° C. and stirred for 10 min. Then the mixture was allowed to warm to rt and stirred for 4 h. The mixture was concentrated under reduced pressure at 45° C., saturated aqueous NH₄Cl solution was added and extracted with ethyl acetate (2×). The combined organic layers were washed with water, brine and dried over anhydrous Na₂SO₄. The organic layer was filtered and concentrated under reduced pressure to yield the title compound as a pale yellow liquid (1.0 g, 83%). [TLC R$_f$=0.16 (ethyl acetate/hexane 30:70)].

b) 3-(chloromethyl)-2-methyl-1-tosyl-1H-indole

To a stirred solution of (2-methyl-1-tosyl-1H-indol-3-yl) methanol (500 mg, 1.59 mmol) in chloroform (20 mL), thionyl chloride (0.23 mL, 3.18 mmol) was added dropwise at 0° C. and stirred for 10 min. Then the mixture was heated under reflux for 3.5 h. The reaction mixture was concentrated under reduced pressure. The residue was taken up in diethyl ether and evaporated to dryness under reduced pressure to yield the title compound (550 mg, quant.). The compound was directly used for the next step without further purification. [TLC R$_f$=0.58 (ethyl acetate/hexane 20:80)].

Building block K147:
2-(3-(bromomethyl)phenyl)-5-methyloxazole

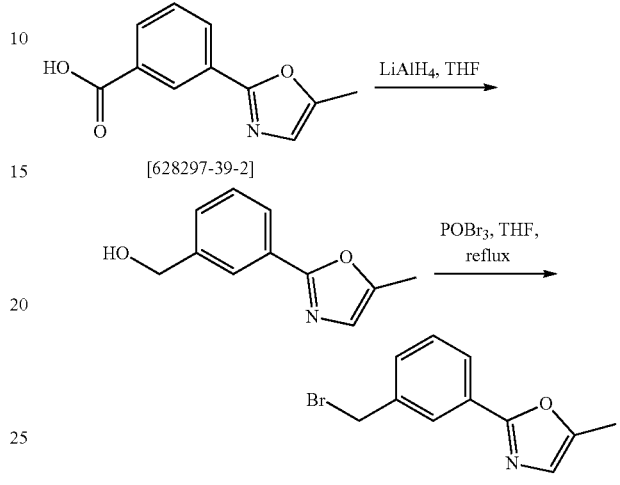

a) (3-(5-methyloxazol-2-yl)phenyl)methanol

To a stirred suspension of LiAlH₄ (0.29 g, 7.41 mmol) in THF (12 mL) a solution of 3-(5-methyloxazol-2-yl)benzoic acid [628297-39-2] (1.21 g, 5.84 mmol) in THF (3 mL) was added dropwise at 25° C. (exothermic) and the mixture was stirred at 35° C. for 30 min. The mixture was poured into 1N aqueous HCl solution and extracted with ethyl acetate (2×). The combined organic layers were washed with brine, dried over anhydrous Na₂SO₄, filtered and concentrated under reduced pressure. The residue was purified by flash-column chromatography over silicagel (eluent: gradient 10%-100% ethyl acetate/heptane) to yield the title compound (0.88 g, 80%). [¹H NMR (400 MHz, CHLOROFORM-d) ♀ ppm 8.00 (s, 1H), 7.87-7.93 (m, 1H), 7.42 (d, J=4.8 Hz, 2H), 6.82 (s, 1H), 4.75 (br. s., 2H), 2.39 (s, 3H); LCMS Rt$_{A}$=0.75, [M+H]⁺=190.1].

b) 2-(3-(bromomethyl)phenyl)-5-methyloxazole

To a stirred solution of (3-(5-methyloxazol-2-yl)phenyl) methanol (0.79 g, 4.13 mmol) in THF (15 mL), POBr₃ (1.93 g, 6.61 mmol) was added in portions at 5° C. The reaction mixture was allowed to warm to rt and then heated at 60° C. for 4 h. The mixture was cooled to rt, poured into saturated aqueous NaHCO₃ solution and extracted with TBME (2×). The combined organic layers were dried over anhydrous Na₂SO₄, filtered and concentrated under reduced pressure. The residue was purified by flash-column chromatography over silicagel (eluent: gradient 5%-40% ethyl acetate/heptane) to yield the title compound (0.88 g, 84%). [¹H NMR (400 MHz, CHLOROFORM-d) ♀ ppm 8.01-8.07 (m, 1H), 7.93 (ddd, J=6.7, 2.1, 1.9 Hz, 1H), 7.39-7.47 (m, 2H), 6.85 (d, J=1.3 Hz, 1H), 4.53 (s, 2H), 2.41 (d, J=1.3 Hz, 3H); LCMS Rt$_{A}$=1.10, [M+H]⁺=252.1/254.1].

Radioligand Binding Assay (Examples 1 to 38)

For crude cell membrane preparations, cells (CHO, Chinese hamster ovary or HEK, human embryonic kidney)

expressing human orexin 1 or human orexin 2 receptors, were washed with HEPES (10 mM, pH 7.5), scraped off the culture plates with the same buffer, and centrifuged at 4° C. for 5 min at 2500×g. The cell pellet was either stored at −80° C. or used directly. Before the experiments, cell membranes were re-suspended in binding assay buffer (10 mM HEPES, 0.5% (w/v) bovine serum albumin, pH 7.5) by homogenisation with a Polytron homogeniser at 50 Hz for 20 s. Cell membranes were also used as made available by commercial providers.

In initial saturation experiments (to calculate Bmax), cell homogenates (150 µl) were incubated with 25-300 pM of the radioligand ([$^{125}$I]orexin A, 50 µl), 8 concentrations in triplicates in the presence or absence Orexin A (1 µM, 50 µl) to define non specific binding. Bound radioactivity was measured, and data were analysed with the program XLFIT or Graphpad Prism. Protein concentration was determined according to the Bradford/BioRad Protein Assay Kit.

In competition experiments, cell homogenates (150 µl) were incubated in assay buffer (10 mM HEPES, pH 7.5, 0.5% (w/v) bovine serum albumin, 5 mM $MgCl_2$, 1 mM $CaCl_2$, and tween 0.05%) for 1 h at room temperature with about 100 pM of the radioligand ([$^{125}$I]orexin A, 2100 Ci/mmole, 50 µl), and with various concentrations of compounds of the invention (50 µl) in triplicates; non-specific binding was determined in the presence of Orexin A (1 µM). Reactions were terminated by vacuum filtration, 3 washes of ice cold wash buffer (Tris-HCl pH 7.4/10 mM, with NaCl 154 mM). Competition data is expressed in Table 2 as Kd [µM].

Radioligand Binding Assay (Examples 39 to 176)

For crude cell membrane preparations, cells (CHO, Chinese hamster ovary or HEK, human embryonic kidney) expressing human orexin 1 or human orexin 2 receptors, were washed with HEPES (10 mM, pH 7.5), scraped off the culture plates with the same buffer, and centrifuged at 4° C. for 5 min at 2500×g. The cell pellet was either stored at −80° C. or used directly. Before the experiments, cell membranes were re-suspended in binding assay buffer (10 mM HEPES, 0.5% (w/v) bovine serum albumin, pH 7.5) by homogenisation with a Polytron homogeniser at 50 Hz for 20 s. Cell membranes were also used as made available by commercial providers.

In initial saturation experiments (to calculate Kd and Bmax), cell homogenates (150 µl) were incubated with 0.1 to 15 nM of the radioligand ([$^3$H]-SB649868, 50 µl), 8 concentrations in triplicates in the presence or absence of almorexant (10 µM, 50 µl) to define non specific binding. Bound radioactivity was measured, and data were analysed with the program XLFIT or Graphpad Prism. Protein concentration was determined according to the Bradford/BioRad Protein Assay Kit.

In competition experiments, cell homogenates (150 µl) were incubated in assay buffer (10 mM HEPES, pH 7.5, 0.5% (w/v) bovine serum albumin, 5 mM $MgCl_2$, 1 mM $CaCl_2$, and tween 0.05%) for 1 h at room temperature with about 1 nM of the radioligand [$^3$H]-SB649868, 66 Ci/mmole, 50 µl), and with various concentrations of compounds of the invention (50 µl) in triplicates; non-specific binding was determined in the presence of almorexant (10 µM). Reactions were terminated by vacuum filtration, 3 washes of ice cold wash buffer (Tris-HCl pH 7.4/10 mM, with NaCl 154 mM). Competition data is expressed in Table 2 as Kd [µM].

Calcium Accumulation in Cells (FLIPR):

Cells expressing human orexin 1 or human orexin 2 receptors, were seeded at 8,000 cells/well in 384 well black-walled clear bottom, poly-D-lysine coated plates. After 24 h, the medium was removed and cells were washed once with phosphate buffered saline and serum-deprived overnight in assay buffer (130 mM NaCl, 5.4 mM KCl, 1.8 mM $CaCl_2$, 0.8 mM $MgSO_4$, 0.9 mM $NaH_2PO_4$, 25 mM glucose, 20 mM HEPES, pH 7.4) containing bovine serum albumin (1% w/v).

On the day of the experiment, the cells seeded in black plates were treated with assay buffer containing the $Ca^{2+}$ sensitive fluorescent dye Fluo-4-AM (2 µM), and probenecid (0.1 mM). After 1 h plates were washed twice with, and resuspended in, assay buffer containing probenecid (0.1 mM) using a multi plate washer. The plates were placed into a FLIPR II (Fluorometric Imaging Plate Reader, Molecular Devices, Sunnyvale, Calif., USA) and baseline fluorescence (fluorescence light units, FLU) was measured (5 measurements, 2 S each; laser excitation 488 nm at 0.6-1 W, CCD camera exposure 0.4 s) before addition of buffer alone (basal) or containing test compounds (either compound of formula I alone, agonist alone or agonist in the presence of various concentrations of compounds of formula I). Fluorescence measurements were then continued every 1 S for 120 S followed by every 4 S for 240 S.

The measurements were typically made in two sequences:

In the first round, compounds of formula I were tested alone, to confirm that they do not display any/any significant agonist activity. Compounds of formula I were tested usually in a concentration range from $10^{-9}$ M to $10^{-5}$ M.

In the second round, performed one hour later (to allow for equilibration), Orexin A was tested either in the absence (calibration curves, Orexin A agonist controls) or in the presence of compounds of formula I to determine antagonism.

Inhibition data is expressed in Table 2 as $K_d$ [µM], converted by the Cheng and Prusoff correction ($Kd=IC_{50}/1+(L/EC_{50})$), where $IC_{50}$ is the 50% inhibition value determined in concentration response inhibition curves, $EC_{50}$ is the half maximal activation concentration determined for orexin A in concentration response curves and L is the concentration of orexin A used in inhibition experiments performed in with a submaximal concentration of orexin A in the presence of up to 8 increasing concentrations of compound of formula I.

Inhibition data is also expressed in Table 2 as % inhibition value measured at a concentration of 10 µM of compound of formula I.

TABLE 2

| Example | FLIPR hOx1R Ki [µM] | FLIPR hOx2R Ki [µM] | Binding hOx1R Kd [µM] | Binding hOx2R Kd [µM] |
|---|---|---|---|---|
| 1 | 0.314 | 0.030 | 0.374 | 0.042 |
| 2 | 0.482 | 0.030 | 0.360 | 0.034 |
| 3 | 0.474 | 0.063 | 0.630 | 0.130 |
| 4 | 1.360 | 0.046 | 2.061 | 0.121 |
| 5 | 0.083 | 0.022 | 0.426 | 0.098 |
| 6 | 1.481 | 0.371 | 1.306 | 0.300 |
| 7 | n.d. | n.d. | >10 | 9.870 |
| 8 | 1.222 | 0.399 | 2.326 | 0.585 |
| 9 | 0.904 | 0.035 | 2.350 | 0.413 |
| 10 | 0 [a] | 1.067 | 3.355 | 0.439 |
| 11 | 2.455 | 0.126 | >10 | 0.755 |
| 12 | n.d. | n.d. | >10 | 6.101 |
| 13 | 0.365 | 0.035 | 0.776 | 0.062 |
| 14 | 0.948 | 0.112 | 1.378 | 0.211 |
| 15 | 1.381 | 0.155 | 1.395 | 0.288 |
| 16 | 1.193 | 0.113 | n.d. | n.d. |
| 17 | 1.723 | 0.247 | n.d. | n.d. |
| 18 | 3 [a] | 0.782 | n.d. | n.d. |
| 19 | 12 [a] | 0.495 | n.d. | n.d. |
| 20 | 0.945 | 0.205 | n.d. | n.d. |
| 21 | 1.760 | 0.213 | 3.279 | 0.211 |
| 22 | 0.518 | 0.051 | 1.318 | 0.059 |
| 23 | 2.739 | 0.280 | 4.481 | 1.094 |
| 24 | n.d. | n.d. | >10 | 5.240 |
| 25 | n.d. | n.d. | 5.250 | 3.210 |

TABLE 2-continued

| Example | FLIPR hOx1R Ki [μM] | FLIPR hOx2R Ki [μM] | Binding hOx1R Kd [μM] | Binding hOx2R Kd [μM] |
|---|---|---|---|---|
| 26 | 0.614 | 0.168 | n.d. | n.d. |
| 27 | 0.740 | 0.084 | 0.702 | 0.169 |
| 28 | 33 [a] | 0.160 | n.d. | n.d. |
| 29 | 1.696 | 0.614 | n.d. | n.d. |
| 30 | 17 [a] | 33 [a] | n.d. | n.d. |
| 31 | 3.691 | 1.176 | n.d. | n.d. |
| 32 | 1.281 | 0.138 | n.d. | n.d. |
| 33 | 2.361 | 0.282 | n.d. | n.d. |
| 34 | 1.563 | 0.088 | 4.318 | 0.181 |
| 35 | 26 [a] | 0.272 | n.d. | n.d. |
| 36 | 0.591 | 0.197 | n.d. | n.d. |
| 37 | 8 [a] | 22 [a] | n.d. | n.d. |
| 38 | 0.013 | 0.001 | 0.017 | 0.007 |
| 39 | 1.424 | 0.025 | 2.771 | 0.243 |
| 40 | 1.020 | 0.098 | n.d. | n.d. |
| 41 | 0.077 | 0.016 | 0.100 [b] | 0.036 [b] |
| 42 | 0.020 | 0.003 | 0.036 [b] | 0.012 [b] |
| 43 | 0.236 | 0.047 | 0.205 | 0.196 |
| 44 | 0.064 | 0.048 | 0.056 | 0.125 |
| 45 | 19 [a] | 43 [a] | n.d. | n.d. |
| 46 | 1.095 | 0.247 | 1.286 | 0.473 |
| 47 | 0.159 | 0.013 | 0.318 | 0.034 |
| 48 | 1.036 | 0.032 | 1.839 | 0.147 |
| 49 | 2.113 | 0.039 | 3.255 | 0.115 |
| 50 | n.d. | n.d. | >10 [b] | >10 [b] |
| 51 | 57 [a] | 32 [a] | n.d. | n.d. |
| 52 | 1.362 | 0.178 | n.d. | n.d. |
| 53 | 37 [a] | 24 [a] | n.d. | n.d. |
| 54 | 0.420 | 0.047 | 0.634 [b] | 0.175 [b] |
| 55 | 0.932 | 0.151 | n.d. | n.d. |
| 56 | 2.038 | 0.483 | n.d. | n.d. |
| 57 | 1.034 | 0.092 | 0.959 [b] | 0.159 [b] |
| 58 | 0.570 | 0.217 | n.d. | n.d. |
| 59 | 12 [a] | 31 [a] | n.d. | n.d. |
| 60 | 0.391 | 0.049 | 0.728 | 0.191 |
| 61 | 0.373 | 0.062 | 2.046 | 0.395 |
| 62 | 29 [a] | 0.833 | n.d. | n.d. |
| 63 | 0.900 | 0.083 | 3.819 | 0.903 |
| 64 | 32 [a] | 0.718 | n.d. | n.d. |
| 65 | 0.357 | 0.023 | 1.859 | 0.623 |
| 66 | 1.714 | 0.302 | n.d. | n.d. |
| 67 | 11 [a] | 27 [a] | n.d. | n.d. |
| 68 | 29 [a] | 0.830 | n.d. | n.d. |
| 69 | 1.109 | 0.163 | n.d. | n.d. |
| 70 | 3.425 | 0.258 | n.d. | n.d. |
| 71 | 2.156 | 0.466 | n.d. | n.d. |
| 72 | 3.100 | 0.452 | n.d. | n.d. |
| 73 | 0.438 | 0.055 | 1.148 | 0.219 |
| 74 | 0.675 | 0.185 | n.d. | n.d. |
| 75 | 22 [a] | 35 [a] | n.d. | n.d. |
| 76 | 44 [a] | 0.559 | n.d. | n.d. |
| 77 | 1.152 | 0.098 | 2.326 | 1.465 |
| 78 | 15 [a] | 32 [a] | n.d. | n.d. |
| 79 | 2.150 | 0.232 | n.d. | n.d. |
| 80 | 2.986 | 0.096 | n.d. | n.d. |
| 81 | 13 [a] | 1.579 | n.d. | n.d. |
| 82 | 33 [a] | 0.081 | 5.086 | 0.624 |
| 83 | 1.730 | 0.080 | 2.756 | 0.364 |
| 84 | 40 [a] | 46 [a] | n.d. | n.d. |
| 85 | 15 [a] | 0.822 | n.d. | n.d. |
| 86 | 47 [a] | 0.372 | n.d. | n.d. |
| 87 | 1.544 | 0.739 | n.d. | n.d. |
| 88 | 11 [a] | 25 [a] | n.d. | n.d. |
| 89 | 29 [a] | 24 [a] | n.d. | n.d. |
| 90 | 17 [a] | 12 [a] | n.d. | n.d. |
| 91 | 2.867 | 38 [a] | n.d. | n.d. |
| 92 | 3.056 | 0.649 | n.d. | n.d. |
| 93 | 1.308 | 0.158 | n.d. | n.d. |
| 94 | 1.701 | 0.282 | n.d. | n.d. |
| 95 | 0.223 | 0.008 | 0.429 | 0.036 |
| 96 | 2.395 | 0.631 | n.d. | n.d. |
| 97 | 14 [a] | 33 [a] | n.d. | n.d. |
| 98 | 0.425 | 0.050 | 0.980 | 0.223 |
| 99 | 1.103 | 0.142 | n.d. | n.d. |
| 100 | 29 [a] | 13 [a] | n.d. | n.d. |
| 101 | 2.794 | 1.382 | n.d. | n.d. |
| 102 | 2.430 | 0.225 | n.d. | n.d. |
| 103 | 2.488 | 1.188 | n.d. | n.d. |
| 104 | 1.007 | 0.106 | 4.579 | 1.369 |
| 105 | 47 [a] | 1.382 | n.d. | n.d. |
| 106 | 35 [a] | 1.358 | n.d. | n.d. |
| 107 | 0.728 | 0.115 | n.d. | n.d. |
| 108 | 1.397 | 0.196 | n.d. | n.d. |
| 109 | 3.138 | 1.236 | n.d. | n.d. |
| 110 | 4.210 | 0.945 | n.d. | n.d. |
| 111 | 1.286 | 0.085 | 3.824 | 0.559 |
| 112 | 3.521 | 1.600 | n.d. | n.d. |
| 113 | 1.362 | 0.082 | 3.505 | 0.630 |
| 114 | 3.789 | 0.831 | n.d. | n.d. |
| 115 | 57 [a] | 1.203 | n.d. | n.d. |
| 116 | 3.789 | 53 [a] | n.d. | n.d. |
| 117 | 2.382 | 0.249 | n.d. | n.d. |
| 118 | 1.838 | 0.197 | n.d. | n.d. |
| 119 | 1.896 | 0.291 | n.d. | n.d. |
| 120 | 0.700 | 0.125 | n.d. | n.d. |
| 121 | 2.526 | 1.663 | n.d. | n.d. |
| 122 | 31 [a] | 0.725 | n.d. | n.d. |
| 123 | 11 [a] | 24 [a] | n.d. | n.d. |
| 124 | 0.932 | 0.140 | n.d. | n.d. |
| 125 | 2.288 | 0.137 | 4.993 | 0.324 |
| 126 | 1.250 | 0.267 | n.d. | n.d. |
| 127 | 2.344 | 0.299 | n.d. | n.d. |
| 128 | 0.967 | 0.073 | >10 | 0.160 |
| 129 | 0.126 | 0.009 | 0.105 | 0.025 |
| 130 | 0.422 | 0.029 | 1.279 | 0.134 |
| 131 | 48 [a] | 0.524 | n.d. | n.d. |
| 132 | 3.178 | 0.555 | n.d. | n.d. |
| 133 | 1.152 | 0.244 | n.d. | n.d. |
| 134 | 1.443 | 0.161 | n.d. | n.d. |
| 135 | 0.242 | 0.185 | n.d. | n.d. |
| 136 | 0.657 | 0.011 | 1.414 [b] | 0.096 [b] |
| 137 | 0.509 | 0.656 | n.d. | n.d. |
| 138 | 3.789 | 1.969 | n.d. | n.d. |
| 139 | 0.541 | 0.105 | n.d. | n.d. |
| 140 | 0.662 | 0.081 | 1.578 | 0.379 |
| 141 | 1.985 | 0.404 | n.d. | n.d. |
| 142 | 0.925 | 0.212 | n.d. | n.d. |
| 143 | 0.747 | 0.039 | 0.307 | 0.050 |
| 144 | 3.250 | 0.596 | n.d. | n.d. |
| 145 | 4.012 | 0.636 | n.d. | n.d. |
| 146 | 29 [a] | 0.621 | n.d. | n.d. |
| 147 | 0.094 | 0.007 | 0.228 | 0.063 |
| 148 | 30 [a] | 32 [a] | n.d. | n.d. |
| 149 | 0.981 | 0.019 | 3.449 | 0.268 |
| 150 | 0.744 | 0.045 | 2.100 | 0.185 |
| 151 | 14 [a] | 0.675 | n.d. | n.d. |
| 152 | 1.563 | 0.069 | 0.939 | 0.084 |
| 153 | 22 [a] | 35 [a] | n.d. | n.d. |
| 154 | 0.646 | 0.115 | n.d. | n.d. |
| 155 | 1.526 | 0.239 | n.d. | n.d. |
| 156 | 0.623 | 0.023 | 1.024 | 0.139 |
| 157 | 1.695 | 0.320 | n.d. | n.d. |
| 158 | 21 [a] | 0.545 | n.d. | n.d. |
| 159 | 24 [a] | 0.745 | n.d. | n.d. |
| 160 | 0.571 | 0.068 | 0.806 | 0.111 |
| 161 | 40 [a] | 0.713 | n.d. | n.d. |
| 162 | 1.245 | 0.564 | n.d. | n.d. |
| 163 | 23 [a] | 0.483 | n.d. | n.d. |
| 164 | 0.115 | 0.014 | 0.090 | 0.012 |
| 165 | 0.468 | 0.115 | n.d. | n.d. |
| 166 | 1.164 | 0.156 | n.d. | n.d. |
| 167 | 0.665 | 0.081 | 1.672 | 0.152 |
| 168 | 2.382 | 0.184 | n.d. | n.d. |
| 169 | 0.966 | 0.070 | 0.926 | 0.123 |
| 170 | 1.807 | 0.535 | n.d. | n.d. |
| 171 | 2.481 | 0.786 | n.d. | n.d. |
| 172 | 14 [a] | 20 [a] | n.d. | n.d. |
| 173 | 1.391 | 0.343 | n.d. | n.d. |
| 174 | 0.259 | 0.032 | 0.143 | 0.041 |

TABLE 2-continued

| Example | FLIPR hOx1R Ki [μM] | FLIPR hOx2R Ki [μM] | Binding hOx1R Kd [μM] | Binding hOx2R Kd [μM] |
|---|---|---|---|---|
| 175 | <10 [a] | 12 [a] | n.d. | n.d. |
| 176 | <10 [a] | <10 [a] | n.d. | n.d. | n.d. = not determined
[a] % inhibition value measured at a concentration of 10 μM of compound of formula I.
[b] radioligand ([$^{125}$I]orexin A was used instead of [$^{3}$H]-SB649868 in the binding assay:

In competition experiments, cell homogenates (150 μl) were incubated in assay buffer (10 mM HEPES, pH 7.5, 0.5% (w/v) bovine serum albumin, 5 mM $MgCl_2$, 1 mM $CaCl_2$, and tween 0.05%) for 1 h at room temperature with about 100 pM of the radioligand ([$^{125}$I]orexin A, 2100 Ci/mmole, 50 μl), and with various concentrations of compounds of the invention (50 μl) in triplicates; non-specific binding was determined in the presence of Orexin A (1 μM). Reactions were terminated by vacuum filtration, 3 washes of ice cold wash buffer (Tris-HCl pH 7.4/10 mM, with NaCl 154 mM). Competition data is expressed in Table 2 as Kd [μM].

Beam Braking Motor Activity Behavior (BBM)

In the morning (9:00 h) of experimental day 1, the animals (C75/Bl6 mice; Janvier, France) are singly placed into home cages (Type 3, only containing sawdust, as well as food and water ad libitum). The cages are put into frames equipped with infrared beams to record the activity/inactivity of the mice (Moti 4.25, TSE Systems, Germany). The first 1.5 days are used for habituation (see Figure). Five minutes before lights-off of the second day, the animals (n=6/groups) are orally treated with vehicle, the compounds or a positive control (e.g. almorexant 100 mg/kg). Then, the animals stay in the setups for the following lights-off period and activity monitored.

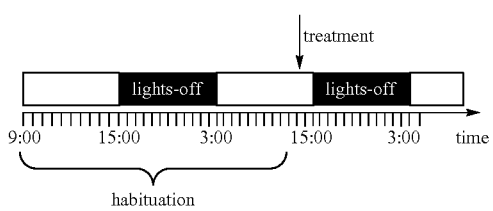

Data Analysis: The raw data files are imported into Excel and for each animal, the minutes spent inactive (no beam breaks within this minute) per hour are calculated. This measure is also 'normalized' for each animal, i.e. the number of minutes spent inactive of the habituation/vehicle day are subtracted for each hour from the minutes spent inactive of the corresponding hour of the treatment day. The data are expressed as means±SEM (standard error of the means) of these difference scores for each hour as well as for the first four hours after administration, the time period which is most sensible to the effects of sleep-promoting compounds. Statistical analysis of the data is done with Systat 11 software. Since the data are normally distributed, analysis of variance (ANOVA) with treatment as between subject factor and the Dunnett test for post-hoc pairwise comparison were used. Furthermore, Student t-tests are used for single pair wise comparisons.

Sleep Electroencephalography (Sleep EEG):

The sleep pattern of tethered mice (C75/Bl6 mice; Janvier, France), chronically implanted with cortical EEG electrodes and an EMG electrode (neck muscle), is scored using the rodent scoring module of Somnologica software. Activity is monitored with an infrared sensor placed in the top of the cage and video recordings are collected with a day/night camera and infrared light during the dark phase (12 hours, lights off at 15:00). Mice are repeatedly acclimated to the recording setup and for a minimum of 3 days before each experiment. All treatments occur 5-10 min before lights off. On Day 1 mice are handled and the oral gavage introduced without application, on Day 2 vehicle is applied, on Day 3 compound is applied, and on Day 4 vehicle is applied. 22 hour recordings are scored in 10 s epochs and the total minutes per hour in Active wake (wake with locomotion), Quiet wake, and sleep are determined. Significance (p<0.05) is tested between vehicle and compound with Systat12 using the Restricted Maximum Likelihood test followed by post-hoc analysis using Fisher's Least Significant Differences test when either treatment or the interaction between treatment and hour had p<0.05.

In Vivo Results:

In the BBM, compound of example 1 was applied at 100 mg/kg p.o. Compound of example 1 induced inactivity for up to 6-7 hours (by 15-22 minutes/hour in the first 3 hours vs controls); typically almorexant 100 mg/kg p.o. induces inactivity over the first 5-7 hours (by 18-21 minutes/hour in the first 3 hours).

In the sleep EEG, compound of example 1 (100 mg/kg p.o.) reduced active wake and increased sleep for up to 7 hours (by 7-16 minutes/hour vs controls), whereas the compound had minimal effects on quiet wake. Typically, almorexant 100 mg/kg p.o. reduces active wake and increases sleep over the first 5-6 hours (by 9-16 minutes/hour), without noticeable effect on quiet wake.

The following are further embodiments of the invention:

Embodiment 1

A compound of the formula (I)

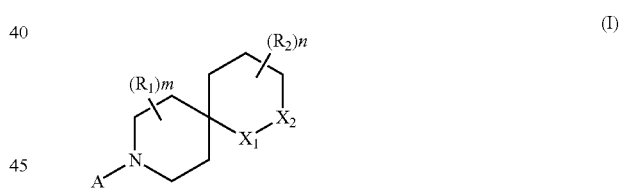

wherein
A is a eight- to ten-membered fused bicyclic aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may be substituted once or more than once by $R_3$, and wherein a substituent on a nitrogen in a heterocyclic ring system may not be halogen;

each $R_3$ independently is $C_{1-6}$alkyl, $C_{1-6}$halogenalkyl, $C_{1-6}$alkoxy, $C_{1-6}$halogenalkoxy, halogen, cyano or a three- to seven-membered monocyclic ring system which may be aromatic, saturated or unsaturated non-aromatic and which may contain from 1 to 4 hetero atoms selected from nitrogen, oxygen and sulfur, and wherein each ring system may contain not more than 2 oxygen atoms and not more than 2 sulfur atoms, and wherein each ring system may in turn be substituted once or more than once by $R_4$, and wherein a substituent on a nitrogen in a heterocyclic ring system may not be halogen;

each $R_4$ independently is $C_{1-6}$alkyl, $C_{1-6}$halogenalkyl, $C_{1-6}$alkoxy, $C_{1-6}$halogenalkoxy, halogen or cyano, or two $R_4$ at the same ring atom together are oxo;

or A is a five- to six-membered monocyclic aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system is substituted by A1 and wherein the ring system may be further substituted once or more than once by $R_5$, and wherein a substituent on a nitrogen in a heterocyclic ring system may not be halogen;

A1 is a five- to six-membered monocyclic aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may be substituted once or more than once by $R_6$, and wherein a substituent on a nitrogen in a heterocyclic ring system may not be halogen;

each $R_5$ or $R_6$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy;

m is 0, 1, 2, 3, 4, 5 or 6;

n is 0, 1, 2, 3, 4, 5 or 6;

each $R_1$ or $R_2$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy;

—$X_1$— is —C(O)— and —$X_2$— is —N(L-B)—;

or —$X_1$— is —N(L-B)— and —$X_2$— is —C(O)—;

L is —C($R_7$)$_2$—;

each $R_7$ independently is hydrogen, $C_{1-6}$alkyl, $C_{1-6}$halogenalkyl, $C_{3-7}$cycloalkyl or $C_{3-7}$cycloalkyl($C_{1-4}$alkyl);

B is a five- to ten-membered monocyclic or fused polycyclic aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may be substituted once or more than once by $R_8$, and wherein a substituent on a nitrogen in a heterocyclic ring system may not be halogen;

each $R_8$ independently $C_{1-6}$alkyl, $C_{1-6}$halogenalkyl, $C_{1-6}$hydroxyalkyl, $C_{1-4}$alkoxy-$C_{1-6}$alkyl, $C_{1-6}$-aminoalkyl, $C_{1-4}$alkylamino-$C_{1-6}$alkyl, di($C_{1-4}$alkyl)amino-$C_{1-6}$alkyl, $C_{2-6}$alkenyl, $C_{2-6}$halogenalkenyl, $C_{2-6}$alkynyl, $C_{2-6}$halogenalkynyl, $C_{1-6}$alkoxy, $C_{1-6}$halogenalkoxy, $C_{1-4}$alkoxy-$C_{1-6}$alkoxy, $C_{1-6}$alkylamino, di($C_{1-6}$alkyl)amino, halogen, hydroxy, cyano, amino or a three- to seven-membered monocyclic ring system which may be aromatic, saturated or unsaturated non-aromatic and which may contain from 1 to 4 hetero atoms selected from nitrogen, oxygen and sulfur, and wherein each ring system may be attached directly to ring system B or via a $C_{1-4}$alkylene, and wherein each ring system may contain not more than 2 oxygen atoms and not more than 2 sulfur atoms, and wherein each ring system may in turn be substituted once or more than once by $C_{1-6}$alkyl, $C_{1-6}$halogenalkyl, $C_{1-6}$alkoxy, $C_{1-6}$halogenalkoxy, halogen or cyano, and wherein a substituent on a nitrogen in a heterocyclic ring system may not be halogen;

or two $R_8$ at adjacent ring atoms form together with said ring atoms a fused five- to seven-membered unsaturated non-aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may in turn be substituted once or more than once by $R_9$, and wherein a substituent on a nitrogen in a heterocyclic ring system may not be halogen; and wherein each $R_9$ independently is halogen or $C_{1-6}$alkyl, or two $R_9$ at the same ring atom together are oxo;

in free form or in salt form.

Embodiment 2

A compound of formula I

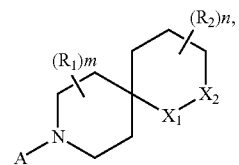

wherein

A is a eight- to ten-membered fused bicyclic aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may be substituted once or more than once by $R_3$, and wherein a substituent on a nitrogen in a heterocyclic ring system may not be halogen;

each $R_3$ independently is $C_{1-6}$alkyl, $C_{1-6}$halogenalkyl, $C_{1-6}$alkoxy, $C_{1-6}$halogenalkoxy, halogen, cyano or a three- to seven-membered monocyclic ring system which may be aromatic, saturated or unsaturated non-aromatic and which may contain from 1 to 4 hetero atoms selected from nitrogen, oxygen and sulfur, and wherein each ring system may contain not more than 2 oxygen atoms and not more than 2 sulfur atoms, and wherein each ring system may in turn be substituted once or more than once by $R_4$, and wherein a substituent on a nitrogen in a heterocyclic ring system may not be halogen;

each $R_4$ independently is $C_{1-6}$alkyl, $C_{1-6}$halogenalkyl, $C_{1-6}$alkoxy, $C_{1-6}$halogenalkoxy, halogen or cyano, or two $R_4$ at the same ring atom together are oxo;

or A is a five- to six-membered monocyclic aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system is substituted by A1 and wherein the ring system may be further substituted once or more than once by $R_5$, and wherein a substituent on a nitrogen in a heterocyclic ring system may not be halogen;

A1 is a five- to six-membered monocyclic aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may be substituted once or more than once by $R_6$, and wherein a substituent on a nitrogen in a heterocyclic ring system may not be halogen;

each $R_5$ or $R_6$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy;

m is 0, 1, 2, 3, 4, 5 or 6;

n is 0, 1, 2, 3, 4, 5 or 6;

each $R_1$ or $R_2$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy;

—X$_1$— is —C(O)— and —X$_2$— is —N(L-B)—;
or —X$_1$— is —N(L-B)— and —X$_2$— is —C(O)—;
L is —C(R$_7$)$_2$—;
each R$_7$ independently is hydrogen, C$_{1-6}$alkyl, C$_{1-6}$halogenalkyl, C$_{3-7}$cycloalkyl or C$_{3-7}$cycloalkyl(C$_{1-4}$alkyl);
B is a five- to ten-membered monocyclic or fused polycyclic aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may be substituted once or more than once by R$_8$, and wherein a substituent on a nitrogen in a heterocyclic ring system may not be halogen;
each R$_8$ independently is C$_{1-6}$alkyl, C$_{1-6}$halogenalkyl, C$_{1-6}$alkoxy, C$_{1-6}$halogenalkoxy, halogen, cyano or a three- to seven-membered monocyclic ring system which may be aromatic, saturated or unsaturated non-aromatic and which may contain from 1 to 4 hetero atoms selected from nitrogen, oxygen and sulfur, and wherein each ring system may contain not more than 2 oxygen atoms and not more than 2 sulfur atoms, and wherein each ring system may in turn be substituted once or more than once by C$_{1-6}$alkyl, C$_{1-6}$halogenalkyl, C$_{1-6}$alkoxy, C$_{1-6}$halogenalkoxy, halogen or cyano, and wherein a substituent on a nitrogen in a heterocyclic ring system may not be halogen;
or two R$_8$ at adjacent ring atoms form together with said ring atoms a fused five- to seven-membered ununsaturated non-aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may in turn be substituted once or more than once by R$_9$, and wherein a substituent on a nitrogen in a heterocyclic ring system may not be halogen; and wherein each R$_9$ independently is halogen or C$_{1-6}$alkyl, or two R$_9$ at the same ring atom together are oxo;
in free form or in salt form.

Embodiment 3

A compound of formula (I) according to embodiment 1 or 2, wherein —X$_1$— is —C(O)— and —X$_2$— is —N(L-B)—.

Embodiment 4

A compound of formula (I) according to any one of embodiments 1 to 3, wherein A is a eight- to ten-membered fused bicyclic aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may be substituted once or more than once by R$_3$, and wherein a substituent on a nitrogen in a heterocyclic ring system may not be halogen; and m and n are both 0.

Embodiment 5

A compound of formula (I) according to any one of embodiments 1 to 4, wherein L is —CH$_2$—; and B is an eight- to ten-membered fused bicyclic aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may be substituted once or more than once by R$_8$, and wherein a substituent on a nitrogen in a heterocyclic ring system may not be halogen.

Embodiment 6

A compound of formula (I) according to embodiment 1, wherein —X$_1$— is —N(L-B)— and —X$_2$— is —C(O)—.

Embodiment 7

A compound of formula (I) according to embodiment 6, wherein A is a eight- to ten-membered fused bicyclic aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may be substituted once or more than once by R$_3$, and wherein a substituent on a nitrogen in a heterocyclic ring system may not be halogen; m and n are both 0; L is —CH$_2$—; and B is an eight- to ten-membered fused bicyclic aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may be substituted once or more than once by R$_8$, and wherein a substituent on a nitrogen in a heterocyclic ring system may not be halogen.

Embodiment 8

A compound of formula (I) according to any of embodiments 1 to 7, wherein B is indol-3-yl which may be substituted once or more than once by R$_{8a}$, wherein a substituent on the nitrogen of the indol-3-yl may not be halogen; and each R$_{8a}$ independently is C$_{1-6}$alkyl, C$_{1-6}$alkoxy, C$_{1-6}$halogenalkyl or halogen.

Embodiment 9

A compound of formula (I) according to any of embodiments 1 to 7, wherein B is a six-membered monocyclic aromatic ring system which may contain 1 to 2 nitrogen atoms, wherein the ring system is substituted once by R$_{8b}$, and wherein the ring system may be further substituted once or more than once by R$_{8c}$;
R$_{8b}$ is a five-membered monocyclic aromatic ring system, which contains from 1 to 4 hetero atoms selected from nitrogen, oxygen and sulfur, and wherein the ring system may in turn be substituted once or more than once by C$_{1-6}$alkyl, C$_{1-6}$halogenalkyl, C$_{1-6}$alkoxy, C$_{1-6}$halogenalkoxy, halogen or cyano, and wherein a substituent on a nitrogen in a heterocyclic ring system may not be halogen; and
each R$_{8c}$ independently is C$_{1-6}$alkyl, C$_{1-6}$halogenalkyl, C$_{1-6}$alkoxy, C$_{1-6}$halogenalkoxy, halogen or cyano.

Embodiment 10

A compound of formula (I) according to embodiment 1 or 2 which is selected from the group consisting of
2-((1H-indol-3-yl)methyl)-9-(quinoxalin-2-yl)-2,9-diazaspiro[5.5]undecan-1-one;
2-(naphthalen-1-ylmethyl)-9-(quinoxalin-2-yl)-2,9-diazaspiro[5.5]undecan-1-one;
2-((1H-indol-4-yl)methyl)-9-(quinoxalin-2-yl)-2,9-diazaspiro[5.5]undecan-1-one;
2-((2,3-dihydrobenzo[b][1,4]dioxin-5-yl)methyl)-9-(quinoxalin-2-yl)-2,9-diazaspiro[5.5]undecan-1-one;
2-(3-(pyridin-3-yl)benzyl)-9-(quinoxalin-2-yl)-2,9-diazaspiro[5.5]undecan-1-one;
2-benzyl-9-(quinoxalin-2-yl)-2,9-diazaspiro[5.5]undecan-1-one;

2-(naphthalen-2-ylmethyl)-9-(quinoxalin-2-yl)-2,9-diazaspiro[5.5]undecan-1-one;
2-(benzo[d][1,3]dioxol-5-ylmethyl)-9-(quinoxalin-2-yl)-2,9-diazaspiro[5.5]undecan-1-one;
2-(benzo[d][1,3]dioxol-4-ylmethyl)-9-(quinoxalin-2-yl)-2,9-diazaspiro[5.5]undecan-1-one;
9-(1H-benzo[d]imidazol-2-yl)-2-benzyl-2,9-diazaspiro[5.5]undecan-1-one;
9-(1H-benzo[d]imidazol-2-yl)-2-(naphthalen-1-ylmethyl)-2,9-diazaspiro[5.5]undecan-1-one;
9-(1-methyl-1H-benzo[d]imidazol-2-yl)-2-(naphthalen-1-ylmethyl)-2,9-diazaspiro[5.5]undecan-1-one;
2-((2-methyl-1H-indol-4-yl)methyl)-9-(quinoxalin-2-yl)-2,9-diazaspiro[5.5]undecan-1-one;
9-(quinoxalin-2-yl)-2-(3-(trifluoromethyl)benzyl)-2,9-diazaspiro[5.5]undecan-1-one;
2-(3-methylbenzyl)-9-(quinoxalin-2-yl)-2,9-diazaspiro[5.5]undecan-1-one;
2-(3,5-dimethylbenzyl)-9-(quinoxalin-2-yl)-2,9-diazaspiro[5.5]undecan-1-one;
2-(2,3-dimethylbenzyl)-9-(quinoxalin-2-yl)-2,9-diazaspiro[5.5]undecan-1-one;
2-(2,3-dimethoxybenzyl)-9-(quinoxalin-2-yl)-2,9-diazaspiro[5.5]undecan-1-one;
2-(2-methylbenzyl)-9-(quinoxalin-2-yl)-2,9-diazaspiro[5.5]undecan-1-one;
2-(2,5-dimethylbenzyl)-9-(quinoxalin-2-yl)-2,9-diazaspiro[5.5]undecan-1-one;
2-(quinolin-8-ylmethyl)-9-(quinoxalin-2-yl)-2,9-diazaspiro[5.5]undecan-1-one;
2-(biphenyl-3-ylmethyl)-9-(quinoxalin-2-yl)-2,9-diazaspiro[5.5]undecan-1-one;
9-(quinoxalin-2-yl)-2-(2-(trifluoromethyl)benzyl)-2,9-diazaspiro[5.5]undecan-1-one;
9-(quinoxalin-2-yl)-2-(4-(trifluoromethyl)benzyl)-2,9-diazaspiro[5.5]undecan-1-one;
2-((2,3-dihydrobenzo[b][1,4]dioxin-6-yl)methyl)-9-(quinoxalin-2-yl)-2,9-diazaspiro[5.5]undecan-1-one;
2-((1-methyl-1H-indol-4-yl)methyl)-9-(quinoxalin-2-yl)-2,9-diazaspiro[5.5]undecan-1-one;
2-(3-chlorobenzyl)-9-(quinoxalin-2-yl)-2,9-diazaspiro[5.5]undecan-1-one;
9-(1H-benzo[d]imidazol-2-yl)-2-(3-chlorobenzyl)-2,9-diazaspiro[5.5]undecan-1-one;
2-(3-chlorobenzyl)-9-(4-phenylpyrimidin-2-yl)-2,9-diazaspiro[5.5]undecan-1-one;
2-yl-methyl-1H-benzo[d]imidazol-2-yl)methyl)-9-(quinoxalin-2-yl)-2,9-diazaspiro[5.5]undecan-1-one;
2-((5-(4-methoxyphenyl)-1,3,4-oxadiazol-2-yl)methyl)-9-(quinoxalin-2-yl)-2,9-diazaspiro[5.5]undecan-1-one;
2-((3-methyl-5-phenylisoxazol-4-yl)methyl)-9-(quinoxalin-2-yl)-2,9-diazaspiro[5.5]undecan-1-one;
2-((2-methylquinolin-4-yl)methyl)-9-(quinoxalin-2-yl)-2,9-diazaspiro[5.5]undecan-1-one;
2-((5-methyl-3-phenylisoxazol-4-yl)methyl)-9-(quinoxalin-2-yl)-2,9-diazaspiro[5.5]undecan-1-one;
2-(3-(1H-pyrrol-1-yl)benzyl)-9-(quinoxalin-2-yl)-2,9-diazaspiro[5.5]undecan-1-one;
2-(benzo[d]isoxazol-3-ylmethyl)-9-(quinoxalin-2-yl)-2,9-diazaspiro[5.5]undecan-1-one;
2-((3,5-dimethylisoxazol-4-yl)methyl)-9-(quinoxalin-2-yl)-2,9-diazaspiro[5.5]undecan-1-one;
1-((1H-indol-4-yl)methyl)-9-(quinoxalin-2-yl)-1,9-diazaspiro[5.5]undecan-2-one;
2-(2-(3-methyl-1,2,4-oxadiazol-5-yl)benzyl)-9-(quinoxalin-2-yl)-2,9-diazaspiro[5.5]undecan-1-one;
2-((1H-indol-3-yl)methyl)-9-(benzo[d]oxazol-2-yl)-2,9-diazaspiro[5.5]undecan-1-one;
1-(2,5-dimethylbenzyl)-9-(quinoxalin-2-yl)-1,9-diazaspiro[5.5]undecan-2-one;
1-((1H-indol-4-yl)methyl)-9-(benzo[d]oxazol-2-yl)-1,9-diazaspiro[5.5]undecan-2-one;
1-((1H-indol-3-yl)methyl)-9-(quinoxalin-2-yl)-1,9-diazaspiro[5.5]undecan-2-one;
1-((1-methyl-1H-indol-4-yl)methyl)-9-(quinoxalin-2-yl)-1,9-diazaspiro[5.5]undecan-2-one;
2-((2-methoxypyridin-4-yl)methyl)-9-(quinoxalin-2-yl)-2,9-diazaspiro[5.5]undecan-1-one;
2-(3-(1H-1,2,3-triazol-1-yl)benzyl)-9-(quinoxalin-2-yl)-2,9-diazaspiro[5.5]undecan-1-one;
2-(3-(2H-1,2,3-triazol-2-yl)benzyl)-9-(quinoxalin-2-yl)-2,9-diazaspiro[5.5]undecan-1-one;
2-((1H-indol-3-yl)methyl)-9-(quinolin-3-yl)-2,9-diazaspiro[5.5]undecan-1-one;
2-(2-(2H-1,2,3-triazol-2-yl)benzyl)-9-(quinoxalin-2-yl)-2,9-diazaspiro[5.5]undecan-1-one;
2-benzyl-9-(1-methyl-1H-benzo[d]imidazol-2-yl)-2,9-diazaspiro[5.5]undecan-1-one;
2-(2-(1-methyl-1H-pyrazol-4-yl)benzyl)-9-(quinoxalin-2-yl)-2,9-diazaspiro[5.5]undecan-1-one;
2-((1H-indol-3-yl)methyl)-9-(benzo[d]thiazol-2-yl)-2,9-diazaspiro[5.5]undecan-1-one;
2-(benzo[c][1,2,5]oxadiazol-5-ylmethyl)-9-(quinoxalin-2-yl)-2,9-diazaspiro[5.5]undecan-1-one;
2-(3-(pyridin-2-yl)benzyl)-9-(quinoxalin-2-yl)-2,9-diazaspiro[5.5]undecan-1-one;
2-(isoquinolin-5-ylmethyl)-9-(quinoxalin-2-yl)-2,9-diazaspiro[5.5]undecan-1-one;
2-((2-morpholinopyridin-4-yl)methyl)-9-(quinoxalin-2-yl)-2,9-diazaspiro[5.5]undecan-1-one;
2-((1H-pyrrolo[2,3-b]pyridin-3-yl)methyl)-9-(quinoxalin-2-yl)-2,9-diazaspiro[5.5]undecan-1-one;
2-(3-(pyridin-4-yl)benzyl)-9-(quinoxalin-2-yl)-2,9-diazaspiro[5.5]undecan-1-one;
2-(3-morpholinobenzyl)-9-(quinoxalin-2-yl)-2,9-diazaspiro[5.5]undecan-1-one;
2-(3-(1H-pyrazol-1-yl)benzyl)-9-(quinoxalin-2-yl)-2,9-diazaspiro[5.5]undecan-1-one;
2-(3-(pyrimidin-2-yl)benzyl)-9-(quinoxalin-2-yl)-2,9-diazaspiro[5.5]undecan-1-one;
2-(pyridin-2-ylmethyl)-9-(quinoxalin-2-yl)-2,9-diazaspiro[5.5]undecan-1-one;
2-((2-(1H-pyrazol-1-yl)pyridin-4-yl)methyl)-9-(quinoxalin-2-yl)-2,9-diazaspiro[5.5]undecan-1-one;
2-(pyridin-3-ylmethyl)-9-(quinoxalin-2-yl)-2,9-diazaspiro[5.5]undecan-1-one;
2-(3-(pyrazin-2-yl)benzyl)-9-(quinoxalin-2-yl)-2,9-diazaspiro[5.5]undecan-1-one;
2-((1H-benzo[d][1,2,3]triazol-1-yl)methyl)-9-(quinoxalin-2-yl)-2,9-diazaspiro[5.5]undecan-1-one;
2-(pyridin-4-ylmethyl)-9-(quinoxalin-2-yl)-2,9-diazaspiro[5.5]undecan-1-one;
2-((2-methylpyridin-4-yl)methyl)-9-(quinoxalin-2-yl)-2,9-diazaspiro[5.5]undecan-1-one;
2-((2-methyl-5-m-tolylthiazol-4-yl)methyl)-9-(quinoxalin-2-yl)-2,9-diazaspiro[5.5]undecan-1-one;
2-(imidazo[1,2-a]pyridin-3-ylmethyl)-9-(quinoxalin-2-yl)-2,9-diazaspiro[5.5]undecan-1-one;
2-((2-methylimidazo[1,2-a]pyridin-3-yl)methyl)-9-(quinoxalin-2-yl)-2,9-diazaspiro[5.5]undecan-1-one;
2-((2-bromopyridin-4-yl)methyl)-9-(quinoxalin-2-yl)-2,9-diazaspiro[5.5]undecan-1-one;

2-((5-(3-fluorophenyl)-2-methylthiazol-4-yl)methyl)-9-(quinoxalin-2-yl)-2,9-diazaspiro[5.5]undecan-1-one;
2-(1-(1H-indol-3-yl)ethyl)-9-(quinoxalin-2-yl)-2,9-diazaspiro[5.5]undecan-1-one;
2-([1,2,4]triazolo[4,3-a]pyridin-3-ylmethyl)-9-(quinoxalin-2-yl)-2,9-diazaspiro[5.5]undecan-1-one;
2-((2-methyl-2H-indazol-3-yl)methyl)-9-(quinoxalin-2-yl)-2,9-diazaspiro[5.5]undecan-1-one;
2-(benzo[c][1,2,5]oxadiazol-4-ylmethyl)-9-(quinoxalin-2-yl)-2,9-diazaspiro[5.5]undecan-1-one;
2-((6-chloropyridin-3-yl)methyl)-9-(quinoxalin-2-yl)-2,9-diazaspiro[5.5]undecan-1-one;
2-(pyrazolo[1,5-a]pyridin-3-ylmethyl)-9-(quinoxalin-2-yl)-2,9-diazaspiro[5.5]undecan-1-one;
2-(3-(methoxymethyl)benzyl)-9-(quinoxalin-2-yl)-2,9-diazaspiro[5.5]undecan-1-one;
2-(4-(1H-1,2,4-triazol-1-yl)benzyl)-9-(quinoxalin-2-yl)-2,9-diazaspiro[5.5]undecan-1-one;
2-((2,3-dihydrobenzo[b][1,4]dioxin-5-yl)methyl)-9-(furo[3,2-c]pyridin-4-yl)-2,9-diazaspiro[5.5]undecan-1-one;
2-((6-(1H-pyrazol-1-yl)pyridin-2-yl)methyl)-9-(quinoxalin-2-yl)-2,9-diazaspiro[5.5]undecan-1-one;
2-((1,5-dimethyl-1H-pyrazol-3-yl)methyl)-9-(quinoxalin-2-yl)-2,9-diazaspiro[5.5]undecan-1-one;
2-(2-(1H-pyrazol-1-yl)benzyl)-9-(quinoxalin-2-yl)-2,9-diazaspiro[5.5]undecan-1-one;
2-((1-benzyl-1H-imidazol-2-yl)methyl)-9-(quinoxalin-2-yl)-2,9-diazaspiro[5.5]undecan-1-one;
2-((6-chloro-4H-benzo[d][1,3]dioxin-8-yl)methyl)-9-(quinoxalin-2-yl)-2,9-diazaspiro[5.5]undecan-1-one;
2-((5-methylisoxazol-3-yl)methyl)-9-(quinoxalin-2-yl)-2,9-diazaspiro[5.5]undecan-1-one;
2-((5-cyclobutyl-1,2,4-oxadiazol-3-yl)methyl)-9-(quinoxalin-2-yl)-2,9-diazaspiro[5.5]undecan-1-one;
9-(quinoxalin-2-yl)-2-((6-(trifluoromethyl)pyridin-3-yl)methyl)-2,9-diazaspiro[5.5]undecan-1-one;
2-((3,4-dimethoxypyridin-2-yl)methyl)-9-(quinoxalin-2-yl)-2,9-diazaspiro[5.5]undecan-1-one;
3-((1-oxo-9-(quinoxalin-2-yl)-2,9-diazaspiro[5.5]undecan-2-yl)methyl)benzonitrile
2-(isoquinolin-1-ylmethyl)-9-(quinoxalin-2-yl)-2,9-diazaspiro[5.5]undecan-1-one;
2-fluoro-5-((1-oxo-9-(quinoxalin-2-yl)-2,9-diazaspiro[5.5]undecan-2-yl)methyl)benzonitrile
2-((5-phenyloxazol-4-yl)methyl)-9-(quinoxalin-2-yl)-2,9-diazaspiro[5.5]undecan-1-one;
4-((1-oxo-9-(quinoxalin-2-yl)-2,9-diazaspiro[5.5]undecan-2-yl)methyl)quinolin-2(1H)-one;
2-((6-methylpyridin-2-yl)methyl)-9-(quinoxalin-2-yl)-2,9-diazaspiro[5.5]undecan-1-one;
2-((5-methyl-1,2,4-oxadiazol-3-yl)benzyl)-9-(quinoxalin-2-yl)-2,9-diazaspiro[5.5]undecan-1-one;
4-fluoro-3-((1-oxo-9-(quinoxalin-2-yl)-2,9-diazaspiro[5.5]undecan-2-yl)methyl)benzonitrile
5-((1-oxo-9-(quinoxalin-2-yl)-2,9-diazaspiro[5.5]undecan-2-yl)methyl)picolinonitrile
2-(4-(pyrimidin-2-yl)benzyl)-9-(quinoxalin-2-yl)-2,9-diazaspiro[5.5]undecan-1-one;
2-(2-fluoro-3-methoxybenzyl)-9-(quinoxalin-2-yl)-2,9-diazaspiro[5.5]undecan-1-one;
2-((6-(pyrrolidin-1-yl)pyridin-2-yl)methyl)-9-(quinoxalin-2-yl)-2,9-diazaspiro[5.5]undecan-1-one;
2-(3-(3-methyl-1,2,4-oxadiazol-5-yl)benzyl)-9-(quinoxalin-2-yl)-2,9-diazaspiro[5.5]undecan-1-one;
2-((3-methylisoxazol-5-yl)methyl)-9-(quinoxalin-2-yl)-2,9-diazaspiro[5.5]undecan-1-one;
2-((4,6-dimethylpyridin-2-yl)methyl)-9-(quinoxalin-2-yl)-2,9-diazaspiro[5.5]undecan-1-one;
2-((1-methyl-1H-indazol-7-yl)methyl)-9-(quinoxalin-2-yl)-2,9-diazaspiro[5.5]undecan-1-one;
2-((1-methyl-1H-indazol-4-yl)methyl)-9-(quinoxalin-2-yl)-2,9-diazaspiro[5.5]undecan-1-one;
2-(4-(5-methyl-1,3,4-oxadiazol-2-yl)benzyl)-9-(quinoxalin-2-yl)-2,9-diazaspiro[5.5]undecan-1-one;
2-((1-phenyl-1H-imidazol-5-yl)methyl)-9-(quinoxalin-2-yl)-2,9-diazaspiro[5.5]undecan-1-one;
2-((1-(3-methoxyphenyl)-1H-imidazol-5-yl)methyl)-9-(quinoxalin-2-yl)-2,9-diazaspiro[5.5]undecan-1-one;
2-((1-(2-methoxyphenyl)-1H-imidazol-2-yl)methyl)-9-(quinoxalin-2-yl)-2,9-diazaspiro[5.5]undecan-1-one;
2-(benzo[c][1,2,5]thiadiazol-4-ylmethyl)-9-(quinoxalin-2-yl)-2,9-diazaspiro[5.5]undecan-1-one;
2-((5-methyl-2-(thiazol-4-yl)oxazol-4-yl)methyl)-9-(quinoxalin-2-yl)-2,9-diazaspiro[5.5]undecan-1-one;
2-(2-(3,5-dimethyl-1H-pyrazol-1-yl)benzyl)-9-(quinoxalin-2-yl)-2,9-diazaspiro[5.5]undecan-1-one;
2-((2-(furan-3-yl)-5-methyloxazol-4-yl)methyl)-9-(quinoxalin-2-yl)-2,9-diazaspiro[5.5]undecan-1-one;
9-(quinoxalin-2-yl)-2-((2,2,8-trimethyl-4H-[1,3]dioxino[4,5-c]pyridin-5-yl)methyl)-2,9-diazaspiro[5.5]undecan-1-one;
2-((1-benzyl-1H-imidazol-5-yl)methyl)-9-(quinoxalin-2-yl)-2,9-diazaspiro[5.5]undecan-1-one;
2-((4-methyl-2-phenyloxazol-5-yl)methyl)-9-(quinoxalin-2-yl)-2,9-diazaspiro[5.5]undecan-1-one;
2-((6-fluoro-4H-benzo[d][1,3]dioxin-8-yl)methyl)-9-(quinoxalin-2-yl)-2,9-diazaspiro[5.5]undecan-1-one;
2-((1H-indol-2-yl)methyl)-9-(quinoxalin-2-yl)-2,9-diazaspiro[5.5]undecan-1-one;
2-((1-phenyl-1H-tetrazol-5-yl)methyl)-9-(quinoxalin-2-yl)-2,9-diazaspiro[5.5]undecan-1-one;
2-((1H-indol-5-yl)methyl)-9-(quinoxalin-2-yl)-2,9-diazaspiro[5.5]undecan-1-one;
2-((1-oxo-9-(quinoxalin-2-yl)-2,9-diazaspiro[5.5]undecan-2-yl)methyl)benzonitrile
2-(5-methyl-2-(2H-1,2,3-triazol-2-yl)benzyl)-9-(quinoxalin-2-yl)-2,9-diazaspiro[5.5]undecan-1-one;
2-(indolin-4-ylmethyl)-9-(quinoxalin-2-yl)-2,9-diazaspiro[5.5]undecan-1-one;
2-((4-(1H-pyrazol-1-yl)pyridin-2-yl)methyl)-9-(quinoxalin-2-yl)-2,9-diazaspiro[5.5]undecan-1-one;
2-(2-methyl-5-(2H-1,2,3-triazol-2-yl)benzyl)-9-(quinoxalin-2-yl)-2,9-diazaspiro[5.5]undecan-1-one;
2-((1H-indazol-3-yl)methyl)-9-(quinoxalin-2-yl)-2,9-diazaspiro[5.5]undecan-1-one;
2-((1-methyl-1H-indol-3-yl)methyl)-9-(quinoxalin-2-yl)-2,9-diazaspiro[5.5]undecan-1-one;
2-((1H-indol-3-yl)methyl)-9-(5-chlorobenzo[d]oxazol-2-yl)-2,9-diazaspiro[5.5]undecan-1-one;
2-((3,4-dihydro-2H-benzo[b][1,4]oxazin-8-yl)methyl)-9-(quinoxalin-2-yl)-2,9-diazaspiro[5.5]undecan-1-one;
2-((2-methyl-1H-indol-3-yl)methyl)-9-(quinoxalin-2-yl)-2,9-diazaspiro[5.5]undecan-1-one;
1-benzyl-9-(quinoxalin-2-yl)-1,9-diazaspiro[5.5]undecan-2-one;
1-(benzo[d]isoxazol-3-ylmethyl)-9-(quinoxalin-2-yl)-1,9-diazaspiro[5.5]undecan-2-one;
1-((1H-indol-4-yl)methyl)-9-(5-chlorobenzo[d]oxazol-2-yl)-1,9-diazaspiro[5.5]undecan-2-one;
1-((1H-indol-4-yl)methyl)-9-(5-phenyl-1,3,4-oxadiazol-2-yl)-1,9-diazaspiro[5.5]undecan-2-one;
1-((1H-indol-4-yl)methyl)-9-(1H-benzo[d]imidazol-2-yl)-1,9-diazaspiro[5.5]undecan-2-one;

1-((1H-indol-4-yl)methyl)-9-(6-chlorobenzo[d]oxazol-2-yl)-1,9-diazaspiro[5.5]undecan-2-one;
1-((1H-indol-4-yl)methyl)-9-(5-methylbenzo[d]oxazol-2-yl)-1,9-diazaspiro[5.5]undecan-2-one;
1-((1H-pyrrolo[2,3-b]pyridin-3-yl)methyl)-9-(quinoxalin-2-yl)-1,9-diazaspiro[5.5]undecan-2-one;
2-((1-methyl-1H-indazol-3-yl)methyl)-9-(quinoxalin-2-yl)-2,9-diazaspiro[5.5]undecan-1-one;
1-((1-methyl-1H-pyrrolo[2,3-b]pyridin-3-yl)methyl)-9-(quinoxalin-2-yl)-1,9-diazaspiro[5.5]undecan-2-one;
2-((4-methyl-3,4-dihydro-2H-benzo[b][1,4]oxazin-8-yl)methyl)-9-(quinoxalin-2-yl)-2,9-diazaspiro[5.5]undecan-1-one;
2-((1-methylindolin-4-yl)methyl)-9-(quinoxalin-2-yl)-2,9-diazaspiro[5.5]undecan-1-one;
2-((1H-indol-3-yl)methyl)-9-(pyrido[3,2-b]pyrazin-7-yl)-2,9-diazaspiro[5.5]undecan-1-one;
2-(3-(5-methyloxazol-2-yl)benzyl)-9-(quinoxalin-2-yl)-2,9-diazaspiro[5.5]undecan-1-one;
2-(2-(1-methyl-1H-pyrazol-5-yl)benzyl)-9-(quinoxalin-2-yl)-2,9-diazaspiro[5.5]undecan-1-one;
2-(2-(oxazol-2-yl)benzyl)-9-(quinoxalin-2-yl)-2,9-diazaspiro[5.5]undecan-1-one;
2-(2-(furan-2-yl)benzyl)-9-(quinoxalin-2-yl)-2,9-diazaspiro[5.5]undecan-1-one;
2-(2-(pyrimidin-2-yl)benzyl)-9-(quinoxalin-2-yl)-2,9-diazaspiro[5.5]undecan-1-one;
2-((1H-indol-3-yl)methyl)-9-(1H-benzo[d]imidazol-2-yl)-2,9-diazaspiro[5.5]undecan-1-one;
2-((1H-indol-3-yl)methyl)-9-(6-methylbenzo[d]thiazol-2-yl)-2,9-diazaspiro[5.5]undecan-1-one;
2-((1H-indol-3-yl)methyl)-9-(4-phenylpyrimidin-2-yl)-2,9-diazaspiro[5.5]undecan-1-one;
2-((1H-indol-3-yl)methyl)-9-(7H-pyrrolo[2,3-d]pyrimidin-4-yl)-2,9-diazaspiro[5.5]undecan-1-one;
2-((1H-indol-3-yl)methyl)-9-(furo[3,2-c]pyridin-4-yl)-2,9-diazaspiro[5.5]undecan-1-one;
2-((1H-indol-3-yl)methyl)-9-(4-methylphthalazin-1-yl)-2,9-diazaspiro[5.5]undecan-1-one;
9-(6-(1H-imidazol-1-yl)pyrimidin-4-yl)-2-((1H-indol-3-yl)methyl)-2,9-diazaspiro[5.5]undecan-1-one;
2-((1H-indol-3-yl)methyl)-9-(5-methoxy-1H-benzo[d]imidazol-2-yl)-2,9-diazaspiro[5.5]undecan-1-one;
2-((1H-indol-3-yl)methyl)-9-(quinolin-2-yl)-2,9-diazaspiro[5.5]undecan-1-one;
2-((1H-indol-3-yl)methyl)-9-(5-(thiazol-2-yl)pyridin-2-yl)-2,9-diazaspiro[5.5]undecan-1-one;
2-((1H-indol-3-yl)methyl)-9-(isoquinolin-1-yl)-2,9-diazaspiro[5.5]undecan-1-one;
2-((1H-indol-3-yl)methyl)-9-(5-methyl-1H-benzo[d]imidazol-2-yl)-2,9-diazaspiro[5.5]undecan-1-one;
2-((1H-indol-3-yl)methyl)-9-(4-methylquinolin-2-yl)-2,9-diazaspiro[5.5]undecan-1-one;
2-((1H-indol-3-yl)methyl)-9-(6-phenylpyrimidin-4-yl)-2,9-diazaspiro[5.5]undecan-1-one;
2-((1H-indol-3-yl)methyl)-9-(4-(pyridin-4-yl)pyrimidin-2-yl)-2,9-diazaspiro[5.5]undecan-1-one;
2-((1H-indol-3-yl)methyl)-9-(pyrido[4,3-b]pyrazin-7-yl)-2,9-diazaspiro[5.5]undecan-1-one;
2-((1H-indol-3-yl)methyl)-9-(imidazo[1,2-b]pyridazin-6-yl)-2,9-diazaspiro[5.5]undecan-1-one;
2-((1H-indol-3-yl)methyl)-9-(quinazolin-2-yl)-2,9-diazaspiro[5.5]undecan-1-one;
2-((1H-indol-3-yl)methyl)-9-(3-methylquinoxalin-2-yl)-2,9-diazaspiro[5.5]undecan-1-one;
2-((1H-indol-3-yl)methyl)-9-(5-phenyl-1,3,4-thiadiazol-2-yl)-2,9-diazaspiro[5.5]undecan-1-one;
2-((1H-indol-3-yl)methyl)-9-(4-(4-fluorophenyl)thiazol-2-yl)-2,9-diazaspiro[5.5]undecan-1-one;
2-((1H-indol-3-yl)methyl)-9-(4-methyl-6-(1H-pyrazol-1-yl)pyrimidin-2-yl)-2,9-diazaspiro[5.5]undecan-1-one and
2-((1H-indol-3-yl)methyl)-9-(4-(1H-pyrazol-1-yl)pyrimidin-2-yl)-2,9-diazaspiro[5.5]undecan-1-one.

Embodiment 11

A pharmaceutical composition comprising a therapeutically effective amount of a compound according to any one of embodiments 1 to 10 and one or more pharmaceutically acceptable carriers.

Embodiment 12

A combination comprising a therapeutically effective amount of the compound according to any one of embodiments) to 10 and one or more therapeutically active agents.

Embodiment 13

A combination of embodiment 12, wherein said combination is a pharmaceutical combination.

Embodiment 14

A method of inhibiting orexin receptor activity in a subject, wherein the method comprises administering to the subject a therapeutically effective amount of a compound of formula I according to any one of embodiments 1 to 10.

Embodiment 15

A method of treating a disorder or a disease in a subject mediated by orexin receptors, wherein the method comprises administering to the subject a therapeutically effective amount of the compound according to any one of embodiments 1 to 10.

Embodiment 16

A method according to embodiment 14 or 15, wherein the compound is selected from
2-((1H-indol-3-yl)methyl)-9-(quinoxalin-2-yl)-2,9-diazaspiro[5.5]undecan-1-one;
2-(naphthalen-1-ylmethyl)-9-(quinoxalin-2-yl)-2,9-diazaspiro[5.5]undecan-1-one;
2-((1H-indol-4-yl)methyl)-9-(quinoxalin-2-yl)-2,9-diazaspiro[5.5]undecan-1-one;
2-((2,3-dihydrobenzo[b][1,4]dioxin-5-yl)methyl)-9-(quinoxalin-2-yl)-2,9-diazaspiro[5.5]undecan-1-one;
2-(3-(pyridin-3-yl)benzyl)-9-(quinoxalin-2-yl)-2,9-diazaspiro[5.5]undecan-1-one;
2-benzyl-9-(quinoxalin-2-yl)-2,9-diazaspiro[5.5]undecan-1-one;
2-(naphthalen-2-ylmethyl)-9-(quinoxalin-2-yl)-2,9-diazaspiro[5.5]undecan-1-one;
2-(benzo[d][1,3]dioxol-5-ylmethyl)-9-(quinoxalin-2-yl)-2,9-diazaspiro[5.5]undecan-1-one;
2-(benzo[d][1,3]dioxol-4-ylmethyl)-9-(quinoxalin-2-yl)-2,9-diazaspiro[5.5]undecan-1-one;
9-(1H-benzo[d]imidazol-2-yl)-2-benzyl-2,9-diazaspiro[5.5]undecan-1-one;
9-(1H-benzo[d]imidazol-2-yl)-2-(naphthalen-1-ylmethyl)-2,9-diazaspiro[5.5]undecan-1-one;

9-(1-methyl-1H-benzo[d]imidazol-2-yl)-2-(naphthalen-1-ylmethyl)-2,9-diazaspiro[5.5]undecan-1-one;

2-((2-methyl-1H-indol-4-yl)methyl)-9-(quinoxalin-2-yl)-2,9-diazaspiro[5.5]undecan-1-one;

9-(quinoxalin-2-yl)-2-(3-(trifluoromethyl)benzyl)-2,9-diazaspiro[5.5]undecan-1-one;

2-(3-methylbenzyl)-9-(quinoxalin-2-yl)-2,9-diazaspiro[5.5]undecan-1-one;

2-(3,5-dimethylbenzyl)-9-(quinoxalin-2-yl)-2,9-diazaspiro[5.5]undecan-1-one;

2-(2,3-dimethylbenzyl)-9-(quinoxalin-2-yl)-2,9-diazaspiro[5.5]undecan-1-one;

2-(2,3-dimethoxybenzyl)-9-(quinoxalin-2-yl)-2,9-diazaspiro[5.5]undecan-1-one;

2-(2-methylbenzyl)-9-(quinoxalin-2-yl)-2,9-diazaspiro[5.5]undecan-1-one;

2-(2,5-dimethylbenzyl)-9-(quinoxalin-2-yl)-2,9-diazaspiro[5.5]undecan-1-one;

2-(quinolin-8-ylmethyl)-9-(quinoxalin-2-yl)-2,9-diazaspiro[5.5]undecan-1-one;

2-(biphenyl-3-ylmethyl)-9-(quinoxalin-2-yl)-2,9-diazaspiro[5.5]undecan-1-one;

9-(quinoxalin-2-yl)-2-(2-(trifluoromethyl)benzyl)-2,9-diazaspiro[5.5]undecan-1-one;

9-(quinoxalin-2-yl)-2-(4-(trifluoromethyl)benzyl)-2,9-diazaspiro[5.5]undecan-1-one;

2-((2,3-dihydrobenzo[b][1,4]dioxin-6-yl)methyl)-9-(quinoxalin-2-yl)-2,9-diazaspiro[5.5]undecan-1-one;

2-((1-methyl-1H-indol-4-yl)methyl)-9-(quinoxalin-2-yl)-2,9-diazaspiro[5.5]undecan-1-one;

2-(3-chlorobenzyl)-9-(quinoxalin-2-yl)-2,9-diazaspiro[5.5]undecan-1-one;

9-(1H-benzo[d]imidazol-2-yl)-2-(3-chlorobenzyl)-2,9-diazaspiro[5.5]undecan-1-one;

2-(3-chlorobenzyl)-9-(4-phenylpyrimidin-2-yl)-2,9-diazaspiro[5.5]undecan-1-one;

2-((1-methyl-1H-benzo[d]imidazol-2-yl)methyl)-9-(quinoxalin-2-yl)-2,9-diazaspiro[5.5]undecan-1-one;

2-((5-(4-methoxyphenyl)-1,3,4-oxadiazol-2-yl)methyl)-9-(quinoxalin-2-yl)-2,9-diazaspiro[5.5]undecan-1-one;

2-((3-methyl-5-phenylisoxazol-4-yl)methyl)-9-(quinoxalin-2-yl)-2,9-diazaspiro[5.5]undecan-1-one;

2-((2-methylquinolin-4-yl)methyl)-9-(quinoxalin-2-yl)-2,9-diazaspiro[5.5]undecan-1-one;

2-((5-methyl-3-phenylisoxazol-4-yl)methyl)-9-(quinoxalin-2-yl)-2,9-diazaspiro[5.5]undecan-1-one;

2-(3-(1H-pyrrol-1-yl)benzyl)-9-(quinoxalin-2-yl)-2,9-diazaspiro[5.5]undecan-1-one;

2-(benzo[d]isoxazol-3-ylmethyl)-9-(quinoxalin-2-yl)-2,9-diazaspiro[5.5]undecan-1-one;

2-((3,5-dimethylisoxazol-4-yl)methyl)-9-(quinoxalin-2-yl)-2,9-diazaspiro[5.5]undecan-1-one;

1-((1H-indol-4-yl)methyl)-9-(quinoxalin-2-yl)-1,9-diazaspiro[5.5]undecan-2-one;

2-(2-(3-methyl-1,2,4-oxadiazol-5-yl)benzyl)-9-(quinoxalin-2-yl)-2,9-diazaspiro[5.5]undecan-1-one;

2-((1H-indol-3-yl)methyl)-9-(benzo[d]oxazol-2-yl)-2,9-diazaspiro[5.5]undecan-1-one;

1-(2,5-dimethylbenzyl)-9-(quinoxalin-2-yl)-1,9-diazaspiro[5.5]undecan-2-one;

1-((1H-indol-4-yl)methyl)-9-(benzo[d]oxazol-2-yl)-1,9-diazaspiro[5.5]undecan-2-one;

1-((1H-indol-3-yl)methyl)-9-(quinoxalin-2-yl)-1,9-diazaspiro[5.5]undecan-2-one;

1-((1-methyl-1H-indol-4-yl)methyl)-9-(quinoxalin-2-yl)-1,9-diazaspiro[5.5]undecan-2-one;

2-((2-methoxypyridin-4-yl)methyl)-9-(quinoxalin-2-yl)-2,9-diazaspiro[5.5]undecan-1-one;

2-(3-(1H-1,2,3-triazol-1-yl)benzyl)-9-(quinoxalin-2-yl)-2,9-diazaspiro[5.5]undecan-1-one;

2-(3-(2H-1,2,3-triazol-2-yl)benzyl)-9-(quinoxalin-2-yl)-2,9-diazaspiro[5.5]undecan-1-one;

2-((1H-indol-3-yl)methyl)-9-(quinolin-3-yl)-2,9-diazaspiro[5.5]undecan-1-one;

2-(2-(2H-1,2,3-triazol-2-yl)benzyl)-9-(quinoxalin-2-yl)-2,9-diazaspiro[5.5]undecan-1-one;

2-benzyl-9-(1-methyl-1H-benzo[d]imidazol-2-yl)-2,9-diazaspiro[5.5]undecan-1-one;

2-(2-(1-methyl-1H-pyrazol-4-yl)benzyl)-9-(quinoxalin-2-yl)-2,9-diazaspiro[5.5]undecan-1-one;

2-((1H-indol-3-yl)methyl)-9-(benzo[d]thiazol-2-yl)-2,9-diazaspiro[5.5]undecan-1-one;

2-(benzo[c][1,2,5]oxadiazol-5-ylmethyl)-9-(quinoxalin-2-yl)-2,9-diazaspiro[5.5]undecan-1-one;

2-(3-(pyridin-2-yl)benzyl)-9-(quinoxalin-2-yl)-2,9-diazaspiro[5.5]undecan-1-one;

2-(isoquinolin-5-ylmethyl)-9-(quinoxalin-2-yl)-2,9-diazaspiro[5.5]undecan-1-one;

2-((2-morpholinopyridin-4-yl)methyl)-9-(quinoxalin-2-yl)-2,9-diazaspiro[5.5]undecan-1-one;

2-((1H-pyrrolo[2,3-b]pyridin-3-yl)methyl)-9-(quinoxalin-2-yl)-2,9-diazaspiro[5.5]undecan-1-one;

2-(3-(pyridin-4-yl)benzyl)-9-(quinoxalin-2-yl)-2,9-diazaspiro[5.5]undecan-1-one;

2-(3-morpholinobenzyl)-9-(quinoxalin-2-yl)-2,9-diazaspiro[5.5]undecan-1-one;

2-(3-(1H-pyrazol-1-yl)benzyl)-9-(quinoxalin-2-yl)-2,9-diazaspiro[5.5]undecan-1-one;

2-(3-(pyrimidin-2-yl)benzyl)-9-(quinoxalin-2-yl)-2,9-diazaspiro[5.5]undecan-1-one;

2-(pyridin-2-ylmethyl)-9-(quinoxalin-2-yl)-2,9-diazaspiro[5.5]undecan-1-one;

2-((2-(1H-pyrazol-1-yl)pyridin-4-yl)methyl)-9-(quinoxalin-2-yl)-2,9-diazaspiro[5.5]undecan-1-one;

2-(pyridin-3-ylmethyl)-9-(quinoxalin-2-yl)-2,9-diazaspiro[5.5]undecan-1-one;

2-(3-(pyrazin-2-yl)benzyl)-9-(quinoxalin-2-yl)-2,9-diazaspiro[5.5]undecan-1-one;

2-((1H-benzo[d][1,2,3]triazol-1-yl)methyl)-9-(quinoxalin-2-yl)-2,9-diazaspiro[5.4]undecan-1-one;

2-(pyridin-4-ylmethyl)-9-(quinoxalin-2-yl)-2,9-diazaspiro[5.5]undecan-1-one;

2-((2-methylpyridin-4-yl)methyl)-9-(quinoxalin-2-yl)-2,9-diazaspiro[5.5]undecan-1-one;

2-((2-methyl-5-m-tolylthiazol-4-yl)methyl)-9-(quinoxalin-2-yl)-2,9-diazaspiro[5.5]undecan-1-one;

2-(imidazo[1,2-a]pyridin-3-ylmethyl)-9-(quinoxalin-2-yl)-2,9-diazaspiro[5.5]undecan-1-one;

2-((2-methylimidazo[1,2-a]pyridin-3-yl)methyl)-9-(quinoxalin-2-yl)-2,9-diazaspiro[5.5]undecan-1-one;

2-((2-bromopyridin-4-yl)methyl)-9-(quinoxalin-2-yl)-2,9-diazaspiro[5.5]undecan-1-one;

2-((5-(3-fluorophenyl)-2-methylthiazol-4-yl)methyl)-9-(quinoxalin-2-yl)-2,9-diazaspiro[5.5]undecan-1-one;

2-(1-(1H-indol-3-yl)ethyl)-9-(quinoxalin-2-yl)-2,9-diazaspiro[5.5]undecan-1-one;

2-([1,2,4]triazolo[4,3-a]pyridin-3-ylmethyl)-9-(quinoxalin-2-yl)-2,9-diazaspiro[5.5]undecan-1-one;

2-((2-methyl-2H-indazol-3-yl)methyl)-9-(quinoxalin-2-yl)-2,9-diazaspiro[5.5]undecan-1-one;

2-(benzo[c][1,2,5]oxadiazol-4-ylmethyl)-9-(quinoxalin-2-yl)-2,9-diazaspiro[5.5]undecan-1-one;

2-((6-chloropyridin-3-yl)methyl)-9-(quinoxalin-2-yl)-2,9-diazaspiro[5.5]undecan-1-one;

2-(pyrazolo[1,5-a]pyridin-3-ylmethyl)-9-(quinoxalin-2-yl)-2,9-diazaspiro[5.5]undecan-1-one;

2-(3-(methoxymethyl)benzyl)-9-(quinoxalin-2-yl)-2,9-diazaspiro[5.5]undecan-1-one;

2-(4-(1H-1,2,4-triazol-1-yl)benzyl)-9-(quinoxalin-2-yl)-2,9-diazaspiro[5.5]undecan-1-one;

2-((2,3-dihydrobenzo[b][1,4]dioxin-5-yl)methyl)-9-(furo[3,2-c]pyridin-4-yl)-2,9-diazaspiro[5.5]undecan-1-one;

2-((6-(1H-pyrazol-1-yl)pyridin-2-yl)methyl)-9-(quinoxalin-2-yl)-2,9-diazaspiro[5.5]undecan-1-one;

2-((1,5-dimethyl-1H-pyrazol-3-yl)methyl)-9-(quinoxalin-2-yl)-2,9-diazaspiro[5.5]undecan-1-one;

2-(2-(1H-pyrazol-1-yl)benzyl)-9-(quinoxalin-2-yl)-2,9-diazaspiro[5.5]undecan-1-one;

2-((1-benzyl-1H-imidazol-2-yl)methyl)-9-(quinoxalin-2-yl)-2,9-diazaspiro[5.5]undecan-1-one;

2-((6-chloro-4H-benzo[d][1,3]dioxin-8-yl)methyl)-9-(quinoxalin-2-yl)-2,9-diazaspiro[5.5]undecan-1-one;

2-((5-methylisoxazol-3-yl)methyl)-9-(quinoxalin-2-yl)-2,9-diazaspiro[5.5]undecan-1-one;

2-((5-cyclobutyl-1,2,4-oxadiazol-3-yl)methyl)-9-(quinoxalin-2-yl)-2,9-diazaspiro[5.5]undecan-1-one;

9-(quinoxalin-2-yl)-2-((6-(trifluoromethyl)pyridin-3-yl)methyl)-2,9-diazaspiro[5.5]undecan-1-one;

2-((3,4-dimethoxypyridin-2-yl)methyl)-9-(quinoxalin-2-yl)-2,9-diazaspiro[5.5]undecan-1-one;

3-((1-oxo-9-(quinoxalin-2-yl)-2,9-diazaspiro[5.5]undecan-2-yl)methyl)benzonitrile 2-(isoquinolin-1-ylmethyl)-9-(quinoxalin-2-yl)-2,9-diazaspiro[5.5]undecan-1-one;

2-fluoro-5-((1-oxo-9-(quinoxalin-2-yl)-2,9-diazaspiro[5.5]undecan-2-yl)methyl)benzonitrile 2-((5-phenyloxazol-4-yl)methyl)-9-(quinoxalin-2-yl)-2,9-diazaspiro[5.5]undecan-1-one;

4-((1-oxo-9-(quinoxalin-2-yl)-2,9-diazaspiro[5.5]undecan-2-yl)methyl)quinolin-2(1H)-one;

2-((6-methylpyridin-2-yl)methyl)-9-(quinoxalin-2-yl)-2,9-diazaspiro[5.5]undecan-1-one;

2-(3-(5-methyl-1,2,4-oxadiazol-3-yl)benzyl)-9-(quinoxalin-2-yl)-2,9-diazaspiro[5.5]undecan-1-one;

4-fluoro-3-((1-oxo-9-(quinoxalin-2-yl)-2,9-diazaspiro[5.5]undecan-2-yl)methyl)benzonitrile 5-((1-oxo-9-(quinoxalin-2-yl)-2,9-diazaspiro[5.5]undecan-2-yl)methyl)picolinonitrile 2-(4-(pyrimidin-2-yl)benzyl)-9-(quinoxalin-2-yl)-2,9-diazaspiro[5.5]undecan-1-one;

2-(2-fluoro-3-methoxybenzyl)-9-(quinoxalin-2-yl)-2,9-diazaspiro[5.5]undecan-1-one;

2-((6-(pyrrolidin-1-yl)pyridin-2-yl)methyl)-9-(quinoxalin-2-yl)-2,9-diazaspiro[5.5]undecan-1-one;

2-(3-(3-methyl-1,2,4-oxadiazol-5-yl)benzyl)-9-(quinoxalin-2-yl)-2,9-diazaspiro[5.5]undecan-1-one;

2-((3-methylisoxazol-5-yl)methyl)-9-(quinoxalin-2-yl)-2,9-diazaspiro[5.5]undecan-1-one;

2-((4,6-dimethylpyridin-2-yl)methyl)-9-(quinoxalin-2-yl)-2,9-diazaspiro[5.5]undecan-1-one;

2-((1-methyl-1H-indazol-7-yl)methyl)-9-(quinoxalin-2-yl)-2,9-diazaspiro[5.5]undecan-1-one;

2-((1-methyl-1H-indazol-4-yl)methyl)-9-(quinoxalin-2-yl)-2,9-diazaspiro[5.5]undecan-1-one;

2-(4-(5-methyl-1,3,4-oxadiazol-2-yl)benzyl)-9-(quinoxalin-2-yl)-2,9-diazaspiro[5.5]undecan-1-one;

2-((1-phenyl-1H-imidazol-5-yl)methyl)-9-(quinoxalin-2-yl)-2,9-diazaspiro[5.5]undecan-1-one;

2-((1-(3-methoxyphenyl)-1H-imidazol-5-yl)methyl)-9-(quinoxalin-2-yl)-2,9-diazaspiro[5.5]undecan-1-one;

2-((1-(2-methoxyphenyl)-1H-imidazol-2-yl)methyl)-9-(quinoxalin-2-yl)-2,9-diazaspiro[5.5]undecan-1-one;

2-(benzo[c][1,2,5]thiadiazol-4-ylmethyl)-9-(quinoxalin-2-yl)-2,9-diazaspiro[5.5]undecan-1-one;

2-((5-methyl-2-(thiazol-4-yl)oxazol-4-yl)methyl)-9-(quinoxalin-2-yl)-2,9-diazaspiro[5.5]undecan-1-one;

2-(2-(3,5-dimethyl-1H-pyrazol-1-yl)benzyl)-9-(quinoxalin-2-yl)-2,9-diazaspiro[5.5]undecan-1-one;

2-((2-(furan-3-yl)-5-methyloxazol-4-yl)methyl)-9-(quinoxalin-2-yl)-2,9-diazaspiro[5.5]undecan-1-one;

9-(quinoxalin-2-yl)-2-((2,2,8-trimethyl-4H-[1,3]dioxino[4,5-c]pyridin-5-yl)methyl)-2,9-diazaspiro[5.5]undecan-1-one;

2-((1-benzyl-1H-imidazol-5-yl)methyl)-9-(quinoxalin-2-yl)-2,9-diazaspiro[5.5]undecan-1-one;

2-((4-methyl-2-phenyloxazol-5-yl)methyl)-9-(quinoxalin-2-yl)-2,9-diazaspiro[5.5]undecan-1-one;

2-((6-fluoro-4H-benzo[d][1,3]dioxin-8-yl)methyl)-9-(quinoxalin-2-yl)-2,9-diazaspiro[5.5]undecan-1-one;

2-((1H-indol-2-yl)methyl)-9-(quinoxalin-2-yl)-2,9-diazaspiro[5.5]undecan-1-one;

2-((1-phenyl-1H-tetrazol-5-yl)methyl)-9-(quinoxalin-2-yl)-2,9-diazaspiro[5.5]undecan-1-one;

2-((1H-indol-5-yl)methyl)-9-(quinoxalin-2-yl)-2,9-diazaspiro[5.5]undecan-1-one;

2-((1-oxo-9-(quinoxalin-2-yl)-2,9-diazaspiro[5.5]undecan-2-yl)methyl)benzonitrile 2-(5-methyl-2-(2H-1,2,3-triazol-2-yl)benzyl)-9-(quinoxalin-2-yl)-2,9-diazaspiro[5.5]undecan-1-one;

2-(indolin-4-ylmethyl)-9-(quinoxalin-2-yl)-2,9-diazaspiro[5.5]undecan-1-one;

2-((4-(1H-pyrazol-1-yl)pyridin-2-yl)methyl)-9-(quinoxalin-2-yl)-2,9-diazaspiro[5.5]undecan-1-one;

2-(2-methyl-5-(2H-1,2,3-triazol-2-yl)benzyl)-9-(quinoxalin-2-yl)-2,9-diazaspiro[5.5]undecan-1-one;

2-((1H-indazol-3-yl)methyl)-9-(quinoxalin-2-yl)-2,9-diazaspiro[5.5]undecan-1-one;

2-((1-methyl-1H-indol-3-yl)methyl)-9-(quinoxalin-2-yl)-2,9-diazaspiro[5.5]undecan-1-one;

2-((1H-indol-3-yl)methyl)-9-(5-chlorobenzo[d]oxazol-2-yl)-2,9-diazaspiro[5.5]undecan-1-one;

2-((3,4-dihydro-2H-benzo[b][1,4]oxazin-8-yl)methyl)-9-(quinoxalin-2-yl)-2,9-diazaspiro[5.5]undecan-1-one;

2-((2-methyl-1H-indol-3-yl)methyl)-9-(quinoxalin-2-yl)-2,9-diazaspiro[5.5]undecan-1-one;

1-benzyl-9-(quinoxalin-2-yl)-1,9-diazaspiro[5.5]undecan-2-one;

1-(benzo[d]isoxazol-3-ylmethyl)-9-(quinoxalin-2-yl)-1,9-diazaspiro[5.5]undecan-2-one;

1-((1H-indol-4-yl)methyl)-9-(5-chlorobenzo[d]oxazol-2-yl)-1,9-diazaspiro[5.5]undecan-2-one;

1-((1H-indol-4-yl)methyl)-9-(5-phenyl-1,3,4-oxadiazol-2-yl)-1,9-diazaspiro[5.5]undecan-2-one;

1-((1H-indol-4-yl)methyl)-9-(1H-benzo[d]imidazol-2-yl)-1,9-diazaspiro[5.5]undecan-2-one;

1-((1H-indol-4-yl)methyl)-9-(6-chlorobenzo[d]oxazol-2-yl)-1,9-diazaspiro[5.5]undecan-2-one;

1-((1H-indol-4-yl)methyl)-9-(5-methylbenzo[d]oxazol-2-yl)-1,9-diazaspiro[5.5]undecan-2-one;

1-((1H-pyrrolo[2,3-b]pyridin-3-yl)methyl)-9-(quinoxalin-2-yl)-1,9-diazaspiro[5.5]undecan-2-one;

2-((1-methyl-1H-indazol-3-yl)methyl)-9-(quinoxalin-2-yl)-2,9-diazaspiro[5.5]undecan-1-one;

1-((1-methyl-1H-pyrrolo[2,3-b]pyridin-3-yl)methyl)-9-(quinoxalin-2-yl)-1,9-diazaspiro[5.5]undecan-2-one;

2-((4-methyl-3,4-dihydro-2H-benzo[b][1,4]oxazin-8-yl)methyl)-9-(quinoxalin-2-yl)-2,9-diazaspiro[5.5]undecan-1-one;
2-((1-methylindolin-4-yl)methyl)-9-(quinoxalin-2-yl)-2,9-diazaspiro[5.5]undecan-1-one;
2-((1H-indol-3-yl)methyl)-9-(pyrido[3,2-b]pyrazin-7-yl)-2,9-diazaspiro[5.5]undecan-1-one;
2-(3-(5-methyloxazol-2-yl)benzyl)-9-(quinoxalin-2-yl)-2,9-diazaspiro[5.5]undecan-1-one;
2-(2-(1-methyl-1H-pyrazol-5-yl)benzyl)-9-(quinoxalin-2-yl)-2,9-diazaspiro[5.5]undecan-1-one;
2-(2-(oxazol-2-yl)benzyl)-9-(quinoxalin-2-yl)-2,9-diazaspiro[5.5]undecan-1-one;
2-(2-(furan-2-yl)benzyl)-9-(quinoxalin-2-yl)-2,9-diazaspiro[5.5]undecan-1-one;
2-(2-(pyrimidin-2-yl)benzyl)-9-(quinoxalin-2-yl)-2,9-diazaspiro[5.5]undecan-1-one;
2-((1H-indol-3-yl)methyl)-9-(1H-benzo[d]imidazol-2-yl)-2,9-diazaspiro[5.5]undecan-1-one;
2-((1H-indol-3-yl)methyl)-9-(6-methylbenzo[d]thiazol-2-yl)-2,9-diazaspiro[5.5]undecan-1-one;
2-((1H-indol-3-yl)methyl)-9-(4-phenyl pyrimidin-2-yl)-2,9-diazaspiro[5.5]undecan-1-one;
2-((1H-indol-3-yl)methyl)-9-(7H-pyrrolo[2,3-d]pyrimidin-4-yl)-2,9-diazaspiro[5.5]undecan-1-one;
2-((1H-indol-3-yl)methyl)-9-(furo[3,2-c]pyridin-4-yl)-2,9-diazaspiro[5.5]undecan-1-one;
2-((1H-indol-3-yl)methyl)-9-(4-methylphthalazin-1-yl)-2,9-diazaspiro[5.5]undecan-1-one;
9-(6-(1H-imidazol-1-yl)pyrimidin-4-yl)-2-((1H-indol-3-yl)methyl)-2,9-diazaspiro[5.5]undecan-1-one;
2-((1H-indol-3-yl)methyl)-9-(5-methoxy-1H-benzo[d]imidazol-2-yl)-2,9-diazaspiro[5.5]undecan-1-one;
2-((1H-indol-3-yl)methyl)-9-(quinolin-2-yl)-2,9-diazaspiro[5.5]undecan-1-one;
2-((1H-indol-3-yl)methyl)-9-(5-(thiazol-2-yl)pyridin-2-yl)-2,9-diazaspiro[5.5]undecan-1-one;
2-((1H-indol-3-yl)methyl)-9-(isoquinolin-1-yl)-2,9-diazaspiro[5.5]undecan-1-one;
2-((1H-indol-3-yl)methyl)-9-(5-methyl-1H-benzo[d]imidazol-2-yl)-2,9-diazaspiro[5.5]undecan-1-one;
2-((1H-indol-3-yl)methyl)-9-(4-methylquinolin-2-yl)-2,9-diazaspiro[5.5]undecan-1-one;
2-((1H-indol-3-yl)methyl)-9-(6-phenylpyrimidin-4-yl)-2,9-diazaspiro[5.5]undecan-1-one;
2-((1H-indol-3-yl)methyl)-9-(4-(pyridin-4-yl)pyrimidin-2-yl)-2,9-diazaspiro[5.5]undecan-1-one;
2-((1H-indol-3-yl)methyl)-9-(pyrido[4,3-b]pyrazin-7-yl)-2,9-diazaspiro[5.5]undecan-1-one;
2-((1H-indol-3-yl)methyl)-9-(imidazo[1,2-b]pyridazin-6-yl)-2,9-diazaspiro[5.5]undecan-1-one;
2-((1H-indol-3-yl)methyl)-9-(quinazolin-2-yl)-2,9-diazaspiro[5.5]undecan-1-one;
2-((1H-indol-3-yl)methyl)-9-(3-methylquinoxalin-2-yl)-2,9-diazaspiro[5.5]undecan-1-one;
2-((1H-indol-3-yl)methyl)-9-(5-phenyl-1,3,4-thiadiazol-2-yl)-2,9-diazaspiro[5.5]undecan-1-one;
2-((1H-indol-3-yl)methyl)-9-(4-(4-fluorophenyl)thiazol-2-yl)-2,9-diazaspiro[5.5]undecan-1-one;
2-((1H-indol-3-yl)methyl)-9-(4-methyl-6-(1H-pyrazol-1-yl)pyrimidin-2-yl)-2,9-diazaspiro[5.5]undecan-1-one and
2-((1H-indol-3-yl)methyl)-9-(4-(1H-pyrazol-1-yl)pyrimidin-2-yl)-2,9-diazaspiro[5.5]undecan-1-one.

Embodiment 17

A method of any of embodiments 14 to 16, wherein said disorder or said disease is selected from sleep disorders, eating disorders, substance-related disorders, mental health disorders or Alzheimer's disease.

Embodiment 18

A compound according to any one of embodiments 1 to 10, for use as a medicament.

Embodiment 19

A compound according to any one of embodiments 1 to 10, for use in the treatment of a disorder or disease in a subject mediated by orexin receptors.

Embodiment 20

A compound according to any one of embodiments 1 to 10, for use in the treatment of a disorder or disease in a subject characterized by an abnormal activity of orexin receptors.

Embodiment 21

A compound for use according to any one of embodiments 19 or 20, wherein the treatment of a disorder or disease is selected from sleep disorders, eating disorders, substance-related disorders, mental health disorders or Alzheimer's disease.

Embodiment 22

Use of a compound according to any one of embodiments 1 to 10, for the treatment of a disorder or disease in a subject mediated by orexin receptors.

Embodiment 23

Use of a compound according to any one of embodiments 1 to 10, for the treatment of a disorder or disease in a subject characterized by an abnormal activity of orexin receptors.

Embodiment 24

Use of a compound according to any one of embodiments 1 to 10, in the manufacture of a medicament for the treatment of a disorder or disease in a subject mediated by orexin receptors.

Embodiment 25

Use according to any one of embodiments 22 to 24, wherein said disorder or said disease is selected from sleep disorders, eating disorders, substance-related disorders, mental health disorders or Alzheimer's disease.

Embodiment 26

Pharmaceutical composition for treating a disorder or disease in a subject mediated by orexin receptors comprising a compound according to any one of embodiments 1 to 10 as an active ingredient.

Embodiment 27

A pharmaceutical composition according to embodiment 25, wherein said disorder or said disease is selected from sleep disorders, eating disorders, substance-related disorders, mental health disorders or Alzheimer's disease.

Embodiment 28

A pharmaceutical composition according to embodiment 25 or 26, wherein said compound is selected from

- 2-((1H-indol-3-yl)methyl)-9-(quinoxalin-2-yl)-2,9-diazaspiro[5.5]undecan-1-one;
- 2-(naphthalen-1-ylmethyl)-9-(quinoxalin-2-yl)-2,9-diazaspiro[5.5]undecan-1-one;
- 2-((1H-indol-4-yl)methyl)-9-(quinoxalin-2-yl)-2,9-diazaspiro[5.5]undecan-1-one;
- 2-((2,3-dihydrobenzo[b][1,4]dioxin-5-yl)methyl)-9-(quinoxalin-2-yl)-2,9-diazaspiro[5.5]undecan-1-one;
- 2-(3-(pyridin-3-yl)benzyl)-9-(quinoxalin-2-yl)-2,9-diazaspiro[5.5]undecan-1-one;
- 2-benzyl-9-(quinoxalin-2-yl)-2,9-diazaspiro[5.5]undecan-1-one;
- 2-(naphthalen-2-ylmethyl)-9-(quinoxalin-2-yl)-2,9-diazaspiro[5.5]undecan-1-one;
- 2-(benzo[d][1,3]dioxol-5-ylmethyl)-9-(quinoxalin-2-yl)-2,9-diazaspiro[5.5]undecan-1-one;
- 2-(benzo[d][1,3]dioxol-4-ylmethyl)-9-(quinoxalin-2-yl)-2,9-diazaspiro[5.5]undecan-1-one;
- 9-(1H-benzo[d]imidazol-2-yl)-2-benzyl-2,9-diazaspiro[5.5]undecan-1-one;
- 9-(1H-benzo[d]imidazol-2-yl)-2-(naphthalen-1-ylmethyl)-2,9-diazaspiro[5.5]undecan-1-one;
- 9-(1-methyl-1H-benzo[d]imidazol-2-yl)-2-(naphthalen-1-ylmethyl)-2,9-diazaspiro[5.5]undecan-1-one;
- 2-((2-methyl-1H-indol-4-yl)methyl)-9-(quinoxalin-2-yl)-2,9-diazaspiro[5.5]undecan-1-one;
- 9-(quinoxalin-2-yl)-2-(3-(trifluoromethyl)benzyl)-2,9-diazaspiro[5.5]undecan-1-one;
- 2-(3-methylbenzyl)-9-(quinoxalin-2-yl)-2,9-diazaspiro[5.5]undecan-1-one;
- 2-(3,5-dimethylbenzyl)-9-(quinoxalin-2-yl)-2,9-diazaspiro[5.5]undecan-1-one;
- 2-(2,3-dimethylbenzyl)-9-(quinoxalin-2-yl)-2,9-diazaspiro[5.5]undecan-1-one;
- 2-(2,3-dimethoxybenzyl)-9-(quinoxalin-2-yl)-2,9-diazaspiro[5.5]undecan-1-one;
- 2-(2-methylbenzyl)-9-(quinoxalin-2-yl)-2,9-diazaspiro[5.5]undecan-1-one;
- 2-(2,5-dimethylbenzyl)-9-(quinoxalin-2-yl)-2,9-diazaspiro[5.5]undecan-1-one;
- 2-(quinolin-8-ylmethyl)-9-(quinoxalin-2-yl)-2,9-diazaspiro[5.5]undecan-1-one;
- 2-(biphenyl-3-ylmethyl)-9-(quinoxalin-2-yl)-2,9-diazaspiro[5.5]undecan-1-one;
- 9-(quinoxalin-2-yl)-2-(2-(trifluoromethyl)benzyl)-2,9-diazaspiro[5.5]undecan-1-one;
- 9-(quinoxalin-2-yl)-2-(4-(trifluoromethyl)benzyl)-2,9-diazaspiro[5.5]undecan-1-one;
- 2-((2,3-dihydrobenzo[b][1,4]dioxin-6-yl)methyl)-9-(quinoxalin-2-yl)-2,9-diazaspiro[5.5]undecan-1-one;
- 2-((1-methyl-1H-indol-4-yl)methyl)-9-(quinoxalin-2-yl)-2,9-diazaspiro[5.5]undecan-1-one;
- 2-(3-chlorobenzyl)-9-(quinoxalin-2-yl)-2,9-diazaspiro[5.5]undecan-1-one;
- 9-(1H-benzo[d]imidazol-2-yl)-2-(3-chlorobenzyl)-2,9-diazaspiro[5.5]undecan-1-one;
- 2-(3-chlorobenzyl)-9-(4-phenylpyrimidin-2-yl)-2,9-diazaspiro[5.5]undecan-1-one;
- 2-((1-methyl-1H-benzo[d]imidazol-2-yl)methyl)-9-(quinoxalin-2-yl)-2,9-diazaspiro[5.5]undecan-1-one;
- 2-((5-(4-methoxyphenyl)-1,3,4-oxadiazol-2-yl)methyl)-9-(quinoxalin-2-yl)-2,9-diazaspiro[5.5]undecan-1-one;
- 2-((3-methyl-5-phenylisoxazol-4-yl)methyl)-9-(quinoxalin-2-yl)-2,9-diazaspiro[5.5]undecan-1-one;
- 2-((2-methylquinolin-4-yl)methyl)-9-(quinoxalin-2-yl)-2,9-diazaspiro[5.5]undecan-1-one;
- 2-((5-methyl-3-phenylisoxazol-4-yl)methyl)-9-(quinoxalin-2-yl)-2,9-diazaspiro[5.5]undecan-1-one;
- 2-(3-(1H-pyrrol-1-yl)benzyl)-9-(quinoxalin-2-yl)-2,9-diazaspiro[5.5]undecan-1-one;
- 2-(benzo[d]isoxazol-3-ylmethyl)-9-(quinoxalin-2-yl)-2,9-diazaspiro[5.5]undecan-1-one;
- 2-((3,5-dimethylisoxazol-4-yl)methyl)-9-(quinoxalin-2-yl)-2,9-diazaspiro[5.5]undecan-1-one;
- 1-((1H-indol-4-yl)methyl)-9-(quinoxalin-2-yl)-1,9-diazaspiro[5.5]undecan-2-one;
- 2-(2-(3-methyl-1,2,4-oxadiazol-5-yl)benzyl)-9-(quinoxalin-2-yl)-2,9-diazaspiro[5.5]undecan-1-one;
- 2-((1H-indol-3-yl)methyl)-9-(benzo[d]oxazol-2-yl)-2,9-diazaspiro[5.5]undecan-1-one;
- 1-(2,5-dimethylbenzyl)-9-(quinoxalin-2-yl)-1,9-diazaspiro[5.5]undecan-2-one;
- 1-((1H-indol-4-yl)methyl)-9-(benzo[d]oxazol-2-yl)-1,9-diazaspiro[5.5]undecan-2-one;
- 1-((1H-indol-3-yl)methyl)-9-(quinoxalin-2-yl)-1,9-diazaspiro[5.5]undecan-2-one;
- 1-((1-methyl-1H-indol-4-yl)methyl)-9-(quinoxalin-2-yl)-1,9-diazaspiro[5.5]undecan-2-one;
- 2-((2-methoxypyridin-4-yl)methyl)-9-(quinoxalin-2-yl)-2,9-diazaspiro[5.5]undecan-1-one;
- 2-(3-(1H-1,2,3-triazol-1-yl)benzyl)-9-(quinoxalin-2-yl)-2,9-diazaspiro[5.5]undecan-1-one;
- 2-(3-(2H-1,2,3-triazol-2-yl)benzyl)-9-(quinoxalin-2-yl)-2,9-diazaspiro[5.5]undecan-1-one;
- 2-((1H-indol-3-yl)methyl)-9-(quinolin-3-yl)-2,9-diazaspiro[5.5]undecan-1-one;
- 2-(2-(2H-1,2,3-triazol-2-yl)benzyl)-9-(quinoxalin-2-yl)-2,9-diazaspiro[5.5]undecan-1-one;
- 2-benzyl-9-(1-methyl-1H-benzo[d]imidazol-2-yl)-2,9-diazaspiro[5.5]undecan-1-one;
- 2-(2-(1-methyl-1H-pyrazol-4-yl)benzyl)-9-(quinoxalin-2-yl)-2,9-diazaspiro[5.5]undecan-1-one;
- 2-((1H-indol-3-yl)methyl)-9-(benzo[d]thiazol-2-yl)-2,9-diazaspiro[5.5]undecan-1-one;
- 2-(benzo[c][1,2,5]oxadiazol-5-ylmethyl)-9-(quinoxalin-2-yl)-2,9-diazaspiro[5.5]undecan-1-one;
- 2-(3-(pyridin-2-yl)benzyl)-9-(quinoxalin-2-yl)-2,9-diazaspiro[5.5]undecan-1-one;
- 2-(isoquinolin-5-ylmethyl)-9-(quinoxalin-2-yl)-2,9-diazaspiro[5.5]undecan-1-one;
- 2-((2-morpholinopyridin-4-yl)methyl)-9-(quinoxalin-2-yl)-2,9-diazaspiro[5.5]undecan-1-one;
- 2-((1H-pyrrolo[2,3-b]pyridin-3-yl)methyl)-9-(quinoxalin-2-yl)-2,9-diazaspiro[5.5]undecan-1-one;
- 2-(3-(pyridin-4-yl)benzyl)-9-(quinoxalin-2-yl)-2,9-diazaspiro[5.5]undecan-1-one;
- 2-(3-morpholinobenzyl)-9-(quinoxalin-2-yl)-2,9-diazaspiro[5.5]undecan-1-one;
- 2-(3-(1H-pyrazol-1-yl)benzyl)-9-(quinoxalin-2-yl)-2,9-diazaspiro[5.5]undecan-1-one;
- 2-(3-(pyrimidin-2-yl)benzyl)-9-(quinoxalin-2-yl)-2,9-diazaspiro[5.5]undecan-1-one;
- 2-(pyridin-2-ylmethyl)-9-(quinoxalin-2-yl)-2,9-diazaspiro[5.5]undecan-1-one;
- 2-((2-(1H-pyrazol-1-yl)pyridin-4-yl)methyl)-9-(quinoxalin-2-yl)-2,9-diazaspiro[5.5]undecan-1-one;
- 2-(pyridin-3-ylmethyl)-9-(quinoxalin-2-yl)-2,9-diazaspiro[5.5]undecan-1-one;

2-(3-(pyrazin-2-yl)benzyl)-9-(quinoxalin-2-yl)-2,9-diazaspiro[5.5]undecan-1-one;
2-((1H-benzo[d][1,2,3]triazol-1-yl)methyl)-9-(quinoxalin-2-yl)-2,9-diazaspiro[5.5]undecan-1-one;
2-(pyridin-4-ylmethyl)-9-(quinoxalin-2-yl)-2,9-diazaspiro[5.5]undecan-1-one;
2-((2-methylpyridin-4-yl)methyl)-9-(quinoxalin-2-yl)-2,9-diazaspiro[5.5]undecan-1-one;
2-((2-methyl-5-m-tolylthiazol-4-yl)methyl)-9-(quinoxalin-2-yl)-2,9-diazaspiro[5.5]undecan-1-one;
2-(imidazo[1,2-a]pyridin-3-ylmethyl)-9-(quinoxalin-2-yl)-2,9-diazaspiro[5.5]undecan-1-one;
2-((2-methylimidazo[1,2-a]pyridin-3-yl)methyl)-9-(quinoxalin-2-yl)-2,9-diazaspiro[5.5]undecan-1-one;
2-((2-bromopyridin-4-yl)methyl)-9-(quinoxalin-2-yl)-2,9-diazaspiro[5.5]undecan-1-one;
2-((5-(3-fluorophenyl)-2-methylthiazol-4-yl)methyl)-9-(quinoxalin-2-yl)-2,9-diazaspiro[5.5]undecan-1-one;
2-(1-(1H-indol-3-yl)ethyl)-9-(quinoxalin-2-yl)-2,9-diazaspiro[5.5]undecan-1-one;
2-([1,2,4]triazolo[4,3-a]pyridin-3-ylmethyl)-9-(quinoxalin-2-yl)-2,9-diazaspiro[5.5]undecan-1-one;
2-((2-methyl-2H-indazol-3-yl)methyl)-9-(quinoxalin-2-yl)-2,9-diazaspiro[5.5]undecan-1-one;
2-(benzo[c][1,2,5]oxadiazol-4-ylmethyl)-9-(quinoxalin-2-yl)-2,9-diazaspiro[5.5]undecan-1-one;
2-((6-chloropyridin-3-yl)methyl)-9-(quinoxalin-2-yl)-2,9-diazaspiro[5.5]undecan-1-one;
2-(pyrazolo[1,5-a]pyridin-3-ylmethyl)-9-(quinoxalin-2-yl)-2,9-diazaspiro[5.5]undecan-1-one;
2-(3-(methoxymethyl)benzyl)-9-(quinoxalin-2-yl)-2,9-diazaspiro[5.5]undecan-1-one;
2-(4-(1H-1,2,4-triazol-1-yl)benzyl)-9-(quinoxalin-2-yl)-2,9-diazaspiro[5.5]undecan-1-one;
2-((2,3-dihydrobenzo[b][1,4]dioxin-5-yl)methyl)-9-(furo[3,2-c]pyridin-4-yl)-2,9-diazaspiro[5.5]undecan-1-one;
2-((6-(1H-pyrazol-1-yl)pyridin-2-yl)methyl)-9-(quinoxalin-2-yl)-2,9-diazaspiro[5.5]undecan-1-one;
2-((1,5-dimethyl-1H-pyrazol-3-yl)methyl)-9-(quinoxalin-2-yl)-2,9-diazaspiro[5.5]undecan-1-one;
2-(2-(1H-pyrazol-1-yl)benzyl)-9-(quinoxalin-2-yl)-2,9-diazaspiro[5.5]undecan-1-one;
2-((1-benzyl-1H-imidazol-2-yl)methyl)-9-(quinoxalin-2-yl)-2,9-diazaspiro[5.5]undecan-1-one;
2-((6-chloro-4H-benzo[d][1,3]dioxin-8-yl)methyl)-9-(quinoxalin-2-yl)-2,9-diazaspiro[5.5]undecan-1-one;
2-((5-methylisoxazol-3-yl)methyl)-9-(quinoxalin-2-yl)-2,9-diazaspiro[5.5]undecan-1-one;
2-((5-cyclobutyl-1,2,4-oxadiazol-3-yl)methyl)-9-(quinoxalin-2-yl)-2,9-diazaspiro[5.5]undecan-1-one;
9-(quinoxalin-2-yl)-2-((6-(trifluoromethyl)pyridin-3-yl)methyl)-2,9-diazaspiro[5.5]undecan-1-one;
2-((3,4-dimethoxypyridin-2-yl)methyl)-9-(quinoxalin-2-yl)-2,9-diazaspiro[5.5]undecan-1-one;
3-((1-oxo-9-(quinoxalin-2-yl)-2,9-diazaspiro[5.5]undecan-2-yl)methyl)benzonitrile
2-(isoquinolin-1-ylmethyl)-9-(quinoxalin-2-yl)-2,9-diazaspiro[5.5]undecan-1-one;
2-fluoro-5-((1-oxo-9-(quinoxalin-2-yl)-2,9-diazaspiro[5.5]undecan-2-yl)methyl)benzonitrile
2-((5-phenyloxazol-4-yl)methyl)-9-(quinoxalin-2-yl)-2,9-diazaspiro[5.5]undecan-1-one;
4-((1-oxo-9-(quinoxalin-2-yl)-2,9-diazaspiro[5.5]undecan-2-yl)methyl)quinolin-2(1H)-one;
2-((6-methylpyridin-2-yl)methyl)-9-(quinoxalin-2-yl)-2,9-diazaspiro[5.5]undecan-1-one;
2-(3-(5-methyl-1,2,4-oxadiazol-3-yl)benzyl)-9-(quinoxalin-2-yl)-2,9-diazaspiro[5.5]undecan-1-one;
4-fluoro-3-((1-oxo-9-(quinoxalin-2-yl)-2,9-diazaspiro[5.5]undecan-2-yl)methyl)benzonitrile
5-((1-oxo-9-(quinoxalin-2-yl)-2,9-diazaspiro[5.5]undecan-2-yl)methyl)picolinonitrile
2-(4-(pyrimidin-2-yl)benzyl)-9-(quinoxalin-2-yl)-2,9-diazaspiro[5.5]undecan-1-one;
2-(2-fluoro-3-methoxybenzyl)-9-(quinoxalin-2-yl)-2,9-diazaspiro[5.5]undecan-1-one;
2-((6-(pyrrolidin-1-yl)pyridin-2-yl)methyl)-9-(quinoxalin-2-yl)-2,9-diazaspiro[5.5]undecan-1-one;
2-(3-(3-methyl-1,2,4-oxadiazol-5-yl)benzyl)-9-(quinoxalin-2-yl)-2,9-diazaspiro[5.5]undecan-1-one;
2-((3-methylisoxazol-5-yl)methyl)-9-(quinoxalin-2-yl)-2,9-diazaspiro[5.5]undecan-1-one;
2-((4,6-dimethylpyridin-2-yl)methyl)-9-(quinoxalin-2-yl)-2,9-diazaspiro[5.5]undecan-1-one;
2-((1-methyl-1H-indazol-7-yl)methyl)-9-(quinoxalin-2-yl)-2,9-diazaspiro[5.5]undecan-1-one;
2-((1-methyl-1H-indazol-4-yl)methyl)-9-(quinoxalin-2-yl)-2,9-diazaspiro[5.5]undecan-1-one;
2-(4-(5-methyl-1,3,4-oxadiazol-2-yl)benzyl)-9-(quinoxalin-2-yl)-2,9-diazaspiro[5.5]undecan-1-one;
2-((1-phenyl-1H-imidazol-5-yl)methyl)-9-(quinoxalin-2-yl)-2,9-diazaspiro[5.5]undecan-1-one;
2-((1-(3-methoxyphenyl)-1H-imidazol-5-yl)methyl)-9-(quinoxalin-2-yl)-2,9-diazaspiro[5.5]undecan-1-one;
2-((1-(2-methoxyphenyl)-1H-imidazol-2-yl)methyl)-9-(quinoxalin-2-yl)-2,9-diazaspiro[5.5]undecan-1-one;
2-(benzo[c][1,2,5]thiadiazol-4-ylmethyl)-9-(quinoxalin-2-yl)-2,9-diazaspiro[5.5]undecan-1-one;
2-((5-methyl-2-(thiazol-4-yl)oxazol-4-yl)methyl)-9-(quinoxalin-2-yl)-2,9-diazaspiro[5.5]undecan-1-one;
2-(2-(3,5-dimethyl-1H-pyrazol-1-yl)benzyl)-9-(quinoxalin-2-yl)-2,9-diazaspiro[5.5]undecan-1-one;
2-((2-(furan-3-yl)-5-methyloxazol-4-yl)methyl)-9-(quinoxalin-2-yl)-2,9-diazaspiro[5.5]undecan-1-one;
9-(quinoxalin-2-yl)-2-((2,2,8-trimethyl-4H-[1,3]dioxino[4,5-c]pyridin-5-yl)methyl)-2,9-diazaspiro[5.5]undecan-1-one;
2-((1-benzyl-1H-imidazol-5-yl)methyl)-9-(quinoxalin-2-yl)-2,9-diazaspiro[5.5]undecan-1-one;
2-((4-methyl-2-phenyloxazol-5-yl)methyl)-9-(quinoxalin-2-yl)-2,9-diazaspiro[5.5]undecan-1-one;
2-((6-fluoro-4H-benzo[d][1,3]dioxin-8-yl)methyl)-9-(quinoxalin-2-yl)-2,9-diazaspiro[5.5]undecan-1-one;
2-((1H-indol-2-yl)methyl)-9-(quinoxalin-2-yl)-2,9-diazaspiro[5.5]undecan-1-one;
2-((1-phenyl-1H-tetrazol-5-yl)methyl)-9-(quinoxalin-2-yl)-2,9-diazaspiro[5.5]undecan-1-one;
2-((1H-indol-5-yl)methyl)-9-(quinoxalin-2-yl)-2,9-diazaspiro[5.5]undecan-1-one;
2-((1-oxo-9-(quinoxalin-2-yl)-2,9-diazaspiro[5.5]undecan-2-yl)methyl)benzonitrile
2-(5-methyl-2-(2H-1,2,3-triazol-2-yl)benzyl)-9-(quinoxalin-2-yl)-2,9-diazaspiro[5.5]undecan-1-one;
2-(indolin-4-ylmethyl)-9-(quinoxalin-2-yl)-2,9-diazaspiro[5.5]undecan-1-one;
2-((4-(1H-pyrazol-1-yl)pyridin-2-yl)methyl)-9-(quinoxalin-2-yl)-2,9-diazaspiro[5.5]undecan-1-one;
2-(2-methyl-5-(2H-1,2,3-triazol-2-yl)benzyl)-9-(quinoxalin-2-yl)-2,9-diazaspiro[5.5]undecan-1-one;
2-((1H-indazol-3-yl)methyl)-9-(quinoxalin-2-yl)-2,9-diazaspiro[5.5]undecan-1-one;
2-((1-methyl-1H-indol-3-yl)methyl)-9-(quinoxalin-2-yl)-2,9-diazaspiro[5.5]undecan-1-one;

2-((1H-indol-3-yl)methyl)-9-(5-chlorobenzo[d]oxazol-2-yl)-2,9-diazaspiro[5.5]undecan-1-one;
2-((3,4-dihydro-2H-benzo[b][1,4]oxazin-8-yl)methyl)-9-(quinoxalin-2-yl)-2,9-diazaspiro[5.5]undecan-1-one;
2-((2-methyl-1H-indol-3-yl)methyl)-9-(quinoxalin-2-yl)-2,9-diazaspiro[5.5]undecan-1-one;
1-benzyl-9-(quinoxalin-2-yl)-1,9-diazaspiro[5.5]undecan-2-one;
1-(benzo[d]isoxazol-3-ylmethyl)-9-(quinoxalin-2-yl)-1,9-diazaspiro[5.5]undecan-2-one;
1-((1H-indol-4-yl)methyl)-9-(5-chlorobenzo[d]oxazol-2-yl)-1,9-diazaspiro[5.5]undecan-2-one;
1-((1H-indol-4-yl)methyl)-9-(5-phenyl-1,3,4-oxadiazol-2-yl)-1,9-diazaspiro[5.5]undecan-2-one;
1-((1H-indol-4-yl)methyl)-9-(1H-benzo[d]imidazol-2-yl)-1,9-diazaspiro[5.5]undecan-2-one;
1-((1H-indol-4-yl)methyl)-9-(6-chlorobenzo[d]oxazol-2-yl)-1,9-diazaspiro[5.5]undecan-2-one;
1-((1H-indol-4-yl)methyl)-9-(5-methylbenzo[d]oxazol-2-yl)-1,9-diazaspiro[5.5]undecan-2-one;
1-((1H-pyrrolo[2,3-b]pyridin-3-yl)methyl)-9-(quinoxalin-2-yl)-1,9-diazaspiro[5.5]undecan-2-one;
2-((1-methyl-1H-indazol-3-yl)methyl)-9-(quinoxalin-2-yl)-2,9-diazaspiro[5.5]undecan-1-one;
1-((1-methyl-1H-pyrrolo[2,3-b]pyridin-3-yl)methyl)-9-(quinoxalin-2-yl)-1,9-diazaspiro[5.5]undecan-2-one;
2-((4-methyl-3,4-dihydro-2H-benzo[b][1,4]oxazin-8-yl)methyl)-9-(quinoxalin-2-yl)-2,9-diazaspiro[5.5]undecan-1-one;
2-((1-methylindolin-4-yl)methyl)-9-(quinoxalin-2-yl)-2,9-diazaspiro[5.5]undecan-1-one;
2-((1H-indol-3-yl)methyl)-9-(pyrido[3,2-b]pyrazin-7-yl)-2,9-diazaspiro[5.5]undecan-1-one;
2-(3-(5-methyloxazol-2-yl)benzyl)-9-(quinoxalin-2-yl)-2,9-diazaspiro[5.5]undecan-1-one;
2-(2-(1-methyl-1H-pyrazol-5-yl)benzyl)-9-(quinoxalin-2-yl)-2,9-diazaspiro[5.5]undecan-1-one;
2-(2-(oxazol-2-yl)benzyl)-9-(quinoxalin-2-yl)-2,9-diazaspiro[5.5]undecan-1-one;
2-(2-(furan-2-yl)benzyl)-9-(quinoxalin-2-yl)-2,9-diazaspiro[5.5]undecan-1-one;
2-(2-(pyrimidin-2-yl)benzyl)-9-(quinoxalin-2-yl)-2,9-diazaspiro[5.5]undecan-1-one;
2-((1H-indol-3-yl)methyl)-9-(1H-benzo[d]imidazol-2-yl)-2,9-diazaspiro[5.5]undecan-1-one;
2-((1H-indol-3-yl)methyl)-9-(6-methylbenzo[d]thiazol-2-yl)-2,9-diazaspiro[5.5]undecan-1-one;
2-((1H-indol-3-yl)methyl)-9-(4-phenylpyrimidin-2-yl)-2,9-diazaspiro[5.5]undecan-1-one;
2-((1H-indol-3-yl)methyl)-9-(7H-pyrrolo[2,3-d]pyrimidin-4-yl)-2,9-diazaspiro[5.5]undecan-1-one;
2-((1H-indol-3-yl)methyl)-9-(furo[3,2-c]pyridin-4-yl)-2,9-diazaspiro[5.5]undecan-1-one;
2-((1H-indol-3-yl)methyl)-9-(4-methylphthalazin-1-yl)-2,9-diazaspiro[5.5]undecan-1-one;
9-(6-(1H-imidazol-1-yl)pyrimidin-4-yl)-2-((1H-indol-3-yl)methyl)-2,9-diazaspiro[5.5]undecan-1-one;
2-((1H-indol-3-yl)methyl)-9-(5-methoxy-1H-benzo[d]imidazol-2-yl)-2,9-diazaspiro[5.5]undecan-1-one;
2-((1H-indol-3-yl)methyl)-9-(quinolin-2-yl)-2,9-diazaspiro[5.5]undecan-1-one;
2-((1H-indol-3-yl)methyl)-9-(5-(thiazol-2-yl)pyridin-2-yl)-2,9-diazaspiro[5.5]undecan-1-one;
2-((1H-indol-3-yl)methyl)-9-(isoquinolin-1-yl)-2,9-diazaspiro[5.5]undecan-1-one;
2-((1H-indol-3-yl)methyl)-9-(5-methyl-1H-benzo[d]imidazol-2-yl)-2,9-diazaspiro[5.5]undecan-1-one;
2-((1H-indol-3-yl)methyl)-9-(4-methylquinolin-2-yl)-2,9-diazaspiro[5.5]undecan-1-one;
2-((1H-indol-3-yl)methyl)-9-(6-phenylpyrimidin-4-yl)-2,9-diazaspiro[5.5]undecan-1-one;
2-((1H-indol-3-yl)methyl)-9-(4-(pyridin-4-yl)pyrimidin-2-yl)-2,9-diazaspiro[5.5]undecan-1-one;
2-((1H-indol-3-yl)methyl)-9-(pyrido[4,3-b]pyrazin-7-yl)-2,9-diazaspiro[5.5]undecan-1-one;
2-((1H-indol-3-yl)methyl)-9-(imidazo[1,2-b]pyridazin-6-yl)-2,9-diazaspiro[5.5]undecan-1-one;
2-((1H-indol-3-yl)methyl)-9-(quinazolin-2-yl)-2,9-diazaspiro[5.5]undecan-1-one;
2-((1H-indol-3-yl)methyl)-9-(3-methylquinoxalin-2-yl)-2,9-diazaspiro[5.5]undecan-1-one;
2-((1H-indol-3-yl)methyl)-9-(5-phenyl-1,3,4-thiadiazol-2-yl)-2,9-diazaspiro[5.5]undecan-1-one;
2-((1H-indol-3-yl)methyl)-9-(4-(4-fluorophenyl)thiazol-2-yl)-2,9-diazaspiro[5.5]undecan-1-one;
2-((1H-indol-3-yl)methyl)-9-(4-methyl-6-(1H-pyrazol-1-yl)pyrimidin-2-yl)-2,9-diazaspiro[5.5]undecan-1-one and
2-((1H-indol-3-yl)methyl)-9-(4-(1H-pyrazol-1-yl)pyrimidin-2-yl)-2,9-diazaspiro[5.5]undecan-1-one.

Embodiment 29

A process for the production of compounds of the formula (Ia)

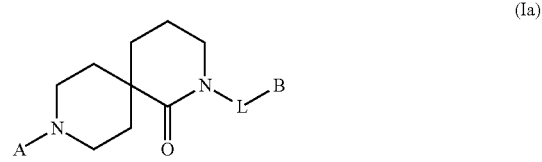

(Ia)

wherein
A is a eight- to ten-membered fused bicyclic aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may be substituted once or more than once by $R_3$, and wherein a substituent on a nitrogen in a heterocyclic ring system may not be halogen;
each $R_3$ independently is $C_{1-6}$alkyl, $C_{1-6}$halogenalkyl, $C_{1-6}$alkoxy, $C_{1-6}$halogenalkoxy, halogen, cyano or a three- to seven-membered monocyclic ring system which may be aromatic, saturated or unsaturated non-aromatic and which may contain from 1 to 4 hetero atoms selected from nitrogen, oxygen and sulfur, and wherein each ring system may contain not more than 2 oxygen atoms and not more than 2 sulfur atoms, and wherein each ring system may in turn be substituted once or more than once by $R_4$, and wherein a substituent on a nitrogen in a heterocyclic ring system may not be halogen;
each $R_4$ independently is $C_{1-6}$alkyl, $C_{1-6}$halogenalkyl, $C_{1-6}$alkoxy, $C_{1-6}$halogenalkoxy, halogen or cyano, or two $R_4$ at the same ring atom together are oxo;
or A is a five- to six-membered monocyclic aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system is substituted by A1 and wherein the ring system may be further substituted once or more than once by $R_5$, and wherein a substituent on a nitrogen in a heterocyclic ring system may not be halogen;
A1 is a five- to six-membered monocyclic aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may be substituted once or more than once by $R_6$, and wherein a substituent on a nitrogen in a heterocyclic ring system may not be halogen;

each $R_5$ or $R_6$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy;

L is —C($R_7$)$_2$—;

each $R_7$ independently is hydrogen, $C_{1-6}$alkyl, $C_{1-6}$halogenalkyl, $C_{3-7}$cycloalkyl or $C_{3-7}$cycloalkyl($C_{1-4}$alkyl);

B is a five- to ten-membered monocyclic or fused polycyclic aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may be substituted once or more than once by $R_8$, and wherein a substituent on a nitrogen in a heterocyclic ring system may not be halogen;

each $R_8$ independently $C_{1-6}$alkyl, $C_{1-6}$halogenalkyl, $C_{1-6}$hydroxyalkyl, $C_{1-4}$alkoxy-$C_{1-6}$alkyl, $C_{1-6}$aminoalkyl, $C_{1-4}$alkylamino-$C_{1-6}$alkyl, di($C_{1-4}$alkyl)amino-$C_{1-6}$alkyl, $C_{2-6}$alkenyl, $C_{2-6}$halogenalkenyl, $C_{2-6}$alkynyl, $C_{2-6}$halogenalkynyl, $C_{1-6}$alkoxy, $C_{1-6}$halogenalkoxy, $C_{1-4}$alkoxy-$C_{1-6}$alkoxy, $C_{1-6}$alkylamino, di($C_{1-6}$alkyl)amino, halogen, hydroxy, cyano, amino or a three- to seven-membered monocyclic ring system which may be aromatic, saturated or unsaturated non-aromatic and which may contain from 1 to 4 hetero atoms selected from nitrogen, oxygen and sulfur, and wherein each ring system may be attached directly to ring system B or via a $C_{1-4}$alkylene, and wherein each ring system may contain not more than 2 oxygen atoms and not more than 2 sulfur atoms, and wherein each ring system may in turn be substituted once or more than once by $C_{1-6}$alkyl, $C_{1-6}$halogenalkyl, $C_{1-6}$alkoxy, $C_{1-6}$halogenalkoxy, halogen or cyano, and wherein a substituent on a nitrogen in a heterocyclic ring system may not be halogen;

or two $R_8$ at adjacent ring atoms form together with said ring atoms a fused five- to seven-membered unsaturated non-aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may in turn be substituted once or more than once by $R_9$, and wherein a substituent on a nitrogen in a heterocyclic ring system may not be halogen; and wherein each $R_9$ independently is halogen or $C_{1-6}$alkyl, or two $R_9$ at the same ring atom together are oxo;

in free form or in salt form;
which comprises reacting a compound of formula IIa

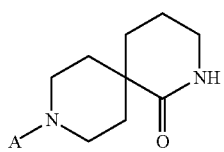

(IIa)

in free form or in salt form;
in which A is as defined under formula Ia, with a compound of formula IIIa, B-L-Hal (IIIa)

in free form or in salt form;
in which B and L are defined under formula Ia and Hal is a halogen atom in the presence of a strong base and a suitable solvent.

Embodiment 30

A process for the production of compounds of the formula (Ia)

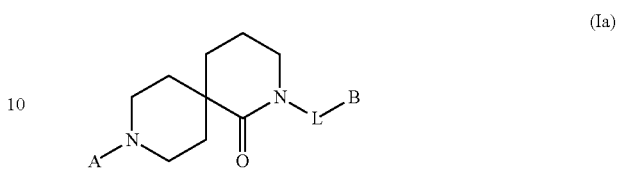

(Ia)

wherein
A is a eight- to ten-membered fused bicyclic aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may be substituted once or more than once by $R_3$, and wherein a substituent on a nitrogen in a heterocyclic ring system may not be halogen;

each $R_3$ independently is $C_{1-6}$alkyl, $C_{1-6}$halogenalkyl, $C_{1-6}$alkoxy, $C_{1-6}$halogenalkoxy, halogen, cyano or a three- to seven-membered monocyclic ring system which may be aromatic, saturated or unsaturated non-aromatic and which may contain from 1 to 4 hetero atoms selected from nitrogen, oxygen and sulfur, and wherein each ring system may contain not more than 2 oxygen atoms and not more than 2 sulfur atoms, and wherein each ring system may in turn be substituted once or more than once by $R_4$, and wherein a substituent on a nitrogen in a heterocyclic ring system may not be halogen;

each $R_4$ independently is $C_{1-6}$alkyl, $C_{1-6}$halogenalkyl, $C_{1-6}$alkoxy, $C_{1-6}$halogenalkoxy, halogen or cyano, or two $R_4$ at the same ring atom together are oxo;

or A is a five- to six-membered monocyclic aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system is substituted by A1 and wherein the ring system may be further substituted once or more than once by $R_5$, and wherein a substituent on a nitrogen in a heterocyclic ring system may not be halogen;

A1 is a five- to six-membered monocyclic aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may be substituted once or more than once by $R_6$, and wherein a substituent on a nitrogen in a heterocyclic ring system may not be halogen;

each $R_5$ or $R_6$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy;

m is 0, 1, 2, 3, 4, 5 or 6;
n is 0, 1, 2, 3, 4, 5 or 6;
each $R_1$ or $R_2$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy;

—$X_1$— is —C(O)— and —$X_2$— is —N(L-B)—;
or —$X_1$— is —N(L-B)— and —$X_2$— is —C(O)—;
L is —C($R_7$)$_2$—;

each $R_7$ independently is hydrogen, $C_{1-6}$alkyl, $C_{1-6}$halogenalkyl, $C_{3-7}$cycloalkyl or $C_{3-7}$cycloalkyl($C_{1-4}$alkyl);

B is a five- to ten-membered monocyclic or fused polycyclic aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may be substituted once or more than once by $R_8$, and wherein a substituent on a nitrogen in a heterocyclic ring system may not be halogen;

each $R_8$ independently is $C_{1-6}$alkyl, $C_{1-6}$halogenalkyl, $C_{1-6}$alkoxy, $C_{1-6}$halogenalkoxy, halogen, cyano or a three- to seven-membered monocyclic ring system which may be aromatic, saturated or unsaturated non-aromatic and which may contain from 1 to 4 hetero atoms selected from nitrogen, oxygen and sulfur, and wherein each ring system may contain not more than 2 oxygen atoms and not more than 2 sulfur atoms, and wherein each ring system may in turn be substituted once or more than once by $C_{1-6}$alkyl, $C_{1-6}$halogenalkyl, $C_{1-6}$alkoxy, $C_{1-6}$halogenalkoxy, halogen or cyano, and wherein a substituent on a nitrogen in a heterocyclic ring system may not be halogen;

or two $R_8$ at adjacent ring atoms form together with said ring atoms a fused five- to seven-membered ununsaturated non-aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may in turn be substituted once or more than once by $R_9$, and wherein a substituent on a nitrogen in a heterocyclic ring system may not be halogen; and wherein each $R_9$ independently is halogen or $C_{1-6}$alkyl, or two $R_9$ at the same ring atom together are oxo;

in free form or in salt form;

which comprises reacting a compound of formula IIa

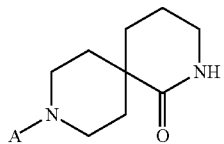

(IIa)

in free form or in salt form;

in which A is as defined under formula Ia, with a compound of formula IIIa,

B-L-Hal (IIIa)

in free form or in salt form;

in which B and L are defined under formula Ia and Hal is a halogen atom in the presence of a strong base and a suitable solvent.

Embodiment 31

A process for the production of compounds of formula (Ib),

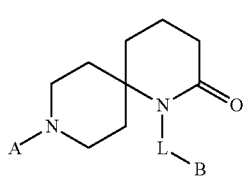

(Ib)

in which A, B and L are as defined in embodiments 28 or 29, in free form or in salt form;

which comprises reacting a compound of formula IIb

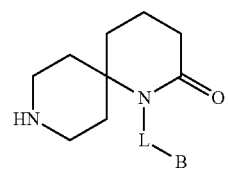

(IIb)

in free form or in salt form;
with a compound of formula Va

A-Hal (Va)

in free form or in salt form;
in which A is as defined under formula Ib and Hal is a halogen atom, in the presence of a base and a suitable solvent.

Embodiment 32

A process of manufacturing a compound of formula (Ia) or (Ib) which is selected from a working example of the experimental section of this application, comprising the reactants, solvents, temperatures, reaction time as disclosed in a corresponding working example.

The invention claimed is:
1. A compound of the formula (I)

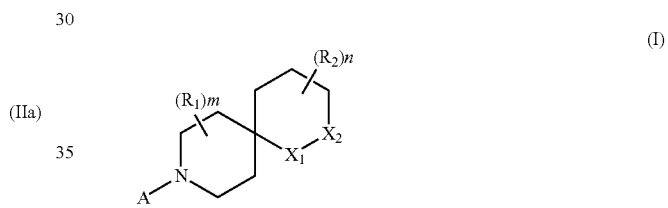

(I)

wherein
A is a eight- to ten-membered fused bicyclic aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may be substituted once or more than once by $R_3$, and wherein a substituent on a nitrogen in a heterocyclic ring system may not be halogen;

each $R_3$ independently is $C_{1-6}$alkyl, $C_{1-6}$halogenalkyl, $C_{1-6}$alkoxy, $C_{1-6}$halogenalkoxy, halogen, cyano or a three- to seven-membered monocyclic ring system which may be aromatic, saturated or unsaturated non-aromatic and which may contain from 1 to 4 hetero atoms selected from nitrogen, oxygen and sulfur, and wherein each ring system may contain not more than 2 oxygen atoms and not more than 2 sulfur atoms, and wherein each ring system may in turn be substituted once or more than once by $R_4$, and wherein a substituent on a nitrogen in a heterocyclic ring system may not be halogen;

each $R_4$ independently is $C_{1-6}$alkyl, $C_{1-6}$halogenalkyl, $C_{1-6}$alkoxy, $C_{1-6}$halogenalkoxy, halogen or cyano, or two $R_4$ at the same ring atom together are oxo;

or A is a five- to six-membered monocyclic aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system is substituted by A1 and wherein the ring system may be further substituted once or more than once by $R_5$, and wherein a substituent on a nitrogen in a heterocyclic ring system may not be halogen;

A1 is a five- to six-membered monocyclic aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may be substituted once or more than once by $R_6$, and wherein a substituent on a nitrogen in a heterocyclic ring system may not be halogen;

each $R_5$ or $R_6$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy;

m is 0, 1, 2, 3, 4, 5 or 6;

n is 0, 1, 2, 3, 4, 5 or 6;

each $R_1$ or $R_2$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy;

—$X_1$— is —C(O)— and —$X_2$— is —N(L-B)—;

or —$X_1$— is —N(L-B)— and —$X_2$— is —C(O)—;

L is —C($R_7$)$_2$—;

each $R_7$ independently is hydrogen, $C_{1-6}$alkyl, $C_{1-6}$halogenalkyl, $C_{3-7}$cycloalkyl or $C_{3-7}$cycloalkyl($C_{1-4}$alkyl);

B is a five- to ten-membered monocyclic or fused polycyclic aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may be substituted once or more than once by $R_8$, and wherein a substituent on a nitrogen in a heterocyclic ring system may not be halogen;

each $R_8$ independently $C_{1-6}$alkyl, $C_{1-6}$halogenalkyl, $C_{1-6}$hydroxyalkyl, $C_{1-4}$alkoxy-$C_{1-6}$alkyl, $C_{1-6}$-aminoalkyl, $C_{1-4}$alkylamino-$C_{1-6}$alkyl, di($C_{1-4}$alkyl)amino-$C_{1-6}$alkyl, $C_{2-6}$alkenyl, $C_{2-6}$halogenalkenyl, $C_{2-6}$alkynyl, $C_{2-6}$halogenalkynyl, $C_{1-6}$alkoxy, $C_{1-6}$halogenalkoxy, $C_{1-4}$alkoxy-$C_{1-6}$alkoxy, $C_{1-6}$alkylamino, di($C_{1-6}$alkyl)amino, halogen, hydroxy, cyano, amino or a three- to seven-membered monocyclic ring system which may be aromatic, saturated or unsaturated non-aromatic and which may contain from 1 to 4 hetero atoms selected from nitrogen, oxygen and sulfur, and wherein each ring system may be attached directly to ring system B or via a $C_{1-4}$-alkylene, and wherein each ring system may contain not more than 2 oxygen atoms and not more than 2 sulfur atoms, and wherein each ring system may in turn be substituted once or more than once by $C_{1-6}$alkyl, $C_{1-6}$halogenalkyl, $C_{1-6}$alkoxy, $C_{1-6}$halogenalkoxy, halogen or cyano, and wherein a substituent on a nitrogen in a heterocyclic ring system may not be halogen;

or two $R_8$ at adjacent ring atoms form together with said ring atoms a fused five- to seven-membered unsaturated non-aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may in turn be substituted once or more than once by $R_9$, and wherein a substituent on a nitrogen in a heterocyclic ring system may not be halogen; and wherein each $R_9$ independently is halogen or $C_{1-6}$alkyl, or two $R_9$ at the same ring atom together are oxo;

in free form or in salt form.

2. The compound of claim 1 of formula I

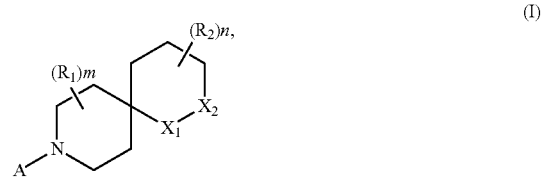

(I)

wherein

A is a eight- to ten-membered fused bicyclic aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may be substituted once or more than once by $R_3$, and wherein a substituent on a nitrogen in a heterocyclic ring system may not be halogen;

each $R_3$ independently is $C_{1-6}$alkyl, $C_{1-6}$halogenalkyl, $C_{1-6}$alkoxy, $C_{1-6}$halogenalkoxy, halogen, cyano or a three- to seven-membered monocyclic ring system which may be aromatic, saturated or unsaturated non-aromatic and which may contain from 1 to 4 hetero atoms selected from nitrogen, oxygen and sulfur, and wherein each ring system may contain not more than 2 oxygen atoms and not more than 2 sulfur atoms, and wherein each ring system may in turn be substituted once or more than once by $R_4$, and wherein a substituent on a nitrogen in a heterocyclic ring system may not be halogen;

each $R_4$ independently is $C_{1-6}$alkyl, $C_{1-6}$halogenalkyl, $C_{1-6}$alkoxy, $C_{1-6}$halogenalkoxy, halogen or cyano, or two $R_4$ at the same ring atom together are oxo;

or A is a five- to six-membered monocyclic aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system is substituted by A1 and wherein the ring system may be further substituted once or more than once by $R_5$, and wherein a substituent on a nitrogen in a heterocyclic ring system may not be halogen;

A1 is a five- to six-membered monocyclic aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may be substituted once or more than once by $R_6$, and wherein a substituent on a nitrogen in a heterocyclic ring system may not be halogen;

each $R_5$ or $R_6$ independently is halogen, $C_{1-6}$alkyl, $C_{1-6}$halogenalkyl, $C_{3-7}$cycloalkyl, $C_{3-7}$cycloalkyl($C_{1-4}$-alkyl), $C_{1-6}$alkoxy, or $C_{1-6}$halogenalkoxy;

m is 0, 1, 2, 3, 4, 5 or 6;

n is 0, 1, 2, 3, 4, 5 or 6;

each $R_1$ or $R_2$ independently is halogen, $C_{1-6}$alkyl, $C_{1-6}$halogenalkyl, $C_{3-7}$cycloalkyl, $C_{3-7}$cycloalkyl($C_{1-4}$-alkyl), $C_{1-6}$alkoxy, or $C_{1-6}$halogenalkoxy;

—$X_1$— is —C(O)— and —$X_2$— is —N(L-B)—;

or —$X_1$— is —N(L-B)— and —$X_2$— is —C(O)—;

L is —C($R_7$)$_2$—;

each $R_7$ independently is hydrogen, $C_{1-6}$alkyl, $C_{1-6}$halogenalkyl, $C_{3-7}$cycloalkyl or $C_{3-7}$cycloalkyl($C_{1-4}$alkyl);

B is a five- to ten-membered monocyclic or fused polycyclic aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may be substituted once or more than once by $R_8$, and wherein a substituent on a nitrogen in a heterocyclic ring system may not be halogen;

each $R_8$ independently is $C_{1-6}$alkyl, $C_{1-6}$halogenalkyl, $C_{1-6}$alkoxy, $C_{1-6}$halogenalkoxy, halogen, cyano or a three- to seven-membered monocyclic ring system which may be aromatic, saturated or unsaturated non-aromatic and which may contain from 1 to 4 hetero atoms selected from nitrogen, oxygen and sulfur, and wherein each ring system may contain not more than 2 oxygen atoms and not more than 2 sulfur atoms, and wherein each ring system may in turn be substituted once or more than once by $C_{1-6}$alkyl, $C_{1-6}$halogenalkyl, $C_{1-6}$alkoxy, $C_{1-6}$halogenalkoxy, halogen or cyano, and wherein a substituent on a nitrogen in a heterocyclic ring system may not be halogen;

or two $R_8$ at adjacent ring atoms form together with said ring atoms a fused five- to seven-membered ununsaturated non-aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may in turn be substituted once or more than once by $R_9$, and wherein a substituent on a nitrogen in a heterocyclic ring system may not be halogen; and wherein each $R_9$ independently is halogen or $C_{1-6}$alkyl, or two $R_9$ at the same ring atom together are oxo;

in free form or in salt form.

3. The compound of claim 1, wherein —$X_1$— is —C(O)— and —$X_2$— is —N(L-B)—.

4. The compound of claim 1, wherein A is a eight- to ten-membered fused bicyclic aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may be substituted once or more than once by $R_3$, and wherein a substituent on a nitrogen in a heterocyclic ring system may not be halogen; and m and n are both 0.

5. The compound of claim 4, wherein L is —$CH_2$—; and B is an eight- to ten-membered fused bicyclic aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may be substituted once or more than once by $R_8$, and wherein a substituent on a nitrogen in a heterocyclic ring system may not be halogen.

6. The compound of claim 1, wherein —$X_1$— is —N(L-B)— and —$X_2$— is —C(O)—.

7. The compound of claim 6, wherein A is a eight- to ten-membered fused bicyclic aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may be substituted once or more than once by $R_3$, and wherein a substituent on a nitrogen in a heterocyclic ring system may not be halogen; m and n are both 0; L is —$CH_2$—; and B is an eight- to ten-membered fused bicyclic aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may be substituted once or more than once by $R_8$, and wherein a substituent on a nitrogen in a heterocyclic ring system may not be halogen.

8. The compound of claim 1, wherein B is indol-3-yl which may be substituted once or more than once by $R_{8a}$, wherein a substituent on the nitrogen of the indol-3-yl may not be halogen; and each $R_{8a}$ independently is $C_{1-6}$alkyl, $C_{1-6}$alkoxy, $C_{1-6}$halogenalkyl or halogen.

9. The compound of claim 1, wherein B is a six-membered monocyclic aromatic ring system which may contain 1 to 2 nitrogen atoms, wherein the ring system is substituted once by $R_{8b}$, and wherein the ring system may be further substituted once or more than once by $R_{8c}$;

$R_{8b}$ is a five-membered monocyclic aromatic ring system, which contains from 1 to 4 hetero atoms selected from nitrogen, oxygen and sulfur, and wherein the ring system may in turn be substituted once or more than once by $C_{1-6}$alkyl, $C_{1-6}$halogenalkyl, $C_{1-6}$alkoxy, $C_{1-6}$halogenalkoxy, halogen or cyano, and wherein a substituent on a nitrogen in a heterocyclic ring system may not be halogen; and each $R_{8c}$ independently is $C_{1-6}$alkyl, $C_{1-6}$halogenalkyl, $C_{1-6}$alkoxy, $C_{1-6}$halogenalkoxy, halogen or cyano.

10. The compound of claim 1 in free form or in pharmaceutically acceptable salt form, wherein said compound is selected from the group consisting of 2-((1H-indol-3-yl)methyl)-9-(quinoxalin-2-yl)-2,9-diazaspiro[5.5]undecan-1-one;

2-(naphthalen-1-ylmethyl)-9-(quinoxalin-2-yl)-2,9-diazaspiro[5.5]undecan-1-one;

2-((1H-indol-4-yl)methyl)-9-(quinoxalin-2-yl)-2,9-diazaspiro[5.5]undecan-1-one;

2-((2,3-dihydrobenzo[b][1,4]dioxin-5-yl)methyl)-9-(quinoxalin-2-yl)-2,9-diazaspiro[5.5]undecan-1-one;

2-(3-(pyridin-3-yl)benzyl)-9-(quinoxalin-2-yl)-2,9-diazaspiro[5.5]undecan-1-one;

2-benzyl-9-(quinoxalin-2-yl)-2,9-diazaspiro[5.5]undecan-1-one;

2-(naphthalen-2-ylmethyl)-9-(quinoxalin-2-yl)-2,9-diazaspiro[5.5]undecan-1-one;

2-(benzo[d][1,3]dioxol-5-ylmethyl)-9-(quinoxalin-2-yl)-2,9-diazaspiro[5.5]undecan-1-one;

2-(benzo[d][1,3]dioxol-4-ylmethyl)-9-(quinoxalin-2-yl)-2,9-diazaspiro[5.5]undecan-1-one;

9-(1H-benzo[d]imidazol-2-yl)-2-benzyl-2,9-diazaspiro[5.5]undecan-1-one;

9-(1H-benzo[d]imidazol-2-yl)-2-(naphthalen-1-ylmethyl)-2,9-diazaspiro[5.5]undecan-1-one;

9-(1-methyl-1H-benzo[d]imidazol-2-yl)-2-(naphthalen-1-ylmethyl)-2,9-diazaspiro[5.5]undecan-1-one;

2-((2-methyl-1H-indol-4-yl)methyl)-9-(quinoxalin-2-yl)-2,9-diazaspiro[5.5]undecan-1-one;

9-(quinoxalin-2-yl)-2-(3-(trifluoromethyl)benzyl)-2,9-diazaspiro[5.5]undecan-1-one;

2-(3-methylbenzyl)-9-(quinoxalin-2-yl)-2,9-diazaspiro[5.5]undecan-1-one;

2-(3,5-dimethylbenzyl)-9-(quinoxalin-2-yl)-2,9-diazaspiro[5.5]undecan-1-one;

2-(2,3-dimethylbenzyl)-9-(quinoxalin-2-yl)-2,9-diazaspiro[5.5]undecan-1-one;

2-(2,3-dimethoxybenzyl)-9-(quinoxalin-2-yl)-2,9-diazaspiro[5.5]undecan-1-one;

2-(2-methylbenzyl)-9-(quinoxalin-2-yl)-2,9-diazaspiro[5.5]undecan-1-one;

2-(2,5-dimethylbenzyl)-9-(quinoxalin-2-yl)-2,9-diazaspiro[5.5]undecan-1-one;
2-(quinolin-8-ylmethyl)-9-(quinoxalin-2-yl)-2,9-diazaspiro[5.5]undecan-1-one;
2-(biphenyl-3-ylmethyl)-9-(quinoxalin-2-yl)-2,9-diazaspiro[5.5]undecan-1-one;
9-(quinoxalin-2-yl)-2-(2-(trifluoromethyl)benzyl)-2,9-diazaspiro[5.5]undecan-1-one;
9-(quinoxalin-2-yl)-2-(4-(trifluoromethyl)benzyl)-2,9-diazaspiro[5.5]undecan-1-one;
2-((2,3-dihydrobenzo[b][1,4]dioxin-6-yl)methyl)-9-(quinoxalin-2-yl)-2,9-diazaspiro[5.5]undecan-1-one;
2-((1-methyl-1H-indol-4-yl)methyl)-9-(quinoxalin-2-yl)-2,9-diazaspiro[5.5]undecan-1-one;
2-(3-chlorobenzyl)-9-(quinoxalin-2-yl)-2,9-diazaspiro[5.5]undecan-1-one;
9-(1H-benzo[d]imidazol-2-yl)-2-(3-chlorobenzyl)-2,9-diazaspiro[5.5]undecan-1-one;
2-(3-chlorobenzyl)-9-(4-phenylpyrimidin-2-yl)-2,9-diazaspiro[5.5]undecan-1-one;
2-((1-methyl-1H-benzo[d]imidazol-2-yl)methyl)-9-(quinoxalin-2-yl)-2,9-diazaspiro[5.5]undecan-1-one;
2-((5-(4-methoxyphenyl)-1,3,4-oxadiazol-2-yl)methyl)-9-(quinoxalin-2-yl)-2,9-diazaspiro[5.5]undecan-1-one;
2-((3-methyl-5-phenylisoxazol-4-yl)methyl)-9-(quinoxalin-2-yl)-2,9-diazaspiro[5.5]undecan-1-one;
2-((2-methylquinolin-4-yl)methyl)-9-(quinoxalin-2-yl)-2,9-diazaspiro[5.5]undecan-1-one;
2-((5-methyl-3-phenylisoxazol-4-yl)methyl)-9-(quinoxalin-2-yl)-2,9-diazaspiro[5.5]undecan-1-one;
2-(3-(1H-pyrrol-1-yl)benzyl)-9-(quinoxalin-2-yl)-2,9-diazaspiro[5.5]undecan-1-one;
2-(benzo[d]isoxazol-3-ylmethyl)-9-(quinoxalin-2-yl)-2,9-diazaspiro[5.5]undecan-1-one;
2-((3,5-dimethylisoxazol-4-yl)methyl)-9-(quinoxalin-2-yl)-2,9-diazaspiro[5.5]undecan-1-one;
1-((1H-indol-4-yl)methyl)-9-(quinoxalin-2-yl)-1,9-diazaspiro[5.5]undecan-2-one;
2-(2-(3-methyl-1,2,4-oxadiazol-5-yl)benzyl)-9-(quinoxalin-2-yl)-2,9-diazaspiro[5.5]undecan-1-one;
2-((1H-indol-3-yl)methyl)-9-(benzo[d]oxazol-2-yl)-2,9-diazaspiro[5.5]undecan-1-one;
1-(2,5-dimethylbenzyl)-9-(quinoxalin-2-yl)-1,9-diazaspiro[5.5]undecan-2-one;
1-((1H-indol-4-yl)methyl)-9-(benzo[d]oxazol-2-yl)-1,9-diazaspiro[5.5]undecan-2-one;
1-((1H-indol-3-yl)methyl)-9-(quinoxalin-2-yl)-1,9-diazaspiro[5.5]undecan-2-one;
1-((1-methyl-1H-indol-4-yl)methyl)-9-(quinoxalin-2-yl)-1,9-diazaspiro[5.5]undecan-2-one;
2-((2-methoxypyridin-4-yl)methyl)-9-(quinoxalin-2-yl)-2,9-diazaspiro[5.5]undecan-1-one;
2-(3-(1H-1,2,3-triazol-1-yl)benzyl)-9-(quinoxalin-2-yl)-2,9-diazaspiro[5.5]undecan-1-one;
2-(3-(2H-1,2,3-triazol-2-yl)benzyl)-9-(quinoxalin-2-yl)-2,9-diazaspiro[5.5]undecan-1-one;
2-((1H-indol-3-yl)methyl)-9-(quinolin-3-yl)-2,9-diazaspiro[5.5]undecan-1-one;
2-(2-(2H-1,2,3-triazol-2-yl)benzyl)-9-(quinoxalin-2-yl)-2,9-diazaspiro[5.5]undecan-1-one;
2-benzyl-9-(1-methyl-1H-benzo[d]imidazol-2-yl)-2,9-diazaspiro[5.5]undecan-1-one;
2-(2-(1-methyl-1H-pyrazol-4-yl)benzyl)-9-(quinoxalin-2-yl)-2,9-diazaspiro[5.5]undecan-1-one;
2-((1H-indol-3-yl)methyl)-9-(benzo[d]thiazol-2-yl)-2,9-diazaspiro[5.5]undecan-1-one;
2-(benzo[c][1,2,5]oxadiazol-5-ylmethyl)-9-(quinoxalin-2-yl)-2,9-diazaspiro[5.5]undecan-1-one;
2-(3-(pyridin-2-yl)benzyl)-9-(quinoxalin-2-yl)-2,9-diazaspiro[5.5]undecan-1-one;
2-(isoquinolin-5-ylmethyl)-9-(quinoxalin-2-yl)-2,9-diazaspiro[5.5]undecan-1-one;
2-((2-morpholinopyridin-4-yl)methyl)-9-(quinoxalin-2-yl)-2,9-diazaspiro[5.5]undecan-1-one;
2-((1H-pyrrolo[2,3-b]pyridin-3-yl)methyl)-9-(quinoxalin-2-yl)-2,9-diazaspiro[5.5]undecan-1-one;
2-(3-(pyridin-4-yl)benzyl)-9-(quinoxalin-2-yl)-2,9-diazaspiro[5.5]undecan-1-one;
2-(3-morpholinobenzyl)-9-(quinoxalin-2-yl)-2,9-diazaspiro[5.5]undecan-1-one;
2-(3-(1H-pyrazol-1-yl)benzyl)-9-(quinoxalin-2-yl)-2,9-diazaspiro[5.5]undecan-1-one;
2-(3-(pyrimidin-2-yl)benzyl)-9-(quinoxalin-2-yl)-2,9-diazaspiro[5.5]undecan-1-one;
2-(pyridin-2-ylmethyl)-9-(quinoxalin-2-yl)-2,9-diazaspiro[5.5]undecan-1-one;
2-((2-(1H-pyrazol-1-yl)pyridin-4-yl)methyl)-9-(quinoxalin-2-yl)-2,9-diazaspiro[5.5]undecan-1-one;
2-(pyridin-3-ylmethyl)-9-(quinoxalin-2-yl)-2,9-diazaspiro[5.5]undecan-1-one;
2-(3-(pyrazin-2-yl)benzyl)-9-(quinoxalin-2-yl)-2,9-diazaspiro[5.5]undecan-1-one;
2-((1H-benzo[d][1,2,3]triazol-1-yl)methyl)-9-(quinoxalin-2-yl)-2,9-diazaspiro[5.5]undecan-1-one;
2-(pyridin-4-ylmethyl)-9-(quinoxalin-2-yl)-2,9-diazaspiro[5.5]undecan-1-one;
2-((2-methylpyridin-4-yl)methyl)-9-(quinoxalin-2-yl)-2,9-diazaspiro[5.5]undecan-1-one;
2-((2-methyl-5-m-tolylthiazol-4-yl)methyl)-9-(quinoxalin-2-yl)-2,9-diazaspiro[5.5]undecan-1-one;
2-(imidazo[1,2-a]pyridin-3-ylmethyl)-9-(quinoxalin-2-yl)-2,9-diazaspiro[5.5]undecan-1-one;
2-((2-methylimidazo[1,2-a]pyridin-3-yl)methyl)-9-(quinoxalin-2-yl)-2,9-diazaspiro[5.5]undecan-1-one;
2-((2-bromopyridin-4-yl)methyl)-9-(quinoxalin-2-yl)-2,9-diazaspiro[5.5]undecan-1-one;
2-((5-(3-fluorophenyl)-2-methylthiazol-4-yl)methyl)-9-(quinoxalin-2-yl)-2,9-diazaspiro[5.5]undecan-1-one;
2-(1-(1H-indol-3-yl)ethyl)-9-(quinoxalin-2-yl)-2,9-diazaspiro[5.5]undecan-1-one;
2-([1,2,4]triazolo[4,3-a]pyridin-3-ylmethyl)-9-(quinoxalin-2-yl)-2,9-diazaspiro[5.5]undecan-1-one;
2-((2-methyl-2H-indazol-3-yl)methyl)-9-(quinoxalin-2-yl)-2,9-diazaspiro[5.5]undecan-1-one;
2-(benzo[c][1,2,5]oxadiazol-4-ylmethyl)-9-(quinoxalin-2-yl)-2,9-diazaspiro[5.5]undecan-1-one;
2-((6-chloropyridin-3-yl)methyl)-9-(quinoxalin-2-yl)-2,9-diazaspiro[5.5]undecan-1-one;
2-(pyrazolo[1,5-a]pyridin-3-ylmethyl)-9-(quinoxalin-2-yl)-2,9-diazaspiro[5.5]undecan-1-one;
2-(3-(methoxymethyl)benzyl)-9-(quinoxalin-2-yl)-2,9-diazaspiro[5.5]undecan-1-one;
2-(4-(1H-1,2,4-triazol-1-yl)benzyl)-9-(quinoxalin-2-yl)-2,9-diazaspiro[5.5]undecan-1-one;
2-((2,3-dihydrobenzo[b][1,4]dioxin-5-yl)methyl)-9-(furo[3,2-c]pyridin-4-yl)-2,9-diazaspiro[5.5]undecan-1-one;
2-((6-(1H-pyrazol-1-yl)pyridin-2-yl)methyl)-9-(quinoxalin-2-yl)-2,9-diazaspiro[5.5]undecan-1-one;
2-((1,5-dimethyl-1H-pyrazol-3-yl)methyl)-9-(quinoxalin-2-yl)-2,9-diazaspiro[5.5]undecan-1-one;
2-(2-(1H-pyrazol-1-yl)benzyl)-9-(quinoxalin-2-yl)-2,9-diazaspiro[5.5]undecan-1-one;

2-((1-benzyl-1H-imidazol-2-yl)methyl)-9-(quinoxalin-2-yl)-2,9-diazaspiro[5.5]undecan-1-one;
2-((6-chloro-4H-benzo[d][1,3]dioxin-8-yl)methyl)-9-(quinoxalin-2-yl)-2,9-diazaspiro[5.5]undecan-1-one;
2-((5-methylisoxazol-3-yl)methyl)-9-(quinoxalin-2-yl)-2,9-diazaspiro[5.5]undecan-1-one;
2-((5-cyclobutyl-1,2,4-oxadiazol-3-yl)methyl)-9-(quinoxalin-2-yl)-2,9-diazaspiro[5.5]undecan-1-one;
9-(quinoxalin-2-yl)-2-((6-(trifluoromethyl)pyridin-3-yl)methyl)-2,9-diazaspiro[5.5]undecan-1-one;
2-((3,4-dimethoxypyridin-2-yl)methyl)-9-(quinoxalin-2-yl)-2,9-diazaspiro[5.5]undecan-1-one;
3-((1-oxo-9-(quinoxalin-2-yl)-2,9-diazaspiro[5.5]undecan-2-yl)methyl)benzonitrile
2-(isoquinolin-1-ylmethyl)-9-(quinoxalin-2-yl)-2,9-diazaspiro[5.5]undecan-1-one;
2-fluoro-5-((1-oxo-9-(quinoxalin-2-yl)-2,9-diazaspiro[5.5]undecan-2-yl)methyl)benzonitrile
2-((5-phenyloxazol-4-yl)methyl)-9-(quinoxalin-2-yl)-2,9-diazaspiro[5.5]undecan-1-one;
4-((1-oxo-9-(quinoxalin-2-yl)-2,9-diazaspiro[5.5]undecan-2-yl)methyl)quinolin-2(1H)-one;
2-((6-methylpyridin-2-yl)methyl)-9-(quinoxalin-2-yl)-2,9-diazaspiro[5.5]undecan-1-one;
2-(3-(5-methyl-1,2,4-oxadiazol-3-yl)benzyl)-9-(quinoxalin-2-yl)-2,9-diazaspiro[5.5]undecan-1-one;
4-fluoro-3-((1-oxo-9-(quinoxalin-2-yl)-2,9-diazaspiro[5.5]undecan-2-yl)methyl)benzonitrile
5-((1-oxo-9-(quinoxalin-2-yl)-2,9-diazaspiro[5.5]undecan-2-yl)methyl)picolinonitrile
2-(4-(pyrimidin-2-yl)benzyl)-9-(quinoxalin-2-yl)-2,9-diazaspiro[5.5]undecan-1-one;
2-(2-fluoro-3-methoxybenzyl)-9-(quinoxalin-2-yl)-2,9-diazaspiro[5.5]undecan-1-one;
2-((6-(pyrrolidin-1-yl)pyridin-2-yl)methyl)-9-(quinoxalin-2-yl)-2,9-diazaspiro[5.5]undecan-1-one;
2-(3-(3-methyl-1,2,4-oxadiazol-5-yl)benzyl)-9-(quinoxalin-2-yl)-2,9-diazaspiro[5.5]undecan-1-one;
2-((3-methylisoxazol-5-yl)methyl)-9-(quinoxalin-2-yl)-2,9-diazaspiro[5.5]undecan-1-one;
2-((4,6-dimethylpyridin-2-yl)methyl)-9-(quinoxalin-2-yl)-2,9-diazaspiro[5.5]undecan-1-one;
2-((1-methyl-1H-indazol-7-yl)methyl)-9-(quinoxalin-2-yl)-2,9-diazaspiro[5.5]undecan-1-one;
2-((1-methyl-1H-indazol-4-yl)methyl)-9-(quinoxalin-2-yl)-2,9-diazaspiro[5.5]undecan-1-one;
2-(4-(5-methyl-1,3,4-oxadiazol-2-yl)benzyl)-9-(quinoxalin-2-yl)-2,9-diazaspiro[5.5]undecan-1-one;
2-((1-phenyl-1H-imidazol-5-yl)methyl)-9-(quinoxalin-2-yl)-2,9-diazaspiro[5.5]undecan-1-one;
2-((1-(3-methoxyphenyl)-1H-imidazol-5-yl)methyl)-9-(quinoxalin-2-yl)-2,9-diazaspiro[5.5]undecan-1-one;
2-((1-(2-methoxyphenyl)-1H-imidazol-2-yl)methyl)-9-(quinoxalin-2-yl)-2,9-diazaspiro[5.5]undecan-1-one;
2-(benzo[c][1,2,5]thiadiazol-4-ylmethyl)-9-(quinoxalin-2-yl)-2,9-diazaspiro[5.5]undecan-1-one;
2-((5-methyl-2-(thiazol-4-yl)oxazol-4-yl)methyl)-9-(quinoxalin-2-yl)-2,9-diazaspiro[5.5]undecan-1-one;
2-(2-(3,5-dimethyl-1H-pyrazol-1-yl)benzyl)-9-(quinoxalin-2-yl)-2,9-diazaspiro[5.5]undecan-1-one;
2-((2-(furan-3-yl)-5-methyloxazol-4-yl)methyl)-9-(quinoxalin-2-yl)-2,9-diazaspiro[5.5]undecan-1-one;
9-(quinoxalin-2-yl)-2-((2,2,8-trimethyl-4H-[1,3]dioxino[4,5-c]pyridin-5-yl)methyl)-2,9-diazaspiro[5.5]undecan-1-one;
2-((1-benzyl-1H-imidazol-5-yl)methyl)-9-(quinoxalin-2-yl)-2,9-diazaspiro[5.5]undecan-1-one;
2-((4-methyl-2-phenyloxazol-5-yl)methyl)-9-(quinoxalin-2-yl)-2,9-diazaspiro[5.5]undecan-1-one;
2-((6-fluoro-4H-benzo[d][1,3]dioxin-8-yl)methyl)-9-(quinoxalin-2-yl)-2,9-diazaspiro[5.5]undecan-1-one;
2-((1H-indol-2-yl)methyl)-9-(quinoxalin-2-yl)-2,9-diazaspiro[5.5]undecan-1-one;
2-((1-phenyl-1H-tetrazol-5-yl)methyl)-9-(quinoxalin-2-yl)-2,9-diazaspiro[5.5]undecan-1-one;
2-((1H-indol-5-yl)methyl)-9-(quinoxalin-2-yl)-2,9-diazaspiro[5.5]undecan-1-one;
2-((1-oxo-9-(quinoxalin-2-yl)-2,9-diazaspiro[5.5]undecan-2-yl)methyl)benzonitrile
2-(5-methyl-2-(2H-1,2,3-triazol-2-yl)benzyl)-9-(quinoxalin-2-yl)-2,9-diazaspiro[5.5]undecan-1-one;
2-(indolin-4-ylmethyl)-9-(quinoxalin-2-yl)-2,9-diazaspiro[5.5]undecan-1-one;
2-((4-(1H-pyrazol-1-yl)pyridin-2-yl)methyl)-9-(quinoxalin-2-yl)-2,9-diazaspiro[5.5]undecan-1-one;
2-(2-methyl-5-(2H-1,2,3-triazol-2-yl)benzyl)-9-(quinoxalin-2-yl)-2,9-diazaspiro[5.5]undecan-1-one;
2-((1H-indazol-3-yl)methyl)-9-(quinoxalin-2-yl)-2,9-diazaspiro[5.5]undecan-1-one;
2-((1-methyl-1H-indol-3-yl)methyl)-9-(quinoxalin-2-yl)-2,9-diazaspiro[5.5]undecan-1-one;
2-((1H-indol-3-yl)methyl)-9-(5-chlorobenzo[d]oxazol-2-yl)-2,9-diazaspiro[5.5]undecan-1-one;
2-((3,4-dihydro-2H-benzo[b][1,4]oxazin-8-yl)methyl)-9-(quinoxalin-2-yl)-2,9-diazaspiro[5.5]undecan-1-one;
2-((2-methyl-1H-indol-3-yl)methyl)-9-(quinoxalin-2-yl)-2,9-diazaspiro[5.5]undecan-1-one;
1-benzyl-9-(quinoxalin-2-yl)-1,9-diazaspiro[5.5]undecan-2-one;
1-(benzo[d]isoxazol-3-ylmethyl)-9-(quinoxalin-2-yl)-1,9-diazaspiro[5.5]undecan-2-one;
1-((1H-indol-4-yl)methyl)-9-(5-chlorobenzo[d]oxazol-2-yl)-1,9-diazaspiro[5.5]undecan-2-one;
1-((1H-indol-4-yl)methyl)-9-(5-phenyl-1,3,4-oxadiazol-2-yl)-1,9-diazaspiro[5.5]undecan-2-one;
1-((1H-indol-4-yl)methyl)-9-(1H-benzo[d]imidazol-2-yl)-1,9-diazaspiro[5.5]undecan-2-one;
1-((1H-indol-4-yl)methyl)-9-(6-chlorobenzo[d]oxazol-2-yl)-1,9-diazaspiro[5.5]undecan-2-one;
1-((1H-indol-4-yl)methyl)-9-(5-methylbenzo[d]oxazol-2-yl)-1,9-diazaspiro[5.5]undecan-2-one;
1-((1H-pyrrolo[2,3-b]pyridin-3-yl)methyl)-9-(quinoxalin-2-yl)-1,9-diazaspiro[5.5]undecan-2-one;
2-((1-methyl-1H-indazol-3-yl)methyl)-9-(quinoxalin-2-yl)-2,9-diazaspiro[5.5]undecan-1-one;
1-((1-methyl-1H-pyrrolo[2,3-b]pyridin-3-yl)methyl)-9-(quinoxalin-2-yl)-1,9-diazaspiro[5.5]undecan-2-one;
2-((4-methyl-3,4-dihydro-2H-benzo[b][1,4]oxazin-8-yl)methyl)-9-(quinoxalin-2-yl)-2,9-diazaspiro[5.5]undecan-1-one;
2-((1-methylindolin-4-yl)methyl)-9-(quinoxalin-2-yl)-2,9-diazaspiro[5.5]undecan-1-one;
2-((1H-indol-3-yl)methyl)-9-(pyrido[3,2-b]pyrazin-7-yl)-2,9-diazaspiro[5.5]undecan-1-one;
2-(3-(5-methyloxazol-2-yl)benzyl)-9-(quinoxalin-2-yl)-2,9-diazaspiro[5.5]undecan-1-one;
2-(2-(1-methyl-1H-pyrazol-5-yl)benzyl)-9-(quinoxalin-2-yl)-2,9-diazaspiro[5.5]undecan-1-one;
2-(2-(oxazol-2-yl)benzyl)-9-(quinoxalin-2-yl)-2,9-diazaspiro[5.5]undecan-1-one;
2-(2-(furan-2-yl)benzyl)-9-(quinoxalin-2-yl)-2,9-diazaspiro[5.5]undecan-1-one;
2-(2-(pyrimidin-2-yl)benzyl)-9-(quinoxalin-2-yl)-2,9-diazaspiro[5.5]undecan-1-one;

2-((1H-indol-3-yl)methyl)-9-(1H-benzo[d]imidazol-2-yl)-2,9-diazaspiro[5.5]undecan-1-one;
2-((1H-indol-3-yl)methyl)-9-(6-methylbenzo[d]thiazol-2-yl)-2,9-diazaspiro[5.5]undecan-1-one;
2-((1H-indol-3-yl)methyl)-9-(4-phenylpyrimidin-2-yl)-2,9-diazaspiro[5.5]undecan-1-one;
2-((1H-indol-3-yl)methyl)-9-(7H-pyrrolo[2,3-d]pyrimidin-4-yl)-2,9-diazaspiro[5.5]undecan-1-one;
2-((1H-indol-3-yl)methyl)-9-(furo[3,2-c]pyridin-4-yl)-2,9-diazaspiro[5.5]undecan-1-one;
2-((1H-indol-3-yl)methyl)-9-(4-methylphthalazin-1-yl)-2,9-diazaspiro[5.5]undecan-1-one;
9-(6-(1H-imidazol-1-yl)pyrimidin-4-yl)-2-((1H-indol-3-yl)methyl)-2,9-diazaspiro[5.5]undecan-1-one;
2-((1H-indol-3-yl)methyl)-9-(5-methoxy-1H-benzo[d]imidazol-2-yl)-2,9-diazaspiro[5.5]undecan-1-one;
2-((1H-indol-3-yl)methyl)-9-(quinolin-2-yl)-2,9-diazaspiro[5.5]undecan-1-one;
2-((1H-indol-3-yl)methyl)-9-(5-(thiazol-2-yl)pyridin-2-yl)-2,9-diazaspiro[5.5]undecan-1-one;
2-((1H-indol-3-yl)methyl)-9-(isoquinolin-1-yl)-2,9-diazaspiro[5.5]undecan-1-one;
2-((1H-indol-3-yl)methyl)-9-(5-methyl-1H-benzo[d]imidazol-2-yl)-2,9-diazaspiro[5.5]undecan-1-one;
2-((1H-indol-3-yl)methyl)-9-(4-methylquinolin-2-yl)-2,9-diazaspiro[5.5]undecan-1-one;
2-((1H-indol-3-yl)methyl)-9-(6-phenylpyrimidin-4-yl)-2,9-diazaspiro[5.5]undecan-1-one;
2-((1H-indol-3-yl)methyl)-9-(4-(pyridin-4-yl)pyrimidin-2-yl)-2,9-diazaspiro[5.5]undecan-1-one;
2-((1H-indol-3-yl)methyl)-9-(pyrido[4,3-b]pyrazin-7-yl)-2,9-diazaspiro[5.5]undecan-1-one;
2-((1H-indol-3-yl)methyl)-9-(imidazo[1,2-b]pyridazin-6-yl)-2,9-diazaspiro[5.5]undecan-1-one;
2-((1H-indol-3-yl)methyl)-9-(quinazolin-2-yl)-2,9-diazaspiro[5.5]undecan-1-one;
2-((1H-indol-3-yl)methyl)-9-(3-methylquinoxalin-2-yl)-2,9-diazaspiro[5.5]undecan-1-one;
2-((1H-indol-3-yl)methyl)-9-(5-phenyl-1,3,4-thiadiazol-2-yl)-2,9-diazaspiro[5.5]undecan-1-one;
2-((1H-indol-3-yl)methyl)-9-(4-(4-fluorophenyl)thiazol-2-yl)-2,9-diazaspiro[5.5]undecan-1-one;
2-((1H-indol-3-yl)methyl)-9-(4-methyl-6-(1H-pyrazol-1-yl)pyrimidin-2-yl)-2,9-diazaspiro[5.5]undecan-1-one and
2-((1H-indol-3-yl)methyl)-9-(4-(1H-pyrazol-1-yl)pyrimidin-2-yl)-2,9-diazaspiro[5.5]undecan-1-one.

11. A pharmaceutical composition comprising a therapeutically effective amount of a compound of claim 1 and one or more pharmaceutically acceptable carriers.

12. A combination comprising a therapeutically effective amount of the compound of claim 1 and one or more therapeutically active agents.

13. A compound in free form or in pharmaceutically acceptable salt form, wherein said compound is:

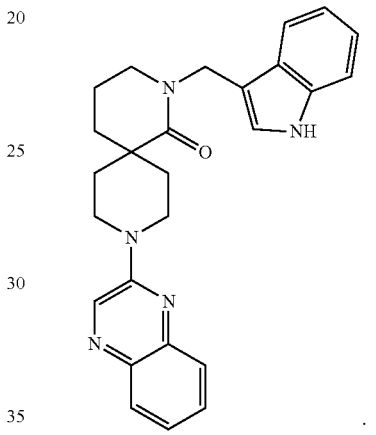

* * * * *